US012807943B2

(12) United States Patent
Doudna et al.

(10) Patent No.: US 12,807,943 B2
(45) Date of Patent: Nov. 24, 2026

(54) COMPOSITIONS AND METHODS FOR DELIVERING CRISPR/CAS EFFECTOR POLYPEPTIDES

(71) Applicant: The Regents of the University of California, Oakland, CA (US)

(72) Inventors: Jennifer A. Doudna, Berkeley, CA (US); Jennifer Rose Hamilton, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1266 days.

(21) Appl. No.: 17/287,392

(22) PCT Filed: Nov. 15, 2019

(86) PCT No.: PCT/US2019/061778
§ 371 (c)(1),
(2) Date: Apr. 21, 2021

(87) PCT Pub. No.: WO2020/102709
PCT Pub. Date: May 22, 2020

(65) Prior Publication Data

US 2023/0193255 A1 Jun. 22, 2023

Related U.S. Application Data

(60) Provisional application No. 62/889,867, filed on Aug. 21, 2019, provisional application No. 62/843,139, filed on May 3, 2019, provisional application No. 62/768,508, filed on Nov. 16, 2018.

(51) Int. Cl.
*C12N 15/11* (2006.01)
*C07K 14/005* (2006.01)
*C12N 7/00* (2006.01)
*C12N 15/86* (2006.01)
*C12N 15/113* (2010.01)

(52) U.S. Cl.
CPC ............ *C12N 15/11* (2013.01); *C07K 14/005* (2013.01); *C12N 7/00* (2013.01); *C12N 15/1138* (2013.01); *C12N 2310/20* (2017.05); *C12N 2320/32* (2013.01); *C12N 2740/16023* (2013.01)

(58) Field of Classification Search
CPC ................ C12N 15/11; C12N 15/1138; C12N 2310/20; C12N 2740/16023; C12N 15/86; C12N 2740/16043; C07K 14/005
See application file for complete search history.

(56) References Cited

U.S. PATENT DOCUMENTS

| | | | | |
|---|---|---|---|---|
| 5,175,099 | A | 12/1992 | Wills | |
| 9,322,037 | B2 | 4/2016 | Liu et al. | |
| 10,968,253 | B2 | 4/2021 | Ohlmann | |
| 11,649,264 | B2 | 5/2023 | Ohlmann | |
| 12,049,480 | B2 | 7/2024 | Ohlmann | |
| 12,202,860 | B2 | 1/2025 | Ohlmann | |
| 2002/0168346 | A1 | 11/2002 | Leboulch et al. | |
| 2005/0009743 | A1 | 1/2005 | Sundquist et al. | |
| 2018/0200188 | A1 * | 7/2018 | Luo | C07K 14/163 |
| 2018/0200359 | A1 | 7/2018 | Puckette et al. | |
| 2019/0055288 | A1 | 2/2019 | Ohlmann et al. | |
| 2020/0255864 | A1 | 8/2020 | Frost et al. | |
| 2022/0403379 | A1 | 12/2022 | Doudna et al. | |
| 2023/0071283 | A1 | 3/2023 | Golosov et al. | |

FOREIGN PATENT DOCUMENTS

| | | | | |
|---|---|---|---|---|
| WO | WO 2010/040023 | | 4/2010 | |
| WO | WO 2017/068077 | | 4/2017 | |
| WO | WO-2017068077 | A1 * | 4/2017 | C07K 14/005 |
| WO | WO 2017/181119 | | 10/2017 | |
| WO | WO 2022/183072 | A1 | 9/2022 | |
| WO | 2023/102550 | A2 | 6/2023 | |
| WO | WO 2024/015605 | A1 | 1/2024 | |
| WO | 2024/044557 | A1 | 2/2024 | |

OTHER PUBLICATIONS

Hübner W. et al. Sequence of human immunodeficiency virus type 1 (HIV-1) Gag localization and oligomerization monitored with live confocal imaging of a replication-competent, fluorescently tagged HIV-1. J Virol. Nov. 2007;81(22):12596-607. doi: 10.1128/JVI.01088-07. Epub Aug. 29, 2007. (Year: 2007).*

Cebrian-Serrano, et al.; "CRISPR-Cas orthologues and variants: optimizing the repertoire, specificity and delivery of genome engineering tools"; Mamm Genome; vol. 28, ps. 247-261 (2017).

Choi, et al.; "Lentivirus pre-packed with Cas9 protein for safer gene editing"; Gene Therapy; vol. 23, pp. 627-633 (2016).

Cronin, et al.; "Altering the Tropism of Lentiviral Vectors through Pseudotyping"; Curr Gene Ther; vol. 5, No. 4, pp. 387-398 (Aug. 2005).

Hewitt; "The MHC class I antigen presentation pathway: strategies for viral immune evasion"; Immunology; vol. 110, pp. 163-169 (2003).

Mangeot, et al.; "Efficient genome editing in primary cells and in vivo using viral-derived "Nanoblades" loaded with Cas9/sgRNA ribonucleoproteins"; bioRxiv; doi: https://doi.org/10.1101/202010 (Oct. 12, 2017).

Montagna, et al.; "VSV-G-Enveloped Vesicles for Traceless Delivery of CRISPR-Cas9"; Molecular Therapy: Nucleic Acids; vol. 12, pp. 453-462 (Sep. 2018).

Muriaux, et al.; "Properties and functions of the nucleocapsid protein in virus assembly"; RNA Biology; vol. 7, No. 6, pp. 744-753 (Nov./Dec 2010).

(Continued)

*Primary Examiner* — Maria G Leavitt
*Assistant Examiner* — Vyoma Shubham Tiwari
(74) *Attorney, Agent, or Firm* — Kyle A. Gurley; Bozicevic, Field & Francis LLP

(57) ABSTRACT

The present disclosure provides a virus-like particle (VLP) comprising a therapeutic polypeptide, and nucleic acids comprising nucleotide sequences encoding the components of the VLP. The present disclosure provides a virus-like particle (VLP) comprising a CRISPR/Cas effector polypeptide, and nucleic acids comprising nucleotide sequences encoding the components of the VLP. The present disclosure provides a system for making a VLP of the present disclosure, as well as methods of making the VLP.

54 Claims, 93 Drawing Sheets

Specification includes a Sequence Listing.

(56) References Cited

OTHER PUBLICATIONS

Pyzocha, et al.; "Diverse Class 2 CRISPR-Cas Effector Proteins for Genome Engineering Applications"; ACS Chemical Biology; vol. 13, pp. 347-356 (2018).
Shao, et al.; "Inhibition of antigen presentation during AAV gene therapy using virus peptides"; Human Molecular Genetics; vol. 27, No. 4, pp. 601-613 (2018).
Staahl, et al.; "Efficient genome editing in the mouse brain by local delivery of engineered Cas9 ribonucleoprotein complexes"; Nature Biotechnology; vol. 35, No. 5, pp. 431-434 (May 2017).
Yewdell, et al.; "Mechanisms of Viral Interference with MHC Class I Antigen Processing and Presentation"; Annu Rev Cell Dev Biol; vol. 15, pp. 579-606 (1999).
Anzalone, et al.; "Search-and-replace genome editing without double-strand breaks or donor DNA"; Nature; vol. 576, pp. 149-157 (2019).
Banskota, et al.; "Engineered virus-like particles for efficient in vivo delivery of therapeutic proteins"; Cell; vol. 185, No. 2, pp. 250-265 (Jan. 20, 2022).
Dobson, et al.; "Antigen identification and high-throughput interaction mapping by reprogramming viral entry"; Nature Methods; vol. 19, pp. 449-460 (2022).
Hamilton, et al.; "In vivo human T cell engineering with enveloped delivery vehicles"; Nature Biotechnology; vol. 42, pp. 1684-1692 (Nov. 2024).
Hamilton, et al.; "Targeted delivery of CRISPR-Cas9 and transgenes enables complex immune cell engineering"; Cell Reports; vol. 35, No. 9, Article 109207, pp. 1-11 (Jun. 1, 2021).
Koblan, et al.; "Improving cytidine and adenine base editors by expression optimization and ancestral reconstruction"; Nature Biotechnology; vol. 36, pp. 843-846 (2018).
Liu, et al.; "CRISPR-Cas9-mediated multiplex gene editing in CAR-T cells"; Cell Research; vol. 27, pp. 154-157 (2017).
Mangeot et al. (2019) "Genome editing in primary cells and in vivo using viral-derived Nanoblades loaded with Cas9-sgRNA ribonucleoproteins", Nature Communications 10:45 1-15.
Münch, et al.; "DARPins: An Efficient Targeting Domain for Lentiviral Vectors"; Molecular Therapy; vol. 19, No. 4, pp. 686-693 (Apr. 2011).
Ngo, et al.; "Mechanism-guided engineering of a minimal biological particle for genome editing"; PNAS; vol. 122, No. 1, e2413519121, pp. 1-9 (Dec 30, 2024), includes Supporting Information.
Nikolic, et al.; "Structural basis for the recognition of LDL-receptor family members by VSV glycoprotein"; Nature Communications; vol. 9, No. 1029, pp. 1-12 (2018).
Richardson, et al.; "Enhancing homology-directed genome editing by catalytically active and inactive CRISPR-Cas9 using asymmetric donor DNA"; Nature Biotechnology; vol. 34, pps. pp. 339-344 (2016).
Yu, et al.; "Systematic discovery of receptor-ligand biology by engineered cell entry and single-cell genomics"; bioRxiv; pp. 1-53 (Dec 14, 2021).
Gutierrez-Guerrero et al. (2021) "Baboon Envelope Pseudotyped "Nanoblades" Carrying Cas9/gRNA Complexes Allow Efficient Genome Editing in Human T, B, and CD34+ Cells and Knock-in of AAV6-Encoded Donor DNA in CD34+ Cells", Front Genome Ed., 3: 604371 1-21.
Zila et al. (2021) "Cone-shaped HIV-1 capsids are transported through intact nuclear pores", Cell, 184:4 1032-1046.
Guo, et al.; "Structural insights into a high fidelity variant of SpCas9"; Cell Research; vol. 29, pp. 183-192 (2019).
Paul, et al.; "CRISPR-Cas12a: Functional overview and applications"; Biomedical Journal; vol. 43, No. 1, pp. 8-17 (Feb. 2020).
Voelkel, et al.; "Protein transduction from retroviral Gag precursors"; PNAS; vol. 107, No. 17, pp. 7805-7810 (Apr. 27, 2010).
Voet, et al.; "3. Chemical Evolution"; Biochemistry, John Wiley and Sons; pp. 126-129 (1990).
Potempa, et al.; "HIV-1 Protease Uses Bi-Specific S2/S2' Subsites to Optimize Cleavage of Two Classes of Target Sites"; Journal of Molecular Biology; vol. 430, No. 24, pp. 5182-5195 (Dec 7, 2018).
Cheng; "Virus-Like Particles Enable Low Levels of CRISPR-Cas9-Mediated Homology-Directed Repair"; Department of Biology, Swarthmore College—Thesis; pp. 1-51 (Nov. 6, 2021).

* cited by examiner

Protein-coding regions of Gag-Pol and Gag-Cas9 plasmids

FIG. 4A (SEQ ID NO:1077)

*ATGGGTGCGAGAGCGTCAGTATTAAGCGGGGGAGAATTAGATCGATGGGAAAAAATTCGGTTAAGGCCAGGGGGAAAGAAAAA*
*ATATAAATTAAAACATATAGTATGGGCAAGCAGGGAGCTAGAACGATTCGCAGTTAATCCTGGCCTGTTAGAAACATCAGAAGGC*
*TGTAGACAAATACTGGGACAGCTACAACCATCCCTTCAGACAGGATCAGAAGAACTTAGATCATTATATAATACAGTAGCAACCC*
*TCTATTGTGTGCATCAAAGGATAGAGATAAAAGACACCAAGGAAGCTTTAGACAAGATAGAGGAAGAGCAAAACAAAAGTAAGAA*
*AAAAGCACAGCAAGCAGCAGCTGACACAGGACACAGCAATCAGGTCAGCCAAAATTAC*GAAAACCTGTATTTCCAATCTCCTAT
AGTGCAGAACATCCAGGGGCAAATGGTACATCAGGCCATATCACCTAGAACTTTAAATGCATGGGTAAAAGTAGTAGAAGAGAA
GGCTTTCAGCCCAGAAGTGATACCCATGTTTTCAGCATTATCAGAAGGAGCCACCCCACAAGATTTAAACACCATGCTAAACACA
GTGGGGGGACATCAAGCAGCCATGCAAATGTTAAAAGAGACCATCAATGAGGAAGCTGCAGAATGGGATAGAGTGCATCCAGT
GCATGCAGGGCCTATTGCACCAGGCCAGATGAGAGAACCAAGGGGAAGTGACATAGCAGGAACTACTAGTACCCTTCAGGAAC
AAATAGGATGGATGACACATAATCCACCTATCCCAGTAGGAGAAATCTATAAAAGATGGATAATCCTGGGATTAAATAAAATAGTA
AGAATGTATAGCCCTACCAGCATTCTGGACATAAGACAAGGACCAAAGGAACCCTTTAGAGACTATGTAGACCGATTCTATAAAA
CTCTAAGAGCCGAGCAAGCTTCACAAGAGGTAAAAAATTGGATGACAGAAACCTTGTTGGTCCAAAATGCGAACCCAGATTGTAA
GACTATTTTAAAAGCATTGGGACCAGGAGCGACACTAGAAGAAATGATGACAGCATGTCAGGGAGTGGGGGGACCCGGCCATA
AAGCAAGAGTTTTGGAAAACTTGTATTTTCAGTCTgctgaagcaatgagccaagtaacaaatccagctaccataatgGAAAACCTGTATTTCCAATC
Tatacagaaaggcaattttaggaaccaaagaaagactgttaagtgtttcaattgtggcaaagaagggcacatagccaaaaattgcagggcccctaggaaaaagggctgttg
gaaatgtggaaaggaaggacaccaaatgaaagattgtactgagagacaggctaatttttttagggaagatctggccttcccacaagggaaggccagggaattttcttcagagc
agaccagagccaacagccccaccagaagagagcttcaggtttggggaagagacaacaactccctctcagaagcaggagccgatagacaaggaactgtatcctttagcttc
cctcagatcactctttggcagcgacccctcgtcacaataa

MATRIX -- italicized
CAPSID -- underlined
P2 -- double underlined
NUCLEOCAPSID; P1; P6 -- bold (P1 also underlined)

TEV CLEAVAGE SITE (ENLYFQ/S) -- bold and underlined
(SEQ ID NO:1112)

FIG. 4B (SEQ ID NO:1078)

*MGARASVLSGGELDRWEKIRLRPGGKKKYKLKHIVWASRELERFAVNPGLLETSEGCRQILGQLQPSLQTGSEELRSLYNTVATLYCVHQRIEIKDTK*

*EALDKIEEEQNKSKKKAQQAAADTGHSNQVSQNY*ENLYFQSPIVQNIQGQMVHQAISPRTLNAWVKVVEEKAFSPEVIPMFSALSEGATPQDLNTMLN

TVGGHQAAMQMLKETINEEAAEWDRVHPVHAGPIAPGQMREPRGSDIAGTTSTLQEQIGWMTHNPPIPVGEIYKRWIILGLNKIVRMYSPTSILDIRQ

GPKEPFRDYVDRFYKTLRAEQASQEVKNWMTETLLVQNANPDCKTILKALGPGATLEEMMTACQGVGGPGHKARVLENLYFQSAEAMSQVTNPATIME

NLYFQSIQKGNFRNQRKTVKCFNCGKEGHIAKNCRAPRKKGCWKCGKEGHQMKDCTERQANFLGKIWPSHKGRPGNFLQSRPEPTAPPEESFRFGEET

TTPSQKQEPIDKELYPLASLRSLFGSDPSSQ

MA -- italicized
TEV cleavage site (ENLYFQS) -- bold and underlined (SEQ ID NO:880)
CA -- underlined
p2 -- double underlined
NC-p1-p6 -- bold

FIG. 5A (SEQ ID NO:1079)

*ATGGGTGCGAGAGCGTCAGTATTAAGCGGGGGAGAATTAGATCGATGGGAAAAAATTCGGTTAAGGCCAGGGGGAAAGAAAAA*

*ATATAAATTAAAACATATAGTATGGGCAAGCAGGGAGCTAGAACGATTCGCAGTTAATCCTGGCCTGTTAGAAACATCAGAAGGC*

*TGTAGACAAATACTGGGACAGCTACAACCATCCCTTCAGACAGGATCAGAAGAACTTAGATCATTATATAATACAGTAGCAACCC*

*TCTATTGTGTGCATCAAAGGATAGAGATAAAAGACACCAAGGAAGCTTTAGACAAGATAGAGGAAGAGCAAAACAAAAGTAAGAA*

*AAAAGCACAGCAAGCAGCAGCTGACACAGGACACAGCAATCAGGTCAGCCAAAATTAC*GAAAACCTGTATTTCCAATCTCCTAT

AGTGCAGAACATCCAGGGGCAAATGGTACATCAGGCCATATCACCTAGAACTTTAAATGCATGGGTAAAAGTAGTAGAAGAGAA

GGCTTTCAGCCCAGAAGTGATACCCATGTTTTCAGCATTATCAGAAGGAGCCACCCCACAAGATTTAAACACCATGCTAAACACA

GTGGGGGGACATCAAGCAGCCATGCAAATGTTAAAAGAGACCATCAATGAGGAAGCTGCAGAATGGGATAGAGTGCATCCAGT

GCATGCAGGGCCTATTGCACCAGGCCAGATGAGAGAACCAAGGGGAAGTGACATAGCAGGAACTACTAGTACCCTTCAGGAAC

AAATAGGATGGATGACACATAATCCACCTATCCCAGTAGGAGAAATCTATAAAAGATGGATAATCCTGGGATTAAATAAAATAGTA

AGAATGTATAGCCCTACCAGCATTCTGGACATAAGACAAGGACCAAAGGAACCCTTTAGAGACTATGTAGACCGATTCTATAAAA

CTCTAAGAGCCGAGCAAGCTTCACAAGAGGTAAAAAATTGGATGACAGAAACCTTGTTGGTCCAAAATGCGAACCCAGATTGTAA

GACTATTTTAAAAGCATTGGGACCAGGAGCGACACTAGAAGAAATGATGACAGCATGTCAGGGAGTGGGGGGACCCGGCCATA

AAGCAAGAGTTTTGGAAAACTTGTATTTTCAGTCTgctgaagcaatgagccaagtaacaaatccagctaccataatgGAAAACCTGTATTTCCAATC

Tatacagaaaggcaattttaggaaccaaagaaagactgttaagtgtttcaattgtggcaaagaagggcacatagccaaaaattgcagggcccctaggaaaaagggctgttg gaaatgtggaaaggaaggacaccaaatgaaagattgtactgagagacaggctaattttttagggaagatctggccttcccacaagggaaggccagggaattttcttcagagc agaccagagccaacagccccaccagaagagagcttcaggtttggggaagagacaacaactccctctcagaagcaggagccgatagacaaggaactgtatcctttagcttc cctcagatcactctttggcagcgacccctcgtcacaaAACTTTGAAAACCTGTATTTCCAATCT*atgg*

FIG. 5A (Cont.)

acaagaagtacagcatcggcctggacatcggcaccaactctgtgggctgggccgtgatcaccgacgagtacaaggtgcccagcaagaaattcaaggtgctgggcaacaccgaccggc
acagcatcaagaagaacctgatcggcgccctgctgttcgacagcggagaaacagccgaggccacccggctgaagagaaccgccagaagaagatacaccagacggaagaaccgg
atctgctatctgcaagagatcttcagcaacgagatggccaaggtggacgacagcttcttccacagactggaagagtccttcctggtggaagaggataagaagcacgagcggcaccccatc
ttcggcaacatcgtggacgaggtggcctaccacgagaagtaccccaccatctaccacctgagaaagaaactggtggacagcaccgacaaggccgacctgcggctgatctatctggccct
ggcccacatgatcaagttccggggccacttcctgatcgagggcgacctgaaccccgacaacagcgacgtggacaagctgttcatccagctggtgcagacctacaaccagctgttcgagg
aaaaccccatcaacgccagcggcgtggacgccaaggccatcctgtctgccagactgagcaagagcagacggctggaaaatctgatcgcccagctgcccggcgagaagaagaatggc
ctgttcggcaacctgattgccctgagcctgggcctgacccccaacttcaagagcaacttcgacctggccgaggatgccaaactgcagctgagcaaggacacctacgacgacgacctgga
caacctgctggcccagatcggcgaccagtacgccgacctgtttctggccgccaagaacctgtccgacgccatcctgctgagcgacatcctgagagtgaacaccgagatcaccaaggccc
ccctgagcgcctctatgatcaagagatacgacgagcaccaccaggacctgaccctgctgaaagctctcgtgcggcagcagctgcctgagaagtacaaagagattttcttcgaccagagca
agaacggctacgccggctacatcgatggcggagccagccaggaagagttctacaagttcatcaagcccatcctggaaaagatggacggcaccgaggaactgctcgtgaagctgaaca
gagaggacctgctgcggaagcagcggaccttcgacaacggcagcatcccccaccagatccacctgggagagctgcacgccattctgcggcggcaggaagatttttacccattcctgaag
gacaaccgggaaaagatcgagaagatcctgaccttccgcatcccctactacgtgggccctctggccaggggaaacagcagattcgcctggatgaccagaaagagcgaggaaaccatc
acccccctggaacttcgaggaagtggtggacaagggcgccagcgcccagagcttcatcgagcggatgaccaacttcgataagaacctgcccaacgagaaggtgctgcccaagcacagc
ctgctgtacgagtacttcaccgtgtacaacgagctgaccaaagtgaaatacgtgaccgagggaatgagaaagcccgccttcctgagcggcgagcagaaaaaagccatcgtggacctgct
gttcaagaccaaccggaaagtgaccgtgaagcagctgaaagaggactacttcaagaaaatcgagtgcttcgactccgtggaaatctccggcgtggaagatcggttcaacgcctccctgg
gcacataccacgatctgctgaaaattatcaaggacaaggacttcctggacaatgaggaaaacgaggacattctggaagatatcgtgctgaccctgacactgtttgaggacagagagatga
tcgaggaacggctgaaaacctatgcccacctgttcgacgacaaagtgatgaagcagctgaagcggcggagatacaccggctggggcaggctgagccggaagctgatcaacggcatcc
gggacaagcagtccggcaagacaatcctggatttcctgaagtccgacggcttcgccaacagaaacttcatgcagctgatccacgacgacagcctgacctttaaagaggacatccagaaa
gcccaggtgtccggccagggcgatagcctgcacgagcacattgccaatctggccggcagccccgccattaagaagggcatcctgcagacagtgaaggtggtggacgagctcgtgaaa
gtgatgggccggcacaagcccgagaacatcgtgatcgaaatggccagagagaaccagaccacccagaagggacagaagaacagccgcgagagaatgaagcggatcgaagagg
gcatcaaagagctgggcagccagatcctgaaagaacaccccgtggaaaacacccagctgcagaacgagaagctgtacctgtactacctgcagaatgggcgggatatgtacgtggacc
aggaactggacatcaaccggctgtccgactacgatgtggaccatatcgtgcctcagagctttctgaaggacgactccatcgataacaaagtgctgactcggagcgacaagaaccggggc
aagagcgacaacgtgccctccgaagaggtcgtgaagaagatgaagaactactggcgccagctgctgaatgccaagctgattacccagaggaagttcgacaatctgaccaaggccgag
agaggcggcctgagcgaactggataaggccggcttcatcaagagacagctggtggaaacccggcagatcacaaagcacgtggcacagatcctggactcccggatgaacactaagtac
gacgagaacgacaaactgatccgggaagtgaaagtgatcaccctgaagtccaagctggtgtccgatttccggaaggatttccagtttta

FIG. 5A (Cont.)

*caaagtgcgcgagatcaacaactaccaccacgcccacgacgcctacctgaacgccgtcgtgggaaccgccctgatcaaaaagtaccctaagctggaaagcgagttcgtgtacggcga*
*ctacaaggtgtacgacgtgcggaagatgatcgccaagagcgagcaggaaatcggcaaggctaccgccaagtacttcttctacagcaacatcatgaactttttcaagaccgagattaccctg*
*gccaacggcgagatccggaagcggcctctgatcgagacaaacggcgaaacaggcgagatcgtgtgggataagggccgggactttgccaccgtgcggaaagtgctgtctatgccccaa*
*gtgaatatcgtgaaaaagaccgaggtgcagacaggcggcttcagcaaagagtctatcctgcccaagaggaacagcgacaagctgatcgccagaaagaaggactgggaccctaagaa*
*gtacggcggcttcgacagccccaccgtggcctattctgtgctggtggtggccaaagtggaaaagggcaagtccaagaaactgaagagtgtgaaagagctgctggggatcaccatcatgg*
*aaagaagcagcttcgagaagaatcccatcgactttctggaagccaagggctacaaagaagtgaaaaaggacctgatcatcaagctgcctaagtactccctgttcgagctggaaaacggc*
*cggaagagaatgctggcctctgccggcgaactgcagaagggaaacgaactggccctgccctccaaatatgtgaacttcctgtacctggccagccactatgagaagctgaagggctcccc*
*cgaggataatgagcagaaacagctgtttgtggaacagcacaaacactacctggacgagatcatcgagcagatcagcgagttctccaagagagtgatcctggccgacgctaatctggaca*
*aggtgctgagcgcctacaacaagcacagagacaagcctatcagagagcaggccgagaatatcatccacctgtttaccctgaccaatctgggagcccctgccgccttcaagtactttgaca*
*ccaccatcgaccggaagaggtacaccagcaccaaagaggtgctggacgccaccctgatccaccagagcatcaccggcctgtacgagacacggatcgacctgtctcagctgggaggc*
*gac*gccgactataaggaccacgacggagactacaaggatcatgatattgattacaaagacgatgacgataagagcctgggcagcggctccccaagaaaaaaacgcaaggtggaaga
tcctaagaaaaagcggaaagtgtaa MATRIX – italicized
CAPSID – underlined
P2 double underlined
NUCLEOCAPSID; P1; P6 – bold (P1 also underlined)
Cas9 – underlined and italicized
3X FLAG sequence: gactataaggaccacgacggagactacaaggatcatgatattgattacaaagacgatgacgataag (underlined) (SEQ ID NO:1096)
SV40 NLS: cccaagaaaaaacgcaaggtg (SEQ ID NO:1110) and cctaagaaaaagcggaaagtg (SEQ ID NO:1111) (underlined)
TEV CLEAVAGE SITE (ENLYFQ/S) – bold and underlined (SEQ ID NO:1112)

FIG. 5B (SEQ ID NO:1080)

MGARASVLSGGELDRWEKIRLRPGGKKKYKLKHIVWASRELERFAVNPGLLETSEGCRQILGQLQPSLQTGSEELRSLYNTVATLYCVHQRIEIKDTK
EALDKIEEEQNKSKKKAQQAAADTGHSNQVSQNYENLYFQSPIVQNIQGQMVHQAISPRTLNAWVKVVEEKAFSPEVIPMFSALSEGATPQDLNTMLN
TVGGHQAAMQMLKETINEEAAEWDRVHPVHAGPIAPGQMREPRGSDIAGTTSTLQEQIGWMTHNPPIPVGEIYKRWIILGLNKIVRMYSPTSILDIRQ
GPKEPFRDYVDRFYKTLRAEQASQEVKNWMTETLLVQNANPDCKTILKALGPGATLEEMMTACQGVGGPGHKARVLENLYFQSAEAMSQVTNPATIME
NLYFQSIQKGNFRNQRKTVKCFNCGKEGHIAKNCRAPRKKGCWKCGKEGHQMKDCTERQANFLGKIWPSHKGRPGNFLQSRPEPTAPPEESFRFGEET
TTPSQKQEPIDKELYPLASLRSLFGSDPSSQNFENLYFQSMDKKYSIGLDIGTNSVGWAVITDEYKVPSKKFKVLGNTDRHSIKKNLIGALLFDSGET
AEATRLKRTARRRYTRRKNRICYLQEIFSNEMAKVDDSFFHRLEESFLVEEDKKHERHPIFGNIVDEVAYHEKYPTIYHLRKKLVDSTDKADLRLIYL
ALAHMIKFRGHFLIEGDLNPDNSDVDKLFIQLVQTYNQLFEENPINASGVDAKAILSARLSKSRRLENLIAQLPGEKKNGLFGNLIALSLGLTPNFKS
NFDLAEDAKLQLSKDTYDDDLDNLLAQIGDQYADLFLAAKNLSDAILLSDILRVNTEITKAPLSASMIKRYDEHHQDLTLLKALVRQQLPEKYKEIFF
DQSKNGYAGYIDGGASQEEFYKFIKPILEKMDGTEELLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVLPKHSLLYEYFTVYNELTKVKYVTEGMRKPAFLSGEQKKAI
VDLLFKTNRKVTVKQLKEDYFKKIECFDSVEISGVEDRFNASLGTYHDLLKIIKDKDFLDNEENEDILEDIVLTLTLFEDREMIEERLKTYAHLFDDK
VMKQLKRRRYTGWGRLSRKLINGIRDKQSGKTILDFLKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQLQNEKLYLYYLQNGRDMYVDQELDINRLSDYDVDHIV
PQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMN
TKYDENDKLIREVKVITLKSKLVSDFRKDFQFYKVREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTGGFSKESILPKRNSDKLIARKKDWDPKKYGGFDS
PTVAYSVLVVAKVEKGKSKKLKSVKELLGITIMERSSFEKNPIDFLEAKGYKEVKKDLIIKLPKYSLFELENGRKRMLASAGELQKGNELALPSKYVN
FLYLASHYEKLKGSPEDNEQKQLFVEQHKHYLDEIIEQISEFSKRVILADANLDKVLSAYNKHRDKPIREQAENIIHLFTLTNLGAPAAFKYFDTTID
RKRYTSTKEVLDATLIHQSITGLYETRIDLSQLGGDADYKDHDGDYKDHDIDYKDDDDKSLGSGSPKKKRKVEDPKKKRKV

FIG. 5B (Cont.)

MA – italicized (SEQ ID NO:880)
TEV cleavage site (ENLYFQS) – bold and underlined
CA -- underlined
p2 – double underlined
NC-p1-p6 – bold
Cas9 – underlined and italicized
3X FLAG: *DYKDHDG*DYKDHDIDYKDDDD (double underlined) (SEQ ID NO:1113)
NLS: PKKKRKV (double underlined)
(SEQ ID NO:909)

FIG. 6A (SEQ ID NO:1081)

ATGGGTGCGAGAGCGTCAGTATTAAGCGGGGGAGAATTAGATCGATGGGAAAAAATTCGGTTAAGGCCAGGGGGAAAGAAAAA
ATATAAATTAAAACATATAGTATGGGCAAGCAGGGAGCTAGAACGATTCGCAGTTAATCCTGGCCTGTTAGAAACATCAGAAGGC
TGTAGACAAATACTGGGACAGCTACAACCATCCCTTCAGACAGGATCAGAAGAACTTAGATCATTATATAATACAGTAGCAACCC
TCTATTGTGTGCATCAAAGGATAGAGATAAAAGACACCAAGGAAGCTTTAGACAAGATAGAGGAAGAGCAAAACAAAAGTAAGAA
AAAAGCACAGCAAGCAGCAGCTGACACAGGACACAGCAATCAGGTCAGCCAAAATTACGAAAACCTGTATTTCCAATCTCCTAT
AGTGCAGAACATCCAGGGGCAAATGGTACATCAGGCCATATCACCTAGAACTTTAAATGCATGGGTAAAAGTAGTAGAAGAGAA
GGCTTTCAGCCCAGAAGTGATACCCATGTTTTCAGCATTATCAGAAGGAGCCACCCCACAAGATTTAAACACCATGCTAAACACA
GTGGGGGGACATCAAGCAGCCATGCAAATGTTAAAAGAGACCATCAATGAGGAAGCTGCAGAATGGGATAGAGTGCATCCAGT
GCATGCAGGGCCTATTGCACCAGGCCAGATGAGAGAACCAAGGGGAAGTGACATAGCAGGAACTACTAGTACCCTTCAGGAAC
AAATAGGATGGATGACACATAATCCACCTATCCCAGTAGGAGAAATCTATAAAAGATGGATAATCCTGGGATTAAATAAAATAGTA
AGAATGTATAGCCCTACCAGCATTCTGGACATAAGACAAGGACCAAAGGAACCCTTTAGAGACTATGTAGACCGATTCTATAAAA
CTCTAAGAGCCGAGCAAGCTTCACAAGAGGTAAAAAATTGGATGACAGAAACCTTGTTGGTCCAAAATGCGAACCCAGATTGTAA
GACTATTTTAAAAGCATTGGGACCAGGAGCGACACTAGAAGAAATGATGACAGCATGTCAGGGAGTGGGGGGACCCGGCCATA
AAGCAAGAGTTTTGGAAAACTTGTATTTTCAGTCTgctgaagcaatgagccaagtaacaaatccagctaccataatgGAAAACCTGTATTTCCAATC
Tatacagaaaggcaattttaggaaccaaagaaagactgttaagtgtttcaattgtggcaaagaagggcacatagccaaaaattgcagggcccctaggaaaaagggctgttg
gaaatgtggaaaggaaggacaccaaatgaaagattgtactgagagacaggctaatttttagggaagatctggccttcccacaagggaaggccagggaattttcttcagagc
agaccagagccaacagccccaccagaagagagcttcaggtttggggaagagacaacaactccctctcagaagcaggagccgatagacaaggaactgtatccttagcttc
cctcagatcactctttggcagcgacccctcgtcacaataaagGAAAACCTGTATTTCCAATCTGAATCCTTGTTTAAAGGTCCGCGAGATTACAATC
CGATCTCATCCACAATCTGTCATCTGACGAACGAGTCCGACGGGCATACCACGAGTCTGTACGGTATTGGATTTGGTCCTTTC
ATTATCACAAATAAGCACTTGTTTCGCCGCAATAATGGTACACTGCTGGTTCAGTCCCTCCACGGCGTTTTTAAAGTAAAGAAT
ACTACAACACTCCAACAGCACCTGATAGACGGGCGAGATATGATCATTATAAGAATGCCGAAAGACTTTCCGCCATTTCCCCA
GAAGCTCAAATTCAGAGAACCTCAGAGGGAAGAACGGATATGCCTCGTCACAACAAATTTTCAAACAAAGTCAATGTCTAGC
ATGGTTTCTGATACGAGCTGCACTTTCCCTTCTAGTGATGGAATATTTTGGAAGCATTGGATACAGACAAAGGACGGCCAGTG
TGGCTCCCCTTTGGTTTCAACACGCGATGGGTTCATTGTAGGAATACATAGCGCTAGCAACTTCACAAATACAAATAACTACTT
TACCAGCGTACCGAAAAATTTTATGGAGCTTCTCACCAACCAGGAGGCGCAGCAGTGGGTCTCCGGATGGCGCCTTAACGCA
GATTCAGTATTGTGGGGAGGACACAAAGTTTTCATGGTCAAACCGGAAGAGCCCTTCCAGCCGGTGAAAGAGGCAACCCAAT
TGATGAATtaa

FIG. 6A (Cont.)

MATRIX -- italicized
CAPSID -- underlined
P2 – double underlined
NUCLEOCAPSID – bold
TF – bold and italicized
TEV protease – bold and double underlined TEV CLEAVAGE SITE (ENLYFQ/S) – bold and underlined
(SEQ ID NO:1112)

FIG. 6B (SEQ ID NO:1082)

*MGARASVLSGGELDRWEKIRLRPGGKKKYKLKHIVWASRELERFAVNPGLLETSEGCRQILGQLQPSLQTGSEELRSLYNTVATLYCVHQRIEIKDTK*

*EALDKIEEEQNKSKKKAQQAAADTGHSNQVSQNY*ENLYFQSPIVQNIQGQMVHQAISPRTLNAWVKVVEEKAFSPEVIPMFSALSEGATPQDLNTMLN

TVGGHQAAMQMLKETINEEAAEWDRVHPVHAGPIAPGQMREPRGSDIAGTTSTLQEQIGWMTHNPPIPVGEIYKRWIILGLNKIVRMYSPTSILDIRQ

GPKEPFRDYVDRFYKTLRAEQASQEVKNWMTETLLVQNANPDCKTILKALGPGATLEEMMTACQGVGGPGHKARVLENLYFQSAEAMSQVTNPATIME

NLYFQSIQKGNFRNQRKTVKCFNCGKEGHIAKNCRAPRKKGCWKCGKEGHQMKDCTERQANFLGKIWPSHKGRPGNFLQSRPEPTAPPEESFRFGEET

TTPSQKQEPIDKELYPLASLRSLFGSDPSSQENLYFQSESLFKGPRDYNPISSTICHLTNESDGHTTSLYGIGFGPFIITNKHLFRRNNGTLLVQSLH

GVFKVKNTTTLQQHLIDGRDMIIIRMPKDFPPFPQKLKFREPQREERICLVTTNFQTKSMSSMVSDTSCTFPSSDGIFWKHWIQTKDGQCGSPLVSTR

DGFIVGIHSASNFTNTNNYFTSVPKNFMELLTNQEAQQWVSGWRLNADSVLWGGHKVFMVKPEEPFQPVKEATQLMN

Matrix – italicized (SEQ ID NO:880)
TEV cleavage site (ENLYFQS) – bold and underlined
CA – underlined
p2 – double underlined
NC – bold
TEV protease – bold and double underlined

FIG. 8A (SEQ ID NO:1083)

*Streptococcus pyogenes* Cas9

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDHIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 8B (SEQ ID NO:1084)

nSpCas9 (SpCas9 D10A)

MDKKYSIGL<u>A</u>IGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLKDDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD

FIG. 8C (SEQ ID NO:1085)

SpCas9 (H840A)

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 8D (SEQ ID NO:1086)

SpCas9 (D10A; H840A)

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD

FIG. 8E (SEQ ID NO:1087)

enSpCas9 (nCas9 with K848A/K1003A/R1060A mutations

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLADDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPALESEFVYGDYKVYDVRKMIAKSEQEIGKATAKYFFYSNIMNFFKTEITLANGEIRKAPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD

FIG. 8F (SEQ ID NO:1088)
nSpCas9-HF1

DKKYSIGLAIGTNSVGWAVITDEYKVPSKKFKVLGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWNFEEVVDKGASAQSFIERMTAFDKN
LPNEKVLPKHSLLYEYFTVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVMKQLKRRRYTGWGALSRK
LINGIRDKQSGKTILDFLKSDGFANRNFMALIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYYLQNGRDMYVDQELD
INRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRAITKHVAQILDSRMNTKYDENDKLIREVKVITLKSKLVSDFRKDFQFYKVREINNYHHAHDAYLNAV
VGTALIKKYPKLESEFVYGDYKVYDVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD

FIG. 9

(SEQ ID NO:1089)

*Staphylococcus aureus* Cas9

MKRNYILGLDIGITSVGYGIIDYETRDVIDAGVRLFKEANVENNEGRRSKRGARRLKRRRRHRIQRVKKLLFDYNLLTDHSEL
SGINPYEARVKGLSQKLSEEEFSAALLHLAKRRGVHNVNEVEEDTGNELSTKEQISRNSKALEEKYVAELQLERLKKDGEV
RGSINRFKTSDYVKEAKQLLKVQKAYHQLDQSFIDTYIDLLETRRTYYEGPGEGSPFGWKDIKEWYEMLMGHCTYFPEELR
SVKYAYNADLYNALNDLNNLVITRDENEKLEYYEKFQIIENVFKQKKKPTLKQIAKEILVNEEDIKGYRVTSTGKPEFTNLKVY
HDIKDITARKEIIENAELLDQIAKILTIYQSSEDIQEELTNLNSELTQEEIEQISNLKGYTGTHNLSLKAINLILDELWHTNDNQIAI
FNRLKLVPKKVDLSQQKEIPTTLVDDFILSPVVKRSFIQSIKVINAIIKKYGLPNDIIIELAREKNSKDAQKMINEMQKRNRQTN
ERIEEIIRTTGKENAKYLIEKIKLHDMQEGKCLYSLEAIPLEDLLNNPFNYEVDHIIPRSVSFDNSFNNKVLVKQEENSKKGNR
TPFQYLSSSDSKISYETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFEEKQAESMPEIETEQEY
KEIFITPHQIKHIKDFKDYKYSHRVDKKPNRELINDTLYSTRKDDKGNTLIVNNLNGLYDKDNDKLKKLINKSPEKLLMYHHDP
QTYQKLKLIMEQYGDEKNPLYKYYEETGNYLTKYSKKDNGPVIKKIKYYGNKLNAHLDITDDYPNSRNKVVKLSLKPYRFDV
YLDNGVYKFVTVKNLDVIKKENYYEVNSKCYEEAKKLKKISNQAEFIASFYNNDLIKINGELYRVIGVNNDLLNRIEVNMIDITY
REYLENMNDKRPPRIIKTIASKTQSIKKYSTDILGNLYEVKSKKHPQIIKKG

FIG. 10A (SEQ ID NO:1090)

*Francisella tularensis* Cpf1

```
   1 MSIYQEFVNK YSLSKTLRFE LIPQGKTLEN IKARGLILDD EKRAKDYKKA KQIIDKYHQF
  61 FIEEILSSVC ISEDLLQNYS DVYFKLKKSD DDNLQKDFKS AKDTIKKQIS EYIKDSEKFK
 121 NLFNQNLIDA KKGQESDLIL WLKQSKDNGI ELFKANSDIT DIDEALEIIK SFKGWTTYFK
 181 GFHENRKNVY SSNDIPTSII YRIVDDNLPK FLENKAKYES LKDKAPEAIN YEQIKKDLAE
 241 ELTFDIDYKT SEVNQRVFSL DEVFEIANFN NYLNQSGITK FNTIIGGKFV NGENTKRKGI
 301 NEYINLYSQQ INDKTLKKYK MSVLFKQILS DTESKSFVID KLEDDSDVVT TMQSFYEQIA
 361 AFKTVEEKSI KETLSLLFDD LKAQKLDLSK IYFKNDKSLT DLSQQVFDDY SVIGTAVLEY
 421 ITQQIAPKNL DNPSKKEQEL IAKKTEKAKY LSLETIKLAL EEFNKHRDID KQCRFEEILA
 481 NFAAIPMIFD EIAQNKDNLA QISIKYQNQG KKDLLQASAE DDVKAIKDLL DQTNNLLHKL
 541 KIFHISQSED KANILDKDEH FYLVFEECYF ELANIVPLYN KIRNYITQKP YSDEKFKLNF
 601 ENSTLANGWD KNKEPDNTAI LFIKDDKYYL GVMNKKNNKI FDDKAIKENK GEGYKKIVYK
 661 LLPGANKMLP KVFFSAKSIK FYNPSEDILR IRNHSTHTKN GSPQKGYEKF EFNIEDCRKF
 721 IDFYKQSISK HPEWKDFGFR FSDTQRYNSI DEFYREVENQ GYKLTFENIS ESYIDSVVNQ
 781 GKLYLFQIYN KDFSAYSKGR PNLHTLYWKA LFDERNLQDV VYKLNGEAEL FYRKQSIPKK
 841 ITHPAKEAIA NKNKDNPKKE SVFEYDLIKD KRFTEDKFFF HCPITINFKS SGANKFNDEI
 901 NLLLKEKAND VHILSIDRGE RHLAYYTLVD GKGNIIKQDT FNIIGNDRMK TNYHDKLAAI
 961 EKDRDSARKD WKKINNIKEM KEGYLSQVVH EIAKLVIEYN AIVVFEDLNF GFKRGRFKVE
1021 KQVYQKLEKM LIEKLNYLVF KDNEFDKTGG VLRAYQLTAP FETFKKMGKQ TGIIYYVPAG
1081 FTSKICPVTG FVNQLYPKYE SVSKSQEFFS KFDKICYNLD KGYFEFSFDY KNFGDKAAKG
1141 KWTIASFGSR LINFRNSDKN HNWDTREVYP TKELEKLLKD YSIEYGHGEC IKAAICGESD
1201 KKFFAKLTSV LNTILQMRNS KTGTELDYLI SPVADVNGNF FDSRQAPKNM PQDADANGAY
1261 HIGLKGLMLL GRIKNNQEGK KLNLVIKNEE YFEFVQNRNN
```

FIG. 10B (SEQ ID NO:1091)

*Acidaminococcus sp. BV3L6* type V CRISPR-associated protein Cpf1

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSNAATGEDYINSPVRDLNGVCFDSRFQN
PEWPMDADANGAYHIALKGQLLLNHLKESKDLKLQNGISNQDWLAYIQELRN

FIG. 10C (SEQ ID NO:1092)

Cpf1 (AsCpf1 R1225A)

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMANSNAATGEDYINSPVRDLNGVCFDSRFQN
PEWPMDADANGAYHIALKGQLLLNHLKESKDLKLQNGISNQDWLAYIQELRN

Top band = unedited or small 1-2bp indels
Middle band = single repeat deletion
Bottom band = double repeat deletion pattern FIG. 16
Gag-Cas9 VLPs co-packaging anti-tdTomato sgRNA
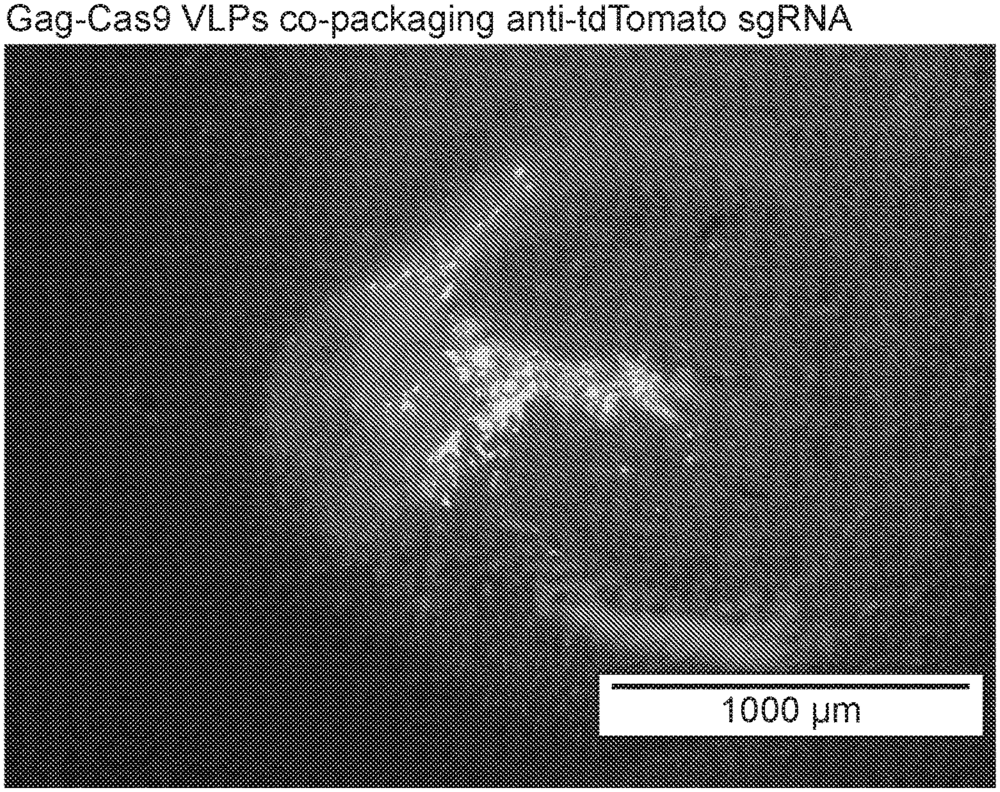
Gag-Cas9 VLPs w/o sgRNA
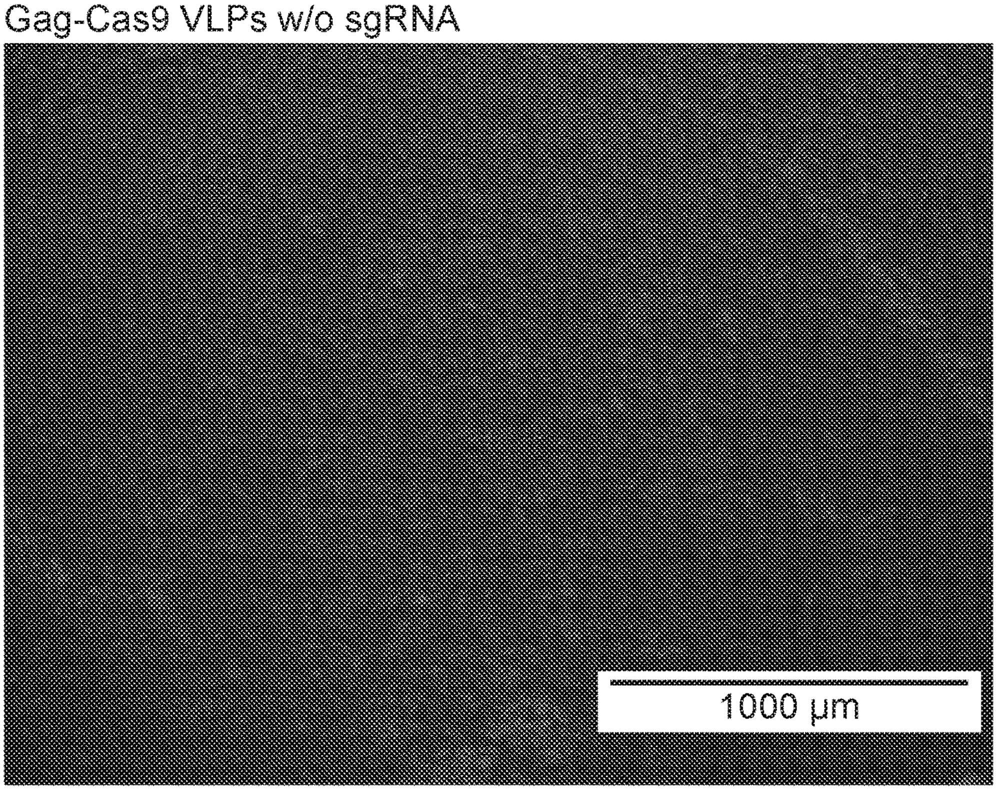

FIG. 21

Gag-1%TCS-Cas9 plasmid nucleotide sequence

CAG enhancer -- bold

Beta actin promoter – upper case; underlined

Kozak – bold and underlined

Gag – lower case and italicized

Spacer between Gag and Cas9 (contains 1%TEV cleavage site coding sequence (AACTTTGAGAATGTTTACTTCCAGAGCGGC) (SEQ ID NO:1093)
and an AgeI restriction site (ACCGGT)): (SEQ ID NO:1094)

AACTTTGAGAATGTTTACTTCCAGAGCGGCACCGGT (SEQ ID NO:1095)

Cas9 – lower case; underlined

3x FLAG: actataaggaccacgacggagactacaaggatcatgatattgattacaaagacgatgacgataag
(SEQ ID NO:1096)

2x SV40 NLS: cccaagaaaaaacgcaaggtggaagatcctaagaaaaagcggaaagtg
(SEQ ID NO:1100)

(SEQ ID NO:1097)

GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCC
AATAGGGACTTTCCATTGACGTCAATGGGTGGACTATTTACGGTAAACTGCCCACTT
GGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTG
GCAGTACATCTACGTATTAGTCATCGCTATTACCATGGGTCGAGGTGAGCCCCACGTTC
TGCTTCACTCTCCCCATCTCCCCCCCCTCCCCACCCCCAATTTTGTATTTATTTATTTTTT
AATTATTTTGTGCAGCGATGGGGGCGGGGGGGGGGGGGCGCGCGCCAGGCGGGGCGGG
GCGGGGCGAGGGGCGGGGCGGGGCGAGGCGGAGAGGTGCGGCGGCAGCCAATCAGAGCG
GCGCGCTCCGAAAGTTTCCTTTTATGGCGAGGCGGCGGCGGCGGCGGCCCTATAAAAAGC
GAAGCGCGCGGCGGGCGGGAGTCGCTGCGTTGCCTTCGCCCCGTGCCCCGCTCCGCGCCGC
CTCGCGCCGCCCGCCCCGGCTCTGACTGACCGCGTTACTCCCACAGGTGAGCGGGCGGGAC
GGCCCTTCTCCTCCGGGCTGTAATTAGCGCTTGGTTTAATGACGGCTCGTTTCTTTTCTG
TGGCTGCGTGAAAGCCTTAAAGGGCTCCGGGAGGGCCCTTTGTGCGGGGGGGAGCGGCTC
GGGGGGTGCGTGCGTGTGTGTGTGCGTGGGGAGCGCCGCGTGCGGCCCGCGCTGCCCGGC

FIG. 21 (Cont.)

GGCTGTGAGCGCTGCGGGCGCGGCGCGGGGCTTTGTGCGCTCCGCGTGTGCGCGAGGGGA
GCGCGGCCGGGGGCGGTGCCCCGCGGTGCGGGGGGGCTGCGAGGGGAACAAAGGCTGCGT
GCGGGGTGTGTGCGTGGGGGGGTGAGCAGGGGGTGTGGGCGCGGCGGTCGGGCTGTAAC
CCCCCCCTGCACCCCCCTCCCCGAGTTGCTGAGCACGGCCCGGCTTCGGGTGCGGGGCTCC
GTGCGGGGCGTGGCGCGGGGCTCGCCGTGCCGGGCGGGGGGTGGCGGCAGGTGGGGGTGC
CGGGCGGGGCGGGGCCGCCTCGGGCCGGGGAGGGCTCGGGGGAGGGGCGCGGCGGCCCCG
GAGCGCCGGCGGCTGTCGAGGCGCGGCGAGCCGCAGCCATTGCCTTTTATGGTAATCGTG
CGAGAGGGCGCAGGGACTTCCTTTGTCCCAAATCTGGCGGAGCCGAAATCTGGGAGGCGC
CGCCGCACCCCCTCTAGCGGGCGCGGGCGAAGCGGTGCGGCGCCGGCAGGAAGGAAATGG
GCGGGGAGGGCCTTCGTGCGTCGCCGCGCCGCCGTCCCCTTCTCCATCTCCAGCCTCGGGG
CTGCCGCAGGGGGACGGCTGCCTTCGGGGGGGACGGGGCAGGGCGGGGTTCGGCTTCTGG
CGTGTGACCGGCGGCTCTAGAGCCTCTGCTAACCATGTTCATGCCTTCTTCTTTTTCCTA
CAGCTCCTGGGCAACGTGCTGGTTGTTGTGCTGTCTCATCATTTTGGCAAAGAATTCgcca
cc*atgggtgcgagagcgtcagtattaagcgggggagaattagatcgatgggaaaaaattcggttaaggccagggg*
*gaaagaaaaaatataaattaaaacatatagtatgggcaagcagggagctagaacgattcgcagttaatcctggcct*
*gttagaaacatcagaaggctgtagacaaatactgggacagctacaaccatcccttcagacaggatcagaagaactt*
*agatcattatataatacagtagcaaccctctattgtgtgcatcaaaggatagagataaaagacaccaaggaagcttt*
*agacaagatagaggaagagcaaaacaaaagtaagaaaaaagcacagcaagcagcagctgacacaggacaca*
*gcaatcaggtcagccaaaattaccctatagtgcagaacatccaggggcaaatggtacatcaggccatatcacctag*
*aactttaaatgcatgggtaaaagtagtagaagagaaggctttcagcccagaagtgatacccatgttttcagcattatc*
*agaaggagccaccccacaagatttaaacaccatgctaaacacagtggggggacatcaagcagccatgcaaatgtt*
*aaaagagaccatcaatgaggaagctgcagaatgggatagagtgcatccagtgcatgcagggcctattgcaccagg*
*ccagatgagagaaccaaggggaagtgacatagcaggaactactagtacccttcaggaacaaataggatggatga*
*cacataatccacctatcccagtaggagaaatctataaaagatggataatcctgggattaaataaaatagtaagaat*
*gtatagccctaccagcattctggacataagacaaggaccaaaggaaccctttagagactatgtagaccgattctata*
*aaactctaagagccgagcaagcttcacaagaggtaaaaaattggatgacagaaaccttgttggtccaaaatgcga*
*acccagattgtaagactattttaaaagcattgggaccaggagcgacactagaagaaatgatgacagcatgtcaggg*
*agtggggggacccggccataaagcaagagttttggctgaagcaatgagccaagtaacaaatccagctaccataat*
*gatacagaaaggcaattttaggaaccaaagaaagactgttaagtgtttcaattgtggcaaagaagggcacatagcc*
*aaaaattgcagggcccctaggaaaaagggctgttggaaatgtggaaaggaaggacaccaaatgaaagattgtac*
*tgagagacaggctaattttttagggaagatctggccttcccacaagggaaggccagggaattttcttcagagcagac*
*cagagccaacagccccaccagaagagagcttcaggtttggggaagagacaacaactccctctcagaagcaggagc*
*cgatagacaaggaactgtatccttagcttccctcagatcactctttggcagcgacccctcgtcacaa*

FIG. 21 (Cont.)

AACTTTGAGAATGTTTACTTCCAGAGCGGCACCGGTatggacaagaagtacagcatcggcctggaca
tcggcaccaactctgtgggctgggccgtgatcaccgacgagtacaaggtgcccagcaagaaattcaaggtgctgggcaa
caccgaccggcacagcatcaagaagaacctgatcggcgccctgctgttcgacagcggagaaacagccgaggccacccg
gctgaagagaaccgccagaagaagatacaccagacggaagaaccggatctgctatctgcaagagatcttcagcaacga
gatggccaaggtggacgacagcttcttccacagactggaagagtccttcctggtggaagaggataagaagcacgagcgg
caccccatcttcggcaacatcgtggacgaggtggcctaccacgagaagtaccccaccatctaccacctgagaaagaaac
tggtggacagcaccgacaaggccgacctgcggctgatctatctggccctggcccacatgatcaagttccggggccacttc
ctgatcgagggcgacctgaaccccgacaacagcgacgtggacaagctgttcatccagctggtgcagacctacaaccagc
tgttcgaggaaaaccccatcaacgccagcggcgtggacgccaaggccatcctgtctgccagactgagcaagagcagac
ggctggaaaatctgatcgcccagctgcccggcgagaagaagaatggcctgttcggcaacctgattgccctgagcctggg
cctgacccccaacttcaagagcaacttcgacctggccgaggatgccaaactgcagctgagcaaggacacctacgacgac
gacctggacaacctgctggcccagatcggcgaccagtacgccgacctgtttctggccgccaagaacctgtccgacgccat
cctgctgagcgacatcctgagagtgaacaccgagatcaccaaggcccccctgagcgcctctatgatcaagagatacgac
gagcaccaccaggacctgaccctgctgaaagctctcgtgcggcagcagctgcctgagaagtacaaagagattttcttcga
ccagagcaagaacggctacgccggctacatcgatggcggagccagccaggaagagttctacaagttcatcaagcccatc
ctggaaaagatggacggcaccgaggaactgctcgtgaagctgaacagagaggacctgctgcggaagcagcggaccttc
gacaacggcagcatccccccaccagatccacctgggagagctgcacgccattctgcggcggcaggaagatttttacccatt
cctgaaggacaaccgggaaaagatcgagaagatcctgaccttccgcatcccctactacgtgggccctctggccaggggga
aacagcagattcgcctggatgaccagaaagagcgaggaaaccatcaccccctggaacttcgaggaagtggtggacaag
ggcgccagcgcccagagcttcatcgagcggatgaccaacttcgataagaacctgcccaacgagaaggtgctgcccaagc
acagcctgctgtacgagtacttcaccgtgtacaacgagctgaccaaagtgaaatacgtgaccgagggaatgagaaagcc
cgccttcctgagcggcgagcagaaaaaagccatcgtggacctgctgttcaagaccaaccggaaagtgaccgtgaagca
gctgaaagaggactacttcaagaaaatcgagtgcttcgactccgtggaaatctccggcgtggaagatcggttcaacgcct
ccctgggcacataccacgatctgctgaaaattatcaaggacaaggacttcctggacaatgaggaaaacgaggacattct
ggaagatatcgtgctgaccctgacactgtttgaggacagagagatgatcgaggaacggctgaaaacctatgcccacctgt
tcgacgacaaagtgatgaagcagctgaagcggcggagatacaccggctggggcaggctgagccggaagctgatcaac
ggcatccgggacaagcagtccggcaagacaatcctggatttcctgaagtccgacggcttcgccaacagaaacttcatgca
gctgatccacgacgacagcctgacctttaaagaggacatccagaaagcccaggtgtccggccagggcgatagcctgcac
gagcacattgccaatctggccggcagccccgccattaagaagggcatcctgcagacagtgaaggtggtggacgagctcg
tgaaagtgatgggccggcacaagcccgagaacatcgtgatcgaaatggccagagagaaccagaccacccagaaggga
cagaagaacagccgcgagagaatgaagcggatcgaagagggcatcaaagagctgggcagccagatcctgaaagaac
accccgtggaaaacacccagctgcagaacgagaagctgtacctgtactacctgcagaatgggcgggatatgtacgtgga
ccaggaactggacatcaaccggctgtccgactacgatgtggaccatatcgtgcctcagagctttctgaaggacgactccat
cgataacaaagtgctgactcggagcgacaagaaccggggcaagagcgacaacgtgccctccgaagaggtcgtgaaga

FIG. 21 (Cont.)

agatgaagaactactggcgccagctgctgaatgccaagctgattacccagaggaagttcgacaatctgaccaaggccga
gagaggcggcctgagcgaactggataaggccggcttcatcaagagacagctggtggaaacccggcagatcacaaagca
cgtggcacagatcctggactcccggatgaacactaagtacgacgagaacgacaaactgatccgggaagtgaaagtgat
caccctgaagtccaagctggtgtccgatttccggaaggatttccagttttacaaagtgcgcgagatcaacaactaccacca
cgcccacgacgcctacctgaacgccgtcgtgggaaccgccctgatcaaaaagtaccctaagctggaaagcgagttcgtg
tacggcgactacaaggtgtacgacgtgcggaagatgatcgccaagagcgagcaggaaatcggcaaggctaccgccaag
tacttcttctacagcaacatcatgaactttttcaagaccgagattaccctggccaacggcgagatccggaagcggcctctg
atcgagacaaacggcgaaacaggcgagatcgtgtgggataagggccgggactttgccaccgtgcggaaagtgctgtcta
tgccccaagtgaatatcgtgaaaaagaccgaggtgcagacaggcggcttcagcaaagagtctatcctgcccaagagga
acagcgacaagctgatcgccagaaagaaggactgggaccctaagaagtacggcggcttcgacagccccaccgtggcct
attctgtgctggtggtggccaaagtggaaaagggcaagtccaagaaactgaagagtgtgaaagagctgctggggatcac
catcatggaaagaagcagcttcgagaagaatcccatcgactttctggaagccaagggctacaaagaagtgaaaaagga
cctgatcatcaagctgcctaagtactccctgttcgagctggaaaacggccggaagagaatgctggcctctgccggcgaac
tgcagaagggaaacgaactggccctgccctccaaatatgtgaacttcctgtacctggccagccactatgagaagctgaag
ggctcccccgaggataatgagcagaaacagctgtttgtggaacagcacaaacactacctggacgagatcatcgagcaga
tcagcgagttctccaagagagtgatcctggccgacgctaatctggacaaggtgctgagcgcctacaacaagcacagaga
caagcctatcagagagcaggccgagaatatcatccacctgtttaccctgaccaatctgggagcccctgccgccttcaagta
ctttgacaccaccatcgaccggaagaggtacaccagcaccaaagaggtgctggacgccaccctgatccaccagagcatc
accggcctgtacgagacacggatcgacctgtctcagctgggaggcgacgccgactataaggaccacgacggagactac
aaggatcatgatattgattacaaagacgatgacgataagagcctgggcagcggctcccccaagaaaaaacgcaaggtg
gaagatcctaagaaaaagcggaaagtgtaaGCTAGCAGATCTTTTTCCCTCTGCCAAAAATTATGG
GGACATCATGAAGCCCCTTGAGCATCTGACTTCTGGCTAATAAAGGAAATTTATTTTCAT
TGCAATAGTGTGTTGGAATTTTTTGTGTCTCTCACTCGGAAGGACATATGGGAGGGCAA
ATCATTTAAAACATCAGAATGAGTATTTGGTTTAGAGTTTGGCAACATATGCCCATATG
CTGGCTGCCATGAACAAAGGTTGGCTATAAAGAGGTCATCAGTATATGAAACAGCCCCCT
GCTGTCCATTCCTTATTCCATAGAAAAGCCTTGACTTGAGGTTAGATTTTTTTTATATTT
TGTTTTGTGTTATTTTTTTCTTTAACATCCCTAAAATTTTCCTTACATGTTTTACTAGCC
AGATTTTTCCTCCTCTCCTGACTACTCCCAGTCATAGCTGTCCCTCTTCTCTTATGAAGA
TCCCTCGACCTGCAGCCCAAGCTTGGCGTAATCATGGTCATAGCTGTTTCCTGTGTGAAA
TTGTTATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTTCCA
GTCGGGAAACCTGTCGTGCCAGCGGATCCGCATCTCAATTAGTCAGCAACCATAGTCCCG
CCCCTAACTCCGCCCATCCCGCCCCTAACTCCGCCCAGTTCCGCCCATTCTCCGCCCCATG

FIG. 21 (Cont.)

GCTGACTAATTTTTTTTATTTATGCAGAGGCCGAGGCCGCCTCGGCCTCTGAGCTATTCC
AGAAGTAGTGAGGAGGCTTTTTTGGAGGCCTAGGCTTTTGCAAAAAGCTAACTTGTTTA
TTGCAGCTTATAATGGTTACAAATAAAGCAATAGCATCACAAATTTCACAAATAAAGCA
TTTTTTTCACTGCATTCTAGTTGTGGTTTGTCCAAACTCATCAATGTATCTTATCATGTC
TGGATCCGCTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCGGCGAGCGGT
ATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATT
TTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAA
TCAGTGAGGCACCTATCTCAGCGATCTGTCTATTTCGTTCATCCATAGTTGCCTGACTCC
CCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAA
GGGCCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCATTG
CTACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGAGT
ACTCAACCAAGTCATTCTGAGAATAGTGTATGCGGCGACCGAGTTGCTCTTGCCCGGCGT

FIG. 21 (Cont.)

CAATACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCAT
GAGCGGATACATATTTGAATGTATTTAGAAAAATAAACAAATAGGGGTTCCGCGCACAT
TTCCCCGAAAAGTGCCACCTG (SEQ ID NO:1097)

FIG. 22

Gag-10%TCS-Cas9 plasmid nucleotide sequence

CAG enhancer – bold

Beta actin promoter – upper case; underlined

Kozak – bold and underlined

Gag – lower case and italicized

Spacer between Gag and Cas9 (contains 10%TEV cleavage site coding sequence (AACTTTGAGAACCTGTTCTTCCAAAGTGGG) (SEQ ID NO:1098)
and AgeI restriction site (ACCGGT)): (SEQ ID NO:1094)

AACTTTGAGAACCTGTTCTTCCAAAGTGGGACCGGT (SEQ ID NO:1099)

Cas9 – lower case; underlined

3x FLAG: actataaggaccacgacggagactacaaggatcatgatattgattacaaagacgatgacgataag (SEQ ID NO:1096)

2x SV40 NLS: cccaagaaaaaacgcaaggtggaagatcctaagaaaaagcggaaagtg (SEQ ID NO:1100)

(SEQ ID NO:1101)

GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCC
AATAGGGACTTTCCATTGACGTCAATGGGTGGACTATTTACGGTAAACTGCCCACTT
GGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTG
GCAGTACATCTACGTATTAGTCATCGCTATTACCATGGGTCGAGGTGAGCCCCACGTTC
TGCTTCACTCTCCCCATCTCCCCCCCCTCCCCACCCCCAATTTTGTATTTATTTATTTTTT
AATTATTTTGTGCAGCGATGGGGGCGGGGGGGGGGGGGGCGCGCGCCAGGCGGGGCGGG
GCGGGGCGAGGGGCGGGGCGGGGCGAGGCGGAGAGGTGCGGCGGCAGCCAATCAGAGCG
GCGCGCTCCGAAAGTTTCCTTTTATGGCGAGGCGGCGGCGGCGGCGGCCCTATAAAAAGC
GAAGCGCGCGGCGGGCGGGAGTCGCTGCGTTGCCTTCGCCCCGTGCCCCGCTCCGCGCCGC
CTCGCGCCGCCCGCCCCGGCTCTGACTGACCGCGTTACTCCCACAGGTGAGCGGGCGGGAC
GGCCCTTCTCCTCCGGGCTGTAATTAGCGCTTGGTTTAATGACGGCTCGTTTCTTTTCTG
TGGCTGCGTGAAAGCCTTAAAGGGCTCCGGGAGGGCCCTTTGTGCGGGGGGGAGCGGCTC

FIG. 22 (Cont.)

GGGGGGTGCGTGCGTGTGTGTGTGCGTGGGGAGCGCCGCGTGCGGCCCGCGCTGCCCGGC
GGCTGTGAGCGCTGCGGGCGCGGCGCGGGGCTTTGTGCGCTCCGCGTGTGCGCGAGGGGA
GCGCGGCCGGGGGCGGTGCCCCGCGGTGCGGGGGGGCTGCGAGGGGAACAAAGGCTGCGT
GCGGGGTGTGTGCGTGGGGGGGTGAGCAGGGGGTGTGGGCGCGGCGGTCGGGCTGTAAC
CCCCCCCTGCACCCCCCTCCCCGAGTTGCTGAGCACGGCCCGGCTTCGGGTGCGGGGCTCC
GTGCGGGGCGTGGCGCGGGGCTCGCCGTGCCGGGCGGGGGGTGGCGGCAGGTGGGGGTGC
CGGGCGGGGCGGGGCCGCCTCGGGCCGGGGAGGGCTCGGGGGAGGGGCGCGGCGGCCCCG
GAGCGCCGGCGGCTGTCGAGGCGCGGCGAGCCGCAGCCATTGCCTTTTATGGTAATCGTG
CGAGAGGGCGCAGGGACTTCCTTTGTCCCAAATCTGGCGGAGCCGAAATCTGGGAGGCGC
CGCCGCACCCCCTCTAGCGGGCGCGGGCGAAGCGGTGCGGCGCCGGCAGGAAGGAAATGG
GCGGGGAGGGCCTTCGTGCGTCGCCGCGCCGCCGTCCCCTTCTCCATCTCCAGCCTCGGGG
CTGCCGCAGGGGGACGGCTGCCTTCGGGGGGGACGGGGCAGGGCGGGGTTCGGCTTCTGG
CGTGTGACCGGCGGCTCTAGAGCCTCTGCTAACCATGTTCATGCCTTCTTCTTTTTCCTA
CAGCTCCTGGGCAACGTGCTGGTTGTTGTGCTGTCTCATCATTTTGGCAAAGAATTCgcca
cc*atgggtgcgagagcgtcagtattaagcgggggagaattagatcgatgggaaaaaattcggttaaggccagggg*
*gaaagaaaaaatataaattaaaacatatagtatgggcaagcagggagctagaacgattcgcagttaatcctggcct*
*gttagaaacatcagaaggctgtagacaaatactgggacagctacaaccatcccttcagacaggatcagaagaactt*
*agatcattatataatacagtagcaaccctctattgtgtgcatcaaaggatagagataaaagacaccaaggaagcttt*
*agacaagatagaggaagagcaaaacaaaagtaagaaaaaagcacagcaagcagcagctgacacaggacaca*
*gcaatcaggtcagccaaaattaccctatagtgcagaacatccaggggcaaatggtacatcaggccatatcacctag*
*aactttaaatgcatgggtaaaagtagtagaagagaaggctttcagcccagaagtgatacccatgttttcagcattatc*
*agaaggagccaccccacaagatttaaacaccatgctaaacacagtggggggacatcaagcagccatgcaaatgtt*
*aaaagagaccatcaatgaggaagctgcagaatgggatagagtgcatccagtgcatgcagggcctattgcaccagg*
*ccagatgagagaaccaaggggaagtgacatagcaggaactactagtacccttcaggaacaaataggatggatga*
*cacataatccacctatcccagtaggagaaatctataaaagatggataatcctgggattaaataaaatagtaagaat*
*gtatagccctaccagcattctggacataagacaaggaccaaaggaaccctttagagactatgtagaccgattctata*
*aaactctaagagccgagcaagcttcacaagaggtaaaaaattggatgacagaaaccttgttggtccaaaatgcga*
*acccagattgtaagactattttaaaagcattgggaccaggagcgacactagaagaaatgatgacagcatgtcaggg*
*agtggggggacccggccataaagcaagagttttggctgaagcaatgagccaagtaacaaatccagctaccataat*
*gatacagaaaggcaattttaggaaccaaagaaagactgttaagtgtttcaattgtggcaaagaagggcacatagcc*
*aaaaattgcagggcccctaggaaaaagggctgttggaaatgtggaaaggaaggacaccaaatgaaagattgtac*
*tgagagacaggctaattttttagggaagatctggccttcccacaagggaaggccagggaattttcttcagagcagac*

FIG. 22 (Cont.)

*cagagccaacagccccaccagaagagagcttcaggtttggggaagagacaacaactccctctcagaagcaggagc*
*cgatagacaaggaactgtatcctttagcttccctcagatcactctttggcagcgacccctcgtcacaa*
AACTTTGAGAACCTGTTCTTCCAAAGTGGACCGGTatggacaagaagtacagcatcggcctggaca
tcggcaccaactctgtgggctgggccgtgatcaccgacgagtacaaggtgcccagcaagaaattcaaggtgctgggcaa
caccgaccggcacagcatcaagaagaacctgatcggcgccctgctgttcgacagcggagaaacagccgaggccacccg
gctgaagagaaccgccagaagaagatacaccagacggaagaaccggatctgctatctgcaagagatcttcagcaacga
gatggccaaggtggacgacagcttcttccacagactggaagagtccttcctggtggaagaggataagaagcacgagcgg
caccccatcttcggcaacatcgtggacgaggtggcctaccacgagaagtaccccaccatctaccacctgagaaagaaac
tggtggacagcaccgacaaggccgacctgcggctgatctatctggccctggcccacatgatcaagttccggggccacttc
ctgatcgagggcgacctgaaccccgacaacagcgacgtggacaagctgttcatccagctggtgcagacctacaaccagc
tgttcgaggaaaaccccatcaacgccagcggcgtggacgccaaggccatcctgtctgccagactgagcaagagcagac
ggctggaaaatctgatcgcccagctgcccggcgagaagaagaatggcctgttcggcaacctgattgccctgagcctggg
cctgacccccaacttcaagagcaacttcgacctggccgaggatgccaaactgcagctgagcaaggacacctacgacgac
gacctggacaacctgctggcccagatcggcgaccagtacgccgacctgtttctggccgccaagaacctgtccgacgccat
cctgctgagcgacatcctgagagtgaacaccgagatcaccaaggcccccctgagcgcctctatgatcaagagatacgac
gagcaccaccaggacctgaccctgctgaaagctctcgtgcggcagcagctgcctgagaagtacaaagagattttcttcga
ccagagcaagaacggctacgccggctacatcgatggcggagccagccaggaagagttctacaagttcatcaagcccatc
ctggaaaagatggacggcaccgaggaactgctcgtgaagctgaacagagaggacctgctgcggaagcagcggaccttc
gacaacggcagcatccccccaccagatccacctgggagagctgcacgccattctgcggcggcaggaagatttttacccatt
cctgaaggacaaccgggaaaagatcgagaagatcctgaccttccgcatcccctactacgtgggccctctggccaggggga
aacagcagattcgcctggatgaccagaaagagcgaggaaaccatcaccccctggaacttcgaggaagtggtggacaag
ggcgccagcgcccagagcttcatcgagcggatgaccaacttcgataagaacctgcccaacgagaaggtgctgcccaagc
acagcctgctgtacgagtacttcaccgtgtacaacgagctgaccaaagtgaaatacgtgaccgagggaatgagaaagcc
cgccttcctgagcggcgagcagaaaaaagccatcgtggacctgctgttcaagaccaaccggaaagtgaccgtgaagca
gctgaaagaggactacttcaagaaaatcgagtgcttcgactccgtggaaatctccggcgtggaagatcggttcaacgcct
ccctgggcacataccacgatctgctgaaaattatcaaggacaaggacttcctggacaatgaggaaaacgaggacattct
ggaagatatcgtgctgaccctgacactgtttgaggacagagagatgatcgaggaacggctgaaaacctatgcccacctgt
tcgacgacaaagtgatgaagcagctgaagcggcggagatacaccggctggggcaggctgagccggaagctgatcaac
ggcatccgggacaagcagtccggcaagacaatcctggatttcctgaagtccgacggcttcgccaacagaaacttcatgca
gctgatccacgacgacagcctgacctttaaagaggacatccagaaagcccaggtgtccggccagggcgatagcctgcac
gagcacattgccaatctggccggcagccccgccattaagaagggcatcctgcagacagtgaaggtggtggacgagctcg
tgaaagtgatgggccggcacaagcccgagaacatcgtgatcgaaatggccagagagaaccagaccacccagaaggga

FIG. 22 (Cont.)

cagaagaacagccgcgagagaatgaagcggatcgaagagggcatcaaagagctgggcagccagatcctgaaagaac
accccgtggaaaacacccagctgcagaacgagaagctgtacctgtactacctgcagaatgggcgggatatgtacgtgga
ccaggaactggacatcaaccggctgtccgactacgatgtggaccatatcgtgcctcagagctttctgaaggacgactccat
cgataacaaagtgctgactcggagcgacaagaaccggggcaagagcgacaacgtgccctccgaagaggtcgtgaaga
agatgaagaactactggcgccagctgctgaatgccaagctgattacccagaggaagttcgacaatctgaccaaggccga
gagaggcggcctgagcgaactggataaggccggcttcatcaagagacagctggtggaaacccggcagatcacaaagca
cgtggcacagatcctggactcccggatgaacactaagtacgacgagaacgacaaactgatccgggaagtgaaagtgat
caccctgaagtccaagctggtgtccgatttccggaaggatttccagttttacaaagtgcgcgagatcaacaactaccacca
cgcccacgacgcctacctgaacgccgtcgtgggaaccgccctgatcaaaaagtaccctaagctggaaagcgagttcgtg
tacggcgactacaaggtgtacgacgtgcggaagatgatcgccaagagcgagcaggaaatcggcaaggctaccgccaag
tacttcttctacagcaacatcatgaactttttcaagaccgagattaccctggccaacggcgagatccggaagcggcctctg
atcgagacaaacggcgaaacaggcgagatcgtgtgggataagggccgggactttgccaccgtgcggaaagtgctgtcta
tgccccaagtgaatatcgtgaaaaagaccgaggtgcagacaggcggcttcagcaaagagtctatcctgcccaagagga
acagcgacaagctgatcgccagaaagaaggactgggaccctaagaagtacggcggcttcgacagccccaccgtggcct
attctgtgctggtggtggccaaagtggaaaagggcaagtccaagaaactgaagagtgtgaaagagctgctggggatcac
catcatggaaagaagcagcttcgagaagaatcccatcgactttctggaagccaagggctacaaagaagtgaaaaagga
cctgatcatcaagctgcctaagtactccctgttcgagctggaaaacggccggaagagaatgctggcctctgccggcgaac
tgcagaagggaaacgaactggccctgccctccaaatatgtgaacttcctgtacctggccagccactatgagaagctgaag
ggctcccccgaggataatgagcagaaacagctgtttgtggaacagcacaaacactacctggacgagatcatcgagcaga
tcagcgagttctccaagagagtgatcctggccgacgctaatctggacaaggtgctgagcgcctacaacaagcacagaga
caagcctatcagagagcaggccgagaatatcatccacctgtttaccctgaccaatctgggagcccctgccgccttcaagta
ctttgacaccaccatcgaccggaagaggtacaccagcaccaaagaggtgctggacgccaccctgatccaccagagcatc
accggcctgtacgagacacggatcgacctgtctcagctgggaggcgacgccgactataaggaccacgacggagactac
aaggatcatgatattgattacaaagacgatgacgataagagcctgggcagcggctcccccaagaaaaacgcaaggtg
gaagatcctaagaaaaagcggaaagtgtaaGCTAGCAGATCTTTTTCCCTCTGCCAAAAATTATGG
GGACATCATGAAGCCCCTTGAGCATCTGACTTCTGGCTAATAAAGGAAATTTATTTTCAT
TGCAATAGTGTGTTGGAATTTTTTGTGTCTCTCACTCGGAAGGACATATGGGAGGGCAA
ATCATTTAAAACATCAGAATGAGTATTTGGTTTAGAGTTTGGCAACATATGCCCATATG
CTGGCTGCCATGAACAAAGGTTGGCTATAAAGAGGTCATCAGTATATGAAACAGCCCCCT
GCTGTCCATTCCTTATTCCATAGAAAAGCCTTGACTTGAGGTTAGATTTTTTTTATATTT
TGTTTTGTGTTATTTTTTTCTTTAACATCCCTAAAATTTTCCTTACATGTTTTACTAGCC
AGATTTTTCCTCCTCTCCTGACTACTCCCAGTCATAGCTGTCCCTCTTCTCTTATGAAGA

FIG. 22 (Cont.)

TCCCTCGACCTGCAGCCCAAGCTTGGCGTAATCATGGTCATAGCTGTTTCCTGTGTGAAA
TTGTTATCCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGCTTTCCA
GTCGGGAAACCTGTCGTGCCAGCGGATCCGCATCTCAATTAGTCAGCAACCATAGTCCCG
CCCCTAACTCCGCCCATCCCGCCCCTAACTCCGCCCAGTTCCGCCCATTCTCCGCCCCATG
GCTGACTAATTTTTTTTATTTATGCAGAGGCCGAGGCCGCCTCGGCCTCTGAGCTATTCC
AGAAGTAGTGAGGAGGCTTTTTTGGAGGCCTAGGCTTTTGCAAAAAGCTAACTTGTTTA
TTGCAGCTTATAATGGTTACAAATAAAGCAATAGCATCACAAATTTCACAAATAAAGCA
TTTTTTTCACTGCATTCTAGTTGTGGTTTGTCCAAACTCATCAATGTATCTTATCATGTC
TGGATCCGCTGCATTAATGAATCGGCCAACGCGCGGGGAGAGGCGGTTTGCGTATTGGGC
GCTCTTCCGCTTCCTCGCTCACTGACTCGCTGCGCTCGGTCGTTCGGCTGCGGCGAGCGGT
ATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCAC
TGGTAACAGGATTAGCAGAGCGAGGTATGTAGGCGGTGCTACAGAGTTCTTGAAGTGGT
GGCCTAACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATT
TTGGTCATGAGATTATCAAAAAGGATCTTCACCTAGATCCTTTTAAATTAAAAATGAAG
TTTTAAATCAATCTAAAGTATATATGAGTAAACTTGGTCTGACAGTTACCAATGCTTAA
TCAGTGAGGCACCTATCTCAGCGATCTGTCTATTTCGTTCATCCATAGTTGCCTGACTCC
CCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAA

FIG. 22 (Cont.)

GGGCCGAGCGCAGAAGTGGTCCTGCAACTTTATCCGCCTCCATCCAGTCTATTAATTGTT
GCCGGGAAGCTAGAGTAAGTAGTTCGCCAGTTAATAGTTTGCGCAACGTTGTTGCCATTG
CTACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGAGT
ACTCAACCAAGTCATTCTGAGAATAGTGTATGCGGCGACCGAGTTGCTCTTGCCCGGCGT
CAATACGGGATAATACCGCGCCACATAGCAGAACTTTAAAAGTGCTCATCATTGGAAAA
CGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCAT
GAGCGGATACATATTTGAATGTATTTAGAAAAATAAACAAATAGGGGTTCCGCGCACAT
TTCCCCGAAAAGTGCCACCTG (SEQ ID NO:1101)

FIG. 23

Gag-1%TCS-TEV plasmid nucleotide sequence

CAG enhancer – bold

Beta actin promoter – upper case; underlined

Kozak – lower case; bold and underlined

Gag (such that the following TCS is in the normal reading frame) – lower case and italicized Spacer between Gag and TEV (contains 1%TEV cleavage site coding sequence):

AACTTTGAGAATGTTTACTTCCAGAGCGGC (SEQ ID NO:1093)

TEV protease – upper case; bold and underlined

GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCC
AATAGGGACTTTCCATTGACGTCAATGGGTGGACTATTTACGGTAAACTGCCCACTT
GGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTG
GCAGTACATCTACGTATTAGTCATCGCTATTACCATGGGTCGAGGTGAGCCCCACGTTC
TGCTTCACTCTCCCCATCTCCCCCCCCTCCCCACCCCCAATTTTGTATTTATTTATTTTT
AATTATTTTGTGCAGCGATGGGGGCGGGGGGGGGGGGGGCGCGCGCCAGGCGGGGCGGG
GCGGGGCGAGGGGCGGGGCGGGGCGAGGCGGAGAGGTGCGGCGGCAGCCAATCAGAGCG
GCGCGCTCCGAAAGTTTCCTTTTATGGCGAGGCGGCGGCGGCGGCGGCCCTATAAAAAGC
GAAGCGCGCGGCGGGCGGGAGTCGCTGCGTTGCCTTCGCCCCGTGCCCCGCTCCGCGCCGC
CTCGCGCCGCCCGCCCCGGCTCTGACTGACCGCGTTACTCCCACAGGTGAGCGGGCGGGAC
GGCCCTTCTCCTCCGGGCTGTAATTAGCGCTTGGTTTAATGACGGCTCGTTTCTTTTCTG
TGGCTGCGTGAAAGCCTTAAAGGGCTCCGGGAGGGCCCTTTGTGCGGGGGGGAGCGGCTC
GGGGGGTGCGTGCGTGTGTGTGTGCGTGGGGAGCGCCGCGTGCGGCCCGCGCTGCCCGGC
GGCTGTGAGCGCTGCGGGCGCGGCGCGGGGCTTTGTGCGCTCCGCGTGTGCGCGAGGGGA
GCGCGGCCGGGGGCGGTGCCCCGCGGTGCGGGGGGGCTGCGAGGGGAACAAAGGCTGCGT
GCGGGGTGTGTGCGTGGGGGGGTGAGCAGGGGGTGTGGGCGCGGCGGTCGGGCTGTAAC
CCCCCCCTGCACCCCCCTCCCCGAGTTGCTGAGCACGGCCCGGCTTCGGGTGCGGGGCTCC
GTGCGGGGCGTGGCGCGGGGCTCGCCGTGCCGGGCGGGGGGTGGCGGCAGGTGGGGGTGC

FIG. 23 (Cont.)

CGGGCGGGGCGGGGCCGCCTCGGGCCGGGGAGGGCTCGGGGGAGGGGCGCGGCGGCCCCG
GAGCGCCGGCGGCTGTCGAGGCGCGGCGAGCCGCAGCCATTGCCTTTTATGGTAATCGTG
CGAGAGGGCGCAGGGACTTCCTTTGTCCCAAATCTGGCGGAGCCGAAATCTGGGAGGCGC
CGCCGCACCCCCTCTAGCGGGCGCGGGCGAAGCGGTGCGGCGCCGGCAGGAAGGAAATGG
GCGGGGAGGGCCTTCGTGCGTCGCCGCGCCGCCGTCCCCTTCTCCATCTCCAGCCTCGGGG
CTGCCGCAGGGGGACGGCTGCCTTCGGGGGGGACGGGGCAGGGCGGGGTTCGGCTTCTGG
CGTGTGACCGGCGGCTCTAGAGCCTCTGCTAACCATGTTCATGCCTTCTTCTTTTTCCTA
CAGCTCCTGGGCAACGTGCTGGTTGTTGTGCTGTCTCATCATTTTGGCAAAGAATTCgcca
ccatgggtgcgagagcgtcagtattaagcgggggagaattagatcgatgggaaaaaattcggttaaggccagggg
gaaagaaaaaatataaattaaaacatatagtatgggcaagcagggagctagaacgattcgcagttaatcctggcct
gttagaaacatcagaaggctgtagacaaatactgggacagctacaaccatcccttcagacaggatcagaagaactt
agatcattatataatacagtagcaaccctctattgtgtgcatcaaaggatagagataaaagacaccaaggaagcttt
agacaagatagaggaagagcaaaacaaaagtaagaaaaaagcacagcaagcagcagctgacacaggacaca
gcaatcaggtcagccaaaattaccctatagtgcagaacatccaggggcaaatggtacatcaggccatatcacctag
aactttaaatgcatgggtaaaagtagtagaagagaaggctttcagcccagaagtgatacccatgttttcagcattatc
agaaggagccaccccacaagatttaaacaccatgctaaacacagtggggggacatcaagcagccatgcaaatgtt
aaaagagaccatcaatgaggaagctgcagaatgggatagagtgcatccagtgcatgcagggcctattgcaccagg
ccagatgagagaaccaaggggaagtgacatagcaggaactactagtacccttcaggaacaaataggatggatga
cacataatccacctatcccagtaggagaaatctataaaagatggataatcctgggattaaataaaatagtaagaat
gtatagccctaccagcattctggacataagacaaggaccaaaggaaccctttagagactatgtagaccgattctata
aaactctaagagccgagcaagcttcacaagaggtaaaaaattggatgacagaaaccttgttggtccaaaatgcga
acccagattgtaagactattttaaaagcattgggaccaggagcgacactagaagaaatgatgacagcatgtcaggg
agtggggggacccggccataaagcaagagttttggctgaagcaatgagccaagtaacaaatccagctaccataat
gatacagaaaggcaattttaggaaccaaagaaagactgttaagtgtttcaattgtggcaaagaagggcacatagcc
aaaaattgcagggcccctaggaaaaagggctgttggaaatgtggaaaggaaggacaccaaatgaaagattgtac
tgagagacaggctaattttttagggaagatctggccttcccacaagggaaggccagggaattttcttcagagcagac
cagagccaacagccccaccagaagagagcttcaggtttggggaagagacaacaactccctctcagaagcaggagc
cgatagacaaggaactgtatcctttagcttccctcagatcactctttggcagcgacccctcgtcacaaAACTTTGA
GAATGTTTACTTCCAGAGCGGCGAATCCTTGTTTAAAGGTCCGCGAGATTACAATCCG
ATCTCATCCACAATCTGTCATCTGACGAACGAGTCCGACGGGCATACCACGAGTCTG
TACGGTATTGGATTTGGTCCTTTCATTATCACAAATAAGCACTTGTTTCGCCGCAAT
AATGGTACACTGCTGGTTCAGTCCCTCCACGGCGTTTTTAAAGTAAAGAATACTACA

FIG. 23 (Cont.)

ACACTCCAACAGCACCTGATAGACGGGCGAGATATGATCATTATAAGAATGCCGAAA
GACTTTCCGCCATTTCCCCAGAAGCTCAAATTCAGAGAACCTCAGAGGGAAGAACGG
ATATGCCTCGTCACAACAAATTTTCAAACAAAGTCAATGTCTAGCATGGTTTCTGAT
ACGAGCTGCACTTTCCCTTCTAGTGATGGAATATTTTGGAAGCATTGGATACAGAC
AAAGGACGGCCAGTGTGGCTCCCCTTTGGTTTCAACACGCGATGGGTTCATTGTAGG
AATACATAGCGCTAGCAACTTCACAAATACAAATAACTACTTTACCAGCGTACCGAA
AAATTTTATGGAGCTTCTCACCAACCAGGAGGCGCAGCAGTGGGTCTCCGGATGGCG
CCTTAACGCAGATTCAGTATTGTGGGGAGGACACAAAGTTTTCATGGTCAAACCGG
AAGAGCCCTTCCAGCCGGTGAAAGAGGCAACCCAATTGATGAATtaaGCTAGCAGATC
TTTTTCCCTCTGCCAAAAATTATGGGGACATCATGAAGCCCCTTGAGCATCTGACTTCTG
GCTAATAAAGGAAATTTATTTTCATTGCAATAGTGTGTTGGAATTTTTTGTGTCTCTCA
CTCGGAAGGACATATGGGAGGGCAAATCATTTAAAACATCAGAATGAGTATTTGGTTTA
GAGTTTGGCAACATATGCCCATATGCTGGCTGCCATGAACAAAGGTTGGCTATAAAGAG
GTCATCAGTATATGAAACAGCCCCCTGCTGTCCATTCCTTATTCCATAGAAAAGCCTTGA
CTTGAGGTTAGATTTTTTTTATATTTTGTTTTGTGTTATTTTTTTCTTTAACATCCCTAA
AATTTTCCTTACATGTTTTACTAGCCAGATTTTTCCTCCTCTCCTGACTACTCCCAGTCA
TAGCTGTCCCTCTTCTCTTATGAAGATCCCTCGACCTGCAGCCCAAGCTTGGCGTAATCA
TGGTCATAGCTGTTTCCTGTGTGAAATTGTTATCCGCTCACAATTCCACACAACATACGA
GCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCGGATCCGCAT
CTCAATTAGTCAGCAACCATAGTCCCGCCCCTAACTCCGCCCATCCCGCCCCTAACTCCGC
CCAGTTCCGCCCATTCTCCGCCCCATGGCTGACTAATTTTTTTTATTTATGCAGAGGCCG
AGGCCGCCTCGGCCTCTGAGCTATTCCAGAAGTAGTGAGGAGGCTTTTTTGGAGGCCTAG
GCTTTTGCAAAAAGCTAACTTGTTTATTGCAGCTTATAATGGTTACAAATAAAGCAATA
GCATCACAAATTTCACAAATAAAGCATTTTTTTCACTGCATTCTAGTTGTGGTTTGTCCA
AACTCATCAATGTATCTTATCATGTCTGGATCCGCTGCATTAATGAATCGGCCAACGCGC
GGGGAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAGATAC

FIG. 23 (Cont.)

CAGGCGTTTCCCCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCAATGCTCACGCTGTA
GGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGGTAGCTCTTGA
TCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAA
CTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTTA
ATAGTTTGCGCAACGTTGTTGCCATTGCTACAGGCATCGTGGTGTCACGCTCGTCGTTTG
GTATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCCG
CAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATG
CGGCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTTA
CCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAA
GGGAATAAGGGCGACACGGAAATGTTGAATACTCATACTCTTCCTTTTTCAATATTATT
GAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTG (SEQ ID NO:1103)

FIG. 24

Gag-100%TCS-TEV plasmid sequence (-1 reading frame)

CAG enhancer – bold
Beta actin promoter – underlined
Kozak – lower case; bold and underlined
Gag (such that the following TCS is in the -1 reading frame) – lower case and italicized
Spacer between Gag and TEV (contains 100%TEV cleavage site coding sequence): GAAAACCTGTATTTCCAATCT (SEQ ID NO:1104)
TEV protease – upper case; bold and underlined GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGAC
CGCCCAACGACCCCCGCCCATTGACGTCAATAATGACGTATGTTCCCATAGTAACGCC
AATAGGGACTTTCCATTGACGTCAATGGGTGGACTATTTACGGTAAACTGCCCACTT
GGCAGTACATCAAGTGTATCATATGCCAAGTACGCCCCCTATTGACGTCAATGACGG
TAAATGGCCCGCCTGGCATTATGCCCAGTACATGACCTTATGGGACTTTCCTACTTG
GCAGTACATCTACGTATTAGTCATCGCTATTACCATGGTCGAGGTGAGCCCCACGTTC
TGCTTCACTCTCCCCATCTCCCCCCCCTCCCCACCCCCAATTTTGTATTTATTTATTTTT
AATTATTTTGTGCAGCGATGGGGGCGGGGGGGGGGGGGCGCGCGCCAGGCGGGGCGGG
GCGGGGCGAGGGGCGGGGCGGGGCGAGGCGGAGAGGTGCGGCGGCAGCCAATCAGAGCG
GCGCGCTCCGAAAGTTTCCTTTTATGGCGAGGCGGCGGCGGCGGCGGCCCTATAAAAAGC
GAAGCGCGCGGCGGGCGGGAGTCGCTGCGTTGCCTTCGCCCCGTGCCCCGCTCCGCGCCGC
CTCGCGCCGCCCGCCCCGGCTCTGACTGACCGCGTTACTCCCACAGGTGAGCGGGCGGGAC
GGCCCTTCTCCTCCGGGCTGTAATTAGCGCTTGGTTTAATGACGGCTCGTTTCTTTTCTG
TGGCTGCGTGAAAGCCTTAAAGGGCTCCGGGAGGGCCCTTTGTGCGGGGGGAGCGGCTC
GGGGGGTGCGTGCGTGTGTGTGTGCGTGGGGAGCGCCGCGTGCGGCCCGCGCTGCCCGGC
GGCTGTGAGCGCTGCGGGCGCGGCGCGGGGCTTTGTGCGCTCCGCGTGTGCGCGAGGGGA
GCGCGGCCGGGGGCGGTGCCCCGCGGTGCGGGGGGGCTGCGAGGGGAACAAAGGCTGCGT
GCGGGGTGTGTGCGTGGGGGGGTGAGCAGGGGGTGTGGGCGCGGCGGTCGGGCTGTAAC
CCCCCCCTGCACCCCCCTCCCCGAGTTGCTGAGCACGGCCCGGCTTCGGGTGCGGGGCTCC
GTGCGGGGCGTGGCGCGGGGCTCGCCGTGCCGGGCGGGGGGTGGCGGCAGGTGGGGGTGC

FIG. 24 (Cont.)

CGGGCGGGGCGGGGCCGCCTCGGGCCGGGGAGGGCTCGGGGGAGGGGCGCGGCGGCCCCG
GAGCGCCGGCGGCTGTCGAGGCGCGGCGAGCCGCAGCCATTGCCTTTTATGGTAATCGTG
CGAGAGGGCGCAGGGACTTCCTTTGTCCCAAATCTGGCGGAGCCGAAATCTGGGAGGCGC
CGCCGCACCCCCTCTAGCGGGCGCGGGCGAAGCGGTGCGGCGCCGGCAGGAAGGAAATGG
GCGGGGAGGGCCTTCGTGCGTCGCCGCGCCGCCGTCCCCTTCTCCATCTCCAGCCTCGGGG
CTGCCGCAGGGGGACGGCTGCCTTCGGGGGGGACGGGGCAGGGCGGGGTTCGGCTTCTGG
CGTGTGACCGGCGGCTCTAGAGCCTCTGCTAACCATGTTCATGCCTTCTTCTTTTTCCTA
CAGCTCCTGGGCAACGTGCTGGTTGTTGTGCTGTCTCATCATTTTGGCAAAGAATTCgcca
cc*atgggtgcgagagcgtcagtattaagcgggggagaattagatcgatgggaaaaaattcggttaaggccagggg*
*gaaagaaaaaatataaattaaaacatatagtatgggcaagcagggagctagaacgattcgcagttaatcctggcct*
*gttagaaacatcagaaggctgtagacaaatactgggacagctacaaccatcccttcagacaggatcagaagaactt*
*agatcattatataatacagtagcaaccctctattgtgtgcatcaaaggatagagataaaagacaccaaggaagcttt*
*agacaagatagaggaagagcaaaacaaaagtaagaaaaaagcacagcaagcagcagctgacacaggacaca*
*gcaatcaggtcagccaaaattaccctatagtgcagaacatccaggggcaaatggtacatcaggccatatcacctag*
*aactttaaatgcatgggtaaaagtagtagaagagaaggctttcagcccagaagtgatacccatgttttcagcattatc*
*agaaggagccaccccacaagatttaaacaccatgctaaacacagtggggggacatcaagcagccatgcaaatgtt*
*aaaagagaccatcaatgaggaagctgcagaatgggatagagtgcatccagtgcatgcagggcctattgcaccagg*
*ccagatgagagaaccaaggggaagtgacatagcaggaactactagtacccttcaggaacaaataggatggatga*
*cacataatccacctatcccagtaggagaaatctataaaagatggataatcctgggattaaataaaatagtaagaat*
*gtatagccctaccagcattctggacataagacaaggaccaaaggaaccctttagagactatgtagaccgattctata*
*aaactctaagagccgagcaagcttcacaagaggtaaaaaattggatgacagaaaccttgttggtccaaaatgcga*
*acccagattgtaagactattttaaaagcattgggaccaggagcgacactagaagaaatgatgacagcatgtcaggg*
*agtggggggacccggccataaagcaagagttttggctgaagcaatgagccaagtaacaaatccagctaccataat*
*gatacagaaaggcaattttaggaaccaaagaaagactgttaagtgtttcaattgtggcaaagaagggcacatagcc*
*aaaaattgcagggcccctaggaaaaagggctgttggaaatgtggaaaggaaggacaccaaatgaaagattgtac*
*tgagagacaggctaattttttagggaagatctggccttcccacaagggaaggccagggaattttcttcagagcagac*
*cagagccaacagccccaccagaagagagcttcaggtttggggaagagacaacaactccctctcagaagcaggagc*
*cgatagacaaggaactgtatcctttagcttccctcagatcactctttggcagcgacccctcgtcacaataaag*GAAA
ACCTGTATTTCCAATCTGAATCCTTGTTTAAAGGTCCGCGAGATTACAATCCGATCTC
ATCCACAATCTGTCATCTGACGAACGAGTCCGACGGGCATACCACGAGTCTGTACGG
TATTGGATTTGGTCCTTTCATTATCACAAATAAGCACTTGTTTCGCCGCAATAATGG

FIG. 24 (Cont.)

TACACTGCTGGTTCAGTCCCTCCACGGCGTTTTTAAAGTAAAGAATACTACAACACT
CCAACAGCACCTGATAGACGGGCGAGATATGATCATTATAAGAATGCCGAAAGACT
TTCCGCCATTTCCCCAGAAGCTCAAATTCAGAGAACCTCAGAGGGAAGAACGGATAT
GCCTCGTCACAACAAATTTTCAAACAAAGTCAATGTCTAGCATGGTTTCTGATACGA
GCTGCACTTTCCCTTCTAGTGATGGAATATTTTGGAAGCATTGGATACAGACAAAG
GACGGCCAGTGTGGCTCCCCTTTGGTTTCAACACGCGATGGGTTCATTGTAGGAATA
CATAGCGCTAGCAACTTCACAAATACAAATAACTACTTTACCAGCGTACCGAAAAAT
TTTATGGAGCTTCTCACCAACCAGGAGGCGCAGCAGTGGGTCTCCGGATGGCGCCTT
AACGCAGATTCAGTATTGTGGGGAGGACACAAAGTTTTCATGGTCAAACCGGAAGA
GCCCTTCCAGCCGGTGAAAGAGGCAACCCAATTGATGAATtaaGCTAGCAGATCTTTTT
CCCTCTGCCAAAAATTATGGGGACATCATGAAGCCCCTTGAGCATCTGACTTCTGGCTAA
TAAAGGAAATTTATTTTCATTGCAATAGTGTGTTGGAATTTTTTGTGTCTCTCACTCGG
AAGGACATATGGGAGGGCAAATCATTTAAAACATCAGAATGAGTATTTGGTTTAGAGTT
TGGCAACATATGCCCATATGCTGGCTGCCATGAACAAAGGTTGGCTATAAAGAGGTCATC
AGTATATGAAACAGCCCCCTGCTGTCCATTCCTTATTCCATAGAAAAGCCTTGACTTGAG
GTTAGATTTTTTTTATATTTTGTTTTGTGTTATTTTTTTCTTTAACATCCCTAAAATTTT
CCTTACATGTTTTACTAGCCAGATTTTTCCTCCTCTCCTGACTACTCCCAGTCATAGCTG
TCCCTCTTCTCTTATGAAGATCCCTCGACCTGCAGCCCAAGCTTGGCGTAATCATGGTCA
TAGCTGTTTCCTGTGTGAAATTGTTATCCGCTCACAATTCCACACAACATACGAGCCGGA
AGCATAAAGTGTAAAGCCTGGGGTGCCTAATGAGTGAGCTAACTCACATTAATTGCGTT
GCGCTCACTGCCCGCTTTCCAGTCGGGAAACCTGTCGTGCCAGCGGATCCGCATCTCAAT
TAGTCAGCAACCATAGTCCCGCCCCTAACTCCGCCCATCCCGCCCCTAACTCCGCCCAGTT
CCGCCCATTCTCCGCCCCATGGCTGACTAATTTTTTTTATTTATGCAGAGGCCGAGGCCG
CCTCGGCCTCTGAGCTATTCCAGAAGTAGTGAGGAGGCTTTTTTGGAGGCCTAGGCTTTT
GCAAAAAGCTAACTTGTTTATTGCAGCTTATAATGGTTACAAATAAAGCAATAGCATCA
CAAATTTCACAAATAAAGCATTTTTTTCACTGCATTCTAGTTGTGGTTTGTCCAAACTCA
TCAATGTATCTTATCATGTCTGGATCCGCTGCATTAATGAATCGGCCAACGCGCGGGGAG
AGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAA
TCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAA

FIG. 24 (Cont.)

AAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCT
GTCCGCCTTTCTCCCTTCGGGAAGCGTGGCGCTTTCTCAATGCTCACGCTGTAGGTATCT
CAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGC
TACAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTCAGTGGAACG
AAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTC
TGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCGTTTGGTATGG
CTTCATTCAGCTCCGGTTCCCAACGATCAAGGCGAGTTACATGATCCCCCATGTTGTGCA
AAAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAA
AAGTGCTCATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGCATT
TATCAGGGTTATTGTCTCATGAGCGGATACATATTTGAATGTATTTAGAAAAATAAACA
AATAGGGGTTCCGCGCACATTTCCCCGAAAAGTGCCACCTG (SEQ ID NO:1105)

FIG. 25

Gag-AcrIIa4 amino acid sequence

Gag -- underlined

Linker between Gag and AcrIIa4 (contains AgeI restriction site for cloning and (SEQ ID NO:882) SQNYPIVQ HIV-1 protease substrate): NFSQNYPIVQTG (SEQ ID NO:1106)

AcrIIa4 -- bold

<u>ARASVLSGGELDRWEKIRLRPGGKKKYKLKHIVWASRELERFAVNPGLLETSEGCRQILGQ</u>
<u>LQPSLQTGSEELRSLYNTVATLYCVHQRIEIKDTKEALDKIEEEQNKSKKKAQQAADTGH</u>
<u>SNQVSQNYPIVQNIQGQMVHQAISPRTLNAWVKVVEEKAFSPEVIPMFSALSEGATPQDL</u>
<u>NTMLNTVGGHQAAMQMLKETINEEAAEWDRVHPVHAGPIAPGQMREPRGSDIAGTTST</u>
<u>LQEQIGWMTHNPPIPVGEIYKRWIILGLNKIVRMYSPTSILDIRQGPKEPFRDYVDRFYKTL</u>
<u>RAEQASQEVKNWMTETLLVQNANPDCKTILKALGPGATLEEMMTACQGVGGPGHKARV</u>
<u>LAEAMSQVTNPATIMIQKGNFRNQRKTVKCFNCGKEGHIAKNCRAPRKKGCWKCGKEGH</u>
<u>QMKDCTERQANFLGKIWPSHKGRPGNFLQSRPEPTAPPEESFRFGEETTTPSQKQEPIDK</u>
<u>ELYPLASLRSLFGSDPSSQ</u>NFSQNYPIVQTGMNINDLIREIKNKDYTVKLSGTDSNSITQLI
IRVNNDGNEYVISESENESIVEKFISAFKNGWNQEYEDEEEFYNDMQTITLKSELN

(SEQ ID NO:1107)

| | MOI to achieve 50% indels |
|---|---|
| 0 Gag-Cas9 | N.D. |
| 1.7ug Gag-Cas9 | 3.551 |
| 3.3ug Gag-Cas9 | 2.249 |
| 5ug Gag-Cas9 | 1.514 |
| 6.7ug Gag-Cas9 | 0.8335 |
| 8.3ug Gag-Cas9 | 0.2598 |

FIG. 40A

Gag-miniABEmax plasmid – nucleotide sequence

CAG enhancer – underlined

Beta actin promoter – bold and underlined

Kozak – gccac (immediately 5' of Gag coding sequence)

Gag – lower case and bold

Spacer between Gag and miniABEmax (contains SQNYPIVQ cleavage site (SEQ ID NO:882) and AgeI restriction site) upper case and bold (immediately 3' of Gag coding sequence)

miniABEmax –lower case and italicized

SV40 NLS – double underlined

GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGACCG
CCCAACGACCCCCGCCCATTGACGTCAATAATGACGTATGTTCCCATAGTAACGCCAATA
GGGACTTTCCATTGACGTCAATGGGTGGACTATTTACGGTAAACTGCCCACTTGGCAGTA
CATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTAC
GTATTAGTCATCGCTATTACCATGGGTCGAGGTGAGCCCCACGTTCTGCTTCACTCTCCC
CATCTCCCCCCCCTCCCCACCCCCAATTTTGTATTTATTTATTTTTTAATTATTTTGTGCA
GCGATGGGGGCGGGGGGGGGGGGGGCGCGCGCCAGGCGGGGCGGGGCGGGGCGAGGGGC
GGGGCGGGGCGAGGCGGAGAGGTGCGGCGGCAGCCAATCAGAGCGGCGCGCTCCGAAAGT
TTCCTTTTATGGCGAGGCGGCGGCGGCGGCGGCCCTATAAAAAGCGAAGCGCGCGGCGGG
CGGGAGTCGCTGCGTTGCCTTCGCCCCGTGCCCCGCTCCGCGCCGCCTCGCGCCGCCCGCC
CCGGCTCTGACTGACCGCGTTACTCCCACAGGTGAGCGGGCGGGACGGCCCTTCTCCTCCG
GGCTGTAATTAGCGCTTGGTTTAATGACGGCTCGTTTCTTTTCTGTGGCTGCGTGAAA
GCCTTAAAGGGCTCCGGGAGGGCCCTTTGTGCGGGGGGGAGCGGCTCGGGGGGTGCG
TGCGTGTGTGTGTGCGTGGGGAGCGCCGCGTGCGGCCCGCGCTGCCCGGCGGCTGTG
AGCGCTGCGGGCGCGGCGCGGGGCTTTGTGCGCTCCGCGTGTGCGCGAGGGGAGCGC

FIG. 40A (Cont.)

GGCCGGGGGCGGTGCCCCGCGGTGCGGGGGGGCTGCGAGGGGAACAAAGGCTGCGTG
CGGGGTGTGTGCGTGGGGGGGTGAGCAGGGGGTGTGGGCGCGGCGGTCGGGCTGTA
ACCCCCCCCTGCACCCCCCTCCCCGAGTTGCTGAGCACGGCCCGGCTTCGGGTGCGGG
GCTCCGTGCGGGGCGTGGCGCGGGGCTCGCCGTGCCGGGCGGGGGGTGGCGGCAGGT
GGGGGTGCCGGGCGGGGCGGGGCCGCCTCGGGCCGGGGAGGGCTCGGGGGAGGGGCG
CGGCGGCCCCGGAGCGCCGGCGGCTGTCGAGGCGCGGCGAGCCGCAGCCATTGCCTTT
TATGGTAATCGTGCGAGAGGGCGCAGGGACTTCCTTTGTCCCAAATCTGGCGGAGCC
GAAATCTGGGAGGCGCCGCCGCACCCCCTCTAGCGGGCGCGGGCGAAGCGGTGCGGC
GCCGGCAGGAAGGAAATGGGCGGGGAGGGCCTTCGTGCGTCGCCGCGCCGCCGTCCC
CTTCTCCATCTCCAGCCTCGGGGCTGCCGCAGGGGGACGGCTGCCTTCGGGGGGGACGGG
GCAGGGCGGGGTTCGGCTTCTGGCGTGTGACCGGCGGCTCTAGAGCCTCTGCTAACCATG
TTCATGCCTTCTTCTTTTTCCTACAGCTCCTGGGCAACGTGCTGGTTGTTGTGCTGTCTC

FIG. 40B

ATCATTTTGGCAAAGAATTCgccaccatgggtgcgagagcgtcagtattaagcgggggagaattagatc
gatgggaaaaaattcggttaaggccagggggaaagaaaaaatataaattaaaacatatagtatgggcaagca
gggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgc
atcaaaggatagagataaaagacaccaaggaagctttagacaagatagaggaagagcaaaacaaaagtaag
aaaaaagcacagcaagcagcagctgacacaggacacagcaatcaggtcagccaaaattaccctatagtgcag
aacatccaggggcaaatggtacatcaggccatatcacctagaactttaaatgcatgggtaaaagtagtagaaga
gaaggctttcagcccagaagtgatacccatgttttcagcattatcagaaggagccaccccacaagatttaaacac
catgctaaacacagtggggggacatcaagcagccatgcaaatgttaaaagagaccatcaatgaggaagctgca
gaatgggatagagtgcatccagtgcatgcagggcctattgcaccaggccagatgagagaaccaaggggaagtg
acatagcaggaactactagtacccttcaggaacaaataggatggatgacacataatccacctatcccagtagga
gaaatctataaaagatggataatcctgggattaaataaaatagtaagaatgtatagccctaccagcattctggac
ataagacaaggaccaaaggaaccctttagagactatgtagaccgattctataaaactctaagagccgagcaag
cttcacaagaggtaaaaaattggatgacagaaaccttgttggtccaaaatgcgaacccagattgtaagactattt
taaaagcattgggaccaggagcgacactagaagaaatgatgacagcatgtcagggagtggggggacccggcc
ataaagcaagagttttggctgaagcaatgagccaagtaacaaatccagctaccataatgatacagaaaggcaa
ttttaggaaccaaagaaagactgttaagtgtttcaattgtggcaaagaagggcacatagccaaaaattgcaggg
cccctaggaaaaagggctgttggaaatgtggaaaggaaggacaccaaatgaaagattgtactgagagacagg
ctaattttttagggaagatctggccttcccacaagggaaggccagggaatttcttcagagcagaccagagccaa
cagccccaccagaagagagcttcaggtttggggaagagacaacaactccctctcagaagcaggagccgataga
caaggaactgtatccctttagcttccctcagatcactctttggcagcgacccctcgtcacaaAACTTTAGCCAG
AACTATCCGATTGTGCAGACCGGT*atgaaacggacagccgacggaagcgagttcgagtcaccaaaga*
*agaagcggaaagtctctgaggtggagttttcccacgagtactggatgagacatgccctgaccctggccaagagggca*
*cgcgatgagagggaggtgcctgtgggagccgtgctggtgctgaacaatagagtgatcggcgagggctggaacaga*
*gccatcggcctgcacgacccaacagcccatgccgaaattatggccctgagacagggcggcctggtcatgcagaact*
*acagactgattgacgccaccctgtacgtgacattcgagccttgcgtgatgtgcgccggcgccatgatccactctaggat*
*cggccgcgtggtgtttggcgtgaggaacgcaaaaaccggcgccgcaggctccctgatggacgtgctgcactacccg*
*gcatgaatcaccgcgtcgaaattaccgagggaatcctggcagatgaatgtgccgccctgctgtgctatttctttcggat*
*gcctagacaggtgttcaatgctcagaagaaggcccagagctccaccgactccggaggatctagcggaggctcctctg*
*gctctgagacacctggcacaagcgagagcgcaacacctgaaagcagcgggggcagcagcgggggtcagacaa*

FIG. 40B (Cont.)

*gaagtacagcatcggcctggccatcggcaccaactctgtgggctgggccgtgatcaccgacgagtacaaggtgccc*
*agcaagaaattcaaggtgctgggcaacaccgaccggcacagcatcaagaagaacctgatcggagccctgctgttcg*
*acagcggcgaaacagccgaggccacccggctgaagagaaccgccagaagaagatacaccagacggaagaaccg*
*gatctgctatctgcaagagatcttcagcaacgagatggccaaggtggacgacagcttcttccacagactggaagagt*
*ccttcctggtggaagaggataagaagcacgagcggcaccccatcttcggcaacatcgtggacgaggtggcctacca*
*cgagaagtaccccaccatctaccacctgagaaagaaactggtggacagcaccgacaaggccgacctgcggctgatc*
*tatctggccctggcccacatgatcaagttccggggccacttcctgatcgagggcgacctgaaccccgacaacagcga*
*cgtggacaagctgttcatccagctggtgcagacctacaaccagctgttcgaggaaaaccccatcaacgccagcggcg*
*tggacgccaaggccatcctgtctgccagactgagcaagagcagacggctggaaaatctgatcgcccagctgcccgg*
*cgagaagaagaatggcctgttcggaaacctgattgccctgagcctgggcctgacccccaacttcaagagcaacttcg*
*acctggccgaggatgccaaactgcagctgagcaaggacacctacgacgacgacctggacaacctgctggcccagat*
*cggcgaccagtacgccgacctgtttctggccgccaagaacctgtccgacgccatcctgctgagcgacatcctgagagt*
*gaacaccgagatcaccaaggcccccctgagcgcctctatgatcaagagatacgacgagcaccaccaggacctgacc*

FIG. 40C

*ctgctgaaagctctcgtgcggcagcagctgcctgagaagtacaaagagattttcttcgaccagagcaagaacggcta
cgccggctacattgacggcggagccagccaggaagagttctacaagttcatcaagcccatcctggaaaagatggac
ggcaccgaggaactgctcgtgaagctgaacagagaggacctgctgcggaagcagcggaccttcgacaacggcagc
atcccccaccagatccacctgggagagctgcacgccattctgcggcggcaggaagatttttacccattcctgaaggac
aaccgggaaaagatcgagaagatcctgaccttccgcatcccctactacgtgggccctctggccaggggaaacagca
gattcgcctggatgaccagaaagagcgaggaaaccatcacccccctggaacttcgaggaagtggtggacaagggcg
cttccgcccagagcttcatcgagcggatgaccaacttcgataagaacctgcccaacgagaaggtgctgcccaagcac
agcctgctgtacgagtacttcaccgtgtataacgagctgaccaaagtgaaatacgtgaccgagggaatgagaaagc
ccgccttcctgagcggcgagcagaaaaaggccatcgtggacctgctgttcaagaccaaccggaaagtgaccgtgaa
gcagctgaaagaggactacttcaagaaaatcgagtgcttcgactccgtggaaatctccggcgtggaagatcggttca
acgcctccctgggcacataccacgatctgctgaaaattatcaaggacaaggacttcctggacaatgaggaaaacga
ggacattctggaagatatcgtgctgaccctgacactgtttgaggacagagagatgatcgaggaacggctgaaaacc
tatgcccacctgttcgacgacaaagtgatgaagcagctgaagcggcggagatacaccggctggggcaggctgagc
cggaagctgatcaacggcatccgggacaagcagtccggcaagacaatcctggatttcctgaagtccgacggcttcgc
caacagaaacttcatgcagctgatccacgacgacagcctgacctttaaagaggacatccagaaagcccaggtgtcc
ggccagggcgatagcctgcacgagcacattgccaatctggccggcagccccgccattaagaagggcatcctgcaga
cagtgaaggtggtggacgagctcgtgaaagtgatgggccggcacaagcccgagaacatcgtgatcgaaatggcca
gagagaaccagaccacccagaagggacagaagaacagccgcgagagaatgaagcggatcgaagagggcatca
aagagctgggcagccagatcctgaaagaacaccccgtggaaaacacccagctgcagaacgagaagctgtacctgt
actacctgcagaatgggcgggatatgtacgtggaccaggaactggacatcaaccggctgtccgactacgatgtgga
ccatatcgtgcctcagagctttctgaaggacgactccatcgacaacaaggtgctgaccagaagcgacaagaaccgg
ggcaagagcgacaacgtgccctccgaagaggtcgtgaagaagatgaagaactactggcggcagctgctgaacgcc
aagctgattacccagagaaagttcgacaatctgaccaaggccgagagaggcggcctgagcgaactggataaggcc
ggcttcatcaagagacagctggtggaaacccggcagatcacaaagcacgtggcacagatcctggactcccggatga
acactaagtacgacgagaatgacaagctgatccgggaagtgaaagtgatcaccctgaagtccaagctggtgtccga
tttccggaaggatttccagttttacaaagtgcgcgagatcaacaactaccaccacgcccacgacgcctacctgaacgc
cgtcgtgggaaccgccctgatcaaaaagtaccctaagctggaaagcgagttcgtgtacggcgactacaaggtgtac
gacgtgcggaagatgatcgccaagagcgagcaggaaatcggcaaggctaccgccaagtacttcttctacagcaac
atcatgaactttttcaagaccgagattaccctggccaacggcgagatccggaagcggcctctgatcgagacaaacgg*

FIG. 40C (Cont.)

*cgaaaccggggagatcgtgtgggataagggccgggattttgccaccgtgcggaaagtgctgagcatgccccaagtg*
*aatatcgtgaaaaagaccgaggtgcagacaggcggcttcagcaaagagtctatcctgcccaagaggaacagcgat*
*aagctgatcgccagaaagaaggactgggaccctaagaagtacggcggcttcgacagccccaccgtggcctattctg*
*tgctggtggtggccaaagtggaaaagggcaagtccaagaaactgaagagtgtgaaagagctgctggggatcacc*
*atcatggaaagaagcagcttcgagaagaatcccatcgactttctggaagccaagggctacaaagaagtgaaaaag*
*gacctgatcatcaagctgcctaagtactccctgttcgagctggaaaacggccggaagagaatgctggcctctgccgg*
*cgaactgcagaagggaaacgaactggccctgccctccaaatatgtgaacttcctgtacctggccagccactatgaga*
*agctgaagggctcccccgaggataatgagcagaaacagctgtttgtggaacagcacaagcactacctggacgaga*
*tcatcgagcagatcagcgagttctccaagagagtgatcctggccgacgctaatctggacaaagtgctgtccgcctac*
*aacaagcaccgggataagcccatcagagagcaggccgagaatatcatccacctgtttaccctgaccaatctgggag*
*cccctgccgccttcaagtactttgacaccaccatcgaccggaagaggtacaccagcaccaaagaggtgctggacgcc*
*accctgatccaccagagcatcaccggcctgtacgagacacggatcgacctgtctcagctgggaggtgactctggcgg*
*ctcaaaaagaaccgccgacggcagcgaattcgag*<u>cccaagaagaagaggaaagtc</u>taaGCTAGCAGATCTTT

FIG. 40D

TTCCCTCTGCCAAAAATTATGGGGACATCATGAAGCCCCTTGAGCATCTGACTTCTGGCT
AATAAAGGAAATTTATTTTCATTGCAATAGTGTGTTGGAATTTTTTGTGTCTCTCACTC
GGAAGGACATATGGGAGGGCAAATCATTTAAAACATCAGAATGAGTATTTGGTTTAGAG
TTTGGCAACATATGCCCATATGCTGGCTGCCATGAACAAAGGTTGGCTATAAAGAGGTC
ATCAGTATATGAAACAGCCCCCTGCTGTCCATTCCTTATTCCATAGAAAAGCCTTGACTT
GAGGTTAGATTTTTTTTATATTTTGTTTTGTGTTATTTTTTTCTTTAACATCCCTAAAAT
TTTCCTTACATGTTTTACTAGCCAGATTTTTCCTCCTCTCCTGACTACTCCCAGTCATAGC
TGTCCCTCTTCTCTTATGAAGATCCCTCGACCTGCAGCCCAAGCTTGGCGTAATCATGGT
CATAGCTGTTTCCTGTGTGAAATTGTTATCCGCTCACAATTCCACACAACATACGAGCCG
GAAGCATAAAGTGTAAAGCCTGGGGTGCCTAATGAGTGAGCTAACTCACATTAATTGCG
TTGCGCTCACTGCCCGCTTTCCAGTCGGGAAACCTGTCGTGCCAGCGGATCCGCATCTCA
ATTAGTCAGCAACCATAGTCCCGCCCCTAACTCCGCCCATCCCGCCCCTAACTCCGCCCAG
TTCCGCCCATTCTCCGCCCCATGGCTGACTAATTTTTTTTATTTATGCAGAGGCCGAGGC
CGCCTCGGCCTCTGAGCTATTCCAGAAGTAGTGAGGAGGCTTTTTTGGAGGCCTAGGCTT
TTGCAAAAAGCTAACTTGTTTATTGCAGCTTATAATGGTTACAAATAAAGCAATAGCAT
CACAAATTTCACAAATAAAGCATTTTTTTCACTGCATTCTAGTTGTGGTTTGTCCAAACT
CATCAATGTATCTTATCATGTCTGGATCCGCTGCATTAATGAATCGGCCAACGCGCGGGG
AGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACA
GAATCAGGGGATAACGCAGGAAAGAACATGTGAGCAAAAGGCCAGCAAAAGGCCAGGAA
CCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTAGGTA
TCTCAGTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGACACGA
CTTATCGCCACTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGCA

FIG. 40D (Cont.)

GAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTA
GATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTAC
CATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCG
CCTCCATCCAGTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCATCCGTAA
GATGCTTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCAGAACTT

FIG. 40E

TAAAAGTGCTCATCATTGGAAAACGTTCTTCGGGGCGAAAACTCTCAAGGATCTTACCGC
TGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGC
ATTTATCAGGGTTATTGTCTCATGAGCGGATACATATTTGAATGTATTTAGAAAAATAA
ACAAATAGGGGTTCCGCGCACATTTCCCCGAAAAGTGCCACCTG (SEQ ID NO:1108)

FIG. 41

Gag-miniABEmax amino acid sequence

Gag – underlined

Spacer between Gag and miniABEmax (contains SQNYPIVQ cleavage site; SEQ ID NO:882) – bold and underlined miniABEmax – italicized SV40 NLS – PKKKRKV (SEQ ID NO:909) at C-terminus MGARASVLSGGELDRWEKIRLRPGGKKKYKLKHIVWASRELERFAVNPGLLETSEGCRQILGQLQPSLQTGSE
ELRSLYNTVATLYCVHQRIEIKDTKEALDKIEEEQNKSKKKAQQAAADTGHSNQVSQNYPIVQNIQGQMVHQ
AISPRTLNAWVKVVEEKAFSPEVIPMFSALSEGATPQDLNTMLNTVGGHQAAMQMLKETINEEAAEWDRV
HPVHAGPIAPGQMREPRGSDIAGTTSTLQEQIGWMTHNPPIPVGEIYKRWIILGLNKIVRMYSPTSILDIRQG
PKEPFRDYVDRFYKTLRAEQASQEVKNWMTETLLVQNANPDCKTILKALGPGATLEEMMTACQGVGGPGH
KARVLAEAMSQVTNPATIMIQKGNFRNQRKTVKCFNCGKEGHIAKNCRAPRKKGCWKCGKEGHQMKDCT
ERQANFLGKIWPSHKGRPGNFLQSRPEPTAPPEESFRFGEETTTPSQKQEPIDKELYPLASLRSLFGSDPSSQN
FSQNYPIVQTG*MKRTADGSEFESPKKKRKVSEVEFSHEYWMRHALTLAKRARDEREVPVGAVLVLNNRVIG*
*EGWNRAIGLHDPTAHAEIMALRQGGLVMQNYRLIDATLYVTFEPCVMCAGAMIHSRIGRVVFGVRNAKTG*
*AAGSLMDVLHYPGMNHRVEITEGILADECAALLCYFFRMPRQVFNAQKKAQSSTDSGGSSGGSSGSETPGT*
*SESATPESSGGSSGGSDKKYSIGLAIGTNSVGWAVITDEYKVPSKKFKVLGNTDRHSIKKNLIGALLFDSGETAE*
*ATRLKRTARRRYTRRKNRICYLQEIFSNEMAKVDDSFFHRLEESFLVEEDKKHERHPIFGNIVDEVAYHEKYPTI*
*YHLRKKLVDSTDKADLRLIYLALAHMIKFRGHFLIEGDLNPDNSDVDKLFIQLVQTYNQLFEENPINASGVDAK*
*AILSARLSKSRRLENLIAQLPGEKKNGLFGNLIALSLGLTPNFKSNFDLAEDAKLQLSKDTYDDDLDNLLAQIGD*
*QYADLFLAAKNLSDAILLSDILRVNTEITKAPLSASMIKRYDEHHQDLTLLKALVRQQLPEKYKEIFFDQSKNGY*
*AGYIDGGASQEEFYKFIKPILEKMDGTEELLVKLNREDLLRKQRTFDNGSIPHQIHLGELHAILRRQEDFYPFLK*
*DNREKIEKILTFRIPYYVGPLARGNSRFAWMTRKSEETITPWNFEEVVDKGASAQSFIERMTNFDKNLPNEKV*
*LPKHSLLYEYFTVYNELTKVKYVTEGMRKPAFLSGEQKKAIVDLLFKTNRKVTVKQLKEDYFKKIECFDSVEISGV*
*EDRFNASLGTYHDLLKIIKDKDFLDNEENEDILEDIVLTLTLFEDREMIEERLKTYAHLFDDKVMKQLKRRRYTG*
*WGRLSRKLINGIRDKQSGKTILDFLKSDGFANRNFMQLIHDDSLTFKEDIQKAQVSGQGDSLHEHIANLAGSP*
*AIKKGILQTVKVVDELVKVMGRHKPENIVIEMARENQTTQKGQKNSRERMKRIEEGIKELGSQILKEHPVENT*
*QLQNEKLYLYYLQNGRDMYVDQELDINRLSDYDVDHIVPQSFLKDDSIDNKVLTRSDKNRGKSDNVPSEEVV*

FIG. 41 (Cont.)

*KKMKNYWRQLLNAKLITQRKFDNLTKAERGGLSELDKAGFIKRQLVETRQITKHVAQILDSRMNTKYDENDK LIREVKVITLKSKLVSDFRKDFQFYKVREINNYHHAHDAYLNAVVGTALIKKYPKLESEFVYGDYKVYDVRKMIA KSEQEIGKATAKYFFYSNIMNFFKTEITLANGEIRKRPLIETNGETGEIVWDKGRDFATVRKVLSMPQVNIVKK TEVQTGGFSKESILPKRNSDKLIARKKDWDPKKYGGFDSPTVAYSVLVVAKVEKGKSKKLKSVKELLGITIMERS SFEKNPIDFLEAKGYKEVKKDLIIKLPKYSLFELENGRKRMLASAGELQKGNELALPSKYVNFLYLASHYEKLKGS PEDNEQKQLFVEQHKHYLDEIIEQISEFSKRVILADANLDKVLSAYNKHRDKPIREQAENIIHLFTLTNLGAPAAF KYFDTTIDRKRYTSTKEVLDATLIHQSITGLYETRIDLSQLGGDSGGSKRTADGSEFE*PKKKRKV (SEQ ID NO:1109)

FIG. 45A

Gag-cre plasmid – nucleotide sequence

CAG enhancer –underlined

Beta actin promoter – bold and underlined

Kozak – gccac (immediately 5' of Gag coding sequence)

Gag – lower case and bold

Spacer between Gag and cre recombinase (contains SQNYPIVQ cleavage site (SEQ ID NO:882) and AgeI restriction site) – upper case and bold (immediately 3' of Gag coding sequence)

Cre recombinase – italicized

3X FLAG tag – actataaggaccacgacggagactacaaggatcatgatattgattacaaagacgatgacgataag (SEQ ID NO:1096)

SV40 NLS

GTCGACATTGATTATTGACTAGTTATTAATAGTAATCAATTACGGGGTCATTAGTTCAT
AGCCCATATATGGAGTTCCGCGTTACATAACTTACGGTAAATGGCCCGCCTGGCTGACCG
CCCAACGACCCCCGCCCATTGACGTCAATAATGACGTATGTTCCCATAGTAACGCCAATA
GGGACTTTCCATTGACGTCAATGGGTGGACTATTTACGGTAAACTGCCCACTTGGCAGTA
CATCAAGTGTATCATATGCCAAGTACGCCCCCTATTGACGTCAATGACGGTAAATGGCCC
GCCTGGCATTATGCCCAGTACATGACCTTATGGGACTTTCCTACTTGGCAGTACATCTAC
GTATTAGTCATCGCTATTACCATGGGTCGAGGTGAGCCCCACGTTCTGCTTCACTCTCCC
CATCTCCCCCCCCTCCCCACCCCCAATTTTGTATTTATTTATTTTTTAATTATTTTGTGCA
GCGATGGGGGCGGGGGGGGGGGGGGCGCGCGCCAGGCGGGGCGGGGCGGGGCGAGGGGC
GGGGCGGGGCGAGGCGGAGAGGTGCGGCGGCAGCCAATCAGAGCGGCGCGCTCCGAAAGT
TTCCTTTTATGGCGAGGCGGCGGCGGCGGCGGCCCTATAAAAAGCGAAGCGCGCGGCGGG
CGGGAGTCGCTGCGTTGCCTTCGCCCCGTGCCCCGCTCCGCGCCGCCTCGCGCCGCCCGCC
CCGGCTCTGACTGACCGCGTTACTCCCACAGGTGAGCGGGCGGGACGGCCCTTCTCCTCCG
GGCTGTAATTAGCGCTTGGTTTAATGACGGCTCGTTTCTTTTCTGTGGCTGCGTGAAA
GCCTTAAAGGGCTCCGGGAGGGCCCTTTGTGCGGGGGGGAGCGGCTCGGGGGGTGCG
TGCGTGTGTGTGTGCGTGGGGAGCGCCGCGTGCGGCCCGCGCTGCCCGGCGGCTGTG
AGCGCTGCGGGCGCGGCGCGGGGCTTTGTGCGCTCCGCGTGTGCGCGAGGGGAGCGC
GGCCGGGGGCGGTGCCCCGCGGTGCGGGGGGGCTGCGAGGGGAACAAAGGCTGCGTG

FIG. 45A (Cont.)

CGGGGTGTGTGCGTGGGGGGGTGAGCAGGGGGTGTGGGCGCGGCGGTCGGGCTGTA
ACCCCCCCCTGCACCCCCCTCCCCGAGTTGCTGAGCACGGCCCGGCTTCGGGTGCGGG
GCTCCGTGCGGGGCGTGGCGCGGGGCTCGCCGTGCCGGGCGGGGGGTGGCGGCAGGT
GGGGGTGCCGGGCGGGGCGGGGCCGCCTCGGGCCGGGGAGGGCTCGGGGGAGGGGCG
CGGCGGCCCCGGAGCGCCGGCGGCTGTCGAGGCGCGGCGAGCCGCAGCCATTGCCTTT
TATGGTAATCGTGCGAGAGGGCGCAGGGACTTCCTTTGTCCCAAATCTGGCGGAGCC
GAAATCTGGGAGGCGCCGCCGCACCCCCTCTAGCGGGCGCGGGCGAAGCGGTGCGGC
GCCGGCAGGAAGGAAATGGGCGGGGAGGGCCTTCGTGCGTCGCCGCGCCGCCGTCCC
CTTCTCCATCTCCAGCCTCGGGGCTGCCGCAGGGGGACGGCTGCCTTCGGGGGGGACGGG
GCAGGGCGGGGTTCGGCTTCTGGCGTGTGACCGGCGGCTCTAGAGCCTCTGCTAACCATG
TTCATGCCTTCTTCTTTTTCCTACAGCTCCTGGGCAACGTGCTGGTTGTTGTGCTGTCTC
ATCATTTTGGCAAAGAATTCgccaccatgggtgcgagagcgtcagtattaagcgggggagaattagatc

FIG. 45B gatgggaaaaaattcggttaaggccagggggaaagaaaaaatataaattaaaacatatagtatgggcaagca
gggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgc
atcaaaggatagagataaaagacaccaaggaagctttagacaagatagaggaagagcaaaacaaaagtaag
aaaaaagcacagcaagcagcagctgacacaggacacagcaatcaggtcagccaaaattaccctatagtgcag
aacatccaggggcaaatggtacatcaggccatatcacctagaactttaaatgcatgggtaaaagtagtagaaga
gaaggctttcagcccagaagtgatacccatgttttcagcattatcagaaggagccaccccacaagatttaaacac
catgctaaacacagtgggggggacatcaagcagccatgcaaatgttaaaagagaccatcaatgaggaagctgca
gaatgggatagagtgcatccagtgcatgcagggcctattgcaccaggccagatgagagaaccaaggggaagtg
acatagcaggaactactagtacccttcaggaacaaataggatggatgacacataatccacctatcccagtagga
gaaatctataaaagatggataatcctgggattaaataaaatagtaagaatgtatagccctaccagcattctggac
ataagacaaggaccaaaggaaccctttagagactatgtagaccgattctataaaactctaagagccgagcaag
cttcacaagaggtaaaaaattggatgacagaaaccttgttggtccaaaatgcgaacccagattgtaagactattt
taaaagcattgggaccaggagcgacactagaagaaatgatgacagcatgtcagggagtgggggggacccggcc
ataaagcaagagttttggctgaagcaatgagccaagtaacaaatccagctaccataatgatacagaaaggcaa
ttttaggaaccaaagaaagactgttaagtgtttcaattgtggcaaagaagggcacatagccaaaaattgcaggg
cccctaggaaaaagggctgttggaaatgtggaaaggaaggacaccaaatgaaagattgtactgagagacagg
ctaatttttttagggaagatctggccttcccacaagggaaggccagggaattttcttcagagcagaccagagccaa
cagccccaccagaagagagcttcaggtttggggaagagacaacaactccctctcagaagcaggagccgataga
caaggaactgtatccctttagcttccctcagatcactctttggcagcgacccctcgtcacaaAACTTTAGCCAG
AACTATCCGATTGTGCAGACCGGT*AAGAAAAAACGGAAGGTCAGCAATCTGCTGACGGTG*
*CATCAGAATCTCCCGGCTTTGCCCGTAGACGCGACCAGTGATGAAGTCAGAAAAAACCTGAT*
*GGATATGTTTCGGGATCGCCAGGCATTCAGCGAACACACATGGAAAATGCTGTTGAGTGTTT*
*GTAGGAGTTGGGCAGCATGGTGTAAACTTAACAATCGCAAATGGTTCCCCGCGGAGCCAGAA*
*GATGTTAGGGATTACCTCCTCTACCTTCAAGCCAGAGGGCTCGCTGTGAAGACGATACAACA*
*GCATTTGGGTCAATTGAATATGCTCCATAGGCGGTCCGGCCTCCCACGCCCTTCAGACTCCAA*
*TGCGGTAAGCCTTGTGATGAGAAGAATACGAAAGGAAAACGTAGATGCTGGTGAACGAGCTA*
*AACAGGCATTGGCGTTCGAGCGCACTGACTTCGATCAAGTACGATCACTTATGGAGAACAGT*
*GACCGATGCCAGGATATACGGAATCTCGCTTTCCTCGGTATAGCATACAACACCTTGCTCAGG*
*ATTGCAGAAATAGCCAGGATAAGGGTCAAAGACATATCACGGACAGACGGGGGCCGGATGCT*
*TATCCATATCGGACGCACCAAGACATTGGTGTCAACTGCTGGTGTGGAAAAGGCATTGTCTC*
*TCGGCGTCACGAAGCTCGTCGAGAGGTGGATAAGCGTTTCTGGAGTAGCGGACGACCCTAAT*

FIG. 45B (Cont.)

*AACTATCTTTTCTGCAGAGTTAGAAAAAACGGAGTGGCCGCACCCTCCGCCACCTCTCAACTT*
*AGCACCAGAGCACTTGAGGGAATTTTTGAAGCTACACATAGGCTCATTTATGGTGCCAAAGA*
*CGATTCCGGGCAGCGGTATCTGGCATGGTCTGGTCACAGTGCGCGGGTTGGGGCTGCCAGAG*
*ATATGGCAAGAGCAGGAGTCTCAATACCTGAGATCATGCAAGCTGGTGGGTGGACAAACGTC*
*AATATCGTCATGAATTATATCCGAAATCTTGATAGTGAGACAGGTGCAATGGTCAGACTCCT*
*CGAAGACGGAGAT*gccgactataaggaccacgacggagactacaaggatcatgatattgattacaaagacgatga
cgataagagcctgggcagcggctcccccaagaaaaaacgcaaggtggaagatcctaagaaaaagcggaaagtgtaaG

FIG. 45C

CTAGCAGATCTTTTTCCCTCTGCCAAAAATTATGGGGACATCATGAAGCCCCTTGAGCAT
CTGACTTCTGGCTAATAAAGGAAATTTATTTTCATTGCAATAGTGTGTTGGAATTTTTT
GTGTCTCTCACTCGGAAGGACATATGGGAGGGCAAATCATTTAAAACATCAGAATGAGT
ATTTGGTTTAGAGTTTGGCAACATATGCCCATATGCTGGCTGCCATGAACAAAGGTTGGC
TATAAAGAGGTCATCAGTATATGAAACAGCCCCCTGCTGTCCATTCCTTATTCCATAGAA
AAGCCTTGACTTGAGGTTAGATTTTTTTTATATTTTGTTTTGTGTTATTTTTTTCTTTAA
CATCCCTAAAATTTTCCTTACATGTTTTACTAGCCAGATTTTTCCTCCTCTCCTGACTAC
TCCCAGTCATAGCTGTCCCTCTTCTCTTATGAAGATCCCTCGACCTGCAGCCCAAGCTTG
GCGTAATCATGGTCATAGCTGTTTCCTGTGTGAAATTGTTATCCGCTCACAATTCCACAC
AACATACGAGCCGGAAGCATAAAGTGTAAAGCCTGGGGTGCCTAATGAGTGAGCTAACT
CACATTAATTGCGTTGCGCTCACTGCCCGCTTTCCAGTCGGGAAACCTGTCGTGCCAGCG
GATCCGCATCTCAATTAGTCAGCAACCATAGTCCCGCCCCTAACTCCGCCCATCCCGCCCC
TAACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTTGG
AGGCCTAGGCTTTTGCAAAAAGCTAACTTGTTTATTGCAGCTTATAATGGTTACAAATA
AAGCAATAGCATCACAAATTTCACAAATAAAGCATTTTTTTCACTGCATTCTAGTTGTG
GTTTGTCCAAACTCATCAATGTATCTTATCATGTCTGGATCCGCTGCATTAATGAATCGG
CCAACGCGCGGGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGC
AAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCAATGCTC
ACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCG
GTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCAGCA
GATTACGCGCAGAAAAAAAGGATCTCAAGAAGATCCTTTGATCTTTTCTACGGGGTCTG
ACGCTCAGTGGAACGAAAACTCACGTTAAGGGATTTTGGTCATGAGATTATCAAAAAGG
ATCTTCACCTAGATCCTTTTAAATTAAAAATGAAGTTTTAAATCAATCTAAAGTATATA

FIG. 45C (Cont.)

TGAGTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGC
TCCAGATTTATCAGCAATAAACCAGCCAGCCGGAAGGGCCGAGCGCAGAAGTGGTCCTGC
AACTTTATCCGCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGTCAT
GCCATCCGTAAGATGCTTTTCTGTGACTGGTGAGTACTCAACCAAGTCATTCTGAGAATA

FIG. 45D

GTGTATGCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAACTGATCTT
CAGCATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTCAA
TATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTG (SEQ
ID NO:1115)

FIG. 46

Gag-cre amino acid sequence

Gag – underlined

Spacer between Gag and cre recombinase (contains SQNYPIVQ cleavage site; SEQ ID NO:882) – bold and underlined Cre recombinase -- italicized 3X FLAG tag – YKDHDGDYKDHDIDYKDDDDK (at C-terminus of Cre recombinase) (SEQ ID NO:1117)

SV40 NLS – 2x PKKKRKV – double underlined (SEQ ID NO:909)

MGARASVLSGGELDRWEKIRLRPGGKKKYKLKHIVWASRELERFAVNPGLLETSEGCRQILGQLQPSLQTGSE
ELRSLYNTVATLYCVHQRIEIKDTKEALDKIEEEQNKSKKKAQQAADTGHSNQVSQNYPIVQNIQGQMVHQ
AISPRTLNAWVKVVEEKAFSPEVIPMFSALSEGATPQDLNTMLNTVGGHQAAMQMLKETINEEAAEWDRV
HPVHAGPIAPGQMREPRGSDIAGTTSTLQEQIGWMTHNPPIPVGEIYKRWIILGLNKIVRMYSPTSILDIRQG
PKEPFRDYVDRFYKTLRAEQASQEVKNWMTETLLVQNANPDCKTILKALGPGATLEEMMTACQGVGGPGH
KARVLAEAMSQVTNPATIMIQKGNFRNQRKTVKCFNCGKEGHIAKNCRAPRKKGCWKCGKEGHQMKDCT
ERQANFLGKIWPSHKGRPGNFLQSRPEPTAPPEESFRFGEETTTPSQKQEPIDKELYPLASLRSLFGSDPSSQN
FSQNYPIVQTG*KKKRKVSNLLTVHQNLPALPVDATSDEVRKNLMDMFRDRQAFSEHTWKMLLSVCRSWAA*
*WCKLNNRKWFPAEPEDVRDYLLYLQARGLAVKTIQQHLGQLNMLHRRSGLPRPSDSNAVSLVMRRIRKENV*
*DAGERAKQALAFERTDFDQVRSLMENSDRCQDIRNLAFLGIAYNTLLRIAEIARIRVKDISRTDGGRMLIHIGR*
*TKTLVSTAGVEKALSLGVTKLVERWISVSGVADDPNNYLFCRVRKNGVAAPSATSQLSTRALEGIFEATHRLIY*
*GAKDDSGQRYLAWSGHSARVGAARDMARAGVSIPEIMQAGGWTNVNIVMNYIRNLDSETGAMVRLLED*
*GDAD*YKDHDGDYKDHDIDYKDDDDKSLGSGSPKKKRKVEDPKKKRKV (SEQ ID NO:1116)

COMPOSITIONS AND METHODS FOR DELIVERING CRISPR/CAS EFFECTOR POLYPEPTIDES

CROSS-REFERENCE

This application claims the benefit of U.S. Provisional Patent Application No. 62/768,508, filed Nov. 16, 2018, U.S. Provisional Patent Application No. 62/843,139, filed May 3, 2019 and U.S. Provisional Patent Application No. 62/889,867, filed Aug. 21, 2019, which applications are incorporated herein by reference in their entirety.

STATEMENT REGARDING FEDERALLY SPONSORED RESEARCH

This invention was made with government support under Grant No. HG009490 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-399WO_SEQ_LISTING_RevSept2021_ST25" created on Sep. 2, 2021 and having a size of 8602 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. Genome editing can be carried out using a CRISPR/Cas system comprising a CRISPR/Cas effector polypeptide and a guide RNA. CRISPR/Cas systems are revolutionizing the field of gene editing and genome engineering. Efficient methods for delivering CRISPR/Cas genome editing components into target cells are needed, for both ex vivo and in vivo applications. Current delivery strategies have drawbacks. For example, delivery of a recombinant virus encoding a CRISPR/Cas effector polypeptide leads to prolonged CRISPR/Cas effector polypeptide expression in target cells, thus increasing the likelihood for off-target gene editing events. Others have used a ribonucleoprotein (RNP) comprising a CRISPR/Cas effector polypeptide and guide RNA (gRNA) to deliver the genome editing components into a cell. There is a need in the art for additional strategies for trafficking RNPs into target cells.

SUMMARY

The present disclosure provides a virus-like particle (VLP) comprising a therapeutic polypeptide, and nucleic acids comprising nucleotide sequences encoding the components of the VLP. The present disclosure provides a virus-like particle (VLP) comprising a CRISPR/Cas effector polypeptide, and nucleic acids comprising nucleotide sequences encoding the components of the VLP. The present disclosure provides a system for making a VLP of the present disclosure, as well as methods of making the VLP.

BRIEF DESCRIPTION OF THE DRAWINGS

FIG. 4A-4B provide a nucleotide sequence encoding an HIV gag polyprotein (FIG. 4A) and an amino acid sequence (FIG. 4B) of the encoded gag polyprotein with heterologous protease cleavage sites.

FIG. 5A-5B provide a nucleotide sequence encoding an HIV gag-Cas9 polyprotein (FIG. 5A) and an amino acid sequence (FIG. 5B) of the encoded gag-Cas9 polyprotein with heterologous protease cleavage sites.

FIG. 6A-6B provide a nucleotide sequence encoding an HIV gag polyprotein and TEV protease (FIG. 6A) and an amino acid sequence (FIG. 6B) of the encoded gag polyprotein and TEV protease, with heterologous protease cleavage sites.

FIG. 8A-8F provides amino acid sequences of *Streptococcus pyogenes* Cas9 (FIG. 8A) and variants of *Streptococcus pyogenes* Cas9 (FIG. 8B-8F).

FIG. 9 provides an amino acid sequence of *Staphylococcus aureus* Cas9.

FIG. 10A-10C provide amino acid sequences of *Francisella tularensis* Cpf1 (FIG. 10A), *Acidaminococcus* sp. BV3L6 Cpf1 (FIG. 10B), and a variant Cpf1 (FIG. 10C).

FIG. 16 depicts Gag-Cas9 VLPs-mediated gene editing in vivo.

FIG. 19A is a drawing of the polypeptides incorporated into VLPs when HIV-1 protease was used for producing the VLPs (upper panel) or when TEV protease was used for producing the VLPs (lower panel). FIG. 19B depicts a Western blot showing intra-VLP release of Cas9 from the Cas9-Gag fusion protein. FIG. 19C is a graph showing editing results in which either a TEV or an HIV-1 protease is used to release the Cas9 polypeptide from the Gag-Cas9 polyprotein. FIG. 19D is a graph showing editing using a "1% TCS," a TEV cleavage site (TCS) that has decreased efficiency as compared to the wild type TCS, where the VLP were generated using: a) 6.7 μg Gag-1% TCS-TEV; b) various amounts of Gag-1% TCS-Cas9; and c) various amounts of a Gag-encoding expression vector.

FIG. 21 provides the nucleotide sequence of the Gag-1% TCS-Cas9 construct described in Example 9.

FIG. 22 provides the nucleotide sequence of the Gag-10% TCS-Cas9 construct described in Example 9.

FIG. 23 provides the nucleotide sequence of the Gag-1% TCS-TEV construct described in Example 9.

FIG. 24 provides the nucleotide sequence of the Gag-10% TCS-TEV construct described in Example 9.

FIG. 25 provides the amino acid sequence of the Cas9-Acr fusion polypeptide described in Example 10.

FIG. 40A-40E provide the nucleotide sequence of the Gag-miniABEmax plasmid.

FIG. 41 provides the amino acid sequence of the Gag-miniABEmax protein.

FIG. 45A-45D provide the nucleotide sequence of the Gag-Cre plasmid.

FIG. 46 provides the amino acid sequence of the Gag-Cre polypeptide.

DEFINITIONS

Figure 1:
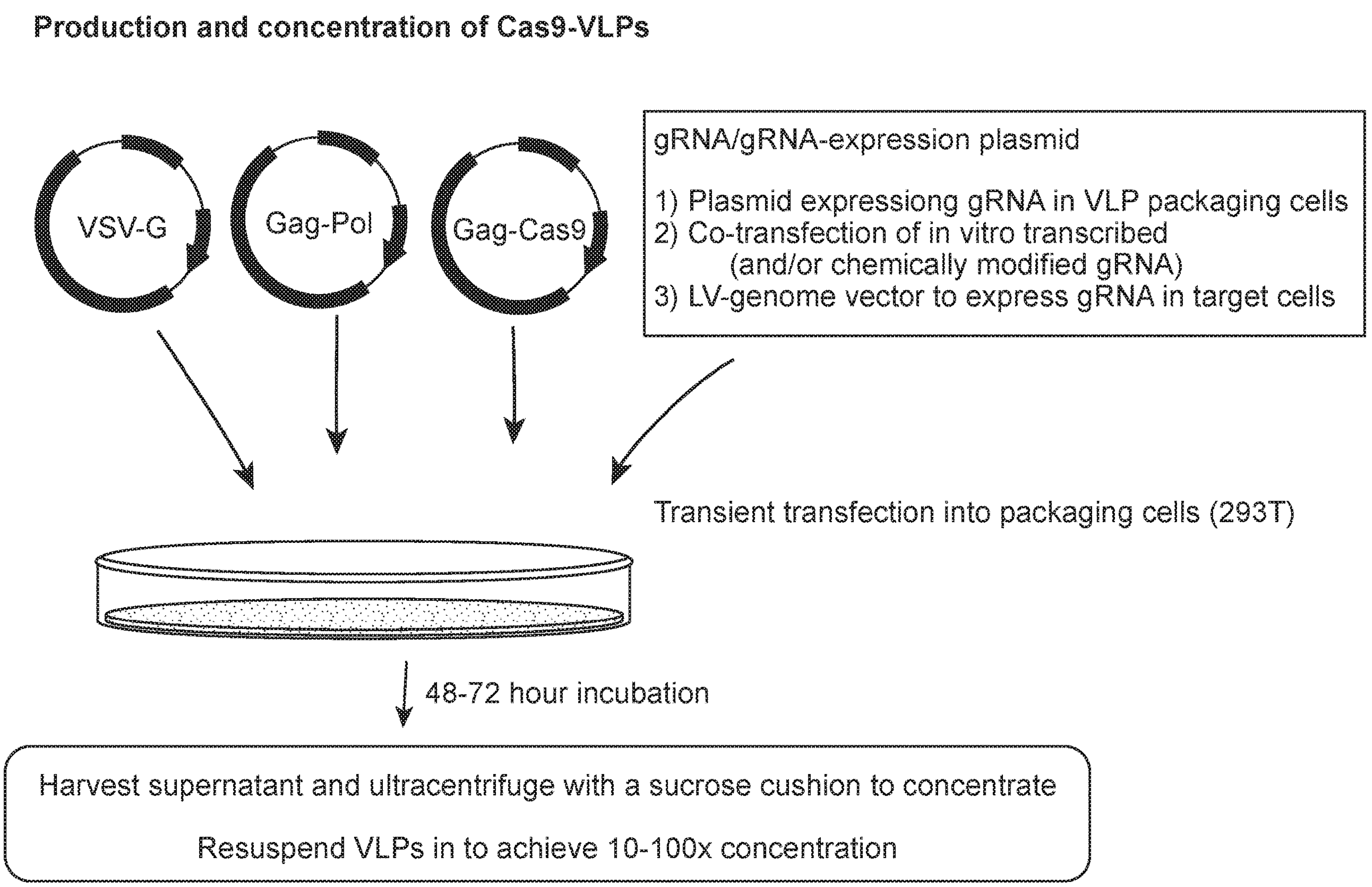
FIG. 1 depicts production and concentration of Cas9 VLPs.

"Heterologous," as used herein, means a nucleotide or polypeptide sequence that is not found in the native nucleic acid or protein, respectively. For example, in the context of a retroviral gag polyprotein, a "heterologous" protease cleavage site is a protease cleavage site that is not found naturally in a retroviral gag polyprotein. Similarly, in the context of a retrovirus, a "heterologous" protease is a protease that is not normally encoded by the retrovirus. As another example, relative to a CRISPR/Cas effector polypeptide, a heterologous polypeptide comprises an amino acid sequence from a protein other than the CRISPR/Cas effector polypeptide. As another example, a CRISPR/Cas effector protein (e.g., a dead CRISPR/Cas effector protein) can be fused to an active domain from a non-CRISPR/Cas effector protein (e.g., a cytidine deaminase), and the sequence of the active domain could be considered a heterologous polypeptide (it is heterologous to the CRISPR/Cas effector protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Heterologous," as used herein, refers to a nucleotide or amino acid sequence that is not found in the native nucleic acid or protein, respectively. For example, relative to a Cas9 polypeptide, a heterologous polypeptide comprises an amino acid sequence from a protein other than the Cas9 polypeptide. Thus, for example, a polymerase polypeptide is heterologous to a Cas9 polypeptide.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, nucleotide sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant nucleotide sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such artificial combination can be carried out to join together nucleic acid segments of desired functions to generate a desired combination of functions.

Similarly, the term "recombinant" polypeptide refers to a polypeptide which is not naturally occurring, e.g., is made by the artificial combination of two otherwise separated segments of amino acid sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change can be achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

The terms "antibodies" and "immunoglobulin" include antibodies or immunoglobulins of any isotype, fragments of antibodies that retain specific binding to antigen, including, but not limited to, Fab, Fv, single-chain Fv (scFv), and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, nanobodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. Also encompassed by the term are Fab', Fv, $F(ab')_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', $F(ab')_2$, and Fv fragments; scFv; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen. "Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies*, vol. 113, Rosenburg and Moore eds., Springer-Verlag, New York, pp. 269-315 (1994). The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, non-human primates, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a virus-like particle" includes a plurality of such virus-like particles and reference to "the CRISPR/Cas effector polypeptide" includes reference to one or more CRISPR/Cas effector polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a virus-like particle (VLP) comprising a therapeutic polypeptide, and nucleic acids comprising nucleotide sequences encoding the components of the VLP. The present disclosure provides a virus-like particle (VLP) comprising a CRISPR/Cas effector polypeptide, and nucleic acids comprising nucleotide sequences encoding the components of the VLP. The present disclosure provides a system for making a VLP of the present disclosure, as well as methods of making the VLP.

Nucleic Acid Encoding Virus-Like Particle

The present disclosure provides a nucleic acid comprising a nucleotide sequence encoding a VLP comprising a fusion polypeptide that comprises: a) a retroviral gag polyprotein comprising a matrix (MA) polypeptide, a capsid (CA) polypeptide, and a nucleocapsid (NC) polypeptide; b) one or more therapeutic polypeptides; and c) one or more heterologous protease cleavage sites, wherein the one or more heterologous protease cleavage sites is between the gag polyprotein and the therapeutic polypeptide(s). Suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody). The present disclosure provides a nucleic acid comprising a nucleotide sequence encoding a VLP comprising a fusion polypeptide that comprises: a) a retroviral gag polyprotein comprising a matrix (MA) polypeptide, a capsid (CA) polypeptide, and a nucleocapsid (NC) polypeptide; b) a CRISPR/Cas effector polypeptide; and c) one or more heterologous protease cleavage sites, wherein the one or more heterologous protease cleavage sites is between the gag polyprotein and the CRISPR/Cas effector polypeptide.

In some cases, the retroviral gag polyprotein also comprises one or more heterologous protease cleavage sites: i) between the MA polypeptide and the CA polypeptide; or ii) between the CA polypeptide and the NC polypeptide; or iii) between the MA polypeptide and the CA polypeptide and between the CA polypeptide and the NC polypeptide.

The presence of the heterologous protease cleavage site(s) provides for reduced protease cleavage within the therapeutic polypeptide. For example, where the therapeutic polypeptide is a CRISPR/Cas effector polypeptide, the presence of the heterologous protease cleavage site(s) provides for reduced protease cleavage within the CRISPR/Cas effector polypeptide. For example, it was found that the retroviral protease that cleaves at native retroviral protease cleavage sites also cleaves a CRISPR/Cas effector polypeptide such as *Streptococcus pyogenes* Cas9. Replacement of one or more native retroviral protease cleavage sites with heterologous protease cleavage sites reduces undesired protease cleavage of the CRISPR/Cas effector polypeptide. Thus, a VLP of the present disclosure can be made with greater efficiency than a VLP made using a retroviral gag/CRISPR/Cas effector polypeptide fusion polypeptide having native retroviral protease cleavage sites.

In some cases, the retroviral gag polyprotein is a lentiviral gag polyprotein. For example, the lentiviral gag polyprotein can be selected from the group consisting of a bovine immunodeficiency virus gag polyprotein, a simian immunodeficiency virus gag polyprotein, a feline immunodeficiency virus gag polyprotein, a human immunodeficiency virus gag polyprotein, an equine infection anemia virus gag polyprotein, and a caprine arthritis encephalitis virus gag polyprotein.

Figure 2:
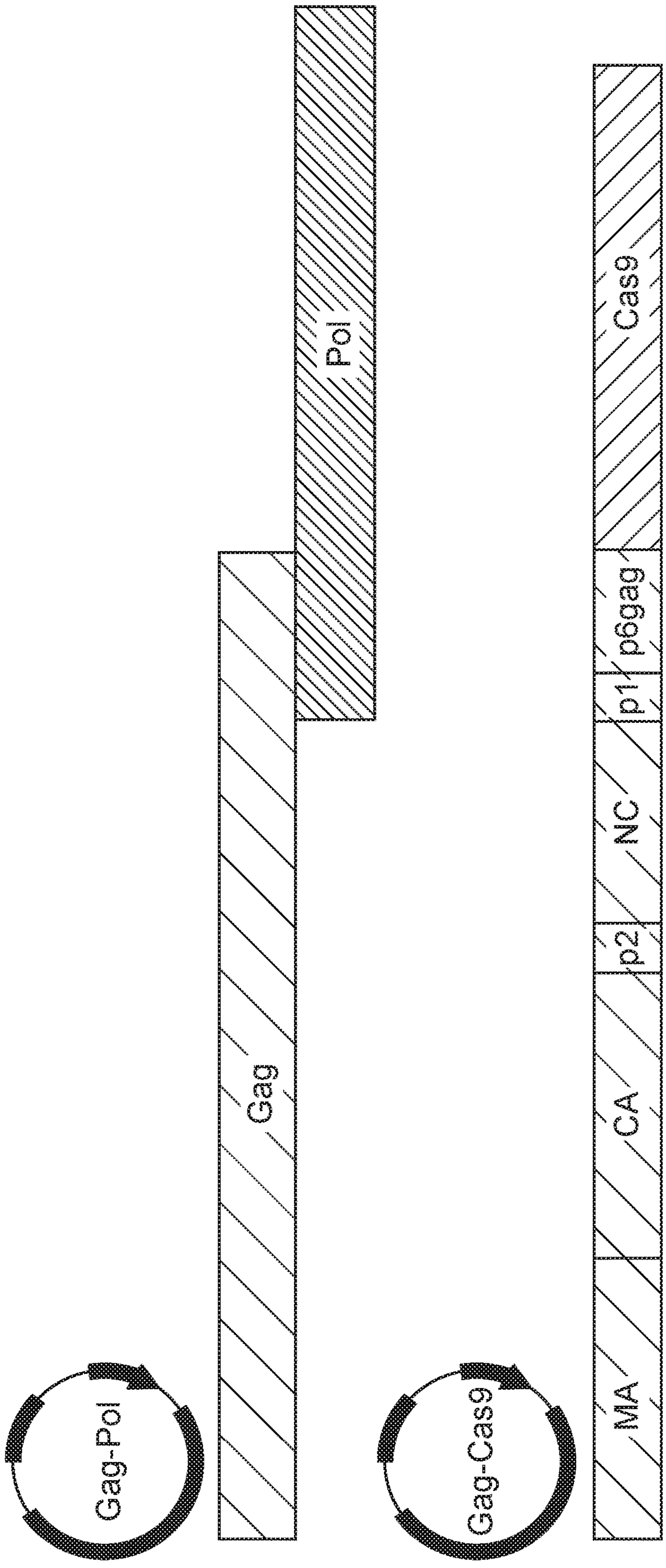
FIG. 2 depicts protein-coding regions of Gag-Pol and Gag-Cas9 constructs.

In some cases, the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide. See, e.g., FIG. 2.

In some cases, the lentiviral gag polyprotein comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence depicted in FIG. 4B. As illustrated in FIG. 4B, a gag polyprotein can comprise: MA-heterologous protease cleavage site-CA-heterologous protease cleavage site-p2-heterologous protease cleavage site-NC-p1-p6. In some cases, the heterologous protease cleavage site is a TEV protease cleavage site: ENLYFQS (SEQ ID NO:880), where cleavage occurs between the Gln and the Ser.

The MA, CA, and NC portions of the gag polyprotein can be of any of a variety of retroviruses. For example, in some cases, a MA polypeptide of the gag polyprotein can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following MA amino acid sequence:

(SEQ ID NO: 847)

MGARASVLSGGELDRWEKIRLRPGGKKKYKLKHIVWASRELERFAVNPGL

LETSEGCRQILGQLQPSLQTGSEELRSLYNTVATLYCVHQRIEIKDTKEA

LDKIEEEQNKSKKKAQQAAADTGHSNQVSQNY.

As another example, in some cases, the CA polypeptide of the gag polyprotein can comprise an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following CA amino acid sequence:

```
                                        (SEQ ID NO: 848)
PIVQNIQGQMVHQAISPRTLNAWVKVVEEKAFSPEVIPMFSALSEGATPQ

DLNTMLNTVGGHQAAMQMLKETINEEAAEWDRVHPVHAGPIAPGQMREPR

GSDIAGTTSTLQEQIGWMTHNPPIPVGEIYKRWIILGLNKIVRMYSPTSI

LDIRQGPKEPFRDYVDRFYKTLRAEQASQEVKNWMTETLLVQNANPDCKT

ILKALGPGATLEEMMTACQGVGGPGHKARVL.
```

In some cases, the retroviral gag polyprotein comprises an MA polypeptide, a CA polypeptide an NC polypeptide, a p1 polypeptide, and a p6 polypeptide. In some cases, the NC-p1-p6 polypeptide of the gag polyprotein comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence:

```
                                        (SEQ ID NO: 849)
IQKGNFRNQRKTVKCFNCGKEGHIAKNCRAPRKKGCWKCGKEGHQMKDCT

ERQANFLGKIWPSHKGRPGNFLQSRPEPTAPPEESFRFGEETTTPSQKQE

PIDKELYPLASLRSLFGSDPSSQ.
```

In some cases, the retroviral gag polyprotein comprises a p2 polypeptide. In some cases, the p2 polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the following amino acid sequence: AEAMSQVTNPATIM (SEQ ID NO:850).

In some cases, the retroviral gag polyprotein is a gag polyprotein of an alpha retrovirus, a beta retrovirus, a gamma retrovirus, a delta retrovirus, an epsilon retrovirus, or a spumavirus. In some cases, the retroviral gag polyprotein is a gag polyprotein of a human immunodeficiency virus.

Therapeutic Polypeptides

As noted above, suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody). A therapeutic polypeptide is heterologous to a retroviral gag polyprotein.

CRISPR/Cas Effector Polypeptides

In some cases, the therapeutic polypeptide is a CRISPR/Cas effector polypeptide. The CRISPR/Cas effector polypeptide can be any of a variety of CRISPR/Cas effector polypeptides. Suitable CRISPR/Cas effector polypeptides are described in detail below. For example, in some cases, the CRISPR/Cas effector polypeptide is a type II CRISPR/Cas effector polypeptide. In some cases, the type II CRISPR/Cas effector polypeptide is a Cas9 polypeptide. In some cases, the CRISPR/Cas effector polypeptide is a type V CRISPR/Cas effector polypeptide, e.g., a Cas12a, a Cas12b, a Cas12c, a Cas12d, or a Cas12e polypeptide. In some cases, the CRISPR/Cas effector polypeptide is a type VI CRISPR/Cas effector polypeptide, e.g., a Cas13a polypeptide, a Cas13b polypeptide, a Cas13c polypeptide, or a Cas13d polypeptide. In some cases, the CRISPR/Cas effector polypeptide is a Cas14 polypeptide. In some cases, the CRISPR/Cas effector polypeptide is a Cas14a polypeptide, a Cas14b polypeptide, or a Cas14c polypeptide. Also suitable for use is a variant CRISPR/Cas effector polypeptide, where the variant CRISPR/Cas effector polypeptide has reduced nucleic acid cleavage activity. Also suitable for use is a CRISPR/Cas effector fusion polypeptide comprising: i) a CRISPR/Cas effector polypeptide is a variant that has reduced nucleic acid cleavage activity; and ii) a heterologous fusion polypeptide. In some cases, the heterologous fusion polypeptide is a protein modifying enzyme. In some cases, the heterologous fusion polypeptide is a nucleic acid modifying enzyme. In some cases, the heterologous fusion polypeptide is a transcription factor. In some cases, the heterologous fusion polypeptide is a transcription activator. In some cases, the heterologous fusion polypeptide is a transcription repressor. Suitable protein-modifying enzymes and nucleic acid modifying enzymes are described in detail below. For example, in some cases, the nucleic acid modifying enzyme is a cytidine deaminase. In some cases, the nucleic acid modifying enzyme is an adenosine deaminase. In some cases, the nucleic acid modifying enzyme is a prime editor. As described in more detail below, in some cases, the CRISPR/Cas effector polypeptide comprises one or more nuclear localization signals.

Suitable CRISPR/Cas effector polypeptides, including CRISPR/Cas effector fusion polypeptides, are described in detail hereinbelow.

Nucleases

Suitable nucleases include, but are not limited to, a homing nuclease polypeptide; a FokI polypeptide; a transcription activator-like effector nuclease (TALEN) polypeptide; a MegaTAL polypeptide; a meganuclease polypeptide; a zinc finger nuclease (ZFN); an ARCUS nuclease; and the like. The meganuclease can be engineered from an LADLIDADG homing endonuclease (LHE). A megaTAL polypeptide can comprise a TALE DNA binding domain and an engineered meganuclease. See, e.g., WO 2004/067736 (homing endonuclease); Urnov et al. (2005) *Nature* 435:646 (ZFN); Mussolino et al. (2011) *Nucle. Acids Res.* 39:9283 (TALE nuclease); Boissel et al. (2013) *Nucl. Acids Res.* 42:2591 (MegaTAL).

Prime Editors

A prime editor is a fusion polypeptide comprising: i) a catalytically impaired CRISPR/Cas effector polypeptide (e.g., a Cas9 polypeptide that exhibits reduced cleavage activity; e.g., a "dead" Cas9); and ii) a reverse transcriptase.

Base Editors

Suitable base editors include, e.g., an adenosine deaminase; a cytidine deaminase (e.g., an activation-induced cytidine deaminase (AID)); APOBEC3G; and the like); and the like.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 894)
MSEVEFSHEYWMRHALTLAKRAWDEREVPVGAVLVHNNRVIGEGWNRPIG

RHDPTAHAEIMALRQGGLVMQNYRLIDATLYVTLEPCVMCAGAMIHSRIG

RVVFGARDAKTGAAGSLMDVLHHPGMNHRVEITEGILADECAALLSDFFR

MRRQEIKAQKKAQSSTD

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 895)
MRRAFITGVFFLSEVEFSHEYWMRHALTLAKRAWDEREVPVGAVLVHNNR

VIGEGWNRPIGRHDPTAHAEIMALRQGGLVMQNYRLIDATLYVTLEPCVM

CAGAMIHSRIGRVVFGARDAKTGAAGSLMDVLHHPGMNHRVEITEGILAD

ECAALLSDFFRMRRQEIKAQKKAQSSTD.

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

(SEQ ID NO: 896)
MGSHMTNDIYFMTLAIEEAKKAAQLGEVPIGAIITKDDEVIARAHNLRET

LQQPTAHAEHIAIERAAKVLGSWRLEGCTLYVTLEPCVMCAGTIVMSRIP

RVVYGADDPKGGCSGSLMNLLQQSNFNHRAIVDKGVLKEACSTLLTTFFK

NLRANKKSTN:

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

(SEQ ID NO: 897)
MTQDELYMKEAIKEAKKAEEKGEVPIGAVLVINGEIIARAHNLRETEQRS

IAHAEMLVIDEACKALGTWRLEGATLYVTLEPCPMCAGAVVLSRVEKVVF

GAFDPKGGCSGTLMNLLQEERFNHQAEVVSGVLEEECGGMLSAFFRELRK

KKKAARKNLSE

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

(SEQ ID NO: 898)
MPPAFITGVTSLSDVELDHEYWMRHALTLAKRAWDEREVPVGAVLVHNHR

VIGEGWNRPIGRHDPTAHAEIMALRQGGLVLQNYRLLDTTLYVTLEPCVM

CAGAMVHSRIGRVVFGARDAKTGAAGSLIDVLHHPGMNHRVEIIEGVLRD

RECATLLSDFFRMRRQEIKALKKADAEGAGPAV

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

(SEQ ID NO: 899)
MDEYWMQVAMQMAEKAEAAGEVPVGAVLVKDGQQIATGYNLSISQHDPTA

HAEILCLRSAGKKLENYRLLDATLYITLEPCAMCAGAMVHSRIARVVYGA

RDEKTGAAGTVVNLLQHPAFNHQVEVTSGVLAEACSAQLSRFFKRRRDEK

KALKLAQRAQQGIE

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

(SEQ ID NO: 900)
MDAAKVRSEFDEKMMRYALELADKAEALGEIPVGAVLVDDARNIIGEGWN

LSIVQSDPTAHAEIIALRNGAKNIQNYRLLNSTLYVTLEPCTMCAGAILH

SRIKRLVFGASDYKTGAIGSRFHFFDDYKMNHTLEITSGVLAEECSQKLS

TFFQKRREEKKIEKALLKSLSDK

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

(SEQ ID NO: 901)
MRTDESEDQDHRMMRLALDAARAAAEAGETPVGAVILDPSTGEVIATAGN

GPIAAHDPTAHAEIAAMRAAAAKLGNYRLTDLTLVVTLEPCAMCAGAISH

ARIGRVVFGADDPKGGAVVHGPKFFAQPTCHWRPEVTGGVLADESADLLR

GFFRARRKAKI

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

(SEQ ID NO: 902)
MSSLKKTPIRDDAYWMGKAIREAAKAAARDEVPIGAVIVRDGAVIGRGHN

LREGSNDPSAHAEMIAIRQAARRSANWRLTGATLYVTLEPCLMCMGAIIL

ARLERVVFGCYDPKGGAAGSLYDLSADPRLNHQVRLSPGVCQEECGTMLS

DFFRDLRRRKKAKATPALFIDERKVPPEP

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 903)
MDSLLMNRRKFLYQFKNVRWAKGRRETYLCYVVKRRDSATSFSLDFGYLR
NKNGCHVELLFLRYISDWDLDPGRCYRVTWFTSWSPCYDCARHVADFLRG
NPNLSLRIFTARLYFCEDRKAEPEGLRRLHRAGVQIAIMTFKDYFYCWNT
FVENHERTFKAWEGLHENSVRLSRQLRRILLPLYEVDDLRDAFRTLGL

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 904)
MDSLLMNRRK FLYQFKNVRW AKGRRETYLC YVVKRRDSAT
SFSLDFGYLR NKNGCHVELL FLRYISDWDL DPGRCYRVTW
FTSWSPCYDC ARHVADFLRG NPNLSLRIFT ARLYFCEDRK
AEPEGLRRLH RAGVQIAIMT FKENHERTFK AWEGLHENSV
RLSRQLRRIL LPLYEVDDLR DAFRTLGL.

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 905)
MDSLLMNRRK FLYQFKNVRW AKGRRETYLC YVVKRRDSAT
SFSLDFGYLR NKNGCHVELL FLRYISDWDL DPGRCYRVTW
FTSWSPCYDC ARHVADFLRG NPNLSLRIFT ARLYFCEDRK
AEPEGLRRLH RAGVQIAIMT FKDYFYCWNT FVENHERTFK
AWEGLHENSV RLSRQLRRIL LPLYEVDDLR DAFRTLGL.

Transcription Factors

A transcription factor can include: i) a DNA binding domain; and ii) a transcription activator. A transcription factor can include: i) a DNA binding domain; and ii) a transcription repressor. Suitable transcription factors include polypeptides that include a transcription activator or a transcription repressor domain (e.g., the Kruppel associated box (KRAB or SKD); the Mad mSIN3 interaction domain (SID); the ERF repressor domain (ERD), etc.); zinc-finger-based artificial transcription factors (see, e.g., Sera (2009) *Adv. Drug Deliv.* 61:513); TALE-based artificial transcription factors (see, e.g., Liu et al. (2013) *Nat. Rev. Genetics* 14:781); and the like. In some cases, the transcription factor comprises a VP64 polypeptide (transcriptional activation). In some cases, the transcription factor comprises a Kruppel-associated box (KRAB) polypeptide (transcriptional repression). In some cases, the transcription factor comprises a Mad mSIN3 interaction domain (SID) polypeptide (transcriptional repression). In some cases, the transcription factor comprises an ERF repressor domain (ERD) polypeptide (transcriptional repression). For example, in some cases, the transcription factor is a transcriptional activator, where the transcriptional activator is GAL4-VP16.

Recombinases

Suitable recombinases include, e.g., a Cre recombinase; a Hin recombinase; a Tre recombinase; a FLP recombinase; and the like.

Antibodies

Suitable antibodies include, e.g., single-chain antibodies such as a nanobody, a single chain Fv antibody; a diabody; a minibody; and the like. A suitable antibody can bind an intracellular antigen, an antigen present on a cell surface, or an extracellular antigen.

Reverse Transcriptases

Suitable reverse transcriptases include, e.g., a murine leukemia virus reverse transcriptase; a Rous sarcoma virus reverse transcriptase; a human immunodeficiency virus type I reverse transcriptase; a Moloney murine leukemia virus reverse transcriptase; and the like.

Anti-CRISPR Polypeptides

Suitable anti-CRISPR (Acr) polypeptides include, e.g., AcrIIA1, AcrIIA2, AcrIIA3, AcrIIA4, AcrIIC1, AcrIIC2, AcrIIC3, AcrE1, AcrID1, Acrf10, anti-CRISPR protein 30, Acrf2, and Acrf1. See, e.g., WO 2017/160689; and Nakamura et al. (2019) *Nature Communications* 10:194; Harrington et al. (2017) *Cell* 170:1224; Shin et al. (2017) *Sci. Adv.* 3:e1701620; Zhu et al. (2019) *Mol. Cell* 74:296; Dong et al. (2017) *Nature* 546:436; Bondy-Denomy et al. (2013) *Nature* 493:429; Rauch et al. (2017) *Cell* 168:150; Ka et al. (2018) *Nucl. Acids Res.* 46:485; Basgall et al. (2018) *Microbiol.* 164:464. In some cases, the Acr polypeptide reduces binding to and/or cleavage of a target nucleic acid by a type II CRISPR/Cas effector polypeptide.

In some cases, the Acr polypeptide is an AcrIIA4 polypeptide. An AcrIIA4 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 936)
NDLIREIKNKDYTVKLSGTDSNSITQLIIRVNNDGNEYVISESENESIVE
KFISAFKNGWNQEYEDEEEFYNDMQTITLKSELN.

In some cases, the Acr polypeptide is an AcrIIA1 polypeptide. An AcrIIA1 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 937)
MTIKLLDEFLKKHDLTRYQLSKLTGISQNTLKDQNEKPLNKYTVSILRSL
SLISGLSVSDVLFELEDIEKNSDDLAGFKHLLDKYKLSFPAQEFELYCLI
KEFESANIEVLPFTFNRFENEEHVNIKKDVCKALENAITVLKEKKNELL.

In some cases, the Acr polypeptide is an AcrIIA2 polypeptide. An AcrIIA2 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 938)

```
MTLTRAQKKY AEAMHEFINM VDDFEESTPD FAKEVLHDSD

YVVITKNEKY AVALCSLSTD ECEYDTNLYL DEKLVDYSTV

DVNGVTYYIN IVETNDIDDL EIATDEDEMK SGNQEIILKS ELK.
```

Heterologous Protease Cleavage Sites

A heterologous protease cleavage site can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue (SEQ ID NO:851)), e.g., Pro-X-X-Hy-(Ser/Thr) (SEQ ID NO:1067), e.g., Pro-Leu/Gln-Gly-Met-Thr-Ser (SEQ ID NO:852) or Pro-Leu/Gln-Gly-Met-Thr (SEQ ID NO:853). Another example of a protease cleavage site is a plasminogen activator cleavage site, e.g., a uPA or a tissue plasminogen activator (tPA) cleavage site. In some cases, the cleavage site is a furin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:854), where the protease cleaves between the glutamine and the serine. Another example of a protease cleavage site that can be included in a proteolytically cleavable linker is an enterokinase cleavage site, e.g., DDDDK (SEQ ID NO:855), where cleavage occurs after the lysine residue. Another example of a protease cleavage site that can be included in a proteolytically cleavable linker is a thrombin cleavage site, e.g., LVPR (SEQ ID NO:856). Additional suitable linkers comprising protease cleavage sites include linkers comprising one or more of the following amino acid sequences: LEVLFQGP (SEQ ID NO:857), cleaved by PreScission protease (a fusion protein comprising human rhinovirus 3C protease and glutathione-S-transferase; Walker et al. (1994) *Biotechnol.* 12:601); a thrombin cleavage site, e.g., CGLVPAGSGP (SEQ ID NO:858); SLLKSRMVPNFN (SEQ ID NO:859) or SLLIARRMPNFN (SEQ ID NO:860), cleaved by cathepsin B; SKLVQASASGVN (SEQ ID NO:861) or SSYLKASDAPDN (SEQ ID NO:862), cleaved by an Epstein-Barr virus protease; RPKPQQFFGLMN (SEQ ID NO:863) cleaved by MMP-3 (stromelysin); SLRPLALWRSFN (SEQ ID NO:864) cleaved by MMP-7 (matrilysin); SPQGIAGQRNFN (SEQ ID NO:865) cleaved by MMP-9; DVDERDVRGFASFL SEQ ID NO:866) cleaved by a thermolysin-like MMP; SLPLGLWAPNFN (SEQ ID NO:867) cleaved by matrix metalloproteinase 2 (MMP-2); SLLIFRSWANFN (SEQ ID NO:868) cleaved by cathespin L; SGVVIATVIVIT (SEQ ID NO:869) cleaved by cathepsin D; SLGPQGIWGQFN (SEQ ID NO:870) cleaved by matrix metalloproteinase 1 (MMP-1); KKSPGRVVGGSV (SEQ ID NO:871) cleaved by urokinase-type plasminogen activator; PQGLLGAPGILG (SEQ ID NO:872) cleaved by membrane type 1 matrix metalloproteinase (MT-MMP); HGPEGLRVGFYESDVMGRGHARLVHVEEPHT (SEQ ID NO:873) cleaved by stromelysin 3 (or MMP-11), thermolysin, fibroblast collagenase and stromelysin-1; GPQGLAGQRGIV (SEQ ID NO:874) cleaved by matrix metalloproteinase 13 (collagenase-3); GGSGQRGRKALE (SEQ ID NO:875) cleaved by tissue-type plasminogen activator (tPA); SLSALLSSDIFN (SEQ ID NO:876) cleaved by human prostate-specific antigen; SLPRFKIIGGFN (SEQ ID NO:877) cleaved by kallikrein (hK3); SLLGIAVPGNFN (SEQ ID NO:878) cleaved by neutrophil elastase; and FFKNIVTPRTPP (SEQ ID NO:879) cleaved by calpain (calcium activated neutral protease). In some cases, the protease cleavage site is a TEV protease cleavage site, e.g., ENLYFQS (SEQ ID NO:880), where cleavage occurs between the Gln and the Ser. In some cases, the protease cleavage site is the TEV protease cleavage site ENLYFQP (SEQ ID NO:881). ENLYFQS (SEQ ID NO:880) and ENLYFQP (SEQ ID NO:881) are wildtype recognition sequences (cleavage substrates) for TEV protease (see e.g. Stols et al. (2002) *Prot. Exp. Purif.* 25: 8-12). In some cases, the proteolytically cleavable linker comprises an HIV-1 protease cleavage site (e.g. SQNYPIVQ (SEQ ID NO:882)), where cleavage occurs between the tyrosine and the proline. In some cases, an HIV-1 protease cleavage site (e.g. SQNYPIVQ (SEQ ID NO:882)) is specifically excluded.

In some cases, the protease cleavage site is a TEV protease cleavage site, e.g., ENLYTQS (SEQ ID NO:854), where the protease cleaves between the glutamine and the serine. In some cases, the protease cleavage site is a variant TEV-cleavage substrate, where the variant TEV cleavage site is cleaved by a TEV protease (e.g., a TEV protease comprising the TEV protease amino acid sequence provided in FIG. 6B) less efficiently than cleavage of ENLYTQS (SEQ ID NO:854) by the TEV protease. In some cases, a variant TEV-cleavage site can: (1) mimic the temporal cleavage observed with wild-type gag polyprotein maturation; and/or (2) maximize packaging of a CRISPR/Cas effector polypeptide into a VLP. Suitable variant TEV cleavage sites are described in Tözsér et al. (2005) *FEBS J.* 272:514. Suitable variant TEV cleavage sites include: ENAYFQS (SEQ ID NO:883), ENLRFQS (SEQ ID NO:884), ENLFFQS (SEQ ID NO:885), ETVRFQS (SEQ ID NO:886), ETLRFQS (SEQ ID NO:887), ETARFQS (SEQ ID NO:888), ETVYFQS (SEQ ID NO:889), and ENVYFQS (SEQ ID NO:890).

In some cases, the variant TEV cleavage substrate (also referred to herein as a "TEV cleavage site" or "TCS") is cleaved less efficiently than a TCS having the amino acid sequence ENLYFQS (SEQ ID NO:880) or ENLYFQP (SEQ ID NO:881). For example, a population of Gag-Cas9 polyproteins that comprise, in order from N-terminus to C-terminus, Gag-TCS-Cas9, where the TCS is a variant TCS, is cleaved less efficiently by a TEV protease than a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881).

For example, in some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time is less than 90%, less than 80%, less than 70%, less than 60%, less than 50%, less than 40%, less than 30%, less than 25%, less than 20%, less than 15%, less than 10%, less than 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease over the same period of time (and under the same conditions).

For example, in some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time is from 80% to 90%, from 70%, to 80%, from 60% to 70%, from 50% to 60%, from 40% to 50%, from 30% to 40%, from 25% to 30%, from 20% to 25%, from 15% to 20%, from 10% to 15%, from 5% to 10%, from 1% to 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease over the same period of time (and under the same conditions).

In some cases, the TEV protease comprises the following amino acid sequence:

```
                                      (SEQ ID NO: 892)
ESLFKGPRDYNPISSTICHLTNESDGHTTSLYGIGFGPFIITNKHLFRRN

NGTLLVQSLHGVFKVKNTTTLQQHLIDGRDMIIIRMPKDFPPFPQKLKFR

EPQREERICLVTTNFQTKSMSSMVSDTSCTFPSSDGIFWKHWIQTKDGQC

GSPLVSTRDGFIVGIHSASNFTNTNNYFTSVPKNFMELLTNQEAQQWVSG

WRLNADSVLWGGHKVFMVKPEEPFQPVKEATQLMN.
```

In some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time (e.g., from 5 seconds to 15 minutes; e.g., from 5 seconds to 15 seconds, from 15 seconds to 30 seconds, from 30 seconds to 60 seconds, from 1 minute to 2 minutes, or from 2 minutes to 5 minutes, from 5 minutes to 10 minutes, or from 10 minutes to 15 minutes) is from 80% to 90%, from 70%, to 80%, from 60% to 70%, from 50% to 60%, from 40% to 50%, from 30% to 40%, from 25% to 30%, from 20% to 25%, from 15% to 20%, from 10% to 15%, from 5% to 10%, from 1% to 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease over the same period of time (and under the same conditions).

A TCS that comprises one or more amino acid differences from ENLYFQS (SEQ ID NO:880) can be said to be a "reduced efficiency" TCS, where the reduced efficiency is expressed as a percent of the cleavage efficiency at a TCS that comprises ENLYFQS (SEQ ID NO:880). For example, the TCS comprising ENLFFQS (SEQ ID NO:885) is said to be a "10% efficiency" TCS (or "10% TCS"). One example of a "reduced affinity" TCS is a TCS that comprises ENLFFQS (SEQ ID NO:885). For example, the percent of a population of Gag-Cas9 polyproteins that comprise, in order from N-terminus to C-terminus, Gag-TCS-Cas9, where the TCS is ENLFFQS (SEQ ID NO:885) that are cleaved with a TEV protease over a given period of time (e.g., from 5 seconds to 15 minutes; e.g., from 5 seconds to 15 seconds, from 15 seconds to 30 seconds, from 30 seconds to 60 seconds, from 1 minute to 2 minutes, or from 2 minutes to 5 minutes, from 5 minutes to 10 minutes, or from 10 minutes to 15 minutes) is about 10% of the percent of a population of Gag-Cas9 polyproteins that comprise, in order from N-terminus to C-terminus, Gag-TCS-Cas9, where the TCS comprises ENLYFQS (SEQ ID NO:880) that is cleaved by the same TEV protease over the same period of time (and under the same conditions).

Another example of a "reduced affinity" TCS is a TCS that comprises ENVYFQS (SEQ ID NO:890). For example, the percent of a population of Gag-Cas9 polyproteins that comprise, in order from N-terminus to C-terminus, Gag-TCS-Cas9, where the TCS is ENVYFQS (SEQ ID NO:890) that are cleaved with a TEV protease over a given period of time (e.g., from 5 seconds to 15 minutes; e.g., from 5 seconds to 15 seconds, from 15 seconds to 30 seconds, from 30 seconds to 60 seconds, from 1 minute to 2 minutes, or from 2 minutes to 5 minutes, from 5 minutes to 10 minutes, or from 10 minutes to 15 minutes) is about 1% of the percent of a population of Gag-Cas9 polyproteins that comprise, in order from N-terminus to C-terminus, Gag-TCS-Cas9, where the TCS comprises ENLYFQS (SEQ ID NO:880) that is cleaved by the same TEV protease over the same period of time (and under the same conditions).

Systems

The present disclosure provides a system comprising: a) a first nucleic acid comprising a nucleotide sequence encoding a VLP comprising a fusion polypeptide that comprises: i) a retroviral gag polyprotein comprising a MA polypeptide, a CA polypeptide, and an NC polypeptide; ii) one or more therapeutic polypeptides; and iii) one or more heterologous protease cleavage sites, wherein at least one of the one or more heterologous protease cleavage sites is between the gag polyprotein and the one or more therapeutic polypeptides; and b) a second nucleic acid comprising a nucleotide sequence encoding a heterologous protease that cleaves the one or more heterologous protease cleavage sites. Suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody). The present disclosure provides a system comprising: a) a first nucleic acid comprising a nucleotide sequence encoding a VLP comprising a fusion polypeptide that comprises: i) a retroviral gag polyprotein comprising a MA polypeptide, a CA polypeptide, and an NC polypeptide; ii) a CRISPR/Cas effector polypeptide; and iii) one or more heterologous protease cleavage sites, wherein at least one of the one or more heterologous protease cleavage sites is between the gag polyprotein and the CRISPR/Cas effector polypeptide; and b) a second nucleic acid comprising a nucleotide sequence encoding a heterologous protease that cleaves the one or more heterologous protease cleavage sites. In some cases, a system of the present disclosure comprises a donor nucleic acid. In some cases, a nucleic acid present in a system of the present disclosure comprises a nucleotide sequence encoding a donor nucleic acid. In some cases, a system of the present disclosure includes a nucleic acid comprising a nucleotide sequence encoding an anti-CRISPR (Acr) polypeptide.

In some cases, the first nucleic acid is a nucleic acid as described above; e.g., the first nucleic acid comprises a nucleotide sequence encoding a VLP comprising a fusion polypeptide that comprises: i) a retroviral gag polyprotein comprising a MA polypeptide, a CA polypeptide, and an NC polypeptide; ii) one or more therapeutic polypeptides; and iii) one or more heterologous protease cleavage sites, wherein at least one of the one or more heterologous protease cleavage sites is between the gag polyprotein and the one or more therapeutic polypeptides. In some cases, the first nucleic acid comprises a nucleotide sequence encoding a VLP comprising a fusion polypeptide that comprises: i) a retroviral gag polyprotein comprising a MA polypeptide, a CA polypeptide, and an NC polypeptide, where the retroviral gag polyprotein comprises a heterologous protease cleavage site between the MA polypeptide and the CA polypeptide; ii) one or more therapeutic polypeptides; and iii) a heterologous protease cleavage site between the NC polypeptide and the one or more therapeutic polypeptides. In some cases, the first nucleic acid comprises a nucleotide sequence encoding a VLP comprising a fusion polypeptide that comprises: i) a retroviral gag polyprotein comprising a MA polypeptide, a CA polypeptide, and an NC polypeptide, where the retroviral gag polyprotein comprises a heterologous protease cleavage site between the MA polypeptide and the CA polypeptide and a heterologous protease cleavage site between the CA polypeptide and the NC polypeptide; ii) one or more therapeutic polypeptides; and iii) a heterologous protease cleavage site between the NC polypeptide and the one or more therapeutic polypeptides. Where the fusion polypeptide comprises two or more heterologous protease cleavage sites, the two or more heterologous protease cleavage sites are generally the same as one another, e.g., can be cleaved by the same protease. For example, in some cases, the two or more heterologous protease cleavage sites are all TEV protease cleavage sites.

In some cases, the first nucleic acid is a nucleic acid as described above; e.g., the first nucleic acid comprises a nucleotide sequence encoding a VLP comprising a fusion polypeptide that comprises: i) a retroviral gag polyprotein comprising a MA polypeptide, a CA polypeptide, and an NC polypeptide; ii) a CRISPR/Cas effector polypeptide; and iii) one or more heterologous protease cleavage sites, wherein at least one of the one or more heterologous protease cleavage sites is between the gag polyprotein and the CRISPR/Cas effector polypeptide. In some cases, the first nucleic acid comprises a nucleotide sequence encoding a VLP comprising a fusion polypeptide that comprises: i) a retroviral gag polyprotein comprising a MA polypeptide, a CA polypeptide, and an NC polypeptide, where the retroviral gag polyprotein comprises a heterologous protease cleavage site between the MA polypeptide and the CA polypeptide; ii) a CRISPR/Cas effector polypeptide; and iii) a heterologous protease cleavage site between the NC polypeptide and the CRISPR/Cas effector polypeptide. In some cases, the first nucleic acid comprises a nucleotide sequence encoding a VLP comprising a fusion polypeptide that comprises: i) a retroviral gag polyprotein comprising a MA polypeptide, a CA polypeptide, and an NC polypeptide, where the retroviral gag polyprotein comprises a heterologous protease cleavage site between the MA polypeptide and the CA polypeptide and a heterologous protease cleavage site between the CA polypeptide and the NC polypeptide; ii) a CRISPR/Cas effector polypeptide; and iii) a heterologous protease cleavage site between the NC polypeptide and the CRISPR/Cas effector polypeptide. Where the fusion polypeptide comprises two or more heterologous protease cleavage sites, the two or more heterologous protease cleavage sites are generally the same as one another, e.g., can be cleaved by the same protease. For example, in some cases, the two or more heterologous protease cleavage sites are all TEV protease cleavage sites.

In some cases, retroviral Gag polypeptides include CA (p24), MA (p17) and NC (p7) polypeptides. In some cases, retroviral Gag polypeptides include CA, MA, and NC polypeptides, and in addition one or more of p1, p2, and p6 polypeptides. In some cases, retroviral Gag polypeptides include CA, MA, NC, and p6 polypeptides. In some cases, retroviral Gag polypeptides include CA, MA, NC, p1, p2, and p6 polypeptides. See FIG. 2. See also, e.g., Muriaux and Darlix (2010) *RNA Biol.* 7:744.

In some cases, the retroviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide. Non-limiting examples are depicted in FIGS. 4A-4B and FIG. 5A-5B.

As noted above, the second nucleic acid of a system of the present disclosure comprises a nucleotide sequence encoding a protease that cleaves the heterologous protease cleavage site(s) present in the fusion polypeptide encoded in the first nucleic acid. Any of a variety of proteases (heterologous proteases) can be used. Generally, the heterologous protease is one that does not substantially cleave the therapeutic polypeptide (e.g., the CRISPR/Cas effector polypeptide). In some cases, the second nucleic acid of a system of the present disclosure comprises an HIV gag polyprotein comprising an MA polypeptide, a CA polypeptide, an NC polypeptide, and a p6 polypeptide linked by a cleavable linker to a Cas protein. In some cases, the cleavable linker is found between the transframe (TF) sequence and the sequence encoding the protease (see FIG. 19). In some cases, the cleavable linker is a TCS. In some cases, the TCS is a variant TCS that is cleaved by a TEV protease with reduced efficiency compared to a TCS that comprises ENLYFQS (SEQ ID NO:880) or ENLYFQP (SEQ ID NO:881).

Suitable heterologous proteases are listed above. In some cases, the heterologous protease is a TEV protease.

A suitable TEV protease comprises an amino acid sequence having at least 95%, at least 98%, at least 99%, or 100%, amino acid sequence identity to the following amino acid sequence:

```
                                          (SEQ ID NO: 891)
ESLFKGPRDYNPISSTICHLTNESDGHTTSLYGIGFGPFIITNKHLFRRN

NGTLLVQSLHGVFKVKNTTTLQQHLIDGRDMIIIRMPKDFPPFPQKLKFR

EPQREERICLVTTNFQTKSMSSMVSDTSCTFPSSDGIFWKHWIQTKDGQC

GSPLVSTRDGFIVGIHSASNFTNTNNYFTSVPKNFMELLTNQEAQQWVSG

WRLNADSVLWGGHKSFMVKPEEPFQPVKEATQLMN.
```

In some cases, the TEV protease comprises Ser-to-Val substitution at the amino acid position indicated by bold and underlining (this position is referred to as "5219"). A suitable TEV protease comprises an amino acid sequence having at least 95%, at least 98%, at least 99%, or 100%, amino acid sequence identity to the following amino acid sequence:

(SEQ ID NO: 892)
ESLFKGPRDYNPISSTICHLTNESDGHTTSLYGIGFGPFIITNKHLFRR

NNGTLLVQSLHGVFKVKNTTTLQQHLIDGRDMIIIRMPKDFPPFPQKLK

FREPQREERICLVTTNFQTKSMSSMVSDTSCTFPSSDGIFWKHWIQTKD

GQCGSPLVSTRDGFIVGIHSASNFTNTNNYFTSVPKNFMELLTNQEAQQ

WVSGWRLNADSVLWGGHKVFMVKPEEPFQPVKEATQLMN, where the amino acid indicated by bold and underlining is a Val (i.e., the TEV protease comprises an S219V substitution).

In some cases, the heterologous protease is a PreScission protease. PreScission protease is a fusion protein of glutathione S-transferase and human rhinovirus type 14 3C protease (Walker et al. (1994) *Biotechnology* 12:601; and Cordingley et al. (1990) *J. Biol. Chem.* 265:9062. In some cases, the heterologous protease is a human rhinovirus 3C protease. In some cases, the heterologous protease is an enterokinase. In some cases, the heterologous protease is an Epstein-Barr virus protease. In some cases, the heterologous protease is cathepsin D. In some cases, the heterologous protease is thrombin.

In some cases, the second nucleic acid comprises a nucleotide sequence encoding: i) a retroviral pol polyprotein; and ii) a heterologous protease. In some cases, the second nucleic acid comprises a nucleotide sequence encoding: i) a retroviral pol polyprotein; ii) a heterologous protease; and iii) a heterologous protease cleavage site that is cleaved by the heterologous protease, where the heterologous protease cleavage site is between the retroviral pol polyprotein and the heterologous protease. The retroviral pol polyprotein comprises a retroviral reverse transcriptase and a retroviral integrase. The retroviral pol polyprotein and the heterologous protease are translated as a single polyprotein, which is cleaved post-translationally.

A system of the present disclosure can include a third nucleic acid, where the third nucleic acid comprises a nucleotide sequence encoding a retroviral gag polyprotein without a therapeutic polypeptide. Inclusion of the third nucleic acid can provide for a higher ratio of gag to gag-therapeutic polypeptide in a VLP. For example, where a system of the present disclosure comprises a third nucleic acid comprising a nucleotide sequence encoding a retroviral gag polyprotein, a VLP made using the system has a ratio of gag to gag-therapeutic polypeptide of from 1:1 to 10:1, e.g., from 1:1 to 1.5:1, from 1.5:1 to 2:1, from 2:1 to 2.5:1, from 2.5:1 to 3:1, from 3:1 to 4:1, from 4:1 to 5:1, from 5:1 to 6:1, from 6:1 to 7:1, from 7:1 to 8:1, from 8:1 to 9:1, or from 9:1 to 10:1. In some cases, the gag polyprotein encoded in the third nucleic acid includes a heterologous protease cleavage site between the MA polypeptide and the CA polypeptide and/or between the CA polypeptide and the NC polypeptide.

For example, in some cases, a system of the present disclosure includes a third nucleic acid, where the third nucleic acid comprises a nucleotide sequence encoding a retroviral gag polyprotein without a CRISPR/Cas effector polypeptide. Inclusion of the third nucleic acid can provide for a higher ratio of gag to gag-CRISPR/Cas effector polypeptide in a VLP. For example, where a system of the present disclosure comprises a third nucleic acid comprising a nucleotide sequence encoding a retroviral gag polyprotein, a VLP made using the system has a ratio of gag to gag-CRISPR/Cas effector polypeptide of from 1:1 to 10:1, e.g., from 1:1 to 1.5:1, from 1.5:1 to 2:1, from 2:1 to 2.5:1, from 2.5:1 to 3:1, from 3:1 to 4:1, from 4:1 to 5:1, from 5:1 to 6:1, from 6:1 to 7:1, from 7:1 to 8:1, from 8:1 to 9:1, or from 9:1 to 10:1. In some cases, the gag polyprotein encoded in the third nucleic acid includes a heterologous protease cleavage site between the MA polypeptide and the CA polypeptide and/or between the CA polypeptide and the NC polypeptide.

A system of the present disclosure can further include: i) a CRISPR/Cas effector polypeptide guide RNA (referred to herein as a "CRISPR/Cas guide RNA" or simply "guide RNA"); ii) a nucleic acid comprising a nucleotide sequence encoding the CRISPR/Cas effector polypeptide guide RNA; or iii) a nucleic acid comprising a nucleotide sequence encoding the constant region of a CRISPR/Cas effector polypeptide guide RNA.

In some cases, a system of the present disclosure comprises a CRISPR/Cas effector guide RNA. For example, a VLP produced using a system of the present disclosure can comprise, encapsulated within the VLP a guide RNA. In some cases, the guide RNA is a dual guide RNA, e.g., two separate nucleic acids that together comprise a guide RNA. In other instances, the guide RNA is a single-molecule guide RNA (also referred to herein as a "single guide RNA" or "sgRNA"). Suitable guide RNAs are described hereinbelow. In some cases, the guide RNA comprises one or more of: i) a modified base; ii) a modified sugar; and iii) a modified backbone.

In some cases, a system of the present disclosure includes a nucleic acid comprising a nucleotide sequence encoding an anti-CRISPR (Acr) polypeptide. Where a system of the present disclosure comprises a nucleic acid comprising a nucleotide sequence encoding an Acr polypeptide, the Acr polypeptide can be included in a VLP, along with a CRISPR/Cas effector polypeptide. The Acr can function to limit the activity of the CRISPR/Cas effector polypeptide. In some cases, a nucleic acid comprising a nucleotide sequence encoding an Acr polypeptide comprises, in order from 5' to 3': a) a nucleotide sequence encoding a Gag polyprotein; b) a protease cleavage site; and c) an Acr polypeptide; in such cases, the encoded polyprotein (comprising, in order from N-terminus to C-terminus: a) the Gag polyprotein; b) the protease cleavage site; and c) the Acr polypeptide) is cleaved following contact with a protease that can cleave the protease cleavage site, thereby releasing the Acr. In some cases, the protease cleavage site is a TEV cleavage site (TCS), as described elsewhere herein.

Suitable Acr polypeptides include, e.g., AcrIIA1, AcrIIA2, AcrIIA3, AcrIIA4, AcrIIC1, AcrIIC2, AcrIIC3, AcrE1, AcrID1, Acrf10, anti-CRISPR protein 30, Acrf2, and Acrf1. See, e.g., WO 2017/160689; and Nakamura et al. (2019) *Nature Communications* 10:194; Harrington et al. (2017) *Cell* 170:1224; Shin et al. (2017) *Sci. Adv.* 3:e1701620; Zhu et al. (2019) *Mol. Cell* 74:296; Dong et al. (2017) *Nature* 546:436; Bondy-Denomy et al. (2013) *Nature* 493:429; Rauch et al. (2017) Cell 168:150; Ka et al. (2018) *Nucl. Acids Res.* 46:485; Basgall et al. (2018) *Microbiol.* 164:464. In some cases, the Acr polypeptide reduces binding to and/or cleavage of a target nucleic acid by a type II CRISPR/Cas effector polypeptide.

In some cases, the Acr polypeptide is an AcrIIA4 polypeptide. An AcrIIA4 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 936)
NDLIREIKNKDYTVKLSGTDSNSITQLIIRVNNDGNEYVISESENESIV
EKFISAFKNGWNQEYEDEEEFYNDMQTITLKSELN.

In some cases, the Acr polypeptide is an AcrIIA1 polypeptide. An AcrIIA1 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 937)
MTIKLLDEFLKKHDLTRYQLSKLTGISQNTLKDQNEKPLNKYTVSILRS

LSLISGLSVSDVLFELEDIEKNSDDLAGFKHLLDKYKLSFPAQEFELYC

LIKEFESANIEVLPFTFNRFENEEHVNIKKDVCKALENAITVLKEKKNE

LL.

In some cases, the Acr polypeptide is an AcrIIA2 polypeptide. An AcrIIA2 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 938)
MTLTRAQKKY AEAMHEFINM VDDFEESTPD FAKEVLHDSD
YVVITKNEKY AVALCSLSTD ECEYDTNLYL DEKLVDYSTV
DVNGVTYYIN IVETNDIDDL EIATDEDEMK SGNQEIILKS ELK.

In some cases, an ACR is delivered to a cell in a VLP. In some cases, a Gag-Acr fusion protein is made comprising a protease site between the Gag polypeptide and the Acr polypeptide such that in the presence of the specific protease, the Acr protein is released from the fusion. In some cases, the proteolytic cleavage site is engineered such that cleavage is less efficient, leading to release of the Acr protein inside of the VLP rather than inside the VLP producer cell. In some cases, the glycoprotein chosen for the VLP production of the Acr VLP targets a specific set of cell types. In some cases, the glycoprotein chosen for the VLP production allows targeting of a subset of cells that VLPs comprising a different glycoprotein also target. In some cases, delivery of an Acr to a subset of cells determined by the glycoprotein incorporated into the VLP protects those cells from nuclease cleavage caused by delivery of Cas9 comprising VLPs comprising a different glycoprotein that targets a larger set of cell types. In further cases, the protease used to release the Acr or Cas9 in the target cell is one that is expressed in the target cell and not expressed in another non-target cell. Non-limiting examples of cell-type specific proteases include cathepsin G and elastase expressed in leukocytes, pepsinogen C expressed in gastric cells, thymus-specific serine protease (TSSP) expressed in thymic stromal cells, and Testes-specific protease 50 (TSP50) expressed normally in the human testes but also expressed in some human breast cancers.

In some cases, other chimeric modulators comprising DNA binding domains are used. A "chimeric modulator" is an effector protein comprising a nucleic acid binding domain and an effector domain. In some cases, the nucleic acid is a DNA. In some cases, the effector domain is, for example, a nuclease domain (a "chimeric nuclease"), a transcriptional regulatory domain (a "chimeric transcription factor"), or a domain involved in epigenetic regulation. In some cases, a chimeric zinc finger protein (ZFP) or a chimeric transcription activator like effector protein (TALE) or a megaTAL is delivered using a VLP. In some cases, the ZFP protein comprises a nuclease domain (e.g. a FokI nuclease domain, for example a zinc finger nuclease ZFN) and is delivered via a VLP to a cell or organism comprising a cell such that the gene recognized by the ZFP DNA binding domain is cleaved. In some cases, the TALE protein or megaTAL protein comprises a nuclease domain (e.g. a FokI nuclease domain, for example a TALEN or MegaTAL) is delivered via a VLP to a cell or organism comprising a cell such that the gene recognized by the TALE or megaTAL DNA binding domain is cleaved. In some cases, the ZFP, TALE or megaTAL is fused to a transcription modulator such that expression of a gene is modulated. In some cases, the modulatory domain is an activator domain (for example VP16) while in other cases, the modulatory domain is a repression domain (for example KRAB). In some cases, the chimeric modulator is fused to a Gag sequence, linked by a linker comprising a protease recognition sequence. In some cases, the chimeric modulator comprises a ZFN fused to a Gag sequence via a linker comprising a TEV protease cleavage site. In some cases, the chimeric modulator comprises a TALEN or megaTAL fused to a Gag sequence via a linker comprising a TEV protease cleavage site.

Guide RNA Nucleic Acid

In other instances, a system of the present disclosure comprises a nucleic acid comprising a nucleotide sequence encoding the CRISPR/Cas effector polypeptide guide RNA. In some cases, the system comprises a library of guide RNA-encoding nucleotide sequences. The nucleotide sequence encoding the guide RNA can be operably linked to a transcriptional control element(s). The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. The nucleotide sequence encoding the guide RNA can be operably linked to a promoter, where the promoter can be a constitutive promoter or a regulatable promoter (e.g., an inducible promoter). The nucleotide sequence encoding the guide RNA can be operably linked to a promoter (e.g., an inducible promoter), e.g., one that is operable in a cell type of choice (e.g., a prokaryotic cell, a eukaryotic cell, a plant cell, an animal cell, a mammalian cell, a primate cell, a rodent cell, a human cell, etc.).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding guide RNA is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

As noted above, in some cases, a system of the present disclosure provides a nucleic acid comprising a nucleotide sequence encoding the constant region of a guide RNA, e.g., the tracrRNA portion of a guide RNA. In these instances, the nucleic acid comprising a nucleotide sequence encoding the constant region of a guide RNA can include an insertion site for the crRNA portion of a guide RNA.

Donor Nucleic Acid

In some cases, a system of the present disclosure comprises a donor nucleic acid. By a "donor nucleic acid" or "donor sequence" or "donor polynucleotide" or "donor template" it is meant a nucleic acid sequence to be inserted at the site cleaved by a CRISPR/Cas effector protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair or a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance.

Polypeptides that Inhibit MHC Class I Antigen Presentation Pathway

In some cases, a system of the present disclosure comprises a polypeptide that inhibits a major histocompatibility complex (MHC) class I antigen presentation pathway in a mammalian cell, or a nucleic acid comprising a nucleotide sequence encoding a polypeptide that inhibits the MHC class I antigen presentation pathway in a mammalian cell. A polypeptide that inhibits the MHC class I antigen presentation pathway reduces the likelihood that an immune response to a system of the present disclosure will be mounted in a mammalian host. MHC class I antigen presentation pathway inhibitor polypeptides include, e.g., a transported associated with antigen processing (TAP) inhibitor (such as a UL49.5 polypeptide (e.g., from bovine herpesvirus (BHV)); human cytomegalovirus (HCMV) US3 and US6; herpes simplex virus (HSV) Us12/ICP47; BNLF2a; and the like. MHC class I antigen presentation pathway inhibitor polypeptides also include, e.g., polypeptides that promote degradation of MHC class I heavy chains, e.g., HCMV US2 and US11, and varicella zoster virus ORF66. MHC class I antigen presentation pathway inhibitor polypeptides also include, e.g., Kaposi's sarcoma-associated herpesvirus (KSHV) K3 and K5 polypeptides.

In some cases, nuclease-directed knock out of a beta-2 microglobulin ("β2M") gene can be performed to reduce formation and/or functioning of an MHC class I complex. The β2M polypeptide is a small protein that helps stabilize human cell surface MHC class I molecules and also facilitates their loading with exogenous peptides (Shields et al (1998) *J Biol Chem* 273: 28010-28010.

For example, in some cases, the polypeptide is an ICP47 polypeptide comprising an amino acid sequence having at least 80%, at least 85%, at least 90%, at least 95%, at least 98%, at least 99%, or 100%, amino acid sequence identity to the following amino acid sequence:

```
                                          (SEQ ID NO: 957)
MSWALEMADT FLDTMRVGPR TYADVRDEIN KRGREDREAA
RTAVHDPERP LLRSPGLLPE IAPNASLGVA HRRTGGTVTD
SPRNPVTR;
```

and has a length of from about 70 amino acids to about 88 amino acids (e.g., from about 70 amino acids to about 80 amino acids, from about 80 amino acids to about 85 amino acids, or from about 85 amino acids to 88 amino acids).

In some cases, the polypeptide is an ICP47 polypeptide comprising an amino acid sequence having at least 80%, at least 85%, at least 90%, at least 95%, at least 98%, at least 99%, or 100%, amino acid sequence identity to the following amino acid sequence:

```
                                          (SEQ ID NO: 958)
   WALEMADT FLDTMRVGPR TYADVRDEIN KRGR;
```

and has a length of from about 25 amino acids to about 32 amino acids (e.g., 25 amino acids (aa), 26 aa, 27 aa, 28 aa, 29 aa, 30 aa, 31 aa, or 32 aa).

As another example, in some cases, the polypeptide is a US6 polypeptide comprising an amino acid sequence having at least 80%, at least 85%, at least 90%, at least 95%, at least 98%, at least 99%, or 100%, amino acid sequence identity to the following amino acid sequence:

```
                                          (SEQ ID NO: 956)
MDLLIRLGFL LMCALPTPGE RSSRDPKTLL SLSPRQQACL

PRTKSHRPIC YNDTGDCTDA DDSWKQLGED FAHQCLLAAK

KRPKTHKSRP NDRNLEGRLT CQRVSRLLPC DLDIHPSHRL

LTLMNNCVCD GAVWNAFRLI ERHGFFAVTL YLCCGITLLV

VILALLCSIT YESTGRGIRR CGS;
```

and having a length of from about 150 amino acids to about 183 amino acids (e.g., from about 150 amino acids to about 155 amino acids, from about 155 amino acids to about 160 amino acids, from about 160 amino acids to about 165 amino acids, from about 165 amino acids to about 170 amino acids, from about 170 amino acids to about 175 amino acids, or from about 175 amino acids to about 183 amino acids).

In some cases, a US6 polypeptide comprises an amino acid sequence having at least 80%, at least 85%, at least 90%, at least 95%, at least 98%, at least 99%, or 100%, amino acid sequence identity to the following amino acid sequence:

(SEQ ID NO: 955)
RSSRDPKTLL SLSPRQQACL PRTKSHRPIC YNDTGDCTDA

DDSWKQLGED FAHQCLLAAK KRPKTHKSRP NDRNLEGRLT

CQRVSRLLPC DLDIHPSHRL LTLMNNCVCD GAVWNAFRLI

ERHGFFAVTL YLCCGITLLV VILALLCSIT YESTGRGIRR CGS;

and having a length of from about 150 amino acids to about 164 amino acids.

In some cases, a US6 polypeptide comprises the following amino acid sequence: ALLCSIT YESTGRGIRR CGS (SEQ ID NO:959); and has a length of 20 amino acids. In some cases, a US6 polypeptide comprises the following amino acid sequence LPCDLDIHPSHRLLTLMNNC (SEQ ID NO:960); and has a length of 20 amino acids.

As another example, in some cases, the polypeptide is a US2 polypeptide comprising an amino acid sequence having at least 80%, at least 85%, at least 90%, at least 95%, at least 98%, at least 99%, or 100%, amino acid sequence identity to the following amino acid sequence:

MNNLWKAWVG LWTSMGPLIR LPDGITKAGE DALRPWKSTA

KHPWFEIEDN RCYIDNGKLF ARGSIVGNMS RFVFDPKADY

GGVGENLYVH ADDVEFVPGE SLKWNVRNLD VMPIFETLAL

RLVLQGDVIW LRCVPELRVD YTSSAYMWNM QYGMVRKSYT

HVAWTIVFYS INITLLVLFIVYVTVDCNLS MMWMRFFVC (SEQ ID

NO: 961; GenBank Accession No: YP_081589);

and having a length of from about 170 amino acids to about 199 amino acids (e.g., from about 170 amino acids to about 175 amino acids, from about 175 amino acids to about 180 amino acids, from about 180 amino acids to about 185 amino acids, from about 185 amino acids to about 190 amino acids, from about 190 amino acids to about 195 amino acids, or from about 195 amino acids to about 199 amino acids).

As another example, in some cases, the polypeptide is a US11 polypeptide comprising an amino acid sequence having at least 80%, at least 85%, at least 90%, at least 95%, at least 98%, at least 99%, or 100%, amino acid sequence identity to the following amino acid sequence:

MNLVMLILAL WAPVAGSMPE LSLTLFDEPP PLVETEPLPP

LPDVSEYRVE YSEARCVLRS GGRLEALWTL RGNLSVPTPT

PRVYYQTLEG YADRVPTPVE DVSESLVAKR YWLRDYRVPQ

RTKLVLFYFS PCHQCQTYYV ECEPRCLVPW VPLWSSLEDI

-continued

ERLLFEDRRL MAYYALTIKS AQYTLMMVAV IQVFWGLYVK

GWLHRHFPWM FSDQW (SEQ ID NO: 962; GenBank

Accession No: APG57339);

and having a length of from about 185 amino acids to about 215 amino acids (e.g., from about 185 amino acids to about 190 amino acids, from about 190 amino acids to about 195 amino acids, from about 195 amino acids to about 200 amino acids, from about 200 amino acids to about 205 amino acids, from about 205 amino acids to about 210 amino acids, or from about 210 amino acids to about 215 amino acids).

As another example, in some cases, the polypeptide is an E19 polypeptide comprising an amino acid sequence having at least 80%, at least 85%, at least 90%, at least 95%, at least 98%, at least 99%, or 100%, amino acid sequence identity to the following amino acid sequence:

MRYMILGLLA LAAVCSAAKK VEFKEPACNV TFKSEANECT

TLIKCTTEHE KLIIRHKDKI GKYAVYAIWQ PGDTNDYNVT

VFQGENRKTF MYKFPFYEMC DITMYMSKQY KLWPPQKCLE

NTGTFCSTAL LITALALVCT LLYLKYKSRR SFIDEKKMP (SEQ ID NO: 963; GenBank Accession No: P68978);

and having a length of from about 130 amino acids to about 159 amino acids (e.g., from about 130 amino acids to about 135 amino acids, from about 135 amino acids to about 140 amino acids, from about 140 amino acids to about 145 amino acids, from about 145 amino acids to about 150 amino acids, from about 150 amino acids to about 155 amino acids, or from about 155 amino acids to about 159 amino acids).

As another example, in some cases, the polypeptide is an E19 polypeptide comprising an amino acid sequence having at least 80%, at least 85%, at least 90%, at least 95%, at least 98%, at least 99%, or 100%, amino acid sequence identity to the following amino acid sequence:

AKK VEFKEPACNV TFKSEANECT TLIKCTTEHE KLIIRHKDKI

GKYAVYAIWQ PGDTNDYNVT VFQGENRKTF MYKFPFYEMC

DITMYMSKQY KLWPPQKCLE NTGTFCSTAL LITALALVCT

LLYLKYKSRR SFIDEKKMP (SEQ ID NO: 964; GenBank

Accession No: P68978);

and having a length of from about 115 amino acids to about 142 amino acids (e.g., from about 115 amino acids to about 120 amino acids, from about 120 amino acids to about 120 amino acids, from about 120 amino acids to about 125 amino acids, from about 125 amino acids to about 130 amino acids, from about 130 amino acids to about 135 amino acids, or from about 135 amino acids to about 142 amino acids).

As another example, in some cases, the polypeptide is a US3 polypeptide comprising an amino acid sequence having at least 80%, at least 85%, at least 90%, at least 95%, at least 98%, at least 99%, or 100%, amino acid sequence identity to the following amino acid sequence:

MKPVLVLAIL AVLFLRLADS VPRPLDVVVS EIRSAHFRVE
ENQCWFHMGM LHYKGRMSGN FTEKHFVSVG IVSQSYMDRL
QVSGEQYHHD ERGAYFEWNI GGHPVPHTVD MVDITLSTRW
GDPKKYAACV PQVRMDYSSQ TINWYLQRSI RDDNWGLLFR
TLLVYLFSLV VLVLLTVGVS ARLRFI (SEQ ID NO: 965;
GenBank Accession No: AAS49002);

and having a length of from about 155 amino acids to about 186 amino acids (e.g., from about 155 amino acids to about 160 amino acids, from about 160 amino acids to about 165 amino acids, from about 165 amino acids to about 170 amino acids, from about 170 amino acids to about 175 amino acids, from about 175 amino acids to about 180 amino acids, or from about 180 amino acids to about 186 amino acids).

As another example, in some cases, the polypeptide is a US10 polypeptide comprising an amino acid sequence having at least 80%, at least 85%, at least 90%, at least 95%, at least 98%, at least 99%, or 100%, amino acid sequence identity to the following amino acid sequence:

MLRRGSLRNP LAICLLWWLG VVAAATEETR EPTYFTCGCV
IQNHVLKGAV KLYGQFPSPK TLRASAWLHD GENHERHRQP
ILVEGTATAT EALYILLPTE LSSPEGNRPR NYSATLTLAS
RDCYERFVCP VYDSGTPMGV LMNLTYLWYL GDYGAILKIY
FGLFCGACVI TRSLLLICGY YPPRE (SEQ ID NO: 966;
GenBank Accession No: APG57338), and having a length of from about 155 amino acids to about 185 amino acids (e.g., from about 155 amino acids to about 160 amino acids, from about 160 amino acids to about 165 amino acids, from about 165 amino acids to about 170 amino acids, from about 170 amino acids to about 175 amino acids, from about 175 amino acids to about 180 amino acids, or from about 180 amino acids to about 185 amino acids).

As another example, in some cases, the polypeptide is a U21 polypeptide comprising an amino acid sequence having at least 80%, at least 85%, at least 90%, at least 95%, at least 98%, at least 99% or 100% amino acid sequence identity to the following amino acid sequence:

MWTILLFCVP VIYGELYPDF CPLAVVDFDV NATVDDLLLF
DISLSKQCSD DKIRHSAVAA MTDNAFFFGN SETQIETDFG
KYLAFNCYQV FSTLNHFLFK NFKKTKGLMK RYDKLCLDVE
SYIHIQIICS PFKSFIRLRR MNETGISPRI LETTFYLQNK
RNSTWVAIKN YLGEDDPFTY RIWHTLTHAK NFLINSCEND
FNQLFFWQRK YLSLAKTFEA TFKQGFNPMI EQRNEQRYRT
NNIDCSFSKF RQNGVKVAVC KYTGWGVSGF GSLEVLQKIK
SPFGEEWKRV GFNSTGAFTP LYGSDVLWGL IFLRVEMTTY
VCTCTNKNTG TQIQVTLPDV DLDLLDSEKT SSNVFVDMLC

-continued

YTLIAILFLA FVTAVVLLGV SCLDGVQKVL TWPLQHIQKE
PVSEKIINLT NLMFGQEPLP KKESLKQQCL (SEQ ID
NO: 967; GenBank Accession No: AAC40735);

and having a length of from about 400 amino acids to about 430 amino acids (e.g., from about 400 amino acids to about 405 amino acids, from about 405 amino acids to about 410 amino acids, from about 410 amino acids to about 415 amino acids, from about 415 amino acids to about 420 amino acids, from about 420 amino acids to about 425 amino acids, or from about 425 amino acids to about 430 amino acids).

As another example, in some cases, the polypeptide is a K3 polypeptide comprising an amino acid sequence having at least 80%, at least 85%, at least 90%, at least 95%, at least 98%, at least 99%, or 100%, amino acid sequence identity to the following amino acid sequence:

MEDEDVPVCW ICNEELGNER FRACGCTGEL ENVHRSCLST
WLTISRNTAC QICGVVYNTR VVWRPLREMT LLPRLTYQEG
LELIVFIFIM TLGAAGLAAA TWVWLYIVGG HDPEIDHVAA
AAYYVFFVFY QLFVVFGLGA FFHMMRHVGR AYAAVNTRVE
VFPYRPRPTS PECAVEEIEL QEILPRGDNQ DEEGPAGAAP
GDQNGPAGAA PGDQDGPADG APVHRDSEES VDEAAGYKEA
GEPTHNDGRD DNVEPTAVGC DCNNLGAERY RATYCGGYVG
AQSGDGAYSV SCHNKAGPSS LVDILPQGLP GGGYGSMGVI
RKRSAVSSAL MFH (SEQ ID NO: 968; GenBank
Accession No: P90495);

and having a length of from about 300 amino acids to about 333 amino acids (e.g., from about 300 amino acids to about 305 amino acids, from about 305 amino acids to about 310 amino acids, from about 310 amino acids to about 315 amino acids, from about 315 amino acids to about 320 amino acids, from about 320 amino acids to about 325 amino acids, or from about 325 amino acids to about 333 amino acids).

As another example, in some cases, the polypeptide is a K5 polypeptide comprising an amino acid sequence having at least 80%, at least 85%, at least 90%, at least 95%, at least 98%, at least 99%, or 100%, amino acid sequence identity to the following amino acid sequence:

MASKDVEEGV EGPICWICRE EVGNEGIHPC ACTGELDVVH
PQCLSTWLTV SRNTACQMCR VIYRTRTQWR SRLNLWPEME
RQEIFELFLL MSVVVAGLVG VALCTWTLLV ILTAPAGTFS
PGAVLGFLCF FGFYQIFIVF AFGGICRVSG TVRALYAANN
TRVTVLPYRR PRRPTANEDN IELTVLVGPA GGTDEEPTDE
SSEGDVASGD KERDGSSGDE PDGGPNDRAG LRGTARTDLC
APTKKPVRKN HPKNNG (SEQ ID NO: 969; GenBank
Accession No: ABD28863);

and having a length of from about 225 amino acids to about 256 amino acids (e.g., from about 225 amino acids to about 230 amino acids, from about 230 amino acids to about 235 amino acids, from about 235 amino acids to about 240 amino acids, from about 240 amino acids to about 245 amino acids, from about 245 amino acids to about 250 amino acids, or from about 250 amino acids to about 256 amino acids).

As another example, in some cases, the polypeptide is a Nef polypeptide comprising an amino acid sequence having at least 80%, at least 85%, at least 90%, at least 95%, at least 98%, at least 99%, or 100%, amino acid sequence identity to the following amino acid sequence:

```
MGGKWSKRSV PGWNTIRKRM RRAEPAAEGV GAASRDLEQR
GAITTSNTAS NNAACAWQEA QEEEEVGFPV RPQVPLRPMT
YKSALDLSHF LKEKGGLEGL VYSQKRQDIL DLWVYHTQGF
FPDWQNYTPG PGTRFPLTFG WCFKLVPVEP EKVEEATVGK
NNCLLHPMNL HGMDDPEGEV LVWRFDSRLA FHHMAREKHP
EYYKDC (SEQ ID NO: 970; GenBank Accession
No: AAF35361.1);
```

and having a length of from about 175 amino acids to about 206 amino acids (e.g., from about 175 amino acids to about 180 amino acids, from about 180 amino acids to about 185 amino acids, from about 185 amino acids to about 190 amino acids, from about 190 amino acids to about 195 amino acids, from about 195 amino acids to about 200 amino acids, or from about 200 amino acids to about 206 amino acids).

As another example, in some cases, the polypeptide is an EBNA1 polypeptide comprising an amino acid sequence having at least 80%, at least 85%, at least 90%, at least 95%, at least 98%, at least 99%, or 100%, amino acid sequence identity to the following amino acid sequence:

```
MSDEGPGTGP GNGLGEKGDT SGPEGSGGSG PQRRGGDNHG
RGRGRGRGRG GGRPGAPGGS GSGPRHRDGV RRPQKRPSCI
GCKGTHGGTG AGAGAGGAGA GGAGAGGGAG AGGGAGGAGG
AGGAGAGGGA GAGGGAGGAG GAGAGGGAGA GGGAGGAGAG
GGAGGAGGAG AGGGAGAGGG AGGAGAGGGA GGAGGAGAGG
GAGAGGAGGA GGAGAGGAGA GGGAGGAGGA GAGGAGAGGA
GAGGAGAGGA GGAGAGGAGG AGAGGAGGAG AGGGAGGAGA
GGGAGGAGAG GAGGAGAGGA GGAGAGGAGG AGAGGGAGAG
GAGAGGGGRG RGGSGGRGRG GSGGRGRGGS GGRRGRGRER
ARGGSRERAR GRGRGRGEKR PRSPSSQSSS SGSPPRRPPP
GRRPFFHPVG EADYFEYHQE GGPDGEPDVP PGAIEQGPAD
DPGEGPSTGP RGQGDGGRRK KGGWFGKHRG QGGSNPKFEN
IAEGLRALLA RSHVERTTDE GTWVAGVFVY GGSKTSLYNL
RRGTALAIPQ CRLTPLSRLP FGMAPGPGPQ PGPLRESIVC
YFMVFLQTHI FAEVLKDAIK DLVMTKPAPT CNIRVTVCSF
DDGVDLPPWF PPMVEGAAAE GDDGDDGDEG GDGDEGEEGQ E
(SEQ ID NO: 971; GenBank Accession No: YP_401677);
```

and having a length of from about 610 amino acids to about 641 amino acids (e.g., from about 610 amino acids to about 615 amino acids, from about 615 amino acids to about 620 amino acids, from about 620 amino acids to about 625 amino acids, from about 625 amino acids to about 630 amino acids, from about 630 amino acids to about 635 amino acids, or from about 635 amino acids to about 641 amino acids).

For example, in some cases, the polypeptide is an EBNA1 polypeptide comprising an amino acid sequence having at least 80%, at least 85%, at least 90%, at least 95%, at least 98%, at least 99%, or 100%, amino acid sequence identity to the following amino acid sequence:

```
                                      (SEQ ID NO: 972)
GAGAGAGGAGA GGAGAGGGAG AGGGAGGAGG AGGAGAGGGA
GAGGGAGGAG GAGAGGGAGA GGGAGGAGAG GGAGGAGGAG
AGGGAGAGGG AGGAGAGGGA GGAGGAGAGG GAGAGGAGGA
GGAGAGGAGA GGGAGGAGGA GAGGAGAGGA GAGGAGAGGA
GGAGAGGAGG AGAGGAGGAG AGGGAGGAGA GGGAGGAGAG
GAGGAGAGGA GGAGAGGAGG AGAGGGAGAG GAGAGGGG;
```

and has a length of from about 220 amino acids to about 239 amino acids (e.g., from about 220 amino acids to about 225 amino acids, from about 225 amino acids to about 230 amino acids, or from about 230 amino acids to 239 amino acids).

As another example, in some cases, the polypeptide is an immediate early (IE) polypeptide comprising an amino acid sequence having at least 80%, at least 85%, at least 90%, at least 95%, at least 98%, at least 99%, or 100%, amino acid sequence identity to the following amino acid sequence:

```
MESSAKRKMD PDNPDEGPSP KVPRPETPVT KATTFLQTML
RKEVNSQLSL GDPLFPELAEESLKTFEQVT EDCNENPEKD
VLAELVKQIK VRVDMVRHR (SEQ ID NO: 973; GenBank
Accession No: AAC60730);
```

and having a length of from about 70 amino acids to about 99 amino acids (e.g., from about 70 amino acids to about 75 amino acids, from about 75 amino acids to about 80 amino acids, from about 80 amino acids to about 85 amino acids, from about 85 amino acids to about 90 amino acids, from about 90 amino acids to about 95 amino acids, or from about 95 amino acids to about 99 amino acids).

As another example, in some cases, the polypeptide is an pp65 polypeptide comprising an amino acid sequence having at least 80%, at least 85%, at least 90%, at least 95%, at least 98%, at least 99%, or 100%, amino acid sequence identity to the following amino acid sequence:

```
MESRGRRCPE MISVLGPISG HVLKAVFSRG DTPVLPHETR
LLQTGIHVRV SQPSLILVSQ YTPDSTPCHR GDNQLQVQHT
YFTGSEVENV SVNVHNPTGR SICPSQEPMS IYVYALPLKM
LNIPSINVHH YPSAAERKHR HLPVADAVIH ASGKQMWQAR
LTVSGLAWTR QQNQWKEPDV YYTSAFVFPT KDVALRHVVC
AHELVCSMEN TRATKMQVIG DQYVKVYLES FCEDVPSGKL
FMHVTLGSDV EEDLTMTRNP QPFMRPHERN GFTVLCPKNM
```

-continued

```
IIKPGKISHI MLDVAFTSHE HFGLLCPKSI PGLSISGNLL

MNGQQIFLEV QAIRETVELR QYDPVAALFF FDIDLLLQRG

PQYSEHPTFT SQYRIQGKLE YRHTWDRHDE GAAQGDDDVW

TSGSDSDEEL VTTERKTPRV TGGGAMAGAS TSAGRKRKSA

SSATACTSGV MTRGRLKAES TVAPEEDTDE DSDNEIHNPA

VFTWPPWQAG ILARNLVPMV ATVQGQNLKY QEFFWDANDI

YRIFAELEGV WQPAAQPKRR RHRQDALPGP CIASTPKKHR G

(SEQ ID NO: 974; GenBank Accession No: P06725);
```

and having a length of from about 530 amino acids to about 561 amino acids (e.g., from about 530 amino acids to about 535 amino acids, from about 535 amino acids to about 540 amino acids, from about 540 amino acids to about 545 amino acids, from about 545 amino acids to about 550 amino acids, from about 550 amino acids to about 555 amino acids, or from about 555 amino acids to about 561 amino acids).

As another example, in some cases, the polypeptide is a gp40 polypeptide comprising an amino acid sequence having at least 80%, at least 85%, at least 90%, at least 95%, at least 98%, at least 99%, or 100%, amino acid sequence identity to the following amino acid sequence:

```
MLGAITYLLL SVLINRGETA GSSYMDVRIF EDERVDICQD

LTATFISYRE GPEMFRHSINLEQSSDIFRI EASGEVKHFP

WMNVSELAQE SAFFVEQERF VYEYIMNVFK AGRPVVFEYR

CKFVPFECTV LQMMDGNTLT RYTVDKGVET LGSPPYSPDV

SEDDIARYGQ GSGISILRDN AALLQKRWTS FCRKIVAMDN

PRHNEYSLYS NRGNGYVSCT MRTQVPLAYN ISLANGVDIY

KYMRMYSGGR LKVEAWLDLR DLNGSTDFAF VISSPTGWYA

TVKYSEYPQQ SPGMLLSSID GQFESSAVVS WHRGHGLKHA

PPVSAEYSIF FMDVWSLIAI GVVFVIVFMY LVKLRVVWIN

RVWPRMRYRL VYINCRVW (SEQ ID NO: 975;

GenBank Accession No: CAP08189);
```

and having a length of from about 345 amino acids to about 378 amino acids (e.g., from about 345 amino acids to about 350 amino acids, from about 350 amino acids to about 355 amino acids, from about 355 amino acids to about 360 amino acids, from about 360 amino acids to about 365 amino acids, from about 365 amino acids to about 370 amino acids, or from about 370 amino acids to about 378 amino acids).

As another example, in some cases, the polypeptide is a Vpu polypeptide comprising an amino acid sequence having at least 80%, at least 85%, at least 90%, at least 95%, at least 98%, at least 99%, or 100%, amino acid sequence identity to the following amino acid sequence: MQLLAILAIV GLVVAAILAI VVWFIVFIEY KKILKQKKID RLIDRIRERA EDSGNESEGD QEELSALVEM GHHAPWDVDD L (SEQ ID NO:976; GenBank Accession No: AAF35359); and having a length of from about 50 amino acids to about 81 amino acids (e.g., from about 50 amino acids to about 55 amino acids, from about 55 amino acids to about 60 amino acids, from about 60 amino acids to about 65 amino acids, from about 65 amino acids to about 70 amino acids, from about 70 amino acids to about 75 amino acids, or from about 75 amino acids to about 81 amino acids).

As another example, in some cases, the polypeptide is a gp48 polypeptide comprising an amino acid sequence having at least 80%, at least 85%, at least 90%, at least 95%, at least 98%, at least 99%, or 100%, amino acid sequence identity to the following amino acid sequence:

```
MPSWSDTLTM DTTARGSTRS RPVQLLALVT VLASMTFQMG

ESLIPIIPDF SSFMMNPLPM PQIMPPSTNE TKETKESYVK

TEEPIVGCNV SRTEINRLKN QMKKIPNTFK CFKKDGVRTS

LDMQTTGEKR FACEIPNNVY VNATWYVHWV VGKIAASVSP

IVYFTSTTSS PPTLDGNMHP FYRRKIVTAA NGFKVDEKTG

DITVARSNAS LADSVRCRLI VCLWTKNDSI SDLPDDDPQM

KNMSGVIKLP DYSGPDTLLT VPFDYAAWRQ RMRTEMEEPS

RRRRQLLLVI SVIASLLWLA VGAMLFYTYG REPLARLLKR

YGKRLAAVRI PADGKDQSLT SPLLTK (SEQ ID NO: 977;

GenBank Accession No: CAP08050);
```

and having a length of from about 310 amino acids to about 346 amino acids (e.g., from about 310 amino acids to about 315 amino acids, from about 320 amino acids to about 325 amino acids, from about 330 amino acids to about 335 amino acids, from about 340 amino acids to about 345 amino acids, from about 350 amino acids to about 355 amino acids, or from about 340 amino acids to about 346 amino acids).

In some cases, a gp48 polypeptide comprises an amino acid sequence having at least 80%, at least 85%, at least 90%, at least 95%, at least 98%, at least 99%, or 100% amino acid sequence identity to the following amino acid sequence:

```
                                          (SEQ ID NO: 978)
M DTTARGSTRS RPVQLLALVT VLASMTFQMG

ESLIPIIPDF SSFMMNPLPM PQIMPPSTNE TKESYVK

TEEPIVGCNV SRTEINRLKN QMKKIPNTFK CFKKDGVRTS

LDMQTTGEKR FACEIPNNVY VNATWYVHWV VGKIAASVSP

IVYFTSTTSS PPTLDGNMHP FYRRKIVTAA NGFKVDEKTG

DITVARSNAS LADSVRCRLI VCLWTKNDSI SDLPDDDPQM

KNMSGVIKLP DYSGPDTLLT DGVPFDYAAW RQRMRTEMEE

PSRRRRQLLL VISVIASLLW LAVGAMLFYT YGREPLARLL

KRYGKQLAAV RIPADGKDQS LTSPLLTK;
```

and having a length of from about 300 amino acids to about 336 amino acids (e.g., from about 300 amino acids to about 305 amino acids, from about 305 amino acids to about 310 amino acids, from about 310 amino acids to about 320 amino acids, from about 320 amino acids to about 325 amino acids, from about 325 amino acids to about 330 amino acids, or from about 330 amino acids to about 336 amino acids).

In some cases, a gp34 polypeptide comprises an amino acid sequence having at least 80%, at least 85%, at least 90%, at least 95%, at least 98%, at least 99%, or 100% amino acid sequence identity to the following amino acid sequence:

MSLVCRLVLV TVVLSSLFTF AISSNNDACK KLQKEYEEKM

KYRHPLGCYF KGINPTKVPS SGSHTILKCT LPVVKVNASW

TLEWVVVKLQ NSVDVTSYYE SSPNSGPTFL RAILNFTPMH

GLRTKNLLKV KDGFQVDNST DNGNGGNLYV YPNATTGSAD

SVRCRLRMCP WTSNSKMTAP DEEMLRKMSE VLNLPNYGVP

DLTPPRRDEF YTKNESPNTI VTTLTVIVTL LFVGLLLVLI

YLYGPSLYRR FFSNDCCSNF KPLKSN (SEQ ID NO: 979;

GenBank Accession No: ABM74001);

and having a length of from about 235 amino acids to about 266 amino acids (e.g., from about 235 amino acids to about 240 amino acids, from about 240 amino acids to about 245 amino acids, from about 245 amino acids to about 250 amino acids, from about 250 amino acids to about 255 amino acids, from about 255 amino acids to about 260 amino acids, or from about 260 amino acids to about 266 amino acids).

As another example, in some cases, the polypeptide is a gp34 polypeptide comprising an amino acid sequence having at least 80%, at least 85%, at least 90%, at least 95%, at least 98%, at least 99%, or 100% amino acid sequence identity to the following amino acid sequence:

(SEQ ID NO: 980)

MSLVCRLVLVTVVLSSLFTFVISRNDNECEKMQKEYKEKMKYRHSLGCY

FKGINPTKVPSSDPRTILKCTLPDVKVNASWTLEWVVVNLHTSVDVTSY

YESSPNSEPRFLRAILNFTPMHGLRTKNLLKVKDGFQVDNSTDNGNGGN

LYVYPNATTGSADSVRCRLRMCPWTSNSKMTAPDEEMLRKMSEVLNLPN

YGVPDLTPPRRDEFYTKNESPNTIVTTLTVIVTLLFVGLLLVLIYLYGP

SLYRRFFSNDCCSNFKPLKSN;

and having a length of from about 235 amino acids to about 266 amino acids (e.g., from about 235 amino acids to about 240 amino acids, from about 240 amino acids to about 245 amino acids, from about 245 amino acids to about 250 amino acids, from about 250 amino acids to about 255 amino acids, from about 255 amino acids to about 260 amino acids, or from about 260 amino acids to about 266 amino acids).

Pseudotyping Envelope Proteins

In some cases, a system of the present disclosure comprises a nucleic acid comprising a nucleotide sequence encoding a pseudotyping viral envelope protein and/or an antibody that specifically binds a cell surface receptor. In such instances, a VLP produced using a system of the present disclosure can be targeted to a particular cell type, a particular tissue, or a particular organ.

In some cases, a VLP is pseudotyped. Pseudotyped VLPs include heterologous glycoproteins derived from an enveloped virus other than the virus from which the MA, CA, and NC polypeptides are derived. Such a pseudotyped VLP can be targeted to a cell, tissue, or organ that is targeted by the virus from which the heterologous glycoproteins are derived. A pseudotyped VLP can include, e.g., as the heterologous virus protein used for the pseudotyping, a viral envelope protein selected from a vesicular stomatitis virus (VSV) glycoprotein (VSV-G protein), a Measles virus hemagglutinin (HA) protein and/or a measles virus fusion glycoprotein, Influenza virus neuraminidase (NA) protein, a Measles virus F protein, an Influenza virus HA protein, Moloney virus MLV-A protein, a Moloney virus MLV-E protein, a Baboon Endogenous retrovirus (BAEV) envelope protein, an Ebola virus glycoprotein, a foamy virus envelope protein, or a combination or two or more of the foregoing viral envelope proteins.

In some cases, a VSV-G protein is specifically excluded. In some cases, a measles virus hemagglutinin protein is specifically excluded. In some cases, a measles virus F protein is specifically excluded. In some cases, an influenza virus hemagglutinin protein is specifically excluded. In some cases, a Moloney virus MLV-A protein is specifically excluded. In some cases, a Moloney virus MLV-E protein is specifically excluded. In some cases, a baboon endogenous retrovirus envelope protein is specifically excluded. In some cases, an Ebola virus glycoprotein is specifically excluded. In some cases, a foamy virus envelop protein is specifically excluded.

In some cases, the heterologous glycoprotein used for pseudotyping is a VSV-G protein. A suitable VSV-G protein comprises an amino acid sequence having at least 80%, at least 85%, at least 90%, at least 95%, at least 98%, at least 99%, or 100%, amino acid sequence identity to the following amino acid sequence:

(SEQ ID NO: 981)

IMKCLLYLAFLFIGVNCKFTIVFPHNQKGNWKNVPSNYHYCPSSSDLNW

HNDLIGTALQVKMPKSHKAIQADGWMCHASKWVTTCDFRWYGPKYITHS

IRSFTPSVEQCKESIEQTKQGTWLNPGFPPQSCGYATVTDAEAVIVQVT

PHHVLVDEYTGEWVDSQFINGKCSNYICPTVHNSTTWHSDYKVKGLCDS

NLISMDITFFSEDGELSSLGKEGTGFRSNYFAYETGGKACKMQYCKHWG

VRLPSGVWFEMADKDLFAAARFPECPEGSSISAPSQTSVDVSLIQDVER

ILDYSLCQETWSKIRAGLPISPVDLSYLAPKNPGTGPAFTIINGTLKYF

ETRYIRVDIAAPILSRMVGMISGTTTERELWDDWAPYEDVEIGPNGVLR

TSSGYKFPLYMIGHGMLDSDLHLSSKAQVFEHPHIQDAASQLPDDESLF

FGDTGLSKNPIELVEGWFSSWKSSIASFFFIIGLIIGLFLVLRVGIHLC

IKLKHTKKRQIYTDIEMNRLGK.

In some cases, the heterologous glycoprotein used for pseudotyping is a BAEV-G protein. A suitable BAEV-G protein comprises an amino acid sequence having at least 80%, at least 85%, at least 90%, at least 95%, at least 98%, at least 99%, or 100%, amino acid sequence identity to the following amino acid sequence:

(SEQ ID NO: 982)

MGFTTKIIFLYNLVLVYAGFDDPRKAIELVQKRYGRPCDCSGGQVSEPP

SDRVSQVTCSGKTAYLMPDQRWKCKSIPKDTSPSGPLQECPCNSYQSSV

HSSCYTSYQQCRSGNKTYYTATLLKTQTGGTSDVQVLGSTNKLIQSPCN

GIKGQSICWSTTAPIHVSDGGGPLDTTRIKSVQRKLEEIHKALYPELQY

HPLAIPKVRDNLMVDAQTLNILNATYNLLLMSNTSLVDDCWLCLKLGPP

TPLAIPNFLLSYVTRSSDNISCLIIPPLLVQPMQFSNSSCLFSPSYNST

-continued

EEIDLGHVAFSNCTSITNVTGPICAVNGSVFLCGNNMAYTYLPTNWTGL

CVLATLLPDIDIIPGDEPVPIPAIDHFIYRPKRAIQFIPLLAGLGITAA

FTTGATGLGVSVTQYTKLSNQLISDVQILSSTIQDLQDQVDSLAEVVLQ

NRRGLDLLTAEQGGICLALQEKCCFYVNKSGIVRDKIKTLQEELERRRK

DLASNPLWTGLQGLLPYLLPFLGPLLTLLLLLTIGPCIFNRLTAFINDK

LNIIHAMVLTQQYQVLRTDEEAQD.

In some cases, the heterologous glycoprotein used for pseudotyping is an influenza virus H1N1 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence:

MKAILVVLLY TFATANADTL CIGYHANNST DTVDTVLEKN

VTVTHSVNLL EDKHNGKLCK LRGVAPLHLG KCNIAGWILG

NPECESLSTA SSWSYIVETP SSDNGTCYPG DFIDYEELRE

QLSSVSSFER FEIFPKTSSW PNHDSNKGVT AACPHAGAKS

FYKNLIWLVK KGNSYPKLSK SYINDKGKEV LVLWGIHHPS

TSADQQSLYQ NADAYVFVGS SRYSKKFKPE IAIRPKVRXX

EGRMNYYWTL VEPGDKITFE ATGNLVVPRY AFAMERNAGS

GIIISDTPVH DCNTTCQTPK GAINTSLPFQ NIHPITIGKC

PKYVKSTKLR LATGLRNIPS IQSRGLFGAI AGFIEGGWTG

MVDGWYGYHH QNEQGSGYAA DLKSTQNAID EITNKVNSVI

EKMNTQFTAV GKEFNHLEKR IENLNKKVDD GFLDIWTYNA

ELLVLLENER TLDYHDSNVK NLYEKVRSQL KNNAKEIGNG

CFEFYHKCDN TCMESVKNGT YDYPKYSEEA KLNREEIDGV

KLESTRIYQI LAIYSTVASS LVLVVSLGAI SFWMCSNGSL

QCRICI (SEQ ID NO: 983; GenBank Accession

No: ACP44189).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and natural killer (NK) cells.

In some cases, the heterologous glycoprotein used for pseudotyping is an influenza virus H3N2 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence:

MKTIIALSYI LCLVFAQKLP GNDNSTATLC LGHHAVPNGT

IVKTITNDQI EVTNATELVQ SSSTGGICDS PHQILDGENC

TLIDALLGDP QCDGFQNKKW DLFVERSKAY SNCYPYDVPD

-continued

YASLRSLVAS SGTLEFNNES FNWTGVTQNG TSSACKRRSN

NSFFSRLNWL THLKFKYPAL NVTMPNNEKF DKLYIWGVHH

PGTDNDQISL YAQASGRITV STKRSQQTVI PSIGSRPRIR

DVPSRISIYW TIVKPGDILL INSTGNLIAP RGYFKIRSGK

SSIMRSDAPI GKCNSECITP NGSIPNDKPF QNVNRITYGA

CPRYVKQNTL KLATGMRNVP EKQTRGIFGA IAGFIENGWE

GMVDGWYGFR HQNSEGTGQA ADLKSTQAAI NQINGKLNRL

IGKTNEKFHQ IEKEFSEVEG RIQDLEKYVE DTKIDLWSYN

AELLVALENQ HTIDLTDSEM NKLFERTKKQ LRENAEDMGN

GCFKIYHKCD NACIGSIRNG TYDHDVYRDE ALNNRFQIKG

VELKSGYKDW ILWISFAISC FLLCVALLGF IMWACQKGNI

RCNICI (SEQ ID NO: 984; GenBank Accession

No: YP_308839).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and natural killer (NK) cells.

In some cases, the heterologous glycoprotein used for pseudotyping is an influenza virus A H5N1 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence:

MEKIVLLLAI VSLVKSDQIC IGYHANNSTE QVDTIMEKNV

TVTHAQDILE KTHNGKLCDL NGVKPLILRD CSVAGWLLGN

PMCDEFINVP EWSYIVEKAS PANDLCYPGD FNDYEELKHL

LSRTNHFEKI QIIPKSSWSN HDASSGVSSA CPYHGRSSFF

RNVVWLIKKN SAYPTIKRSY NNTNQEDLLV LWGIHHPNDA

AEQTKLYQNP TTYISVGTST LNQRLVPEIA TRPKVNGQSG

RMEFFWTILK PNDAINFESN GNFIAPEYAY KIVKKGDSAI

MKSELEYGNC NTKCQTPMGA INSSMPFHNI HPLTIGECPK

YVKSNRLVLA TGLRNTPQRE RRRKKRGLFG AIAGFIEGGW

QGMVDGWYGY HHSNEQGSGY AADKESTQKA IDGVTNKVNS

IIDKMNTQFE AVGREFNNLE RRIENLNKQM EDGFLDVWTY

NAELLVLMEN ERTLDFHDSN VKNLYDKVRL QLRDNAKELG

NGCFEFYHKC DNECMESVKN GTYDYPQYSE EARLNREEIS

GVKLESMGTY QILSIYSTVA SSLALAIMVA GLSLWMCSNG

SLQCRICI (SEQ ID NO: 985; GenBank

Accession No: YP_308669).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an influenza virus H7N9 hemagglutinin glycoprotein. A suitable influenza hemagglutinin protein comprises an amino acid sequence having at least 80%, at least 85%, at least 90%, at least 95%, at least 98%, at least 99%, or 100%, amino acid sequence identity to the following amino acid sequence:

```
MNTQILVFAL IAIIPTNADK ICLGHHAVSN GTKVNTLTER
GVEVVNATET VERTNIPRIC SKGKRTVDLG QCGLLGTITG
PPQCDQFLEF SADLIIERRE GSDVCYPGKF VNEEALRQIL
RESGGIDKEA MGFTYSGIRT NGATSACRRS GSSFYAEMKW
LLSNTDNAAF PQMTKSYKNT RKSPALIVWG IHHSVSTAEQ
TKLYGSGNKL VTVGSSNYQQ SFVPSPGARP QVNGLSGRID
FHWLMLNPND TVTFSFNGAF IAPDRASFLR GKSMGIQSGV
QVDANCEGDC YHSGGTIISN LPFQNIDSRA VGKCPRYVKQ
RSLLLATGMK NVPEIPKGRG LFGAIAGFIE NGWEGLIDGW
YGFRHQNAQG EGTAADYKST QSAIDQITGK LNRLIEKTNQ
QFELIDNEFN EVEKQIGNVI NWTRDSITEV WSYNAELLVA
MENQHTIDLA DSEMDKLYER VKRQLRENAE EDGTGCFEIF
HKCDDDCMAS IRNNTYDHSK YREEAMQNRI QIDPVKLSSG
YKDVILWFSF GASCFILLAI VMGLVFICVK NGNMRCTICI (SEQ
ID NO: 986; GenBank Accession No: YP_009118475).
```

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a Hepatitis B Virus (HBV) S glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MENTTSGFLG PLLVLQAGFF LLTRNLTIPQ SLDSWWTSLN
FLGGAPTCPG QNSQSPTSNH SPTSCPPICP GYRWMCLRRF
IIFLFILLLC LIFLLVLLDY QGMLPVCPLL PGTSTTSTGP
CKTCTIPAQG TSMFPSCCCT KPSDGNCTCI PIPSSWAFAR
FLWEWASVRF SWLSLLVPFV QWFVGLSPTV WLSVIWMMWY
WGPSLYNILS PFLPLLPIFF CLWVYI (SEQ ID NO: 987;
GenBank Accession No: ABV02793).
```

Such a heterologous glycoprotein may be useful in directing a VLP of the present disclosure to a liver cell.

In some cases, the heterologous glycoprotein used for pseudotyping is a Hepatitis B Virus (HBV) middle S glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MQWNSTAFHQ ALQDPKVRGL YFPAGGSSSG TVNPAPNIAS
HISSISARTG DPVTNMENIT SGFLGPLLVL QAGFFLLTRI
LTIPQSLDSW WTSLNFLGGS PVCLGQNSQS PTSNHSPTSC
PPICPGYRWM CLRRFIIFLF ILLLCLIFLL VLLDYQGMLP
VCPLIPGSTT TSTGPCKTCT TPAQGNSMFP SCCCTKPTDG
NCTCIPIPSS WAFAKYLWEW ASVRFSWLSL LVPFVQWFVG
LSPTVWLSAI WMMWYWGPSL YSIVSPFIPL LPIFFCLWVY I
(SEQ ID NO: 988; GenBank Accession No: ACJ66136).
```

Such a heterologous glycoprotein may be useful in directing a VLP of the present disclosure to a liver cell.

In some cases, the heterologous glycoprotein used for pseudotyping is a Hepatitis B Virus (HBV) large S glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MGLSWTVPLE WGKNHSTTNP LGFFPDHQLD PAFRANTRNP
DWDHNPNKDH WTEANKVGVG AFGPGFTPPH GGLLGWSPQA
QGMLKTLPAD PPPASTNRQS GRQPTPITPP LRDTHPQAMQ
WNSTTFHQAL QDPKVSALYL PAGGSSSGTV NPVPTTASLI
SSIFSRIGDP APNMESITSG FLGPLLVLQA GFFLLTKILT
IPQSLDSWWT SLNFLGGAPV CLGQNSQSPT SSHSPTSCPP
ICPGYRWMCL RRFIIFLFIL LLCLIFLLVL LDYQGMLPVC
PLIPGSSTTS TGPCRTCTTL AQGTSMFPSC CCSKPSDGNC
TCIPIPSSWA FGKFLWEWAS ARFSWLSLLV PFVQWFAGLS
PTVWLSVIWM MWYWGPSLYN ILSPFIPLLP IFFCLWVYI
(SEQ ID NO: 989; GenBank Accession No: AGR65633).
```

Such a heterologous glycoprotein may be useful in directing a VLP of the present disclosure to a liver cell.

In some cases, the heterologous glycoprotein used for pseudotyping is a Hepatitis B Virus (HBV) small S glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MENITSGFLG PLLVLQAGFF LLTRILTIPQ SLDSWWTSLN
FLGGTTVCLG QNSQSPTSNH SPTSCPPTCP GYRWMCLRRF
IIFLFILLLC LIFLLVLLDY QGMLPVCPLI PGSSTTSTGP
CRTCTTPAQG TSMYPSCCCT KPSDGNCTCI PIPSSWAFGK
FLWEWASARF SWLSLLVPFV QWFVGLSPTV WLSVIWMMWY
WAPNLHNILS PFLPLLPIFL CLWVYI (SEQ ID NO: 990;
GenBank Accession No: AHC69850.
```

Such a heterologous glycoprotein may be useful in directing a VLP of the present disclosure to a liver cell.

In some cases, the heterologous glycoprotein used for pseudotyping is a Hepatitis B Virus (HBV) pre S glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MGGWSSKPRK GMGTNLAVPN PLGFFPDHQL DPAFKANSDN
PDWDLNTHKD YWPDAWKVGV GAFGPGFTPP HGGLLGWSPQ
AQGLLTTVPA APPPASTNRQ SGRQPTPLSP PLRDTHPQAM
KWNSTTFHQT LQDPRVRALY LPAGGSSSGT VSPAQNTVSA
ISSILSKTGD PVPNMESIAS GLLGPLLVLQ AGFFLLTKIL
TIPQSLDSWW TSLNFLGGTP VCLGQNSQSQ ISSHSPTCCP
PTCPGYRWMC LRRFIIFLCI LLLCLIFLLV LLDYQGMLPV
CPLIPGSSTT STGPCKTCTA PAQGTSMFPS CCCTKPTDGN
CTCIPIPSSW AFAKYLWEWA SVRFSWLSLL VPFVQWFVGL
SPTVWLSVIW MMWFWGPSLY NILSPFIPLL PIFFCLWVYI
(SEQ ID NO: 991 ; GenBank Accession No:
CAA66700).
```

Such a heterologous glycoprotein may be useful in directing a VLP of the present disclosure to a liver cell.

In some cases, the heterologous glycoprotein used for pseudotyping is a Hepatitis B Virus (HBV) preS2 glycoprotein. A suitable HBV protein comprises an amino acid sequence having at least 80%, at least 85%, at least 90%, at least 95%, at least 98%, at least 99%, or 100%, amino acid sequence identity to the following amino acid sequence:

```
MQWNSTTFHQ TLQDPRVRGL YFPAGGSSSG TVNPVPTTVS
HISSIFSRIG DPALNMENIT SGFLGPLLVL QAGFFLLTRI
LTIPQSLDSW WTSLNFLGGT TVCLGQNSQS PTSNHSPTSC
PPTCPGYRWM CLRRFIIFLF ILLLCLIFLL VLLDYQGMLS
VCPLIPGSTT TSTGPCKTCTTPAQGTSIHP SCCCTKPSDG
NCTWIPIPSS WAFGKFLWEW ASARFSWLSL LVPFVQWFVG
LSPTVWLSVI WIMWYWGPSL YSILSPFLPL LPIFFCLWVY I
(SEQ ID NO: 992; GenBank Accession No: AAO12662).
```

Such a heterologous glycoprotein may be useful in directing a VLP of the present disclosure to a liver cell.

In some cases, the heterologous glycoprotein used for pseudotyping is a Rabies virus. A suitable Rabies virus protein comprises an amino acid sequence having at least 80%, at least 85%, at least 90%, at least 95%, at least 98%, at least 99%, or 100%, amino acid sequence identity to the following amino acid sequence:

```
MVPQALLFVP LLVFPLCFGK FPIYTIPDKL GPWSPIDIHH
LSCPNNLVVE DEGCTNLSGF SYMELKVGYI SAIKVNGFTC
TGVVTEAETY TNFVGYVTTT FKRKHFRPTP DACRSAYNWK
MAGDPRYEES LHNPYPDYHW LRTVKTTKES LVIISPSVAD
```

-continued

```
LDPYDKSLHS RVFPSGKCSG ITVSSTYCST NHDYTIWMPE
NLRLGTSCDI FINSRGKRAS KGSQTCGFID ERGLYKSLKG
ACKLKLCGVL GLRLMDGTWV AMQTSDETKW CPPDQLVNLH
DFRSDEIEHL VVEELVKKRE ECLDALESIM TTKSVSFRRL
SHLRKLVPGF GKAYTIFNKT LMEADAHYKS VRTWNEIIPS
KGCLRVGGRC HPHVNGVFFN GIILGPEGHV LIPEMQSSLL
QQHMELLESS VIPLMHPLAD PSTVFKEGDE AEDFVEVHLP
DVHKQVSGVN LGLPNWGKYV LLSAGALIAL MLIIFLLTCC
RRVNRPESTQ HSLGGKRRKV SITSQSGKII SSWESYKSGG ETRL
(SEQ ID NO: 993; GenBank Accession No: AWR88358).
```

Such a glycoprotein may be useful for targeting a VLP of the present disclosure to neurons, astrocytes, oligodendrocyctes, glia, and other cells of the of the central nervous system.

In some cases, the heterologous glycoprotein used for pseudotyping is a Mokola virus glycoprotein. A suitable Mokola virus protein comprises an amino acid sequence having at least 80%, at least 85%, at least 90%, at least 95%, at least 98%, at least 99%, or 100%, amino acid sequence identity to the following amino acid sequence:

```
MNIPCFVVIL SLATTHSLGE FPLYTIPEKI EKWTPIDMIH
LSCPNNLLSE EEGCNAESSF TYFELKSGYL AHQKVPGFTC
TGVVNEAETY TNFVGYVTTT FKRKHFRPTV AACRDAYNWK
VSGDPRYEES LHTPYPDSSW LRTVTTTKES LLIISPSIVE
MDIYGRTLHS PMFPSGVCSN VYPSVPSCET NHDYTLWLPE
DPSLSLVCDI FTSSNGKKAM NGSRICGFKD ERGFYRSLKG
ACKLTLCGRP GIRLFDGTWV SFTKPDVHVW CTPNQLINIH
NDRLDEIEHL IVEDIIKKRE ECLDTLETIL MSQSVSFRRL
SHFRKLVPGY GKAYTILNGS LMETNVYYKR VDKWADILPS
KGCLKVGQQC MEPVKGVLFN GIIKGPDGQI LIPEMQSEQL
KQHMDLLKAA VFPLRHPLIS REAVFKKDGD ADDFVDLHMP
DVHKSVSDVD LGLPHWGFWM LIGATIVAFV VLVCLLRVCC
KRVRRRRSGR ATQEIPLSFP SAPVPRAKVV SSWESYKGLP GT
(SEQ ID NO: 994; GenBank Accession No: AAB26292).
```

Such a glycoprotein may be useful for targeting a VLP of the present disclosure to neurons, astrocytes, oligodendrocyctes, glia, and other cells of the of the central nervous system.

In some cases, the heterologous glycoprotein used for pseudotyping is a lymphocytic choriomeningitis virus (LCMV) glycoprotein. A suitable LCMV protein comprises an amino acid sequence having at least 80%, at least 85%, at least 90%, at least 95%, at least 98%, at least 99%, or 100%, amino acid sequence identity to the following amino acid sequence:

```
MGQIVTMFEA LPHIIDEVIN IVIIVLIIIT SIKAVYNFAT
CGILALISFL LLAGRSCGLY GLDGPDIYKG IYQFKSVEFD
```

-continued

MSHLNLTMPN ACSANNSHHY ISMGNSGLEL TFTNDSIISH

NFCNLTSAFN KKTFDHTLMS IVSSLHLSIR GNSNYKAVSC

DFNSGITIQY NLSFSDAQSA LSQCKTFRGR VLDMFRTAFG

GKYMRSGWGW TGSDGKTTWC SQTSYQYLII QNRTWENHCR

YAGPFGMARI LFAQEKTKFL TRRLAGTFTW TLSDSSGVDN

PGGYCLTRWM ILAADLKCFG NTAVAKCNMN HDEEFCDMLR

LIDYNKAALS KFKEDVESAL HLFKVTVNSL VSDQLLMRNH

LRDLMGVPYC NYSRFWYLEH TKTGETSVPK CWLVTNGSYL

NETHFSDQIE QEADNMITDM LRKDYIKRQG STPLALMDLL

MFSTSAYLVS VFLHLVKIPT HRHIKGGSCP KPHRLTNKGI

CSCGAFKVPG VKTVWKRR (SEQ ID NO: 995; GenBank Accession No: AIW66623).

In some cases, the heterologous glycoprotein used for pseudotyping is a lymphocytic choriomeningitis virus (LCMV) glycoprotein C. A suitable LCMV protein comprises an amino acid sequence having at least 80%, at least 85%, at least 90%, at least 95%, at least 98%, at least 99%, or 100%, amino acid sequence identity to the following amino acid sequence:

MGQIVTMFEA LPHIIDEVIN IVIIVLIIIT SIKAVYNFAT

CGILALVSFL FLAGRSCGMY GLNGPDIYKG VYQFKSVEFD

MSHLNLTMPN ACSANNSHHY ISMGSSGLEL TFTNDSILNH

NFCNLTSAFN KKTFDHTLMS IVSSLHLSIR GNSNHKAVSC

DFNNGITIQY NLSFSDPQSA ISQCRTFRGR VLDMFRTAFG

GKYMRSGWGW AGSDGKTTWC SQTSYQYLII QNRTWENHCR

YAGPFGMSRI LFAQEKTKFL TRRLAGTFTW TLSDSSGVEN

PGGYCLTKWM ILAAELKCFG NTAVAKCNVN HDEEFCDMLR

LIDYNKAALS KFKQDVESAL HVFKTTVNSL ISDQLLMRNH

LRDLMGVPYC NYSKFWYLEH AKTGETSVPK CWLVTNGSYL

NETHFSDQIE QEADNMITEM LRKDYIKRQG STPLALMDLL

MFSTSAYLIS IFLHLVKIPT HRHIKGGSCP KPHRLTNKGI

CSCGAFKVPG VKTIWKRR (SEQ ID NO: 996; GenBank Accession No: CAC01231).

In some cases, the heterologous glycoprotein used for pseudotyping is a lymphocytic choriomeningitis virus (LCMV) glycoprotein. A suitable LCMV protein comprises an amino acid sequence having at least 80%, at least 85%, at least 90%, at least 95%, at least 98%, at least 99%, or 100%, amino acid sequence identity to the following amino acid sequence:

MGQIVTMFEA LPHIIDEVIN IVIIVLIVIT GIKAVYNFAT

CGIFALISFL LLAGRSCGMY GLKGPDIYKG VYQFKSVEFD

MSHLNLTMPN ACSANNSHHY ISMGTSGLEL TFTNDSIISH

NFCNLTSAFN KKTFDHTLMS IVSSLHLSIR GNSNYKAVSC

-continued

DFNNGITIQY NLTFSDAQSA QSQCRTFRGR VLDMFRTAFG

GKYMRSGWGW TGSDGKTTWC SQTSYQYLII QNRTWENHCT

YAGPFGMSRI LLSQEKTKFF TRRLAGTFTW TLSDSSGVEN

PGGYCLTKWM ILAAELKCFG NTAVAKCNVN HDAEFCDMLR

LIDYNKAALS KFKEDVESAL HLFKTTVNSL ISDQLLMRNH

LRDLMGVPYC NYSKFWYLEH AKTGETSVPK CWLVTNGSYL

NETHFSDQIE QEADNMITEM LRKDYIKRQG STPLALMDLL

MFSTSAYLVS IFLHLVKIPT HRHIKGGSCP KPHRLTNKGI

CSCGAFKVPG VKTVWKRR (SEQ ID NO: 997; GenBank Accession No: P09991).

In some cases, the heterologous glycoprotein used for pseudotyping is a lymphocytic choriomeningitis virus (LCMV) G1 glycoprotein. A suitable LCMV protein comprises an amino acid sequence having at least 80%, at least 85%, at least 90%, at least 95%, at least 98%, at least 99%, or 100%, amino acid sequence identity to the following amino acid sequence:

MYGLKGPDIYKG VYQFKSVEFD MSHLNLTMPN ACSANNSHHY

ISMGTSGLEL TFTNDSIISH NFCNLTSAFN KKTFDHTLMS

IVSSLHLSIR GNSNYKAVSC DFNNGITIQY NLTFSDAQSA

QSQCRTFRGR VLDMFRTAFG GKYMRSGWGW TGSDGKTTWC

SQTSYQYLII QNRTWENHCT YAGPFGMSRI LLSQEKTKFF TRRLA (SEQ ID NO: 998; GenBank Accession No: P09991).

In some cases, the heterologous glycoprotein used for pseudotyping is a lymphocytic choriomeningitis virus (LCMV) G2 glycoprotein. A suitable LCMV protein comprises an amino acid sequence having at least 80%, at least 85%, at least 90%, at least 95%, at least 98%, at least 99%, or 100%, amino acid sequence identity to the following amino acid sequence:

GTFTW TLSDSSGVEN PGGYCLTKWM ILAAELKCFG NTAVAKCNVN

HDAEFCDMLR LIDYNKAALS KFKEDVESAL HLFKTTVNSL

ISDQLLMRNH LRDLMGVPYC NYSKFWYLEH AKTGETSVPK

CWLVTNGSYL NETHFSDQIE QEADNMITEM LRKDYIKRQG

STPLALMDLL MFSTSAYLVS IFLHLVKIPT HRHIKGGSCP

KPHRLTNKGI CSCGAFKVPG VKTVWKRR (SEQ ID NO: 999; GenBank Accession No: P09991).

In some cases, the heterologous glycoprotein used for pseudotyping is a Ross River virus E1 glycoprotein. A suitable Ross River virus protein comprises an amino acid sequence having at least 80%, at least 85%, at least 90%, at least 95%, at least 98%, at least 99%, or 100%, amino acid sequence identity to the following amino acid sequence:

YEHTATIPNV VGFPYKAHIE RNXFSPMTLQ LEVVXXSLEP
TLNLEYITCE YKTVVPSPFI KCCGTSECSS KEQPDYQCKV
YTGVYPFMWG GAYCFCDSEN TQLSEAYVDR SDVCKHDHAL
AYKAHTASLK ATIRISYGTI NQTTEAFVNG EHAVNVGGSK
FIFGPISTAW SPFDNKIVVY KDDVYNQDFP PYGSGQPGRF
GDIQSRTVES KDLYANTALK LSRPSPGVVH VPYTQTPSGF
KYWLKEKGSS LNTKAPFGCK IKTNPVRAMD CAVGSIPVSM
DIPDSAFTRV VDAPAVTDLS CQVAVCTHSS DFGXVATLSY
KTDKPGKCAV HSHSNVATLQ EATVDVKEDG KVTVHFSXXS
ASPAFKVSVC DAKTTCTAAC EPPKDHIVPY GASHNNQVFP
DMSGTAMTWV QRMASGLGGL ALIAVVVLVL VTCITMRR (SEQ
ID NO: 1000; GenBank Accession No: NP_740686).

Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is a Ross River virus E2 glycoprotein. A suitable Ross River virus protein comprises an amino acid sequence having at least 80%, at least 85%, at least 90%, at least 95%, at least 98%, at least 99%, or 100%, amino acid sequence identity to the following amino acid sequence:

SVIEHFNVYK ATRPYLAXCA DCGDGYFCYS PVAIEKIRDE
ASDGMLKIQV SAQIGLDKAG THAHTKMRYM AGHDVQESKR
DSLRVYTSAA CSIHGTMGHF IVAHCPPGDY LKXSFEDANS
HVKACKVQYK HDPLPVGREK FVVRPHFGVE LPCTSYQLTT
APTDEEIDMH TPPDIPDRTL LSQTAGNVKI TAGGRTIRYN
CTCGRDNVGT TSTDKTINTC KIDQCHAAVT SHDKWXFTSP
FVPRADQTAR KGKVHVPFPL TNVTCRVPLA RAPDVTYGKK
EVTLRLHPDH PTXFSYRSLG AVPHPYEEWV DKFSERIIPV
TEEGIEYQWG NNPPVRLWAQ LTTEGKPHGW PHEIIQYYYG
LYPAATIAAV SGASLMALLT LAATCCMLAT ARRKCLTPYA
LTPGAVVPLT LGLLXCAPRA NA (SEQ ID NO: 1001;
GenBank Accession No: NP_740684).

Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is a Semliki Forest virus E1 glycoprotein. A suitable Semliki Forest virus protein comprises an amino acid sequence having at least 80%, at least 85%, at least 90%, at least 95%, at least 98%, at least 99%, or 100%, amino acid sequence identity to the following amino acid sequence:

YEHSTVMPNV VGFPYKAHIE RPGYSPLTLQ MQVVETSLEP
TLNLEYITCE YKTVVPSPYV KCCGASECST KEKPDYQCKV
YTGVYPFMWG GAYCFCDSEN TQLSEAYVDR SDVCRHDHAS
AYKAHTASLK AKVRVMYGNV NQTVDVYVNG DHAVTIGGTQ
FIFGPLSSAW TPFDNKIVVY KDEVFNQDFP PYGSGQPGRF
GDIQSRTVES NDLYANTALK LARPSPGMVH VPYTQTPSGF
KYWLKEKGTA LNTKAPFGCQ IKTNPVRAMN CAVGNIPVSM
NLPDSAFTRI VEAPTIIDLT CTVATCTHSS DFGGVLTLTY
KTNKNGDCSV HSHSNVATLQ EATAKVKTAG KVTLHFSTAS
ASPSFVVSLC SARATCSASC EPPKDHIVPY AASHSNVVFP
DMSGTALSWV QKISGGLGAF AIGAILVLVV VTCIGLRR
(SEQ ID NO: 1002; GenBank Accession No:
NP_819008).

Such a glycoprotein may be useful for targeting a VLP of the present disclosure to muscle, pancreas, neurons, astrocytes, oligodendrocyctes, glia, and other cells of the of the central nervous system.

In some cases, the heterologous glycoprotein used for pseudotyping is a Semliki Forest virus E2 glycoprotein. A suitable Semliki Forest virus protein comprises an amino acid sequence having at least 80%, at least 85%, at least 90%, at least 95%, at least 98%, at least 99%, or 100%, amino acid sequence identity to the following amino acid sequence:

SVSQHFNVYK ATRPYIAYCA DCGAGHSCHS PVAIEAVRSE
ATDGMLKIQF SAQIGIDKSD NHDYTKIRYA DGHAIENAVR
SSLKVATSGD CFVHGTMGHF ILAKCPPGEF LQVSIQDTRN
AVRACRIQYH HDPQPVGREK FTIRPHYGKE IPCTTYQQTT
AETVEEIDMH MPPDTPDRTL LSQQSGNVKI TVGGKKVKYN
CTCGTGNVGT TNSDMTINTC LIEQCHVSVT DHKKWQFNSP
FVPRADEPAR KGKVHIPFPL DNITCRVPMA REPTVIHGKR
EVTLHLHPDH PTLFSYRTLG EDPQYHEEWV TAAVERTIPV
PVDGMEYHWG NNDPVRLWSQ LTTEGKPHGW PHQIVQYYYG
LYPAATVSAV VGMSLLALIS IFASCYMLVA ARSKCLTPYA
LTPGAAVPWT LGILCCAPRA HA (SEQ ID NO: 1003;
GenBank Accession No: NP_819006).

Such a glycoprotein may be useful for targeting a VLP of the present disclosure to muscle, pancreas, neurons, astrocytes, oligodendrocyctes, glia, and other cells of the of the central nervous system.

In some cases, the heterologous glycoprotein used for pseudotyping is a Sindbis virus E1 glycoprotein. A suitable Sindbis virus protein comprises an amino acid sequence having at least 80%, at least 85%, at least 90%, at least 95%, at least 98%, at least 99%, or 100%, amino acid sequence identity to the following amino acid sequence:

YEHATTVPNV PQIPYKALVE RAGYAPLNLE ITVMSSEVLP

STNQEYITCK FTTVVPSPKI KCCGSLECQP AAHADYTCKV

FGGVYPFMWG GAQCFCDSEN SQMSEAYVEL SADCASDHAQ

AIKVHTAAMK VGLRIVYGNT TSFLDVYVNG VTPGTSKDLK

VIAGPISASF TPFDHKVVIH RGLVYNYDFP EYGAMKPGAF

GDIQATSLTS KDLIASTDIR LLKPSAKNVH VPYTQASSGF

EMWKNNSGRP LQETAPFGCK IAVNPLRAVD CSYGNIPISI

DIPNAAFIRT SDAPLVSTVK CEVSECTYSA DFGGMATLQY

VSDREGQCPV HSHSSTATLQ ESTVHVLEKG AVTVHFSTAS

PQANFIVSLC GKKTTCNAEC KPPADHIVST PHKNDQEFQA

AISKTSWSWL FALFGGASSL LIIGLMIFAC SMMLTSTRR (SEQ ID NO: 1004; GenBank Accession No: NP_740677).

Such a glycoprotein may be useful for targeting a VLP of the present disclosure to muscle, pancreas, neurons, astrocytes, oligodendrocyctes, glia, and other cells of the of the central nervous system.

In some cases, the heterologous glycoprotein used for pseudotyping is a Sindbis virus E2 glycoprotein. A suitable Sindbis virus protein comprises an amino acid sequence having at least 80%, at least 85%, at least 90%, at least 95%, at least 98%, at least 99%, or 100%, amino acid sequence identity to the following amino acid sequence:

SVIDDFTLTS PYLGTCSYCH HTVPCFSPVK IEQVWDEADD

NTIRIQTSAQ FGYDQSGAAS ANKYRYMSLK QDHTVKEGTM

DDIKISTSGP CRRLSYKGYF LLAKCPPGDS VTVSIVSSNS

ATSCTLARKI KPKFVGREKY DLPPVHGKKI PCTVYDRLKE

TTAGYITMHR PRPHAYTSYL EESSGKVYAK PPSGKNITYE

CKCGDYKTGT VSTRTEITGC TAIKQCVAYK SDQTKWVFNS

PDLIRHDDHT AQGKLHLPFK LIPSTCMVPV AHAPNVIHGF

KHISLQLDTD HLTLLTTRRL GANPEPTTEW IVGKTVRNFT

VDRDGLEYIW GNHEPVRVYA QESAPGDPHG WPHEIVQHYY

HRHPVYTILA VASATVAMMI GVTVAVLCAC KARRECLTPY

ALAPNAVIPT SLALLCCVRS ANA (SEQ ID NO: 1005; GenBank Accession No: NP_740675).

Such a glycoprotein may be useful for targeting a VLP of the present disclosure to skeletal muscle, and cells that make up the joints, joint-associated connective tissue, bone, neurons, and lymphatic cells.

In some cases, the heterologous glycoprotein used for pseudotyping is an Ebola Zaire virus glycoprotein. A suitable Ebola Zaire virus protein comprises an amino acid sequence having at least 80%, at least 85%, at least 90%, at least 95%, at least 98%, at least 99%, or 100%, amino acid sequence identity to the following amino acid sequence:

MGVTGILQLP RDRFKRTSFF LWVIILFQRT FSIPLGVIHN

STLQVSDVDK LVCRDKLSST NQLRSVGLNL EGNGVATDVP

-continued

SATKRWGFRS GVPPKVVNYE AGEWAENCYN LEIKKPDGSE

CLPAAPDGIR GFPRCRYVHK VSGTGPCAGD FAFHKEGAFF

LYDRLASTVI YRGTTFAEGV VAFLILPQAK KDFFSSHPLR

EPVNATEDPS SGYYSTTIRY QATGFGTNET EYLFEVDNLT

YVQLESRFTP QFLLQLNETI YTSGKRSNTT GKLIWKVNPE

IDTTIGEWAF WETKKNLTRK IRSEELSFTV VSNGAKNISG

QSPARTSSDP GTNTTTEDHK IMASENSSAM VQVHSQGREA

AVSHLTTLAT ISTSPQSLTT KPGPDNSTHN TPVYKLDISE

ATQVEQHHRR TDNDSTASDT PSATTAAGPP KAENTNTSKS

TDFLDPATTT SPQNHSETAG NNNTHHQDTG EESASSGKLG

LITNTIAGVA GLITGGRRTR REAIVNAQPK CNPNLHYWTT

QDEGAAIGLA WIPYFGPAAE GIYIEGLMHN QDGLICGLRQ

LANETTQALQ LFLRATTELR TFSILNRKAI DFLLQRWGGT

CHILGPDCCI EPHDWTKNIT DKIDQIIHDF VDKTLPDQGD

NDNWWTGWRQ WIPAGIGVTG VIIAVIALFC ICKFVF (SEQ ID NO: 1006; GenBank Accession No: AAB81004).

Such a glycoprotein may be useful for targeting a VLP of the present disclosure to hepatocytes, endothelial cells, dendritic cells, macrophages, and monocytes.

In some cases, the heterologous glycoprotein used for pseudotyping is an Ebola Zaire virus glycoprotein. A suitable Ebola Zaire virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1007)

IPLGVIHN STLQVSDVDK LVCRDKLSST NQLRSVGLNL

EGNGVATDVP SATKRWGFRS GVPPKVVNYE AGEWAENCYN

LEIKKPDGSECLPAAPDGIR GFPRCRYVHK VSGTGPCAGD

FAFHKEGAFF LYDRLASTVI YRGTTFAEGV VAFLILPQAK

KDFFSSHPLR EPVNATEDPS SGYYSTTIRY QATGFGTNET

EYLFEVDNLT YVQLESRFTP QFLLQLNETI YTSGKRSNTT

GKLIWKVNPE IDTTIGEWAF WETKKNLTRK IRSEELSFTV

VSNGAKNISG QSPARTSSDP GTNTTTEDHK IMASENSSAM

VQVHSQGREA AVSHLTTLAT ISTSPQSLTT KPGPDNSTHN

TPVYKLDISE ATQVEQHHRR TDNDSTASDT PSATTAAGPP

KAENTNTSKS TDFLDPATTT SPQNHSETAG NNNTHHQDTG

EESASSGKLG LITNTIAGVA GLITGGRRTR REAIVNAQPK

CNPNLHYWTT QDEGAAIGLA WIPYFGPAAE GIYIEGLMHN

QDGLICGLRQ LANETTQALQ LFLRATTELR TFSILNRKAI

DFLLQRWGGT CHILGPDCCI EPHDWTKNIT DKIDQIIHDF

VDKTLPDQGDNDNWWTGWRQ WIPAGIGVTG VIIAVIALFC ICKFVF.

Such a glycoprotein may be useful for targeting a VLP of the present disclosure to hepatocytes, endothelial cells, dendritic cells, macrophages, and monocytes.

In some cases, the heterologous glycoprotein used for pseudotyping is an Ebola Reston virus glycoprotein. A suitable Ebola Reston virus protein comprises an amino acid sequence having at least 80%, at least 85%, at least 90%, at least 95%, at least 98%, at least 99%, or 100%, amino acid sequence identity to the following amino acid sequence:

```
MGSGYQLLQL PRERFRKTSF LVWVIILFQR AISMPLGIVT
NSTLKATEID QLVCRDKLSS TSQLKSVGLN LEGNGIATDV
PSATKRWGFR SGVPPKVVSY EAGEWAENCY NLEIKKSDGS
ECLPLPPDGV RGFPRCRYVH KVQGTGPCPG DLAFHKNGAF
FLYDRLASTV IYRGTTFAEG VVAFLILSEP KKHFWKATPA
HEPVNTTDDS TSYYMTLTLS YEMSNFGGNE SNTLFKVDNH
TYVQLDRPHT PQFLVQLNET LRRNNRLSNS TGRLTWTLDP
KIEPDVGEWA FWETKKNFSQ QLHGENLHFQ IPSTHTNNSS
DQSPAGTVQG KISYHPPANN SELVPTDSPP VVSVLTAGRT
EEMSTQGLTN GETITGFTAN PMTTTIAPSP TMTSEVDNNV
PSEQPNNTAS IEDSPPSASN ETIYHSEMDP IQGSNNSAQS
PQTKTTPAPT TSPMTQDPQE TANSSKPGTS PGSAAGPSQP
GLTINTVSKV ADSLSPTRKQ KRSVRQNTAN KCNPDLYYWT
AVDEGAAVGL AWIPYFGPAA EGIYIEGVMH NQNGLICGLR
QLANETTQAL QLFLRATTEL RTYSLLNRKA IDFLLQRWGG
TCRILGPSCC IEPHDWTKNI TDEINQIKHD FIDNPLPDHG
DDLNLWTGWR QWIPAGIGII GVIIAIIALL CICKILC (SEQ
ID NO: 1008; GenBank Accession No: NP_690583).
```

Such a glycoprotein may be useful for targeting a VLP of the present disclosure to hepatocytes, endothelial cells, dendritic cells, macrophages, and monocytes.

In some cases, the heterologous glycoprotein used for pseudotyping is a Marburg virus glycoprotein. A suitable Marburg virus protein comprises an amino acid sequence having at least 80%, at least 85%, at least 90%, at least 95%, at least 98%, at least 99%, or 100%, amino acid sequence identity to the following amino acid sequence:

```
MKTTCFLISL ILIQGTKNLP ILEIASNNQP QNVDSVCSGT
LQKTEDVHLM GFTLSGQKVA DSPLEASKRW AFRTGVPPKN
VEYTEGEEAK TCYNISVTDP SGKSLLLDPP TNIRDYPKCK
TIHHIQGQNP HAQGIALHLW GAFFLYDRIA STTMYRGKVF
TEGNIAAMIV NKTVHKMIFS RQGQGYRHMN LTSTNKYWTS
SNGTQTNDTG CFGALQEYNS TKNQTCAPSK IPPPLPTARP
EIKLTSTPTD ATKLNTTDPS SDDEDLATSG SGSGEREPHT
TSDAVTKQGL SSTMPPTPSP QPSTPQQGGN NTNHSQDAVT
ELDKNNTTAQ PSMPPHNTTT ISTNNTSKHN FSTLSAPLQN
TTNDNTQSTI TENEQTSAPS ITTLPPTGNP TTAKSTSSKK
GPATTAPNTT NEHFTSPPPT PSSTAQHLVY FRRKRSILWR
EGDMFPFLDG LINAPIDFDP VPNTKTIFDE SSSSGASAEE
```

-continued

```
DQHASPNISL TLSYFPNINE NTAYSGENEN DCDAELRIWS
VQEDDLAAGL SWIPFFGPGI EGLYTAVLIK NQNNLVCRLR
RLANQTAKSL ELLLRVTTEE RTFSLINRHA IDFLLTRWGG
TCKVLGPDCC IGIEDLSKNI SEQIDQIKKD EQKEGTGWGL
GGKWWTSDWG VLTNLGILLL LSIAVLIALS CICRIFTKYI G
(SEQ ID NO: 1009); GenBank Accession No:
CAA78117).
```

Such a glycoprotein may be useful for targeting a VLP of the present disclosure to hepatocytes, endothelial cells, dendritic cells, macrophages, and monocytes.

In some cases, the heterologous glycoprotein used for pseudotyping is a murine leukemia virus (MLV) glycoprotein. A suitable MLV protein comprises an amino acid sequence having at least 80%, at least 85%, at least 90%, at least 95%, at least 98%, at least 99%, or 100%, amino acid sequence identity to the following amino acid sequence:

```
MESTTLSKPF KNQVNPWGPL IVLLILGGVN PVALGNSPHQ
VFNLTWEVTN GDRETVWAIA GNHPLWTWWP DLTPDLCMLA
LHGPSYWGLE YRAPFSPPPG PPCCSGSSDS TPGCSRDCEE
PLTSYTPRCN TAWNRLKLSK VTHAHNEGFY VCPGPHRPRW
ARSCGGPESF YCASWGCETT GRASWKPSSS WDYITVSNNL
TSDQATPVCK GNEWCNSLTI RFTSFGKQAT SWVTGHWWGL
RLYVSGHDPG LIFGIRLKIT DSGPRVPIGP NPVLSDRRPP
SRPRPTRSPP PSNSTPTETP LTLPEPPPAG VENRLLNLVK
GAYQALNLTS PDKTQECWLC LVSGPPYYEG VAVLGTYSNH
TSAPANCSVA SQHKLTLSEV TGQGLCIGAV PKTHQVLCNT
TQKTSDGSYY LAAPTGTTWA CSTGLTPCIS TTILDLTTDY
CVLVELWPRV TYHSPSYVYH QFEGRAKYKR EPVSLTLALL
LGGLTMGGIA AGVGTGTTAL VATQQFQQLQ AAMHDDLKEV
EKSITNLEKS LTSLSEVVLQ NRRGLDLLFL KEGGLCAALK
EECCFYADHT GLVRDSMAKL RERLSQRQKL FESQQGWFEG
LFNKSPWFTT LISTIMGPLI ILLLILLFGP CILNRLVQFI
KDRISVVQAL VLTQQYHQLK TIRDCKSRE (SEQ ID
NO: 1010; GenBank Accession No: AAA51037).
```

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence:

```
MESTTLSKPF KNQVNPWGPL IVLLILRGVN PVTLGNSPHQ
VFNLTWEVTN GDRETVWAIT GNHPLWTWWP DLTPDLCMLA
LHGPSYWGLE YRAPFSPPPG PPCCSGSSDS TPGCSRDCEE
```

-continued

```
PLTSYTPRCN TAWNRLKLSK VTHAHNGGFY VCPGPHRPRW
ARSCGGPESF YCASWGCETT GRASWKPSSS WDYITVSNNL
TSDQATPVCK GNKWCNSLTI RFTSFGKQAT SWVTGHWWGL
RLYVSGHDPG LIFGIRLKIT DSGPRVPIGP NPVLSDRRPP
SRPRPTRSPP PSNSTPTETP LTLPEPPPAG VENRLLNLVK
GAYQALNLTS PDKTQECWLC LVSGPPYYEG VAVLGTYSNH
TSAPANCSVA SQHKLTLSEV TGQGLCIGAV PKTHQVLCNT
TQKTSDGSYY LAAPTGTTWA CSTGLTPCIS TTILDLTTDY
CVLVELWPRV TYHSPSYVYH QFERRAKYKR EPVSLTLALL
LGGLTMGGIA AGVGTGTTAL VATQQFQQLQ AAMHDDLKEV
EKSITNLEKS LTSLSEVVLQ NRRGLDLLFL KEGGLCAALK
EECCFYADHT GLVRDSMAKL RERLSQRQKL FESQQGWFEG
LFNKSPWFTT LISTIMGPLI ILLLLILLFGP CILNRLVQFI
KDRISVVQAL VLTQQYHQLK IIEDCKSRE (SEQ ID
NO: 1011; GenBank Accession No: AID54959).
```

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence:

```
MARSTLSKPP QDKINPWKPL IVMGVLLGVG MAESPHQVFN
VTWRVTNLMT GRTANATSLL GTVQDAFPKL YFDLCDLVGE
EWDPSDQEPY VGYGCKYPAG RQRTRTFDFY VCPGHTVKSG
CGGPGEGYCG KWGCETTGQA YWKPTSSWDL ISLKRGNTPW
DTGCSKVACG PCYDLSKVSN SFQGATRGGR CNPLVLEFTD
AGKKANWDGP KSWGLRLYRT GTDPITMFSL TRQVLNVGPR
VPIGPNPVLP DQRLPSSPIE IVPAPQPPSP LNTSYPPSTT
STPSTSPTSP SVPQPPPGTG DRLLALVKGA YQALNLTNPD
KTQECWLCLV SGPPYYEGVA VVGTYTNHST APANCTATSQ
HKLTLSEVTG QGLCMGAVPK THQALCNTTQ SAGSGSYYLA
APAGTMWACS TGLTPCLSTT VLNLTTDYCV LVELWPRVIY
HSPDYMYGQL EQRTKYKREP VSLTLALLLG GLTMGGIAAG
IGTGTTALIK TQQFEQLHAA IQTDLNEVEK SITNLEKSLT
SLSEVVLQNR RGLDLLFLKE GGLCAALKEE CCFYADHTGL
VRDSMAKLRE RLNQRQKLFE TGQGWFEGLF NRSPWFTTLI
STIMGPLIVL LLILLFGPCI LNRLVQFVKD RISVVQALVL
TQQYHQLKPI EYEP (SEQ ID NO: 1012; GenBank
Accession No: AAA46515).
```

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence:

```
MEGPAFSKPL KDKINPWKSL MVMGVYLRVG MAESPHQVFN
VTWRVTNLMT GRTANATSLL GTVQDAFPRL YFDLCDLVGE
EWDPSDQEPY VGYGCKYPGG RKRTRTFDFY VCPGHTVKSG
CGGPREGYCG EWGCETTGQA YWKPTSSWDL ISLKRGNTPW
DTGCSKMACG PCYDLSKVSN SFQGATRGGR CNPLVLEFTD
AGKKANWDGP KSWGLRLYRT GTDPITMFSL TRQVLNIGPR
IPIGPNPVIT GQLPPSRPVQ IRLPRPPQPP PTGAASIVPE
TAPPSQQPGT GDRLLNLVEG AYQALNLTNP DKTQECWLCL
VSGPPYYEGV AVVGTYTNHS TAPASCTATS QHKLTLSEVT
GQGLCMGALP KTHQALCNTT QSAGSGSYYL AAPAGTMWAC
STGLTPCLST TMLNLTTDYC VLVELWPRII YHSPDYMYGQ
LEQRTKYKRE PVSLTLALLL GGLTMGGIAA GIGTGTTALI
KTQQFEQLHA AIQTDLNEVE KSITNLEKSL TSLSEVVLQN
RRGLDLLFLK EGGLCAALKE ECCFYADHTG LVRDSMAKLR
ERLNQRQKLF ESGQGWFEGQ FNRSPWFTTL ISTIMGPLIV
LLLILLFGPC ILNRLVQFVK DRISVVQALV LTQQYHQLKP
IEYEP (SEQ ID NO:1013; GenBank Accession
No: AAA46514).
```

In some cases, the heterologous glycoprotein used for pseudotyping is an MLV glycoprotein. A suitable MLV protein comprises an amino acid sequence having at least 80%, at least 85%, at least 90%, at least 95%, at least 98%, at least 99%, or 100%, amino acid sequence identity to the following amino acid sequence:

```
MEGSAFSKPL KDKINPWGPL IVMGILVRAG ASVQRDSPHQ
IFNVTWRVTN LMTGQTANAT SLLGTMTDTF PKLYFDLCDL
VGDYWDDPEP DIGDGCRTPG GRRRTRLYDF YVCPGHTVPI
GCGGPGEGYC GKWGCETTGQ AYWKPSSSWD LISLKRGNTP
KDQGPCYDSS VSSGVQGATP GGRCNPLVLE FTDAGRKASW
DAPKVWGLRL YRSTGADPVT RFSLTRQVLN VGPRVPIGPN
PVITDQLPPS QPVQIMLPRP PHPPPSGTVS MVPGAPPPSQ
QPGTGDRLLN LVEGAYQALN LTSPDKTQEC WLCLVSGPPY
YEGVAVLGTY SNHTSAPANC SVASQHKLTL SEVTGQGLCV
GAVPKTHQAL CNTTQKTSDG SYYLAAPAGT IWACNTGLTP
CLSTTVLNLT TDYCVLVELW PKVTYHSPDY VYGQFEKKTK
YKREPVSLTL ALLLGGLTMG GIAAGVGTGT TALVATKQFE
QLQAAIHTDL GALEKSVSAL EKSLTSLSEV VLQNRRGLDL
LFLKEGGLCA ALKEECCFYA DHTGVVRDSM AKLRERLNQR
QKLFESGQGW FEGLFNRSPW FTTLISTIMG PLIVLLLILL
LGPCILNRLV QFVKDRISVV QALILTQQYH QLKSIEPEEV
ESRE (SEQ ID NO: 1014; GenBank Accession
No: AAA46531).
```

In some cases, the heterologous glycoprotein used for pseudotyping is a polytropic mink cell focus-forming virus glycoprotein. A suitable polytropic mink cell focus-forming virus protein comprises an amino acid sequence having at least 80%, at least 85%, at least 90%, at least 95%, at least 98%, at least 99%, or 100%, amino acid sequence identity to the following amino acid sequence:

VQHDSPHQVF NVTWRVTNLM TGQTANATSL LGTMTDAFPK
LYFDLCDLIG DDWDETGLGC RTPGGRKRAR TFDFYVCPGH
TVPTGCGGPR EGYCGKWGCE TTGQAYWKPS SLWDLISLKR
GNTPQNQGPC YDSSAVSSDI KGATPGGRCN PLVLEFTDAG
KKASWDGPKV WGLRLYRSTG TDPVTRFSLT RRVLNIGPRV
PIGPNPVIID QLPPSRPVQI MLPRPPQPPP PGAASIVPET
APPSNQPGTG DRLLNLVDGA YQALNLTSPD KTQECWLCLV
AEPPYYEGVA VLGTYSNHTS APANCSVASQ HKLTLSEVTG
RGLCIGTVPK THQALCNTTL KTNKGSYYLV APAGTTWACN
TGLTPCLSAT VLNRTTDYCV LVELWPRVTY HPPSYVYSQF
EKSYRHKR (SEQ ID NO: 1015; GenBank
Accession No: 2016415A).

In some cases, the heterologous glycoprotein used for pseudotyping is a gibbon ape leukemia virus (GALV) glycoprotein. A suitable GALV protein comprises an amino acid sequence having at least 80%, at least 85%, at least 90%, at least 95%, at least 98%, at least 99%, or 100%, amino acid sequence identity to the following amino acid sequence:

MVLLPGSMLL TSNLHHLRHQ MSPGSWKRLI ILLSCVFGGG
GTSLQNKNPH QPMTLTWQVL SQTGDVVWDT KAVQPPWTWW
PTLKPDVCAL AASLESWDIP GTDVSSSKRV RPPDSDYTAA
YKQITWGAIG CSYPRARTRM ASSTFYVCPR DGRTLSEARR
CGGLESLYCK EWDCETTGTG YWLSKSSKDL ITVKWDQNSE
WTQKFQQCHQ TGWCNPLKID FTDKGKLSKD WITGKTWGLR
FYVSGHPGVQ FTIRLKITNM PAVAVGPDLV LVEQGPPRTS
LALPPPLPPR EAPPPSLPDS NSTALATSAQ TPTVRKTIVT
LNTPPPTTGD RLFDLVQGAF LTLNATNPGA TESCWLCLAM
GPPYYEAIAS SGEVAYSTDL DRCRWGTQGK LTLTEVSGHG
LCIGKVPFTH QHLCNQTLSI NSSGDHQYLL PSNHSWWACS
TGLTPCLSTS VFNQTRDFCI QVQLIPRIYY YPEEVLLQAY
DNSHPRTKRE AVSLTLAVLL GLGITAGIGT GSTALIKGPI
DLQQGLTSLQ IAIDADLRAL QDSVSKLEDS LTSLSEVVLQ
NRRGLDLLFL KEGGLCAALK EECCFYIDHS GAVRDSMKKL
KEKLDKRQLE RQKSQNWYEG WFNNSPWFTT LLSTIAGPLL
LLLLLLILGP CIINKLVQFI NDRISAVKIL VLRQKYQALE
NEGNL (SEQ ID NO: 1016; GenBank Accession
No: P21415).

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence:

(SEQ ID NO: 1017)
TSLQNKNPH QPMTLTWQVL SQTGDVVWDT KAVQPPWTWW
PTLKPDVCAL AASLESWDIP GTDVSSSKRV RPPDSDYTAA
YKQITWGAIG CSYPRARTRM ASSTFYVCPR DGRTLSEARR
CGGLESLYCK EWDCETTGTG YWLSKSSKDL ITVKWDQNSE
WTQKFQQCHQ TGWCNPLKID FTDKGKLSKD WITGKTWGLR
FYVSGHPGVQ FTIRLKITNM PAVAVGPDLV LVEQGPPRTS
LALPPPLPPR EAPPPSLPDS NSTALATSAQ TPTVRKTIVT
LNTPPPTTGD RLFDLVQGAF LTLNATNPGA TESCWLCLAM
GPPYYEAIAS SGEVAYSTDL DRCRWGTQGK LTLTEVSGHG
LCIGKVPFTH QHLCNQTLSI NSSGDHQYLL PSNHSWWACS
TGLTPCLSTS VFNQTRDFCI QVQLIPRIYY YPEEVLLQAY
DNSHPRTKRE AVSLTLAVLL GLGITAGIGT GSTALIKGPI
DLQQGLTSLQ IAIDADLRAL QDSVSKLEDS LTSLSEVVLQ
NRRGLDLLFL KEGGLCAALK EECCFYIDHS GAVRDSMKKL
KEKLDKRQLE RQKSQNWYEG WFNNSPWFTT LLSTIAGPLL
LLLLLLILGP CIINKLVQFI NDRISAVKIL VLRQKYQALE
NEGNL.

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence:

(SEQ ID NO: 1018)
TSLQNKNPH QPMTLTWQVL SQTGDVVWDT KAVQPPWTWW
PTLKPDVCAL AASLESWDIP GTDVSSSKRV RPPDSDYTAA
YKQITWGAIG CSYPRARTRM ASSTFYVCPR DGRTLSEARR
CGGLESLYCK EWDCETTGTG YWLSKSSKDL ITVKWDQNSE
WTQKFQQCHQ TGWCNPLKID FTDKGKLSKD WITGKTWGLR
FYVSGHPGVQ FTIRLKITNM PAVAVGPDLV LVEQGPPRTS
LALPPPLPPR EAPPPSLPDS NSTALATSAQ TPTVRKTIVT
LNTPPPTTGD RLFDLVQGAF LTLNATNPGA TESCWLCLAM
GPPYYEAIAS SGEVAYSTDL DRCRWGTQGK LTLTEVSGHG
LCIGKVPFTH QHLCNQTLSI NSSGDHQYLL PSNHSWWACS
TGLTPCLSTS VFNQTRDFCI QVQLIPRIYY YPEEVLLQAY
DNSHPRTKRE AVSLTLAVLL GLGITAGIGT GSTALIKGPI

-continued

DLQQGLTSLQ IAIDADLRAL QDSVSKLEDS LTSLSEVVLQ
NRRGLDLLFL KEGGLCAALK EECCFYIDHS GAVRDSMKKL
KEKLDKRQLE RQKSQNWYEG WFNNSPWFTT LLSTIAGPLL
LLLLLLILGP CIINKLVQFI NDRISAVKIL VLRQKYQALE
NEGNL.

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence:

(SEQ ID NO: 1019)
TSLQNKNPH QPMTLTWQVL SQTGDVVWDT KAVQPPWTWW
PTLKPDVCAL AASLESWDIP GTDVSSSKRV RPPDSDYTAA
YKQITWGAIG CSYPRARTRM ASSTFYVCPR DGRTLSEARR
CGGLESLYCK EWDCETTGTG YWLSKSSKDL ITVKWDQNSE
WTQKFQQCHQ TGWCNPLKID FTDKGKLSKD WITGKTWGLR
FYVSGHPGVQ FTIRLKITNM PAVAVGPDLV LVEQGPPRTS
LALPPPLPPR EAPPPSLPDS NSTALATSAQ TPTVRKTIVT
LNTPPPTTGD RLFDLVQGAF LTLNATNPGA TESCWLCLAM
GPPYYEAIAS SGEVAYSTDL DRCRWGTQGK LTLTEVSGHG
LCIGKVPFTH QHLCNQTLSI NSSGDHQYLL PSNHSWWACS
TGLTPCLSTS VFNQTRDFCI QVQLIPRIYY YPEEVLLQAY
DNSHPRTKR.

In some cases, the heterologous glycoprotein used for pseudotyping is a GALV glycoprotein. A suitable GALV protein comprises an amino acid sequence having at least 80%, at least 85%, at least 90%, at least 95%, at least 98%, at least 99%, or 100%, amino acid sequence identity to the following amino acid sequence:

(SEQ ID NO: 1020)
E AVSLTLAVLL GLGITAGIGT GSTALIKGPI DLQQGLTSLQ
IAIDADLRAL QDSVSKLEDS LTSLSEVVLQ NRRGLDLLFL
KEGGLCAALK EECCFYIDHS GAVRDSMKKL KEKLDKRQLE
RQKSQNWYEG WFNNSPWFTT LLSTIAGPLL LLLLLLILGP
CIINKLVQFI NDRISAVKIL.

In some cases, the heterologous glycoprotein used for pseudotyping is a RD114 retrovirus glycoprotein. A suitable RD114 retrovirus protein comprises an amino acid sequence having at least 80%, at least 85%, at least 90%, at least 95%, at least 98%, at least 99%, or 100%, amino acid sequence identity to the following amino acid sequence:

MKLPTGMVIL CSLIIVRAGF DDPRKAIALV QKQHGKPCEC
SGGQVSEAPP NSIQQVTCPG KTAYLMTNQK WKCRVTPKNL

-continued

TPSGGELQNC PCNTFQDSMH SSCYTEYRQC RANNKTYYTA
TLLKIRSGSL NEVQILQNPN QLLQSPCRGS INQPVCWSAT
APIHISDGGG PLDTKRVWTV QKRLEQIHKA MHPELQYHPL
ALPKVRDDLS LDARTFDILN TTFRLLQMSN FSLAQDCWLC
LKLGTPTPLA IPTPSLTYSL ADSLANASCQ IIPPLLVQPM
QFSNSSCLSS PFINDTEQID LGAVTFTNCT SVANVSSPLC
ALNGSVFLCG NNMAYTYLPQ NWTGLCVQAS LLPDIDIIPG
DEPVPIPAID HYIHRPKRAV QFIPLLAGLG ITAAFTTGAT
GLGVSVTQYT KLSHQLISDV QVLSGTIQDL QDQVDSLAEV
VLQNRRGLDL LTAEQGGICL ALQEKCCFYA NKSGIVRNKI
RTLQEELQKR RESLASNPLW TGLQGFLPYL LPLLGPLLTL
LLILTIGPCV FSRLMAFIND RLNVVHAMVL AQQYQALKAE
EEAQD (SEQ ID NO: 1021; GenBank Accession
No: YP_001497149).

In some cases, the heterologous glycoprotein used for pseudotyping is a Sendai virus (SeV) glycoprotein. A suitable SeV protein comprises an amino acid sequence having at least 80%, at least 85%, at least 90%, at least 95%, at least 98%, at least 99%, or 100%, amino acid sequence identity to the following amino acid sequence:

MTAYIQRSQC ISTSLLVVLT TLVSCQIPRD RLSNIGVIVD
EGKSLKIAGS HESRYIVLSL VPGVDFENGC GTAQVIQYKS
LLNRLLIPLR DALDLQEALI TVTNDTTQNA GAPQSRFFGA
VIGTIALGVA TSAQITAGIA LAEAREAKRD IALIKESMTK
THKSIELLQN AVGEQILALK TLQDFVNDEI KPAISELGCE
TAALRLGIKL TQHYSELLTA FGSNFGTIGE KSLTLQALSS
LYSANITEIM TTIKTGQSNI YDVIYTEQIK GTVIDVDLER
YMVTLSVKIP ILSEVPGVLI HKASSISYNI DGEEWYVTVP
SHILSRASFL GGADITDCVE SRLTYICPRD PAQLIPDSQQ
KCILGDTTRC PVTKVVDSLI PKFAFVNGGV VANCIASTCT
CGTGRRPISQ DRSKGVVFLT HDNCGLIGVN GVELYANRRG
HDATWGVQNL TVGPAIAIRP IDISLNLADA TNFLQDSKAE
LEKARKILSE VGRWYNSRET VITIIVVMVV ILVVIIVIII
VLYRLRRSML MGNPDDRIPR DTYTLEPKIR HMYTNGGFDA
MAKER (SEQ ID NO: 1022; GenBank Accession
No: P04855).

In some cases, the heterologous glycoprotein used for pseudotyping is an SeV F0 glycoprotein. A suitable SeV protein comprises an amino acid sequence having at least 80%, at least 85%, at least 90%, at least 95%, at least 98%, at least 99%, or 100%, amino acid sequence identity to the following amino acid sequence:

QIPRD RLSNIGVIVD EGKSLKIAGS HESRYIVLSL VPGVDFENGC

GTAQVIQYKS LLNRLLIPLR DALDLQEALI TVTNDTTQNA

GAPQSRFFGA VIGTIALGVA TSAQITAGIA LAEAREAKRD

IALIKESMTK THKSIELLQN AVGEQILALK TLQDFVNDEI

KPAISELGCE TAALRLGIKL TQHYSELLTA FGSNFGTIGE

KSLTLQALSS LYSANITEIM TTIKTGQSNI YDVIYTEQIK

GTVIDVDLER YMVTLSVKIP ILSEVPGVLI HKASSISYNI

DGEEWYVTVP SHILSRASFL GGADITDCVE SRLTYICPRD

PAQLIPDSQQ KCILGDTTRC PVTKVVDSLI PKFAFVNGGV

VANCIASTCT CGTGRRPISQ DRSKGVVFLT HDNCGLIGVN

GVELYANRRG HDATWGVQNL TVGPAIAIRP IDISLNLADA

TNFLQDSKAE LEKARKILSE VGRWYNSRET VITIIVVMVV

ILVVIIVIII VLYRLRRSML MGNPDDRIPR DTYTLEPKIR

HMYTNGGFDA MAEKR (SEQ ID NO: 1023; GenBank

Accession No: P04855).

In some cases, the heterologous glycoprotein used for pseudotyping is an SeV F2 glycoprotein. A suitable SeV protein comprises an amino acid sequence having at least 80%, at least 85%, at least 90%, at least 95%, at least 98%, at least 99%, or 100%, amino acid sequence identity to the following amino acid sequence:

QIPRD RLSNIGVIVD EGKSLKIAGS HESRYIVLSL VPGVDFENGC

GTAQVIQYKS LLNRLLIPLR DALDLQEALI TVTNDTTQNA

GAPQSR (SEQ ID NO: 1024; GenBank Accession

No: P04855).

In some cases, the heterologous glycoprotein used for pseudotyping is an SeV F1 glycoprotein. A suitable SeV protein comprises an amino acid sequence having at least 80%, at least 85%, at least 90%, at least 95%, at least 98%, at least 99%, or 100%, amino acid sequence identity to the following amino acid sequence:

FFGA VIGTIALGVA TSAQITAGIA LAEAREAKRD IALIKESMTK

THKSIELLQN AVGEQILALK TLQDFVNDEI KPAISELGCE

TAALRLGIKL TQHYSELLTA FGSNFGTIGE KSLTLQALSS

LYSANITEIM TTIKTGQSNI YDVIYTEQIK GTVIDVDLER

YMVTLSVKIP ILSEVPGVLI HKASSISYNI DGEEWYVTVP

SHILSRASFL GGADITDCVE SRLTYICPRD PAQLIPDSQQ

KCILGDTTRC PVTKVVDSLI PKFAFVNGGV VANCIASTCT

CGTGRRPISQ DRSKGVVFLT HDNCGLIGVN GVELYANRRG

HDATWGVQNL TVGPAIAIRP IDISLNLADA TNFLQDSKAE

LEKARKILSE VGRWYNSRET VITIIVVMVV ILVVIIVIII

-continued

VLYRLRRSML MGNPDDRIPR DTYTLEPKIR HMYTNGGFDA

MAKER (SEQ ID NO: 1025; GenBank Accession

No: P04855).

In some cases, the heterologous glycoprotein used for pseudotyping is an SeV hemagglutinin-neuraminidase glycoprotein. A suitable SeV protein comprises an amino acid sequence having at least 80%, at least 85%, at least 90%, at least 95%, at least 98%, at least 99%, or 100%, amino acid sequence identity to the following amino acid sequence:

MDGDRSKRDS YWSTSPGGST TKLVSDSERS GKVDTWLLIL

AFTQWALSIA TVIICIVIAA RQGYSMERYS MTVEALNTSN

KEVKESLTSL IRQEVITRAA NIQSSVQTGI PVLLNKNSRD

VIRLIEKSCN RQELTQLCDS TIAVHHAEGI APLEPHSFWR

CPAGEPYLSS DPEVSLLPGP SLLSGSTTIS GCVRLPSLSI

GEAIYAYSSN LITQGCADIG KSYQVLQLGY ISLNSDMFPD

LNPVVSHTYD INDNRKSCSV VATGTRGYQL CSMPIVDERT

DYSSDGIEDL VLDILDLKGR TKSHRYSNSE IDLDHPFSAL

YPSVGSGIAT EGSLIFLGYG GLTTPLQGDT KCRIQGCQQV

SQDTCNEALK ITWLGGKQVV SVLIQVNDYL SERPRIRVTT

IPITQNYLGA EGRLLKLGDQ VYIYTRSSGW HSQLQIGVLD

VSHPLTISWT PHEALSRPGN EDCNWYNTCP KECISGVYTD

AYPLSPDAAN VATVTLYANT SRVNPTIMYS NTTNIINMLR

IKDVQLEAAY TTTSCITHFG KGYCFHIIEI NQKSLNTLQP

MLFKTSIPKL CKAES (SEQ ID NO: 1026; GenBank

Accession No: BAA24391).

In some cases, the heterologous glycoprotein used for pseudotyping is a Jaagsiekte sheep retrovirus (JSRV) glycoprotein. A suitable JSRV protein comprises an amino acid sequence having at least 80%, at least 85%, at least 90%, at least 95%, at least 98%, at least 99%, or 100%, amino acid sequence identity to the following amino acid sequence:

MPKRRAGFRK GWYARQRNSL THQMQRMTLS EPTSELPTQR

QIEALMRYAW NEAHVQPPVT PTNILIMLLL LLQRIQNGAA

ATFWAYIPDP PMLQSLGWDK ETVPVYVNDT SLLGGKSDIH

ISPQQANISF YGLTTQYPMC FSYQSQHPHC IQVSADISYP

RVTISGIDEK TGMRSYRDGT GPLDIPFCDK HLSIGIGIDT

PWTLCRARIA SVYNINNANT TLLWDWAPGG TPDFPEYRGQ

HPPISSVNTA PIYQTELWKL LAAFGHGNSL YLQPNISGSK

YGDVGVTGFL YPRACVPYPF MVIQGHMEIT PSLNIYYLNC

SNCILTNCIR GVAKGEQVII VKQPAFVMLP VEITEEWYDE

TALELLQRIN TALSRPKRGL SLIILGIVSL ITLIATAVTA

SVSLAQSIQV AHTVDSLSSN VTKVMGTQEN IDKKIEDRLP

-continued

ALYDVVRVLG EQVQSINFRM KIQCHANYKW ICVTKKPYNT
SDFPWDKVKK HLQGIWFNTT VSLDLLQLHN EILDIENSPK
ATLNIADTVD NFLQNLFSNF PSLHSLWRSI IAMGAVLTFV
LIIICLAPCL IRSIVKEFLH MRVLIHKNML QHQHLMELLN
NKERGAAGDD P (SEQ ID NO: 1027; GenBank
Accession No: AB150237).

In some cases, the heterologous glycoprotein used for pseudotyping is a baculovirus gp64 glycoprotein. A suitable baculovirus protein comprises an amino acid sequence having at least 80%, at least 85%, at least 90%, at least 95%, at least 98%, at least 99%, or 100%, amino acid sequence identity to the following amino acid sequence:

MFHLLTLLLL LFINMNLYLA GEHCNVQMKN GPYRIKNLAI
TPPRETLKKD VTVTIVETDY EENVLIGYKG YYQAYGYNGG
SLDANTRLEE TMESLPLTKE DLLTWTYRQE CEVGEELIDR
WGSDSDDCYR NKDGRGVWVK TKELVKRQNN NHFAHHTCNR
SWRCGFSTAK MYSKLVCDDE TNDCKVFILD NTGKPINITT
NEVLYRDGVN MMLKSKPTFT RREEKVACLL VKDELNPDKT
REHCLIDSDI YDLSNNNWFC MFNKCIKRNV DSVVKKRPNK
WMHNLAPKYS EGATATKGDM MHIQEELMYE NDLLKMNIEL
VHAHMNKLNN IIHDLIVSIA KVDERLIGNL MNISVSSVFL
SDDTFLLMPC TNPPQHTSNC YNNSIYREGR WVFNEDTSEC
IDFNNYRELS IDDDIEFWIP TIGNTTYHDS WKDASGWSFV
AQQKSNLIMT MENTKFGGVG TSLSDITSMS EGELTAKLTT
FVFSHIVTFI LIIILIILCI CLLKK (SEQ ID NO:
1028; GenBank Accession No: YP_009182316.

In some cases, the heterologous glycoprotein used for pseudotyping is a baculovirus gp64 glycoprotein. A suitable baculovirus protein comprises an amino acid sequence having at least 80%, at least 85%, at least 90%, at least 95%, at least 98%, at least 99%, or 100%, amino acid sequence identity to the following amino acid sequence:

MLRITLLILF LVRFVSGAEH CNAQMKSGPW RIKNLPIAPP
KETLQKDVDV EIVETDLDEN VIIGYKGYYQ AYAYNGGSLD
PNTSVDETTQ TLNIDKDDLI TWGDRRKCEV GEELIDQWGS
DSDSCFKDKL GRGVWVAGKE LVKRKNNNHF AHHTCNRSWR
CGVSTAKMYT RLECDNETDD CKVTILDING TVINVTENEV
LHRDGVSMIL KQKSTFTRRT EKVACLLIKD DKSDPYSITR
EHCLIDNDIF DLSKNTWNCK FNRCIKRRSE NVVKKRPPTW
RHNEPPKHSE GTTATKGDLM HIQEELMYEN DLLRMNLELL
HAHINKLNNM MHDLIVSVAK VDERLIGNLM NNSVSSTFLS
DDTFLLMPCT NPPPHTSNCY NNSIYKEGRW VANTDSSQCI
DFRNYKELAI DDDIEFWIPT IGNTSYHESW KDASGWSFIA

-continued

QQKSNLISTM ENTKFGGHTT SLSDIGDMAK GELNATLYSF
MLGHGFSFFL IIGVIVFLIC MVRSRVRAF (SEQ ID NO:
1029; GenBank Accession No: YP_473216).

In some cases, the heterologous glycoprotein used for pseudotyping is a Chandipura virus glycoprotein. A suitable Chandipura virus protein comprises an amino acid sequence having at least 80%, at least 85%, at least 90%, at least 95%, at least 98%, at least 99%, or 100%, amino acid sequence identity to the following amino acid sequence:

MTSSVTISVI LLISFIAPSY SSLSIAFPEN TKLDWKPVTK
NTRYCPMGGE WFLEPGLQEE SFLSSTPIGA TPSKSDGFLC
HAAKWVTTCD FRWYGPKYIT HSIHNIKPTR SDCDTALASY
KSGTLVSPGF PPESCGYASV TDSEFLVIMI TPHHVGVDDY
RGHWVDPLFV GGECDQSYCD TIHNSSVWIP ADQTKKNICG
QSFTPLTVTV AYDKTKEIAA GAIVFKSKYH SHMEGARTCR
LSYCGRNGIK FPNGEWVSLD VKTKIQEKPL LPLFKECPAG
TEVRSTLQSD GAQVLTSEIQ RILDYSLCQN TWDKVERKEP
LSPLDLSYLA SKSPGKGLAY TVINGTLSFA HTRYVRMWID
GPVLKEMKGK RESPSGISSD IWTQWFKYGD MEIGPNGLLK
TAGGYKFPWH LIGMGIVDNE LHELSEANPL DHPQLPHAQS
IADDSEEIFF GDTGVSKNPV ELVTGWFTSW KESLAAGVVL
ILVVVLIYGV LRCFPVLCTT CRKPKWKKGV ERSDSFEMRI
FKPNNMRARV (SEQ ID NO: 1030; GenBank
Accession No: YP_007641380).

In some cases, the heterologous glycoprotein used for pseudotyping is a Venezuelan equine encephalitis virus glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence:

MFPFQPMYPM QPMPYRNPFA APRRPWFPRT DPFLAMQVQE
LTRSMANLTF KQRRDAPPEG PSAKKPKKEA SQKQKGGGQG
KKKKNQGKKK AKTGPPNPKA QNGNKKKTNK KPGKRQRMVM
KLESDKTFPI MLEGKINGYA CVVGGKLFRP MHVEGKIDND
VLAALKTKKA SKYDLEYADV PQNMRADTFK YTHEKPQGYY
SWHHGAVQYE NGRFTVPKGV GAKGDSGRPI LDNQGRVVAI
VLGGVNEGSR TALSVVMWNE KGVTVKYTPE NCEQWSLVTT
MCLLANVTFP CAQPPICYDR KPAETLAMLS VNVDNPGYDE
LLEAAVKCPG STEELFKEYK LTRPYMARCI RCAVGSCHSP
IAIEAVKSDG HDGYVRLQTS SQYGLDSSGN LKGRTMRYDM
HGTIKEIPLH QVSLHTSRPC HIVDGHGYFL LARCPAGDSI
TMEFKKDSVT HSCSVPYEVK FNPVGRELYT HPPEHGVEQA

-continued

CQVYAHDAQN RGAYVEMHLP GSEVDSSLVS LSGSSVTVTP
PVGTSALVEC ECGGTKISET INKTKQFSQC TKKEQCRAYR
LQNDKWVYIS DKLPKAAGAT LKGKLHVPFL LADGKCTVPL
APEPMITFGF RSVSLKLHPK NPTYLTTRQL ADEPHYTHEL
ISEPAVRNFT VTGKGWEFVW GNHPPKRFWA QETAPGNPHG
LPHEVITHYY HRYPMSTILG LSICAAIATV SVAASTWLFC
RSRVACLTPY RLTPNARIPF CLAVLCCART ARAETTWESL
DHLWNNNQQM FWIQLLIPLA ALIVVTRLLR CVCCVVPFLV
MAGAAGAGAY EHATTMPSQA GISYNTIVNR AGYAPLPISI
TPTKIKLIPT VNLEYVTCHY KTGMDSPAIK CCGSQECTPT
YRPDEQCKVF TGVYPFMWGG AYCFCDTENT QVSKAYVMKS
DDCLADHAEA YKAHTASVQA FLNITVGEHS IVTTVYVNGE
TPVNFNGVKL TAGPLSTAWT PFDRKIVQYA GEIYNYDFPE
YGAGQPGAFG DIQSRTVSSS DLYANTNLVL QRPKAGAIHV
PYTQAPSGFE QWKKDKAPSL KSTAPFGCEI YTNPIRAENC
AVGSIPLAFD IPDALFTRVS ETPTLSAAEC TLNECVYSSD
FGGIATVKYS ASKSGKCAVH VPSGTATLKE AAVELTEQGS
ATIHFSTANI HPEFRLQICT SYVTCKGDCH PPKDHIVTHP
QYHAQTFTAA VSKTAWTWLT SLLGGSAVII IIGLVLATIV
AMYVLTNQKH N (SEQ ID NO: 1031; GenBank
Accession No: AAU89534).

Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Venezuelan equine encephalitis virus E2 glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence:

STEELFKEYK LTRPYMARCI RCAVGSCHSP IAIEAVKSDG
HDGYVRLQTS SQYGLDSSGN LKGRTMRYDM HGTIKEIPLH
QVSLHTSRPC HIVDGHGYFL LARCPAGDSI TMEFKKDSVT
HSCSVPYEVK FNPVGRELYT HPPEHGVEQA CQVYAHDAQN
RGAYVEMHLP GSEVDSSLVS LSGSSVTVTP PVGTSALVEC
ECGGTKISET INKTKQFSQC TKKEQCRAYR LQNDKWVYIS
DKLPKAAGAT LKGKLHVPFL LADGKCTVPL APEPMITFGF
RSVSLKLHPK NPTYLTTRQL ADEPHYTHEL ISEPAVRNFT
VTGKGWEFVW GNHPPKRFWA QETAPGNPHG LPHEVITHYY

-continued

HRYPMSTILG LSICAAIATV SVAASTWLFC RSRVACLTPY
RLTPNARIPF CLAVLCCART ARA (SEQ ID NO: 1033;
GenBank Accession No: AAU89534).

Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Venezuelan equine encephalitis virus E1 glycoprotein. A suitable Venezuelan equine encephalitis virus protein comprises an amino acid sequence having at least 80%, at least 85%, at least 90%, at least 95%, at least 98%, at least 99%, or 100%, amino acid sequence identity to the following amino acid sequence:

Y EHATTMPSQA GISYNTIVNR AGYAPLPISI TPTKIKLIPT
VNLEYVTCHY KTGMDSPAIK CCGSQECTPT YRPDEQCKVF
TGVYPFMWGG AYCFCDTENT QVSKAYVMKS DDCLADHAEA
YKAHTASVQA FLNITVGEHS IVTTVYVNGE TPVNFNGVKL
TAGPLSTAWT PFDRKIVQYA GEIYNYDFPE YGAGQPGAFG
DIQSRTVSSS DLYANTNLVL QRPKAGAIHV PYTQAPSGFE
QWKKDKAPSL KSTAPFGCEI YTNPIRAENC AVGSIPLAFD
IPDALFTRVS ETPTLSAAEC TLNECVYSSD FGGIATVKYS
ASKSGKCAVH VPSGTATLKE AAVELTEQGS ATIHFSTANI
HPEFRLQICT SYVTCKGDCH PPKDHIVTHP QYHAQTFTAA
VSKTAWTWLT SLLGGSAVII IIGLVLATIV AMYVLTNQKH
N (SEQ ID NO: 1034; GenBank Accession No:
AAU89534).

Such a glycoprotein may be useful for targeting a VLP of the present disclosure to dendritic cells, macrophages, and cells of the spleen, lymph node, thymus, pancreas, skeletal muscle, and central nervous system.

In some cases, the heterologous glycoprotein used for pseudotyping is a Lassa virus glycoprotein. A suitable Lassa virus protein comprises an amino acid sequence having at least 80%, at least 85%, at least 90%, at least 95%, at least 98%, at least 99%, or 100%, amino acid sequence identity to the following amino acid sequence:

MGQIVTFFQE VPHVIEEVMN IVLIALSVLA VLKGLYNFAT
CGLVGLVTFL LLCGRSCTTS LYKGVYELQT LELNMETLNM
TMPLSCTKNN SHHYIMVGNE TGLELTLTNT SIINHKFCNL
SDAHKKNLYD HALMSIISTF HLSIPNFNQY EAMSCDFNGG
KISVQYNLSH SYAGDAANHC GTVANGVLQT FMRMAWGGSY
IALDSGRGNW DCIMTSYQYL IIQNTTWEDH CQFSRPSPIG
YLGLLSQRTR DIYISRRLLG TFTWTLSDSE GKDTPGGYCL
TRWMLIEAEL KCFGNTAVAK CNEKHDEEFC DMLRLFDFNK
QAIQRLKAEA QMSIQLINKA VNALINDQLI MKNHLRDIMG

-continued

IPYCNYSKYW YLNHTTTGRT SLPKCWLVSN GSYLNETHFS
DDIEQQADNM ITEMLQKEYM ERQGKTPLGL VDLFVFSTSF
YLISIFLHLV KIPTHRHIVG KSCPKPHRLN HMGICSCGLY
KQPGVPVKWK R (SEQ ID NO: 1035; GenBank
Accession No: ADY11070).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence:

MEAVIKMRRA LFLQAFLTGR PGKASKKDPK KNPLATSKKD
PEKTPLLPTR VNYILIIGVL VLCEVTGVRA DVHLLEQPGN
LWITWANRTG QTDFCLSTQS ATSPFQTCLI GIPSPISEGD
FKGYVSDNCT TLGTDRLVSS ASITGGPDNS TTLTYRKVSC
LLLKLNVSMW NEPPELQLLG SQSLPNITDI TQISGVAGGC
VGFRPKGVPW YLGWSQGEAT RFLLRHPSFS NLTGPFTVVT
ADRHNLFMGS EYCGAYGYRF WEIYNCSQEG QQYRCGKARR
PRPQSPETQC TRQGGIWVNR SKEINETEPF SFTVNCTASN
LGNASGCCGK AGTILPGIWV DSTQGNFTKP KALPPAIFLI
CGDRAWQGIP SRPVGGPCYL GKLTMLAPNH TDILKILANS
SRTGIRRRRS VSHLDDTCSD EVQLWGPTAR IFASILAPGV
AAAQALREIE RLACWSVKQA NLTTSLLGDL LDDVTSIRHA
VLQNRAAIDF LLLAHGHGCE DIAGMCCFNL SDHSESIQKK
FQLMKEHVNK IGVDSDPIGS WLRGLFGGIG GWAVHLLKGL
LLGLVVILLL VVCLPCFLQF VSSSIRKMIN NSVSYHTEYR
KMQGGAV (SEQ ID NO: 1036; GenBank Accession
No: ADO34853).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence:

MEAVIKMRRA LFLQAFLTGH PGKVSKKDSK KKPPATGKRD
PEKTPLLPTR VNYILIIGVL VLCEVTGVRA DVHLLEQPGN
LWITWANRTG QTDFCLSTQS ATSPFQTCLI GIPSPISEGD
FKGYVSGNCT ALGTHRLVSS GIHGGPDNST TLTYRKVSCL
LLKLNVSLLD EPSELQLLGS QSLPNITNIT QIPSVAGGCI
GFTPYGSPAG VYGWDRRQVT HILLTDPGSN PFFNKASNSS
KPFTVVTADR HNLFMGSEYC GAYGYRFWEM YNCSQMRQNW

-continued

SICMDVWGRG LPESWCTSTG GIWVNQSKEI NETEPFSFTA
NCTGSNLGNV SGCCGESITI LPPGAWVDST QGSFTKPKAL
PPGIFLICGD RAWQGIPSRP VGGPCYLGKL TMLAPNHTDI
LKILANSSQT GVRHKRSVTH LDDTCSDEVQ LWGPTARIFA
SILAPGVAAA QALREIERLA CWSVKQANLT TSLLGDLLDD
VTSIRHAVLQ NRAAIDFLLL AHGHGCEDIA GMCCFNLSDH
SESIQKKFQL MKEHVNKIGV DSDPIGSWLR GLFGGIGEWA
VHLLKGLLLG LVVILLLVVC LPCFLQFVSS SIRKMINNSI
SYHTEYRKMQ GGAV (SEQ ID NO: 1037; GenBank
Accession No: AEF97639).

In some cases, the heterologous glycoprotein used for pseudotyping is an avian leukosis virus glycoprotein. A suitable avian leukosis virus protein comprises an amino acid sequence having at least 80%, at least 85%, at least 90%, at least 95%, at least 98%, at least 99%, or 100%, amino acid sequence identity to the following amino acid sequence:

MEAVIKAFLT GHPGKVSKKD SKKKPPATSK KDPEKTPLLP
SRGYFFFPTI LVCVVIISVV PGVGGVHLLR QPGNVWVTWA
NKTGRTDFCL SLQSATSPFR TCLIGIPQYP LNTFKGYVTN
VTACDNDADL ASQTACLIKA LNTTLPWDPQ ELDILGSQMI
KNGTTRTCVT FGSVCYKENN RSRVCHNFDG NFNGTGGAEA
ELRDFIAKWK SDDLLIRPYV NQSWTMVSPI NVESFSISRR
YCGFTSNETR YYRGDLSNWC GSKRGKWSAG YSNRTKCSSN
TTGCGGNCTT EWNYYAYGFT FGKQPEVLWN NGTAKALPPG
IFLICGDRAW QGIPRNALGG PCYLGQLTML SPNFTTWITY
GPNITGHRRS RRAIRGLSPD CSDEVQLWSA TARIFASFFA
PGVAAAQALK EIERLACWSV KQANLTSLIL NAMLEDMNSI
RHAVLQNRAA IDFLLLAQGH GCQDVEGMCC FNLSDHSESI
HKALQAMKEH TEKIQVEDDP IGDWFTRTFG DLGRWLAKGV
KTLLFALLVI VCLLAIIPCI IKCFQDCLSR TMNQFMDERI
RYHRIREQL (SEQ ID NO: 1038; GenBank
Accession No: AWM62167).

In some cases, the heterologous glycoprotein used for pseudotyping is a human T-lymphotropic virus 1 (HTLV-1) glycoprotein. A suitable HTLV-1 protein comprises an amino acid sequence having at least 80%, at least 85%, at least 90%, at least 95%, at least 98%, at least 99%, or 100%, amino acid sequence identity to the following amino acid sequence:

MGKFLATLIL FFQFCPLILG DYSPSCCTLT VGVSSYHSKP
CNPAQPVCSW TLDLLALSAD QALQPPCPNL VSYSSYHATY
SLYLFPHWIK KPNRNGGGYY SASYSDPCSL KCPYLGCQSW
TCPYTGAVSS PYWKFQQDVN FTQEVSHLNI NLHFSKCGFP

-continued

FSLLVDAPGY DPIWFLNTEP SQLPPTAPPL LSHSNLDHIL
EPSIPWKSKL LTLVQLTLQS TNYTCIVCID RASLSTWHVL
YSPNVSVPSL SSTPLLYPSL ALPAPHLTLP FNWTHCFDPQ
IQAIVSSPCH NSLILPPFSL SPVPTLGSRS RRAVPVAVWL
VSALAMGAGV AGGITGSMSL ASGKSLLHEV DKDISQLTQA
IVKNHKNLLK IAQYAAQNRR GLDLLFWEQG GLCKALQEQC
CFLNITNSHV SILQERPPLE NRVLTGWGLN WDLGLSQWAR
EALQTGITLV ALLLLVILAG PCILRQLRHL PSRVRYPHYS
LINPESSL (SEQ ID NO: 1039; GenBank
Accession No: AAU04884).

Such a glycoprotein may be useful for targeting a VLP of the present disclosure to CD4+ and CD8+ T cells.

In some cases, the heterologous glycoprotein used for pseudotyping is a human foamy virus gp130 glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence:

MAPPMTLQQW IIWKKMNKAH EALQNTTTVT EQQKEQIILD
IQNEEVQPTR RDKFRYLLYT CCATSSRVLA WMFLVCILLI
IVLVSCFVTI SRIQWNKDIQ VLGPVIDWNV TQRAVYQPLQ
TRRIARSLRM QHPVPKYVEV NMTSIPQGVY YEPHPEPIVV
KERVLGLSQI LMINSENIAN NANLTQEVKK LLTEMVNEEM
QSLSDVMIDF EIPLGDPRDQ EQYIHRKCYQ EFANCYLVKY
KEPKPWPKEG LIADQCPLPG YHAGLTYNRQ SIWDYYIKVE
SIRPANWTTK SKYGQARLGS FYIPSSLRQI NVSHVLFCSD
QLYSKWYNIE NTIEQNERFL LNKLNNLTSG TSVLKKRALP
KDWSSQGKNA LFREINVLDI CSKPESVILL NTSYYSFSLW
EGDCNFTKDM ISQLVPECDG FYNNSKWMHM HPYACRFWRS
KKNEKEETKC RDGETKRCLY YPLWDSPEST YDFGYLAYQK
NFPSPICIEQ QKIRDQDYEV YSLYQERKIA SKAYGIDTVL
FSLKNFLNYT GTPVNEMPNA RAFVGLIDPK FPPSYPNVTR
EHYTSCNNRK RRSVDNNYAK LRSMGYALTG AVQTLSQISD
INDENLQQGI YLLRDHVITL MEATLHDISV MEGMFAVQHL
HTHLNHLKTM LLERRIDWTY MSSTWLQQQL QKSDDEMKVI
KRIARSLVYY VKQTHSSPTA TAWEIGLYYE LVIPKHIYLN
NWNVVNIGHL VKSAGQLTHV TIAHPYEIIN KECVETIYLH
LEDCTRQDYV ICDVVKIVQP CGNSSDTSDC PVWAEAVKEP
FVQVNPLKNG SYLVLASSTD CQIPPYVPSI VTVNETTSCF
GLDFKRPLVA EERLSFEPRL PNLQLRLPHL VGIIAKIKGI
KIEVTSSGES IKEQIERAKA ELLRLDIHEG DTPAWIQQLA

-continued

AATKDVWPAA ASALQGIGNF LSGTAQGIFG TAFSLLGYLK
PILIGVGVIL LVILIFKIVS WIPTKKKNQ (SEQ ID NO:
1040; GenBank Accession No: P14351).

In some cases, the heterologous glycoprotein used for pseudotyping is a human foamy virus glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1041)
SLRM QHPVPKYVEV NMTSIPQGVY YEPHPEPIVV KERVLGLSQI
LMINSENIAN NANLTQEVKK LLTEMVNEEM QSLSDVMIDF
EIPLGDPRDQ EQYIHRKCYQ EFANCYLVKY KEPKPWPKEG
LIADQCPLPG YHAGLTYNRQ SIWDYYIKVE SIRPANWTTK
SKYGQARLGS FYIPSSLRQI NVSHVLFCSD QLYSKWYNIE
NTIEQNERFL LNKLNNLTSG TSVLKKRALP KDWSSQGKNA
LFREINVLDI CSKPESVILL NTSYYSFSLW EGDCNFTKDM
ISQLVPECDG FYNNSKWMHM HPYACRFWRS KKNEKEETKC
RDGETKRCLY YPLWDSPEST YDFGYLAYQK NFPSPICIEQ
QKIRDQDYEV YSLYQERKIA SKAYGIDTVL FSLKNFLNYT
GTPVNEMPNA RAFVGLIDPK FPPSYPNVTR EHYTSCNNRK
RR.

In some cases, the heterologous glycoprotein used for pseudotyping is a human foamy virus glycoprotein. A suitable human foamy virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1042)
SVDNNYAK LRSMGYALTG AVQTLSQISD INDENLQQGI
YLLRDHVITL MEATLHDISV MEGMFAVQHL HTHLNHLKTM
LLERRIDWTY MSSTWLQQQL QKSDDEMKVI KRIARSLVYY
VKQTHSSPTA TAWEIGLYYE LVIPKHIYLN NWNVVNIGHL
VKSAGQLTHV TIAHPYEIIN KECVETIYLH LEDCTRQDYV
ICDVVKIVQP CGNSSDTSDC PVWAEAVKEP FVQVNPLKNG
SYLVLASSTD CQIPPYVPSI VTVNETTSCF GLDFKRPLVA
EERLSFEPRL PNLQLRLPHL VGIIAKIKGI KIEVTSSGES
IKEQIERAKA ELLRLDIHEG DTPAWIQQLA AATKDVWPAA
ASALQGIGNF LSGTAQGIFG TAFSLLGYLK PILIGVGVIL
LVILIFKIVS WIPTKKKNQ.

In some cases, the heterologous glycoprotein used for pseudotyping is a visna-maedi virus gp160 glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence:

MASKESKPSR TTRRGMEPPL RETWNQVLQE LVKRQQQEEE
EQQGLVSGKK KSWVSIDLLG TEGKDIKKVN IWEPCEKWFA
QVVWGVLWVL QIVLWGCLMW EVRKGNQCQA EEVIALVSDP
GGFQRVQHVE TVPVTCVTKN FTQWGCQPEG AYPDPELEYR
NISREILEEV YKQDWPWNTY HWPLWQMENM RQWMKENEKE
YKERTNKTKE DIDDLVAGRI RGRFCVPYPY ALLRCEEWCW
YPESINQETG HAEKIKINCT KAKAVSCTEK MSLAAVQRVY
WEKEDEESMK FLNIKACNIS LRCQDEGKSP GGCVQGYPIP
KGAEIIPEAM KYLRGKKSRY GGIKDKNGEL KLPLSVRVWV
RMANLSGWVN GTPPYWSARI NGSTGINGTR WYGIGTLHHL
GCNISSNPER GICNFTGELW IGGDKFPYYY TPSWNCSQNW
TGHPVWHVFR YLDMTEHMTS RCIQRPKRHN ITVGNGTITG
NCSVTNWDGC NCTRSGNHLY NSTSGGLLVI ICRQNSTITG
IMGTNTNWTT MWNIYQNCSR CNNSSLDRTG SGTLGTVNNL
KCSLPHRNES NKWTCKSQRD SYIAGRDFWG KVKAKYSCES
NLGGLDSMMH QQMLLQRYQV IRVRAYTYGV VEMPQSYMEA
QGENKRSRRN LQRKKRGIGL VIVLAIMAII AAAGAGLGVA
NAVQQSYTRT AVQSLANATA AQQEVLEASY AMVQHIAKGI
RILEARVARV EALVDRMMVY QELDCWHYQH YCVTSTRSEV
ANYVNWTRFK DNCTWQQWEE EIEQHEGNLS LLLREAALQV
HIAQRDARRI PDAWKAIQEA FNWSSWFSWL KYIPWIIMGI
VGLMCFRILM CVISMCLQAY KQVKQIRYTQ VTVVIEAPVE
LEEKQKRNGD GTNGCASLER ERRTSHRSFI QIWRATWWAW
KTSPWRHNWR TMPYITLLPI LVIWQWMEEN GWNGENQHKK
KKERVDCQDR EQMPTLENDY VEL (SEQ ID NO: 1043;
GenBank Accession No: P35954).

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1044)
QCQA EEVIALVSDP GGFQRVQHVE TVPVTCVTKN FTQWGCQPEG
AYPDPELEYR NISREILEEV YKQDWPWNTY HWPLWQMENM
RQWMKENEKE YKERTNKTKE DIDDLVAGRI RGRFCVPYPY
ALLRCEEWCW YPESINQETG HAEKIKINCT KAKAVSCTEK
MSLAAVQRVY WEKEDEESMK FLNIKACNIS LRCQDEGKSP
GGCVQGYPIP KGAEIIPEAM KYLRGKKSRY GGIKDKNGEL
KLPLSVRVWV RMANLSGWVN GTPPYWSARI NGSTGINGTR
WYGIGTLHHL GCNISSNPER GICNFTGELW IGGDKFPYYY
TPSWNCSQNW TGHPVWHVFR YLDMTEHMTS RCIQRPKRHN

-continued

ITVGNGTITG NCSVTNWDGC NCTRSGNHLY NSTSGGLLVI
ICRQNSTITG IMGTNTNWTT MWNIYQNCSR CNNSSLDRTG
SGTLGTVNNL KCSLPHRNES NKWTCKSQRD SYIAGRDFWG
KVKAKYSCES NLGGLDSMMH QQMLLQRYQV IRVRAYTYGV
VEMPQSYMEA QGENKRSRRN LQRKKRGIGL VIVLAIMAII
AAAGAGLGVA NAVQQSYTRT AVQSLANATA AQQEVLEASY
AMVQHIAKGI RILEARVARV EALVDRMMVY QELDCWHYQH
YCVTSTRSEV ANYVNWTRFK DNCTWQQWEE EIEQHEGNLS
LLLREAALQV HIAQRDARRI PDAWKAIQEA FNWSSWFSWL
KYIPWIIMGI VGLMCFRILM CVISMCLQAY KQVKQIRYTQ
VTVVIEAPVE LEEKQKRNGD GTNGCASLER ERRTSHRSFI
QIWRATWWAW KTSPWRHNWR TMPYITLLPI LVIWQWMEEN
GWNGENQHKK KKERVDCQDR EQMPTLENDY VEL.

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1045)
QCQA EEVIALVSDP GGFQRVQHVE TVPVTCVTKN FTQWGCQPEG
AYPDPELEYR NISREILEEV YKQDWPWNTY HWPLWQMENM
RQWMKENEKE YKERTNKTKE DIDDLVAGRI RGRFCVPYPY
ALLRCEEWCW YPESINQETG HAEKIKINCT KAKAVSCTEK
MSLAAVQRVY WEKEDEESMK FLNIKACNIS LRCQDEGKSP
GGCVQGYPIP KGAEIIPEAM KYLRGKKSRY GGIKDKNGEL
KLPLSVRVWV RMANLSGWVN GTPPYWSARI NGSTGINGTR
WYGIGTLHHL GCNISSNPER GICNFTGELW IGGDKFPYYY
TPSWNCSQNW TGHPVWHVFR YLDMTEHMTS RCIQRPKRHN
ITVGNGTITG NCSVTNWDGC NCTRSGNHLY NSTSGGLLVI
ICRQNSTITG IMGTNTNWTT MWNIYQNCSR CNNSSLDRTG
SGTLGTVNNL KCSLPHRNES NKWTCKSQRD SYIAGRDFWG
KVKAKYSCES NLGGLDSMMH QQMLLQRYQV IRVRAYTYGV
VEMPQSYMEA QGENKRSRRN LQRKKRGIGL VIVLAIMAII
AAAGAGLGVA NAVQQSYTRT AVQSLANATA AQQEVLEASY
AMVQHIAKGI RILEARVARV EALVDRMMVY QELDCWHYQH
YCVTSTRSEV ANYVNWTRFK DNCTWQQWEE EIEQHEGNLS
LLLREAALQV HIAQRDARRI PDAWKAIQEA FNWSSWFSWL
KYIPWIIMGI VGLMCFRILM CVISMCLQAY KQVKQIRYTQ
VTVVIEAPVE LEEKQKRNGD GTNGCASLER ERRTSHRSFI
QIWRATWWAW KTSPWRHNWR TMPYITLLPI LVIWQWMEEN
GWNGENQHKK KKERVDCQDR EQMPTLENDY VEL.

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1046)

QCQA EEVIALVSDP GGFQRVQHVE TVPVTCVTKN FTQWGCQPEG
AYPDPELEYR NISREILEEV YKQDWPWNTY HWPLWQMENM
RQWMKENEKE YKERTNKTKE DIDDLVAGRI RGRFCVPYPY
ALLRCEEWCW YPESINQETG HAEKIKINCT KAKAVSCTEK
MSLAAVQRVY WEKEDEESMK FLNIKACNIS LRCQDEGKSP
GGCVQGYPIP KGAEIIPEAM KYLRGKKSRY GGIKDKNGEL
KLPLSVRVWV RMANLSGWVN GTPPYWSARI NGSTGINGTR
WYGIGTLHHL GCNISSNPER GICNFTGELW IGGDKFPYYY
TPSWNCSQNW TGHPVWHVFR YLDMTEHMTS RCIQRPKRHN
ITVGNGTITG NCSVTNWDGC NCTRSGNHLY NSTSGGLLVI
ICRQNSTITG IMGTNTNWTT MWNIYQNCSR CNNSSLDRTG
SGTLGTVNNL KCSLPHRNES NKWTCKSQRD SYIAGRDFWG
KVKAKYSCES NLGGLDSMMH QQMLLQRYQV IRVRAYTYGV
VEMPQSYMEA QGENKRSRRN LQRKKR.

In some cases, the heterologous glycoprotein used for pseudotyping is a visna-maedi virus glycoprotein. A suitable visna-maedi virus protein comprises an amino acid sequence having at least 80%, at least 85%, at least 90%, at least 95%, at least 98%, at least 99%, or 100%, amino acid sequence identity to the following amino acid sequence:

(SEQ ID NO: 1047)

GIGL VIVLAIMAII AAAGAGLGVA NAVQQSYTRT AVQSLANATA
AQQEVLEASY AMVQHIAKGI RILEARVARV EALVDRMMVY
QELDCWHYQH YCVTSTRSEV ANYVNWTRFK DNCTWQQWEE
EIEQHEGNLS LLLREAALQV HIAQRDARRI PDAWKAIQEA
FNWSSWFSWL KYIPWIIMGI VGLMCFRILM CVISMCLQAY
KQVKQIRYTQ VTVVIEAPVE LEEKQKRNGD GTNGCASLER
ERRTSHRSFI QIWRATWWAW KTSPWRHNWR TMPYITLLPI
LVIWQWMEEN GWNGENQHKK KKERVDCQDR EQMPTLENDY VEL.

In some cases, the heterologous glycoprotein used for pseudotyping is a severe acute respiratory syndrome-associated coronavirus (SARS-CoV) spike glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence:

MFIFLLFLTL TSGSDLDRCT TFDDVQAPNY TQHTSSMRGV
YYPDEIFRSD TLYLTQDLFL PFYSNVTGFH TINHTFGNPV
IPFKDGIYFA ATEKSNVVRG WVFGSTMNNK SQSVIIINNS

-continued

TNVVIRACNF ELCDNPFFAV SKPMGTQTHT MIFDNAFNCT
FEYISDAFSL DVSEKSGNFK HLREFVFKNK DGFLYVYKGY
QPIDVVRDLP SGFNTLKPIF KLPLGINITN FRAILTAFSP
AQDIWGTSAA AYFVGYLKPT TFMLKYDENG TITDAVDCSQ
NPLAELKCSV KSFEIDKGIY QTSNFRVVPS GDVVRFPNIT
NLCPFGEVFN ATKFPSVYAW ERKKISNCVA DYSVLYNSTF
FSTFKCYGVS ATKLNDLCFS NVYADSFVVK GDDVRQIAPG
QTGVIADYNY KLPDDFMGCV LAWNTRNIDA TSTGNYNYKY
RYLRHGKLRP FERDISNVPF SPDGKPCTPP ALNCYWPLND
YGFYTTTGIG YQPYRVVVLS FELLNAPATV CGPKLSTDLI
KNQCVNFNFN GLTGTGVLTP SSKRFQPFQQ FGRDVSDFTD
SVRDPKTSEI LDISPCSFGG VSVITPGTNA SSEVAVLYQD
VNCTDVSTAI HADQLTPAWR IYSTGNNVFQ TQAGCLIGAE
HVDTSYECDI PIGAGICASY HTVSLLRSTS QKSIVAYTMS
LGADSSIAYS NNTIAIPTNF SISITTEVMP VSMAKTSVDC
NMYICGDSTE CANLLLQYGS FCTQLNRALS GIAAEQDRNT
REVFAQVKQM YKTPTLKYFG GFNFSQILPD PLKPTKRSFI
EDLLFNKVTL ADAGFMKQYG ECLGDINARD LICAQKFNGL
TVLPPLLTDD MIAAYTAALV SGTATAGWTF GAGAALQIPF
AMQMAYRFNG IGVTQNVLYE NQKQIANQFN KAISQIQESL
TTTSTALGKL QDVVNQNAQA LNTLVKQLSS NFGAISSVLN
DILSRLDKVE AEVQIDRLIT GRLQSLQTYV TQQLIRAAEI
RASANLAATK MSECVLGQSK RVDFCGKGYH LMSFPQAAPH
GVVFLHVTYV PSQERNFTTA PAICHEGKAY FPREGVFVFN
GTSWFITQRN FFSPQIITTD NTFVSGNCDV VIGIINNTVY
DPLQPELDSF KEELDKYFKN HTSPDVDLGD ISGINASVVN
IQKEIDRLNE VAKNLNESLI DLQELGKYEQ YIKWPWYVWL
GFIAGLIAIV MVTILLCCMT SCCSCLKGAC SCGSCCKFDE
DDSEPVLKGV KLHYT (SEQ ID NO: 1048;
GenBank Accession No: ABA02260).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a SARS-CoV S2 glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence:

CDI PIGAGICASY HTVSLLRSTS QKSIVAYTMS LGADSSIAYS
NNTIAIPTNF SISITTEVMP VSMAKTSVDC NMYICGDSTE

-continued

```
CANLLLQYGS FCTQLNRALS GIAAEQDRNT REVFAQVKQM
YKTPTLKYFG GFNFSQILPD PLKPTKRSFI EDLLFNKVTL
ADAGFMKQYG ECLGDINARD LICAQKFNGL TVLPPLLTDD
MIAAYTAALV SGTATAGWTF GAGAALQIPF AMQMAYRFNG
IGVTQNVLYE NQKQIANQFN KAISQIQESL TTTSTALGKL
QDVVNQNAQA LNTLVKQLSS NFGAISSVLN DILSRLDKVE
AEVQIDRLIT GRLQSLQTYV TQQLIRAAEI RASANLAATK
MSECVLGQSK RVDFCGKGYH LMSFPQAAPH GVVFLHVTYV
PSQERNFTTA PAICHEGKAY FPREGVFVFN GTSWFITQRN
FFSPQIITTD NTFVSGNCDV VIGIINNTVY DPLQPELDSF
KEELDKYFKN HTSPDVDLGD ISGINASVVN IQKEIDRLNE
VAKNLNESLI DLQELGKYEQ YIKWPWYVWL GFIAGLIVIV
MVTILLCCMT SCCSCLKGAC SCGSCCKFDE DDSEPVLKGV KL
(SEQ ID NO: 1049; GenBank Accession No: ABD73002).
```

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a SARS-CoV spike receptor binding domain glycoprotein. A suitable SARS-CoV protein comprises an amino acid sequence having at least 80%, at least 85%, at least 90%, at least 95%, at least 98%, at least 99%, or 100%, amino acid sequence identity to the following amino acid sequence:

```
PNIT NLCPFGEVFN ATKFPSVYAW ERKKISNCVA DYSVLYNSTF
FSTFKCYGVS ATKLNDLCFS NVYADSFVVK GDDVRQIAPG
QTGVIADYNY KLPDDFMGCV LAWNTRNIDA TSTGNYNYKY
RYLRHGKLRP FERDISNVPF SPDGKPCTPP ALNCYWPLND
YGFYTTTGIG YQPYRVVVLS FELLNAPATV CGPKLSTDLI
KNQCVNFNFN GLTGTGVLTP SSKRFQPFQQ FGRDVSDFTD
SVRDPKTSE (SEQ ID NO: 1050;
GenBank Accession No: ABD73002).
```

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a respiratory syncytial virus (RSV) glycoprotein G. A suitable RSV protein comprises an amino acid sequence having at least 80%, at least 85%, at least 90%, at least 95%, at least 98%, at least 99%, or 100%, amino acid sequence identity to the following amino acid sequence:

```
MSKNKDQRTA KTLERTWDTL NHLLFISSCL YKLNLKSVAQ
ITLSILAMII STSLIIAAII FIASANHKVT PTTAIIQDAT
SQIKNTTPTY LTQNPQLGIS PSNPSEITSQ ITTILASTTP
GVKSTLQSTT VKTKNTTTTQ TQPSKPTTKQRQNKPPSKPN
NDFHFEVFNF VPCSICSNNP TCWAICKRIP
NKKPGKKTTTKPTKKPTLKT TKKDPKPQTT KSKEVPTTKP
TEEPTINTTK TNIITTLLTS NTTGNPELTS QMETFHSTSS
EGNPSPSQVS TTSEYPSQPS SPPNTPRQ
(SEQ ID NO: 1051; UniProtKB: P03423-1).
```

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV glycoprotein F. A suitable RSV protein comprises an amino acid sequence having at least 80%, at least 85%, at least 90%, at least 95%, at least 98%, at least 99%, or 100%, amino acid sequence identity to the following amino acid sequence:

```
MELLILKANA ITTILTAVTF CFASGQNITE EFYQSTCSAV
SKGYLSALRT GWYTSVITIE LSNIKENKCN GTDAKVKLIK
QELDKYKNAV TELQLLMQST PPTNNRARRE LPRFMNYTLN
NAKKTNVTLS KKRKRRFLGF LLGVGSAIAS GVAVSKVLHL
EGEVNKIKSA LLSTNKAVVS LSNGVSVLTS KVLDLKNYID
KQLLPIVNKQ SCSISNIETV IEFQQKNNRL LEITREFSVN
AGVTTPVSTY MLTNSELLSL INDMPITNDQ KKLMSNNVQI
VRQQSYSIMS IIKEEVLAYV VQLPLYGVID TPCWKLHTSP
LCTTNTKEGS NICLTRTDRG WYCDNAGSVS FFPQAETCKV
QSNRVFCDTM NSLTLPSEIN LCNVDIFNPK YDCKIMTSKT
DVSSSVITSL GAIVSCYGKT KCTASNKNRG IIKTFSNGCD
YVSNKGMDTV SVGNTLYYVN KQEGKSLYVK GEPIINFYDP
LVFPSDEFDA SISQVNEKIN QSLAFIRKSD ELLHNVNAGK
STTNIMITTI IIVIIVILLS LIAVGLLLYC KARSTPVTLS
KDQLSGINNI AFSN
(SEQ ID NO: 1052; GenBank Accession No: P03420).
```

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV glycoprotein. A suitable RSV protein comprises an amino acid sequence having at least 80%, at least 85%, at least 90%, at least 95%, at least 98%, at least 99%, or 100%, amino acid sequence identity to the following amino acid sequence:

(SEQ ID NO: 1053)
QNITE EFYQSTCSAV SKGYLSALRT GWYTSVITIE LSNIKENKCN

GTDAKVKLIK QELDKYKNAV TELQLLMQST PPTNNRARRE

LPRFMNYTLN NAKKTNVTLS KKRKRRFLGF LLGVGSAIAS

GVAVSKVLHL EGEVNKIKSA LLSTNKAVVS LSNGVSVLTS

KVLDLKNYID KQLLPIVNKQ SCSISNIETV IEFQQKNNRL

LEITREFSVN AGVTTPVSTY MLTNSELLSL INDMPITNDQ

KKLMSNNVQI VRQQSYSIMS IIKEEVLAYV VQLPLYGVID

TPCWKLHTSP LCTTNTKEGS NICLTRTDRG WYCDNAGSVS

FFPQAETCKV QSNRVFCDTM NSLTLPSEIN LCNVDIFNPK

YDCKIMTSKT DVSSSVITSL GAIVSCYGKT

KCTASNKNRG IIKTFSNGCD YVSNKGMDTV SVGNTLYYVN

KQEGKSLYVK GEPIINFYDP LVFPSDEFDA SISQVNEKIN

QSLAFIRKSD ELLHNVNAGK STTNIMITTI IIVIIVILLS

LIAVGLLLYC KARSTPVTLS KDQLSGINNI AFSN.

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F0 glycoprotein. A suitable RSV protein comprises an amino acid sequence having at least 80%, at least 85%, at least 90%, at least 95%, at least 98%, at least 99%, or 100%, amino acid sequence identity to the following amino acid sequence:

QNITE EFYQSTCSAV SKGYLSALRT GWYTSVITIE

LSNIKENKCN GTDAKVKLIK QELDKYKNAV TELQLLMQST

PPTNNRARRE LPRFMNYTLN NAKKTNVTLS KKRKRRFLGF

LLGVGSAIAS GVAVSKVLHL EGEVNKIKSA LLSTNKAVVS

LSNGVSVLTS KVLDLKNYID KQLLPIVNKQ SCSISNIETV

IEFQQKNNRL LEITREFSVN AGVTTPVSTY MLTNSELLSL

INDMPITNDQ KKLMSNNVQI VRQQSYSIMS IIKEEVLAYV

VQLPLYGVID TPCWKLHTSP LCTTNTKEGS NICLTRTDRG

WYCDNAGSVS FFPQAETCKV QSNRVFCDTM NSLTLPSEIN

LCNVDIFNPK YDCKIMTSKT DVSSSVITSL GAIVSCYGKT

KCTASNKNRG IIKTFSNGCD YVSNKGMDTV SVGNTLYYVN

KQEGKSLYVK GEPIINFYDP LVFPSDEFDA SISQVNEKIN

QSLAFIRKSD ELLHNVNAGK STTNIMITTI IIVIIVILLS

LIAVGLLLYC KARSTPVTLS KDQLSGINNI AFSN (SEQ ID NO: 1054; GenBank Accession No: P03420).

Such a glycoprotein may be useful for targeting a VLP of the present disclosure to cells of respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F2 glycoprotein. A suitable RSV protein comprises an amino acid sequence having at least 80%, at least 85%, at least 90%, at least 95%, at least 98%, at least 99%, or 100%, amino acid sequence identity to the following amino acid sequence:

QNITE EFYQSTCSAV SKGYLSALRT GWYTSVITIE

LSNIKENKCN GTDAKVKLIK QELDKYKNAV TELQLLMQST

PPTNNRARRE LPRFMNYTLN NAKKTNVTLS KKRKRR (SEQ ID NO: 1055; GenBank Accession No: P03420).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is an RSV F1 glycoprotein. A suitable RSV protein comprises an amino acid sequence having at least 80%, at least 85%, at least 90%, at least 95%, at least 98%, at least 99%, or 100%, amino acid sequence identity to the following amino acid sequence:

FLGF LLGVGSAIAS GVAVSKVLHL EGEVNKIKSA LLSTNKAVVS

LSNGVSVLTS KVLDLKNYID KQLLPIVNKQ SCSISNIETV

IEFQQKNNRL LEITREFSVN AGVTTPVSTY MLTNSELLSL

INDMPITNDQ KKLMSNNVQI VRQQSYSIMS IIKEEVLAYV

VQLPLYGVID TPCWKLHTSP LCTTNTKEGS NICLTRTDRG

WYCDNAGSVS FFPQAETCKV QSNRVFCDTM NSLTLPSEIN

LCNVDIFNPK YDCKIMTSKT DVSSSVITSL GAIVSCYGKT

KCTASNKNRG IIKTFSNGCD YVSNKGMDTV SVGNTLYYVN

KQEGKSLYVK GEPIINFYDP LVFPSDEFDA SISQVNEKIN

QSLAFIRKSD ELLHNVNAGK STTNIMITTI IIVIIVILLS

LIAVGLLLYC KARSTPVTLS KDQLSGINNI AFSN (SEQ ID NO: 1056; GenBank Accession No: P03420).

Such a glycoprotein may be useful for targeting a VLP of the present disclosure to cells of the lung/respiratory tract.

In some cases, the heterologous glycoprotein used for pseudotyping is an RSV glycoprotein. A suitable RSV protein comprises an amino acid sequence having at least 80%, at least 85%, at least 90%, at least 95%, at least 98%, at least 99%, or 100%, amino acid sequence identity to the following amino acid sequence:

(SEQ ID NO: 1057)
QNITE EFYQSTCSAV SKGYLSALRT GWYTSVITIE LSNIKENKCN

GTDAKVKLIK QELDKYKNAV TELQLLMQST PPTNNRARRE

LPRFMNYTLN NAKKTNVTLS KKRKRRFLGF LLGVGSAIAS

GVAVSKVLHL EGEVNKIKSA LLSTNKAVVS LSNGVSVLTS

-continued

KVLDLKNYID KQLLPIVNKQ SCSISNIETV IEFQQKNNRL
LEITREFSVN AGVTTPVSTY MLTNSELLSL INDMPITNDQ
KKLMSNNVQI VRQQSYSIMS IIKEEVLAYV VQLPLYGVID
TPCWKLHTSP LCTTNTKEGS NICLTRTDRG WYCDNAGSVS
FFPQAETCKV QSNRVFCDTM NSLTLPSEIN LCNVDIFNPK
YDCKIMTSKT DVSSSVITSL GAIVSCYGKT KCTASNKNRG
IIKTFSNGCD YVSNKGMDTV SVGNTLYYVN KQEGKSLYVK
GEPIINFYDP LVFPSDEFDA SISQVNEKIN QSLAFIRKSD
ELLHNVNAGK STTNIMITTI IIVIIVILLS LIAVGLLLYC
KARSTPVTLS KDQLSGINNI AFSN.

Such a glycoprotein may be useful for targeting a VLP of the present disclosure to cells of the lung/respiratory tract.

In some cases, the heterologous glycoprotein used for pseudotyping is a human parainfluenza virus type 3 hemagglutinin-neuraminidase glycoprotein. A suitable human parainfluenza virus type 3 protein comprises an amino acid sequence having at least 80%, at least 85%, at least 90%, at least 95%, at least 98%, at least 99%, or 100%, amino acid sequence identity to the following amino acid sequence:

MEYWKHTNHG KDAGNELETS MATHGNKLTN KITYILWTII
LVLLSIVFII VLINSIKSEK AHESLLQNIN NEFMEITEKI
QMASDNTNDL IQSGVNTRLL TIQSHVQNYI PISLTQQMSD
LRKFISEITI RNDNQEVLPQ RITHDVGIKP LNPDDFWRCT
SGLPSLMKTP KIRLMPGPGL LAMPTTVDGC IRTPSLVIND
LIYAYTSNLI TRGCQDIGKS YQVLQIGIIT VNSDLVPDLN
PRISHTFNIN DNRKSCSLAL LNTDVYQLCS TPKVDERSDY
ASPGIEDIVL DIVNYDGSIS TTRFKNNNIS FDQPYAALYP
SVGPGIYYKG KIIFLGYGGL EHPINENVIC NTTGCPGKTQ
RDCNQASHSP WFSDRRMVNS IIVVDKGLNS IPKLKVWTIS
MRQNYWGSEG RLLLLGNKIY IYTRSTSWHS KLQLGIIDIT
DYSDIRIKWT WHNVLSRPGN NECPWGHSCP DGCITGVYTD
AYPLNPTGSI VSSVILDSQK SRVNPVITYS TATERVNELA
ILNRTLSAGY TTTSCITHYN KGYCFHIVEI NHKSLNTLQP
MLFKTEIPKS CS (SEQ ID NO: 1058;
GenBank Accession No: AAP35240).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a human parainfluenza virus type 3 glycoprotein F0. A suitable human parainfluenza virus type 3 protein comprises an amino acid sequence having at least 80%, at least 85%, at least 90%, at least 95%, at least 98%, at least 99%, or 100%, amino acid sequence identity to the following amino acid sequence:

MPISILLIIT TMIMASHCQI DITKLQHVGV LVNSPKGMKI
SQNFETRYLI LSLIPKIDDS NSCGDQQIKQ YKRLLDRLII
PLYDGLRLQK DVIVANQESN ENTDPRTERF FGGVIGTIAL
GVATSAQITA AVALVEAKQA RSDIEKLKEA IRDTNKAVQS
VQSSVGNLIV AIKSVQDYVN KEIVPSIARL GCEAAGLQLG
IALTQHYSEL TNIFGDNIGS LQEKGIKLQG IASLYRTNIT
EIFTTSTVDK YDIYDLLFTE SIKVRVIDVD LNDYSITLQV
RLPLLTRLLN TQIYKVDSIS YNIQNREWYI PLPSHIMTKG
AFLGGADVKE CIEAFSSYIC PSDPGFVLNH EMESCLSGNI
SQCPRTTVTS DIVPRYAFVN GGVVANCITT TCTCNGIGNR
INQPPDQGVK IITHKECNTI GINGMLFNTN KEGTLAFYTP
ADITLNNSVA LDPIDISIEL NKAKSDLEES KEWIRRSNQK
LDSIGSWHQS STTIIVILIM MIILFIINIT IITIAIKYYR
IQKRNRVDQN DKPYVLTNK (SEQ ID NO: 1059;
GenBank Accession No: AXA52708).

Such a glycoprotein may be useful for targeting a VLP of the present disclosure to cells of the respiratory tract (e.g., cells of the lung), where such cells include, e.g., epithelial cells, goblet cells, club cells, type I pneumocytes, type II pneumocytes, monocytes, macrophages, dendritic cells, neutrophils, and NK cells.

In some cases, the heterologous glycoprotein used for pseudotyping is a Hepatitis C virus (HCV) E1 glycoprotein. A suitable HCV protein comprises an amino acid sequence having at least 80%, at least 85%, at least 90%, at least 95%, at least 98%, at least 99%, or 100%, amino acid sequence identity to the following amino acid sequence:

YQVRNSSGLY HVTNDCPNSS IVYEAADAIL HTPGCVPCVR
EGNASRCWVA VTPTVATRDG KLPTTQLRRH IDLLVGSATL
CSALYVGDLC GSVFLVGQLF TFSPRRHWTT QDCNCSIYPG
HITGHRMAWD MMMNWSPTAA LVVAQLLRIP QAIMDMIAGA
HWGVLAGIAY FSMVGNWAKV LVVLLLFAGV DA
(SEQ ID NO: 1060; GenBank Accession No: NP_751920).

Such a glycoprotein may be useful for targeting a VLP of the present disclosure to a liver cell.

In some cases, the heterologous glycoprotein used for pseudotyping is an HCV E2 glycoprotein. A suitable HCV protein comprises an amino acid sequence having at least 80%, at least 85%, at least 90%, at least 95%, at least 98%, at least 99%, or 100%, amino acid sequence identity to the following amino acid sequence:

ETHVTGGSAG RTTAGLVGLL TPGAKQNIQL INTNGSWHIN
STALNCNESL NTGWLAGLFY QHKFNSSGCP ERLASCRRLT
DFAQGWGPIS YANGSGLDER PYCWHYPPRP CGIVPAKSVC
GPVYCFTPSP VVVGTTDRSG APTYSWGAND TDVFVLNNTR
PPLGNWFGCT WMNSTGFTKV CGAPPCVIGG VGNNTLLCPT

-continued

DCFRKHPEAT YSRCGSGPWI TPRCMVDYPY RLWHYPCTIN

YTIFKVRMYV GGVEHRLEAA CNWTRGERCD LEDRDRSELS

PLLLSTTQWQ VLPCSFTTLP ALSTGLIHLH QNIVDVQYLY

GVGSSIASWA IKWEYVVLLF LLLADARVCS CLWMMLLISQ AEA (SEQ ID NO: 1061; GenBank Accession No: NP_751921).

Such a glycoprotein may be useful for targeting a VLP of the present disclosure to a liver cell.

In some cases, the heterologous glycoprotein used for pseudotyping is a fowl plague virus glycoprotein. A suitable fowl plague virus protein comprises an amino acid sequence having at least 80%, at least 85%, at least 90%, at least 95%, at least 98%, at least 99%, or 100%, amino acid sequence identity to the following amino acid sequence:

MNTQILVFAL VAVIPTNADK ICLGHHAVSN GTKVNTLTER

GVEVVNATET VERTNIPKIC SKGKRTTDLG QCGLLGTITG

PPQCDQFLEF SADLIIERRE GNDVCYPGKF VNEEALRQIL

RGSGGIDKET MGFTYSGIRT NGTTSACRRS GSSFYAEMEW

LLSNTDNASF PQMTKSYKNT RRESALIVWG IHHSGSTTEQ

TKLYGSGNKL ITVGSSKYHQ SFVPSPGTRP QINGQSGRID

FHWLILDPND TVTFSFNGAF IAPNRASFLR GKSMGIQSDV

QVDANCEGEC YHSGGTITSR LPFQNINSRA VGKCPRYVKQ

ESLLLATGMK NVPEPSKKRE KRGLFGAIAG FIENGWEGLV

DGWYGFRHQN AQGEGTAADY KSTQSAIDQI TGKLNRLIEK

TNQQFELIDN EFTEVEKQIG NLINWTKDFI TEVWSYNAEL

LVAMENQHTI DLADSEMNKL YERVRKQLRE NAEEDGTGCF

EIFHKCDDDC MASIRNNTYD HSKYREEAMQ NRIQIDPVKL

SSGYKDVILW FSFGASCFLL LAIAVGLVFI CVKNGNMRCT ICI (SEQ ID NO: 1062; GenBank Accession No: 0601245A).

In some cases, the heterologous glycoprotein used for pseudotyping is an *Autographa californica* nuclear polyhedrosis virus (AcMNPV) major envelope glycoprotein gp64. A suitable AcMNPV protein comprises an amino acid sequence having at least 80%, at least 85%, at least 90%, at least 95%, at least 98%, at least 99%, or 100%, amino acid sequence identity to the following amino acid sequence:

MVSAIVLYVL LAAAAHSAFA AEHCNAQMKT GPYKIKNLDI

TPPKETLQKD VEITIVETDY NENVIIGYKG YYQAYAYNGG

SLDPNTRVEE TMKTLNVGKE DLLMWSIRQQ CEVGEELIDR

WGSDSDDCFR DNEGRGQWVK GKELVKRQNN NHFAHHTCNK

SWRCGISTSK MYSRLECQDD TDECQVYILD AEGNPINVTV

DTVLHRDGVS MILKQKSTFT TRQIKAACLL IKDDKNNPES

VTREHCLIDN DIYDLSKNTW NCKFNRCIKR KVEHRVKKRP

PTWRHNVRAK YTEGDTATKG DLMHIQEELM YENDLLKMNI

-continued

ELMHAHINKL NNMLHDLIVS VAKVDERLIG NLMNNSVSST

FLSDDTFLLM PCTNPPAHTS NCYNNSIYKE GRWVANTDSS

QCIDFSNYKE LAIDDDVEFW IPTIGNTTYH DSWKDASGWS

FIAQQKSNLI TTMENTKFGG VGTSLSDITS MAEGELAAKL

TSFMFGHVVN FVIILIVILF LYCMIRNRNR QY (SEQ ID NO: 1063; UniProt Accession No: P17501-1).

In some cases, the heterologous glycoprotein used for pseudotyping is an AcMNPV glycoprotein. A suitable AcMNPV protein comprises an amino acid sequence having at least 80%, at least 85%, at least 90%, at least 95%, at least 98%, at least 99%, or 100%, amino acid sequence identity to the following amino acid sequence:

(SEQ ID NO: 1064)

AEHCNAQMKT GPYKIKNLDI TPPKETLQKD VEITIVETDY

NENVIIGYKG YYQAYAYNGG SLDPNTRVEE TMKTLNVGKE

DLLMWSIRQQ CEVGEELIDR WGSDSDDCFR DNEGRGQWVK

GKELVKRQNN NHFAHHTCNK SWRCGISTSK MYSRLECQDD

TDECQVYILD AEGNPINVTV DTVLHRDGVS MILKQKSTFT

TRQIKAACLL IKDDKNNPES VTREHCLIDN DIYDLSKNTW

NCKFNRCIKR KVEHRVKKRP PTWRHNVRAK YTEGDTATKG

DLMHIQEELM YENDLLKMNI ELMHAHINKL NNMLHDLIVS

VAKVDERLIG NLMNNSVSST FLSDDTFLLM PCTNPPAHTS

NCYNNSIYKE GRWVANTDSS QCIDFSNYKE LAIDDDVEFW

IPTIGNTTYH DSWKDASGWS FIAQQKSNLI TTMENTKFGG

VGTSLSDITS MAEGELAAKL TSFMFGHVVN FVIILIVILF

LYCMIRNRNR QY.

In some cases, the heterologous glycoprotein used for pseudotyping is a measles virus hemagglutinin (H) polypeptide. See, e.g., Levy et al. (2017) Blood Adv. 1:2088. A suitable measles virus H polypeptide comprises an amino acid sequence having at least 80%, at least 85%, at least 90%, at least 95%, at least 98%, at least 99%, or 100%, amino acid sequence identity to the following amino acid sequence:

(SEQ ID NO: 1065)

MSPQRDRINA FYKDNPHPKG SRIVINREHL MIDRPYVLLA

VLFVMFLSLI GLLAIAGIRL HRAAIYTAEI HKSLSTNLDV

TNSIEHQVKD VLTPLFKIIG DEVGLRTPQR FTDLVKFISD

KIKFLNPDRE YDFRDLTWCI NPPERIKLDY DQYCADVAAE

ELMNALVNST LLETRTTNQF LAVSKGNCSG PTTIRGQFSN

MSLSLLDLYL SRGYNVSSIV TMTSQGMYGG TYLVEKPNLS

SKGSELSQLS MYRVFEVGVI RNPGLGAPVF HMTNYFEQPV

SNDLSNCMVA LGELKLAALC HGGDSITIPY QGSGKGVSFQ

LVKLGVWKSP TDMQSWVPLS TDDPVIDRLY LSSHRGVIAD

NQAKWAVPTT RTDDKLRMET CFQQACKGKI QALCENPEWA

-continued

```
PLKDNRIPSY GVLSVDLSLT VELKIKIASG FGPLITHGSG

MDLYKSNHNN VYWLTIPPMK NLALGVINTL EWIPRFKVSP

YLFTVPIKEA GEDCHAPTYL PAEVDGDVKL SSNLVILPGQ

DLQYVLATYD TSRVEHAVVY YVYSPSRSFS YFYPFRLPIK

GIPIELQVEC FTWDQKLWCR HFCVLADSES GGHITHSGMV

GMGVSCTVTR EDGTNSR.
```

Such a glycoprotein may be useful for targeting a VLP of the present disclosure to T cells, B cells, monocytes, macrophages, dendritic cells, and hematopoietic stem cells (e.g., $CD34^+$ cells).

In some cases, the heterologous glycoprotein used for pseudotyping is a measles virus fusion (F) polypeptide. A suitable measles virus F polypeptide comprises an amino acid sequence having at least 80%, at least 85%, at least 90%, at least 95%, at least 98%, at least 99%, or 100%, amino acid sequence identity to the following amino acid sequence:

```
                                          (SEQ ID NO: 1066)
MSIMGLKVNV SAIFMAVLLT LQTPTGQIHW GNLSKIGVVG

IGSASYKVMT RSSHQSLVIK LMPNITLLNN CTRVEIAEYR

RLLRTVLEPI RDALNAMTQN IRPVQSVASS RRHKRFAGVV

LAGAALGVAT AAQITAGIAL HQSMLNSQAI DNLRASLETT

NQAIETIRQA GQEMILAVQG VQDYINNELI PSMNQLSCDL

IGQKLGLKLL RYYTEILSLF GPSLRDPISA EISIQALSYA

LGGDINKVLE KLGYSGGDLL GILESGGIKA RITHVDTESY

FIVLSIAYPT LSEIKGVIVH RLEGVSYNIG SQEWYTTVPK

YVATQGYLIS NFDESSCTFM PEGTVCSQNA LYPMSPLLQE

CLRGYTKSCA RTLVSGSFGN RFILSQGNLI ANCASILCKC

YTTGTIINQD PDKILTYIAA DHCPVVEVNG VTIQVGSRRY

PDAVYLHRID LGPPISLERL DVGTNLGNAI AKLEDAKELL

ESSDQILRSM KGLSSTSIVY ILIAVCLGGL IGIPALICCC

RGRCNKKGEQ VGMSRPGLKP DLTGTSKSYV RSL.
```

Such a glycoprotein may be useful for targeting a VLP of the present disclosure to T cells, B cells, monocytes, macrophages, dendritic cells, and hematopoietic stem cells (e.g., $CD34^+$ cells). In some cases, both measles virus hemagglutinin and measles virus F protein are used to pseudotype a VLP of the present disclosure.

In some cases, both measles virus L and measles virus H polypeptides are used to pseudotype a VLP of the present disclosure.

In some cases, a system of the present disclosure comprises a nucleic acid comprising a nucleotide sequence encoding an antibody that specifically binds an antigen on a cell, tissue, or organ, where the antibody provides for selective targeting of the VLP to the cell, tissue, or organ. In some cases, the antibody targets a cancer antigen, thereby targeting the VLP to a cancerous cell that displays the cancer antigen on its cell surface. In some cases, the antibody provides for selective binding to an organ such as kidney, liver, bone, pancreas, brain, lung, heart, and the like. In some cases, the antibody provides for selective binding to a particular cell type. For example, in some cases, the antibody provides for selective binding to a cell such as a skeletal muscle cell, a cardiomyocyte, an adipocyte, an epithelial cell, an endothelial cell, a macrophage, a beta islet cell, or an immune cell (e.g., a T cell, a B cell, a monocyte, a natural killer cell, a dendritic cell, etc.). In some cases, the antibody provides for selective binding to a diseased cell, relative to a non-diseased cell of the same cell type.

Suitable antigens bound by an antibody present in a VLP of the present disclosure include, e.g., CD3, epidermal growth factor receptor (EGFR), CA-125 (highly expressed on epithelial ovarian cancer cells), CD80, CD86, glycoprotein IIb/IIIa receptor, CD51, TNF-α, epithelial adhesion molecule EpcAM (CD326), vascular endothelial growth factor receptor-2 (VEGFR-2), CD52, mesothelin, activin receptor-like kinase 1 (ALK-1), phosphatidyl serine, CD19, vascular endothelial growth factor A (VEGF-A), IL-6 receptor, CD11a, CD25, CD2, CD3 receptor, and the like.

Suitable antigens bound by an antibody present in a VLP of the present disclosure include, e.g., carbonic anhydrase IX, alpha-fetoprotein (AFP), α-actinin-4, A3, ART-4, B7, Ba 733, BAGE, BrE3-antigen, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIF-1α, colon-specific antigen-p (CSAp), CEACAM5, CEACAM6, c-Met, DAM, epidermal growth factor receptor (EGFR), EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, histone H2B, histone H3, histone H4, HMGB-1, hypoxia inducible factor (HIF-1), HSP70-2M, HST-2, insulin-like growth factor-1 receptor (IGF-1R), IFN-γ IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, PD-1, PD-L1, PD-1 receptor, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-α, Tn antigen, tumor necrosis antigens, VEGFR, ED-B fibronectin, WT-1, 17-1A-antigen, complement factors C3, C3a, C3b, C5a, C5; and the like.

Examples of suitable antibodies include, e.g., abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), tocilizumab (anti-IL-6 receptor), basiliximab (anti-CD25), daclizumab (anti-CD25), efalizumab (anti-CD11a), GA101 (anti-CD20; Glycart Roche), muromonab-CD3 (anti-CD3 receptor), natalizumab (anti-at-4 integrin), and the like.

Retroviruses

As discussed above, the present disclosure provides a nucleic acid comprising a nucleotide sequence encoding a fusion polypeptide that comprises a retroviral gag polyprotein and a CRISPR/Cas effector polypeptide. As discussed above, the present disclosure also provides a system comprising a nucleic acid comprising a nucleotide sequence encoding a VLP comprising a fusion polypeptide that comprises a retroviral gag polyprotein and a CRISPR/Cas effector polypeptide. In some cases, the system also comprises a nucleic acid comprising a nucleotide sequence encoding a retroviral gag polypeptide (without a CRISPR/Cas effector polypeptide).

Many retroviruses are known in the art; gag and pol polypeptides, and nucleotide sequences encoding such gag and polypeptides, from any of a variety of retroviruses can be used in a nucleic acid, system, or VLP of the instant disclosure. Examples include: murine leukemia virus (MLV), lentivirus such as human immunodeficiency virus (HIV), equine infectious anemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). Other retroviruses suitable for use include, but are not limited to, Avian Leukosis Virus, Bovine Leukemia Virus, Mink-Cell Focus-Inducing Virus. The core sequence of the retroviral vectors can be derived from a wide variety of retroviruses, including for example, B, C, and D type retroviruses as well as spumaviruses and lentiviruses (see RNA Tumor Viruses, Second Edition, Cold Spring Harbor Laboratory, 1985). An example of a retrovirus suitable for use in the compositions and methods disclosed herein, includes, but is not limited to, lentivirus.

One example of a suitable lentivirus is a human immunodeficiency virus (HIV), for example, type 1 or 2 (i.e., HIV-1 or HIV-2). Other lentivirus vectors include sheep Visna/maedi virus, feline immunodeficiency virus (FIV), bovine lentivirus, simian immunodeficiency virus (SIV), an equine infectious anemia virus (EIAV), and a caprine arthritis-encephalitis virus (CAEV).

Lentiviruses share several structural virion proteins in common, including the envelope glycoproteins SU (gp120) and TM (gp41), which are encoded by the env gene; CA (p24), MA (p17) and NC (p7), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, such as by mutation or deletion.

In some cases, retroviral Gag polypeptides include CA (p24), MA (p17) and NC (p7) polypeptides. In some cases, retroviral Gag polypeptides include CA, MA, and NC polypeptides, and in addition one or more of p1, p2, and p6 polypeptides. In some cases, retroviral Gag polypeptides include CA, MA, NC, and p6 polypeptides. In some cases, retroviral Gag polypeptides include CA, MA, NC, p1, p2, and p6 polypeptides. See, e.g., Muriaux and Darlix (2010) *RNA Biol.* 7:744.

Recombinant lentivirus can be recovered through the in trans co-expression in a permissive cell line of (1) the packaging constructs, i.e., a vector expressing the Gag-Pol precursors together with Rev (alternatively expressed in trans); (2) a vector expressing an envelope receptor, generally of an heterologous nature; and (3) the transfer vector, consisting in the viral cDNA deprived of all open reading frames, but maintaining the sequences required for replication, encapsidation, and expression, in which the sequences to be expressed are inserted.

Retroviral packaging systems for generating producer cells and producer cell lines that produce retroviruses, and methods of making such packaging systems are known in the art. Generally, the retroviral packaging systems include at least two packaging vectors: a first packaging vector which includes a first nucleotide sequence comprising a gag, a pol, or gag and pol genes; and a second packaging vector which includes a second nucleotide sequence comprising a heterologous or functionally modified envelope gene. In some cases, the retroviral elements are derived from a lentivirus, such as HIV. These vectors can lack a functional tat gene and/or functional accessory genes (vif, vpr, vpu, vpx, nef). In other instances, the system further comprises a third packaging vector that comprises a nucleotide sequence comprising a rev gene. The packaging system can be provided in the form of a packaging cell.

Suitable lentiviral vector packaging systems provide separate packaging constructs for gag/pol and env, and typically employ a heterologous or functionally modified envelope protein for safety reasons. In some cases of a lentiviral vector system, the accessory genes, vif, vpr, vpu and nef, are deleted or inactivated. In some cases of a lentiviral vector system, the tat gene has been deleted or otherwise inactivated (e.g., via mutation). Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., liver-specific promoter), or other factors relating to desired control over expression, as is understood in the art. For example, in some cases, an inducible promoter such as tet can be used to achieve controlled expression. The gene encoding rev can be provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known to those of skill in the art. A system of the present disclosure can be introduced into a packaging cell line, via transfection, transduction or infection, to generate a producer cell or cell line. The packaging vectors can be introduced into human cells or cell lines by standard methods including, for example, calcium phosphate transfection, lipofection or electroporation. In some cases, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Methods of Making a VLP

The present disclosure provides a method of making a VLP comprising one or more therapeutic polypeptides. Suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody. Thus, for example, the present disclosure provides a method of making a VLP comprising a CRISPR/Cas effector polypeptide. The methods generally involve introducing into a packaging cell a system of the present disclosure; and harvesting the VLPs produced by the packaging cell. In some cases, the VLPs are harvested from the supernatant (e.g., the cell culture medium) in which the packaging cells are cultures. In some cases, the cell culture medium is filtered (e.g., with a 0.45 μm filter). A non-limiting example of a method of making a VLP is depicted schematically in FIG. 1.

Any suitable permissive or packaging cell known in the art may be employed in the production of a VLP of the present disclosure. In some cases, the cell is a mammalian cell. In some cases, the cell is an insect cell. Examples of cells suitable for production of a VLP of the present disclosure include, e.g., human cell lines, such as VERO, WI38, MRC5, A549, HEK293, HEK293T, B-50 or any other HeLa cells, HepG2, Saos-2, HuH7, Chinese Hamster Ovary (CHO) cells, and HT1080 cell lines.

Also suitable for use as packaging cells are insect cell lines. Any insect cell that allows for production of a VLP of the present disclosure and which can be maintained in culture can be used. Examples include *Spodoptera frugiperda*, such as the Sf9 or Sf21 cell lines, *Drosophila* spp. cell lines, or mosquito cell lines, e.g., *Aedes albopictus* derived cell lines.

The nucleic acids present in a system of the present disclosure can extra-chromosomal or integrated into the cell's chromosomal DNA. In some cases, the packaging cell is a cell line with one or more packaging functions incorporated extrachromosomally or integrated into the cell's chromosomal DNA, or a cell line with helper functions incorporated extra-chromosomally or integrated into the cell's chromosomal DNA. A packaging cell line is a suitable host cell transfected by one or more nucleic acid vectors that, under suitable in vitro culture conditions, produces VLPs comprising a CRISPR/Cas effector polypeptide and, in some cases, the VLPs also include one or more CRIPSR/Cas guide RNA(s) or a nucleic acid comprising a nucleotide sequence encoding same. In some cases, the guide RNAs are derived from a library of guide RNAs.

Virus-Like Particles

The present disclosure provides VLPs. As used herein, the term "virus-like particle" (VLP) refers to a non-replicating, multicomponent structure composed of one or more viral proteins or virally-derived peptides or polypeptides, such as, but not limited to capsid, coat, shell, surface and/or envelope proteins, or variant polypeptides derived from these proteins. In some cases, a VLP of the present disclosure comprises one or more therapeutic polypeptides. Suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody. In some cases, a VLP of the present disclosure comprises a CRISPR/Cas effector polypeptide. In some cases, a VLP of the present disclosure comprises: i) a CRISPR/Cas effector polypeptide; and ii) one or more guide RNAs or a nucleic acid comprising a nucleotide sequence encoding one or more guide RNAs. In some cases, a VLP of the present disclosure comprises: i) a CRISPR/Cas effector polypeptide; ii) one or more guide RNAs or a nucleic acid comprising a nucleotide sequence encoding one or more guide RNAs; and iii) a donor DNA template. In some cases, a VLP of the present disclosure comprises: i) a CRISPR/Cas effector polypeptide; and ii) an anti-CRISPR polypeptide.

In some cases, a VLP of the present disclosure comprises an anti-CRISPR polypeptide and does not include a CRISPR/Cas effector polypeptide. The present disclosure provides a composition comprising: a) a VLP of the present disclosure that comprises a CRISPR/Cas effector polypeptide and that does not include an anti-CRISPR polypeptide; and b) a VLP of the present disclosure comprises an anti-CRISPR polypeptide and does not include a CRISPR/Cas effector polypeptide. The present disclosure provides: a) a first composition comprising a VLP of the present disclosure that comprises a CRISPR/Cas effector polypeptide and that does not include an anti-CRISPR polypeptide; and b) a second composition comprising a VLP of the present disclosure comprises an anti-CRISPR polypeptide and does not include a CRISPR/Cas effector polypeptide. In some cases, the first composition and the second composition are in separate containers.

In some cases, a VLP of the present disclosure has an in vivo half life of less than 7 days. In some cases, a VLP of the present disclosure has an in vivo half life of from about 24 hours to about 48 hours, from about 48 hours to about 3 days, from about 3 days to about 4 days, from about 4 days to about 5 days, from about 5 days to about 6 days, or from about 6 days to about 7 days. In some cases, a VLP of the present disclosure is stable to one or more freeze/thaw cycles.

In some cases, a VLP of the present disclosure comprises: i) retroviral MA, CA, and NC polypeptides; and ii) one or more therapeutic polypeptides (e.g., a CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; an antibody; etc.). In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, and NC polypeptides, and p6 polypeptides; and ii) a CRISPR/Cas effector polypeptide.

In some cases, a VLP of the present disclosure comprises: i) retroviral MA, CA, and NC polypeptides; and ii) one or more therapeutic polypeptides (e.g., a CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; an antibody; etc.), where one or more of the retroviral MA, CA, and NC polypeptides comprises amino acid(s) at the N-terminus and/or the C-terminus from a heterologous protease cleavage site. In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, NC polypeptide, and p6 polypeptides; and ii) one or more therapeutic polypeptides (e.g., a CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; an antibody; etc.), where one or more of the retroviral MA, CA, NC and p6 polypeptides comprises amino acid(s) at the N-terminus and/or the C-terminus from a heterologous protease cleavage site. Generally, the retroviral polypeptide (e.g., the retroviral MA and/or CA and/or NC polypeptide and/or p6 polypeptide) comprises from 1 to 10 heterologous amino acids (e.g., 1, 2, 3, 4, 5, 6, 7, 8, 9, or 10 amino acids) at the N-terminus and/or C-terminus, where the from 1 to 10 heterologous amino acids are from the heterologous protease cleavage site. For example, in some cases, the MA polypeptide comprises, at the C-terminus of the MA polypeptide, amino acid(s) that are N-terminal to the cleavage site within the protease cleavage site; and the CA polypeptide comprises, at the N-terminus of the CA polypeptide, amino acid(s) that are C-terminal to the cleavage site within the protease cleavage site. In some cases, a p6 polypeptide comprises, at the C-terminus of the p6 polypeptide, amino acid(s) that are N-terminal to the cleavage site within the protease cleavage site. As one non-limiting example, where the heterologous protease cleavage site is the TEV protease-cleavable sequence ENLYFQS (SEQ ID NO:880), in some cases, the MA polypeptide comprises, at the C-terminus of the MA polypeptide, the amino acids ENLYFQ, and the CA polypeptide comprises, at the N-terminus of the CA polypeptide, the amino acid Ser. As another example, in some cases, the CA polypeptide comprises, at the C-terminus of the CA polypeptide, amino acid(s) that are N-terminal to the cleavage site within the protease cleavage site; and the NC polypeptide comprises, at the N-terminus of the NC polypeptide, amino acid(s) that are C-terminal to the cleavage site within the protease cleavage site. As one non-limiting example, where the heterologous protease cleavage site is the TEV protease-cleavable sequence ENLYFQS (SEQ ID NO:880), in some cases, the CA polypeptide comprises, at the C-terminus of the CA polypeptide, the amino acids ENLYFQ, and the NC polypeptide comprises, at the N-terminus of the NC polypeptide, the amino acid Ser. As one non-limiting example, where the heterologous protease cleavage site is, e.g., between the p6 polypeptide and the CRISPR/Cas effector polypeptide, and where the protease cleavage site is the TEV protease-cleavable sequence ENLYFQS (SEQ ID NO:880), in some cases, the p6 polypeptide comprises, at the C-terminus of the p6 polypeptide, the amino acids ENLYFQ. In some cases, e.g., where a heterologous protease cleavage site is between the MA polypeptide and the CA polypeptide, and between the CA polypeptide and the NC polypeptide, the CA polypeptide comprises, at its N-terminus, amino acid(s) C-terminal to the protease cleavage site within the heterologous protease cleavage site; and the CA polypeptide also comprises, at its C-terminus, amino acid(s) N-terminal to the protease cleavage site within the heterologous protease cleavage site. As one non-limiting example, where the heterologous protease cleavage site is the TEV protease-cleavable sequence ENLYFQS (SEQ ID NO:880), in some cases, the CA polypeptide comprises, at its N-terminus, a Ser, and at its C-terminus, the amino acid sequence ENLYFQ. In some cases, the therapeutic polypeptide also includes, at its N-terminus, from 1 to 10 heterologous amino acids (e.g., 1, 2, 3, 4, 5, 6, 7, 8, 9, or 10 amino acids) at the N-terminus and/or C-terminus, where the from 1 to 10 heterologous amino acids are from the heterologous protease cleavage site.

In some cases, a VLP of the present disclosure comprises: i) retroviral MA, CA, and NC polypeptides; and ii) a CRISPR/Cas effector polypeptide. In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, and NC polypeptides, and p6 polypeptides; and ii) a CRISPR/Cas effector polypeptide.

In some cases, a VLP of the present disclosure comprises: i) retroviral MA, CA, and NC polypeptides; and ii) a CRISPR/Cas effector polypeptide, where one or more of the retroviral MA, CA, and NC polypeptides comprises amino acid(s) at the N-terminus and/or the C-terminus from a heterologous protease cleavage site. In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, NC polypeptide, and p6 polypeptides; and ii) a CRISPR/Cas effector polypeptide, where one or more of the retroviral MA, CA, NC and p6 polypeptides comprises amino acid(s) at the N-terminus and/or the C-terminus from a heterologous protease cleavage site. Generally, the retroviral polypeptide (e.g., the retroviral MA and/or CA and/or NC polypeptide and/or p6 polypeptide) comprises from 1 to 10 heterologous amino acids (e.g., 1, 2, 3, 4, 5, 6, 7, 8, 9, or 10 amino acids) at the N-terminus and/or C-terminus, where the from 1 to 10 heterologous amino acids are from the heterologous protease cleavage site. For example, in some cases, the MA polypeptide comprises, at the C-terminus of the MA polypeptide, amino acid(s) that are N-terminal to the cleavage site within the protease cleavage site; and the CA polypeptide comprises, at the N-terminus of the CA polypeptide, amino acid(s) that are C-terminal to the cleavage site within the protease cleavage site. In some cases, a p6 polypeptide comprises, at the C-terminus of the p6 polypeptide, amino acid(s) that are N-terminal to the cleavage site within the protease cleavage site. As one non-limiting example, where the heterologous protease cleavage site is the TEV protease-cleavable sequence ENLYFQS (SEQ ID NO:880), in some cases, the MA polypeptide comprises, at the C-terminus of the MA polypeptide, the amino acids ENLYFQ, and the CA polypeptide comprises, at the N-terminus of the CA polypeptide, the amino acid Ser. As another example, in some cases, the CA polypeptide comprises, at the C-terminus of the CA polypeptide, amino acid(s) that are N-terminal to the cleavage site within the protease cleavage site; and the NC polypeptide comprises, at the N-terminus of the NC polypeptide, amino acid(s) that are C-terminal to the cleavage site within the protease cleavage site. As one non-limiting example, where the heterologous protease cleavage site is the TEV protease-cleavable sequence ENLYFQS (SEQ ID NO:880), in some cases, the CA polypeptide comprises, at the C-terminus of the CA polypeptide, the amino acids ENLYFQ, and the NC polypeptide comprises, at the N-terminus of the NC polypeptide, the amino acid Ser. As one non-limiting example, where the heterologous protease cleavage site is, e.g., between the p6 polypeptide and the CRISPR/Cas effector polypeptide, and where the protease cleavage site is the TEV protease-cleavable sequence ENLYFQS (SEQ ID NO:880), in some cases, the p6 polypeptide comprises, at the C-terminus of the p6 polypeptide, the amino acids ENLYFQ. In some cases, e.g., where a heterologous protease cleavage site is between the MA polypeptide and the CA polypeptide, and between the CA polypeptide and the NC polypeptide, the CA polypeptide comprises, at its N-terminus, amino acid(s) C-terminal to the protease cleavage site within the heterologous protease cleavage site; and the CA polypeptide also comprises, at its C-terminus, amino acid(s) N-terminal to the protease cleavage site within the heterologous protease cleavage site. As one non-limiting example, where the heterologous protease cleavage site is the TEV protease-cleavable sequence ENLYFQS (SEQ ID NO:880), in some cases, the CA polypeptide comprises, at its N-terminus, a Ser, and at its C-terminus, the amino acid sequence ENLYFQ. In some cases, the CRISPR/Cas effector polypeptide also includes, at its N-terminus, from 1 to 10 heterologous amino acids (e.g., 1, 2, 3, 4, 5, 6, 7, 8, 9, or 10 amino acids) at the N-terminus and/or C-terminus, where the from 1 to 10 heterologous amino acids are from the heterologous protease cleavage site.

Heterologous Protease Cleavage Sites

A heterologous protease cleavage site can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO:852) or Pro-Leu/Gln-Gly-Met-Thr (SEQ ID NO:853). Another example of a protease cleavage site is a plasminogen activator cleavage site, e.g., a uPA or a tissue plasminogen activator (tPA) cleavage site. In some cases, the cleavage site is a furin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:854), where the protease cleaves between the glutamine and the serine. Another example of a protease cleavage site that can be included in a proteolytically cleavable linker is an enterokinase cleavage site, e.g., DDDDK (SEQ ID NO:855), where cleavage occurs after the lysine residue. Another example of a protease cleavage site that can be included in a proteolytically cleavable linker is a thrombin cleavage site, e.g., LVPR (SEQ ID NO:856). Additional suitable linkers comprising protease cleavage sites include linkers comprising one or more of the following amino acid sequences: LEVLFQGP (SEQ ID NO:857), cleaved by PreScission protease (a fusion protein comprising human rhinovirus 3C protease and glutathione-S-transferase; Walker et al. (1994) *Biotechnol.* 12:601); a thrombin cleavage site, e.g., CGLVPAGSGP (SEQ ID NO:858); SLLKSRMVPNFN (SEQ ID NO:859) or SLLIARRMPNFN (SEQ ID NO:860), cleaved by cathepsin B; SKLVQASASGVN (SEQ ID NO:861) or SSYLKASDAPDN (SEQ ID NO:862), cleaved by an Epstein-Barr virus protease; RPKPQQFFGLMN (SEQ ID NO:863) cleaved by MMP-3 (stromelysin); SLRPLALWRSFN (SEQ ID NO:864) cleaved by MMP-7 (matrilysin); SPQGIAGQRNFN (SEQ ID NO:865) cleaved by MMP-9; DVDERDVRGFASFL SEQ ID NO:866) cleaved by a thermolysin-like MMP; SLPLGLWAPNFN (SEQ ID NO:867) cleaved by matrix metalloproteinase 2 (MMP-2); SLLIFRSWANFN (SEQ ID NO:868) cleaved by cathespin L; SGVVIATVIVIT (SEQ ID NO:869) cleaved by cathepsin D; SLGPQGIWGQFN (SEQ ID NO:870) cleaved by matrix metalloproteinase 1 (MMP-1); KKSPGRVVGGSV (SEQ ID NO:871) cleaved by urokinase-type plasminogen activator; PQGLLGAPGILG (SEQ ID NO:872) cleaved by membrane type 1 matrixmetalloproteinase (MT-MMP); HGPEGLRVGFYESDVMGRGHARLVHVEEPHT (SEQ ID NO:873) cleaved by stromelysin 3 (or MMP-11), thermolysin, fibroblast collagenase and stromelysin-1; GPQGLAGQRGIV (SEQ ID NO:874) cleaved by matrix metalloproteinase 13 (collagenase-3); GGSGQRGRKALE (SEQ ID NO:875) cleaved by tissue-type plasminogen activator (tPA); SLSALLSSDIFN (SEQ ID NO:876) cleaved by human prostate-specific antigen; SLPRFKIIGGFN (SEQ ID NO:877) cleaved by kallikrein (hK3); SLLGIAVPGNFN (SEQ ID NO:878) cleaved by neutrophil elastase; and FFKNIVTPRTPP (SEQ ID NO:879) cleaved by calpain (calcium activated neutral protease).

In some cases, the protease cleavage site is a TEV protease cleavage site, e.g., ENLYTQS (SEQ ID NO:854), where the protease cleaves between the glutamine and the serine. In some cases, the protease cleavage site is the TEV protease cleavage site ENLYFQP (SEQ ID NO:881). In some cases, the protease cleavage site is a variant TEV-cleavage substrate, where the variant TEV cleavage site is cleaved by a TEV protease (e.g., a TEV protease comprising the TEV protease amino acid sequence provided in FIG. 6B) less efficiently than cleavage of ENLYTQS (SEQ ID NO:854) by the TEV protease. In some cases, a variant TEV-cleavage site can: (1) mimic the temporal cleavage observed with wild-type gag polyprotein maturation; and/or (2) maximize packaging of a therapeutic polypeptide, such as a CRISPR/Cas effector polypeptide, into a VLP. Suitable variant TEV cleavage sites are described in Tözsér et al. (2005) *FEBS J.* 272:514. Suitable variant TEV cleavage sites include: ENAYFQS (SEQ ID NO:883), ENLRFQS (SEQ ID NO:884), ENLFFQS (SEQ ID NO:885), ETVRFQS (SEQ ID NO:886), ETLRFQS (SEQ ID NO:887), ETARFQS (SEQ ID NO:888), ETVYFQS (SEQ ID NO:889), and ENVYFQS (SEQ ID NO:890).

In some cases, the variant TEV cleavage substrate (also referred to herein as a "TEV cleavage site" or "TCS") is cleaved less efficiently than a TCS having the amino acid sequence ENLYFQS (SEQ ID NO:880) or ENLYFQP (SEQ ID NO:881). For example, a population of Gag-Cas9 polyproteins that comprise, in order from N-terminus to C-terminus, Gag-TCS-Cas9, where the TCS is a variant TCS, is cleaved less efficiently by a TEV protease than a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881).

For example, in some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time is less than 90%, less than 80%, less than 70%, less than 60%, less than 50%, less than 40%, less than 30%, less than 25%, less than 20%, less than 15%, less than 10%, less than 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease of the same period of time (and under the same conditions).

For example, in some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time is from 80% to 90%, from 70%, to 80%, from 60% to 70%, from 50% to 60%, from 40% to 50%, from 30% to 40%, from 25% to 30%, from 20% to 25%, from 15% to 20%, from 10% to 15%, from 5% to 10%, from 1% to 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease of the same period of time (and under the same conditions).

In some cases, the TEV protease comprises the following amino acid sequence:

```
                                        (SEQ ID NO: 892)
ESLFKGPRDYNPISSTICHLTNESDGHTTSLYGIGFGPFIITNKHLFRRNN

GTLLVQSLHGVFKVKNTTTLQQHLIDGRDMIIIRMPKDFPPFPQKLKFREP

QREERICLVTTNFQTKSMSSMVSDTSCTFPSSDGIFWKHWIQTKDGQCGSP

LVSTRDGFIVGIHSASNFTNTNNYFTSVPKNFMELLTNQEAQQWVSGWRLN

ADSVLWGGHKVFMVKPEEPFQPVKEATQLMN.
```

In some cases, the percent of a population of Gag-Cas9 polyproteins that comprise, in order from N-terminus to C-terminus, Gag-TCS-Cas9, where the TCS is a variant TCS, that are cleaved with a TEV protease over a given period of time (e.g., from 5 seconds to 15 minutes; e.g., from 5 seconds to 15 seconds, from 15 seconds to 30 seconds, from 30 seconds to 60 seconds, from 1 minute to 2 minutes, or from 2 minutes to 5 minutes, from 5 minutes to 10 minutes, or from 10 minutes to 15 minutes) is from 80% to 90%, from 70%, to 80%, from 60% to 70%, from 50% to 60%, from 40% to 50%, from 30% to 40%, from 25% to 30%, from 20% to 25%, from 15% to 20%, from 10% to 15%, from 5% to 10%, from 1% to 5%, or less than 1% (e.g., less than 0.9%, less than 0.8%, less than 0.7%, less than 0.6%, less than 0.5%, less than 0.1%, less than 0.05%, less than 0.01%, less than 0.005%, or less than 0.001%), of the percent of a population of Gag-Cas9 polyproteins that comprise, in order from N-terminus to C-terminus, Gag-TCS-Cas9, where the TCS comprises ENLYFQS (SEQ ID NO:880) or ENLYFQP (SEQ ID NO:881), that is cleaved by the same TEV protease of the same period of time (and under the same conditions).

Therapeutic Polypeptides

As noted above, in some cases, a nucleic acid of the present disclosure comprises a nucleotide sequence encoding one or more therapeutic polypeptides; a system of the present disclosure comprises a nucleic acid comprising a nucleotide sequence encoding one or more therapeutic polypeptides; and a VLP of the present disclosure comprises one or more therapeutic polypeptides. Any known therapeutic is suitable in the context of a nucleic acid of the present disclosure, a system of the present disclosure, or a VLP of the present disclosure. Suitable therapeutic polypeptides include, e.g., CRISPR/Cas effector polypeptide (including, e.g., a fusion polypeptide comprising: i) a CRISPR/Cas effector polypeptide; and ii) one or more heterologous fusion partners (one or more heterologous fusion polypeptides); a nuclease; a base editor; a transcription factor; a recombinase; an anti-CRISPR polypeptide; a reverse transcriptase; a prime editor; and an antibody.

Nucleases

Suitable nucleases include, but are not limited to, a homing nuclease polypeptide; a FokI polypeptide; a transcription activator-like effector nuclease (TALEN) polypeptide; a MegaTAL polypeptide; a meganuclease polypeptide; a zinc finger nuclease (ZFN); an ARCUS nuclease; and the like. The meganuclease can be engineered from an LADLIDADG homing endonuclease (LHE). A megaTAL polypeptide can comprise a TALE DNA binding domain and an engineered meganuclease. See, e.g., WO 2004/067736 (homing endonuclease); Urnov et al. (2005) *Nature* 435:646 (ZFN); Mussolino et al. (2011) *Nucle. Acids Res.* 39:9283 (TALE nuclease); Boissel et al. (2013) *Nucl. Acids Res.* 42:2591 (MegaTAL).

Prime Editors

A prime editor is a fusion polypeptide comprising: i) a catalytically impaired CRISPR/Cas effector polypeptide (e.g., a Cas9 polypeptide that exhibits reduced cleavage activity; e.g., a "dead" Cas9); and ii) a reverse transcriptase.

Base Editors

Suitable base editors include, e.g., an adenosine deaminase; a cytidine deaminase (e.g., an activation-induced cytidine deaminase (AID)); APOBEC3G; and the like); and the like.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                        (SEQ ID NO: 894)
MSEVEFSHEYWMRHALTLAKRAWDEREVPVGAVLVHNNRVIGEGWNRPIGR

HDPTAHAEIMALRQGGLVMQNYRLIDATLYVTLEPCVMCAGAMIHSRIGRV

VFGARDAKTGAAGSLMDVLHHPGMNHRVEITEGILADECAALLSDFFRMRR

QEIKAQKKAQSSTD
```

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                        (SEQ ID NO: 895)
MRRAFITGVFFLSEVEFSHEYWMRHALTLAKRAWDEREVPVGAVLVHNNRV

IGEGWNRPIGRHDPTAHAEIMALRQGGLVMQNYRLIDATLYVTLEPCVMCA

GAMIHSRIGRVVFGARDAKTGAAGSLMDVLHHPGMNHRVEITEGILADECA

ALLSDFFRMRRQEIKAQKKAQSSTD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

(SEQ ID NO: 896)
MGSHMTNDIYFMTLAIEEAKKAAQLGEVPIGAIITKDDEVIARAHNLRETL

QQPTAHAEHIAIERAAKVLGSWRLEGCTLYVTLEPCVMCAGTIVMSRIPRV

VYGADDPKGGCSGSLMNLLQQSNFNHRAIVDKGVLKEACSTLLTTFFK

NLRANKKSTN:

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

(SEQ ID NO: 897)
MTQDELYMKEAIKEAKKAEEKGEVPIGAVLVINGEIIARAHNLRETEQRSI

AHAEMLVIDEACKALGTWRLEGATLYVTLEPCPMCAGAVVLSRVEKVVFGA

FDPKGGCSGTLMNLLQEERFNHQAEVVSGVLEEECGGMLSAFFRELRKKKK

AARKNLSE

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

(SEQ ID NO: 898)
MPPAFITGVTSLSDVELDHEYWMRHALTLAKRAWDEREVPVGAVLVHNHRV

IGEGWNRPIGRHDPTAHAEIMALRQGGLVLQNYRLLDTTLYVTLEPCVMCA

GAMVHSRIGRVVFGARDAKTGAAGSLIDVLHHPGMNHRVEIIEGVLRDECA

TLLSDFFRMRRQEIKALKKADRAEGAGPAV

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

(SEQ ID NO: 899)
MDEYWMQVAMQMAEKAEAAGEVPVGAVLVKDGQQIATGYNLSISQHDPTAH

AEILCLRSAGKKLENYRLLDATLYITLEPCAMCAGAMVHSRIARVVYGARD

EKTGAAGTVVNLLQHPAFNHQVEVTSGVLAEACSAQLSRFFKRRRDEKKAL

KLAQRAQQGIE

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

(SEQ ID NO: 900)
MDAAKVRSEFDEKMMRYALELADKAEALGEIPVGAVLVDDARNIIGEGWNL

SIVQSDPTAHAEIIALRNGAKNIQNYRLLNSTLYVTLEPCTMCAGAILHSR

-continued

IKRLVFGASDYKTGAIGSRFHFFDDYKMNHTLEITSGVLAEECSQKLS

TFFQKRREEKKIEKALLKSLSDK

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

(SEQ ID NO: 901)
MRTDESEDQDHRMMRLALDAARAAAEAGETPVGAVILDPSTGEVIATAGNG

PIAAHDPTAHAEIAAMRAAAAKLGNYRLTDLTLVVTLEPCAMCAGAISHAR

IGRVVFGADDPKGGAVVHGPKFFAQPTCHWRPEVTGGVLADESADLLRGFF

RARRKAKI

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

(SEQ ID NO: 902)
MSSLKKTPIRDDAYWMGKAIREAAKAAARDEVPIGAVIVRDGAVIGRGHNL

REGSNDPSAHAEMIAIRQAARRSANWRLTGATLYVTLEPCLMCMGAIILAR

LERVVFGCYDPKGGAAGSLYDLSADPRLNHQVRLSPGVCQEECGTMLSDFF

RDLRRRKKAKATPALFIDERKVPPEP

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 903)
MDSLLMNRRKFLYQFKNVRWAKGRRETYLCYVVKRRDSATSFSLDFGYL

RNKNGCHVELLFLRYISDWDLDPGRCYRVTWFTSWSPCYDCARHVADFL

RGNPNLSLRIFTARLYFCEDRKAEPEGLRRLHRAGVQIAIMTFKDYFYC

WNTFVENHERTFKAWEGLHENSVRLSRQLRRILLPLYEVDDLRDAFRTL

GL

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 904)
MDSLLMNRRK FLYQFKNVRW AKGRRETYLC YVVKRRDSAT

SFSLDFGYLR NKNGCHVELL FLRYISDWDL DPGRCYRVTW

FTSWSPCYDC ARHVADFLRG NPNLSLRIFT ARLYFCEDRK

AEPEGLRRLH RAGVQIAIMT FKENHERTFK AWEGLHENSV

RLSRQLRRIL LPLYEVDDLR DAFRTLGL.

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 905)
MDSLLMNRRK FLYQFKNVRW AKGRRETYLC YVVKRRDSAT

SFSLDFGYLR NKNGCHVELL FLRYISDWDL DPGRCYRVTW

FTSWSPCYDC ARHVADFLRG NPNLSLRIFT ARLYFCEDRK

AEPEGLRRLH RAGVQIAIMT FKDYFYCWNT FVENHERTFK

AWEGLHENSV RLSRQLRRIL LPLYEVDDLR DAFRTLGL.

Transcription Factors

A transcription factor can include: i) a DNA binding domain; and ii) a transcription activator. A transcription factor can include: i) a DNA binding domain; and ii) a transcription repressor. Suitable transcription factors include polypeptides that include a transcription activator or a transcription repressor domain (e.g., the Kruppel associated box (KRAB or SKD); the Mad mSIN3 interaction domain (SID); the ERF repressor domain (ERD), etc.); zinc-finger-based artificial transcription factors (see, e.g., Sera (2009) *Adv. Drug Deliv.* 61:513); TALE-based artificial transcription factors (see, e.g., Liu et al. (2013) *Nat. Rev. Genetics* 14:781); and the like. In some cases, the transcription factor comprises a VP64 polypeptide (transcriptional activation). In some cases, the transcription factor comprises a Krüppel-associated box (KRAB) polypeptide (transcriptional repression). In some cases, the transcription factor comprises a Mad mSIN3 interaction domain (SID) polypeptide (transcriptional repression). In some cases, the transcription factor comprises an ERF repressor domain (ERD) polypeptide (transcriptional repression). For example, in some cases, the transcription factor is a transcriptional activator, where the transcriptional activator is GAL4-VP16.

Recombinases

Suitable recombinases include, e.g., a Cre recombinase; a Hin recombinase; a Tre recombinase; a FLP recombinase; and the like.

Reverse Transcriptases

Suitable reverse transcriptases include, e.g., a murine leukemia virus reverse transcriptase; a Rous sarcoma virus reverse transcriptase; a human immunodeficiency virus type I reverse transcriptase; a Moloney murine leukemia virus reverse transcriptase; and the like.

Antibodies

Suitable antibodies include, e.g., single-chain antibodies such as a nanobody, a single chain Fv antibody; a diabody; a minibody; and the like. A suitable antibody can bind an intracellular antigen, an antigen present on a cell surface, or an extracellular antigen.

Anti-CRISPR Polypeptides

Suitable anti-CRISPR (Acr) polypeptides include, e.g., AcrIIA1, AcrIIA2, AcrIIA3, AcrIIA4, AcrIIC1, AcrIIC2, AcrIIC3, AcrE1, AcrID1, Acrf10, anti-CRISPR protein 30, Acrf2, and Acrf1. See, e.g., WO 2017/160689; and Nakamura et al. (2019) Nature Communications 10:194; Harrington et al. (2017) Cell 170:1224; Shin et al. (2017) Sci. Adv. 3:e1701620; Zhu et al. (2019) Mol. Cell 74:296; Dong et al. (2017) Nature 546:436; Bondy-Denomy et al. (2013) Nature 493:429; Rauch et al. (2017) Cell 168:150; Ka et al. (2018) Nucl. Acids Res. 46:485; Basgall et al. (2018) Microbiol. 164:464. In some cases, the Acr polypeptide reduces binding to and/or cleavage of a target nucleic acid by a type II CRISPR/Cas effector polypeptide.

In some cases, the Acr polypeptide is an AcrIIA4 polypeptide. An AcrIIA4 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 936)
NDLIREIKNKDYTVKLSGTDSNSITQLIIRVNNDGNEYVISESENESIV
EKFISAFKNGWNQEYEDEEEFYNDMQTITLKSELN.

In some cases, the Acr polypeptide is an AcrIIA1 polypeptide. An AcrIIA1 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 937)
MTIKLLDEFLKKHDLTRYQLSKLTGISQNTLKDQNEKPLNKYTVSILRS

LSLISGLSVSDVLFELEDIEKNSDDLAGFKHLLDKYKLSFPAQEFELYC

LIKEFESANIEVLPFTFNRFENEEHVNIKKDVCKALENAITVLKEKKNE

LL.

In some cases, the Acr polypeptide is an AcrIIA2 polypeptide. An AcrIIA2 polypeptide can comprise an amino acid sequence having at least 80%, at least 85%, at least 90%, at least 95%, at least 98%, at least 99%, or 100%, amino acid sequence identity to the following amino acid sequence:

(SEQ ID NO: 938)
MTLTRAQKKY AEAMHEFINM VDDFEESTPD FAKEVLHDSD

YVVITKNEKY AVALCSLSTD ECEYDTNLYL DEKLVDYSTV

DVNGVTYYIN IVETNDIDDL EIATDEDEMK SGNQEIILKS

ELK.

CRISPR/Cas Effector Polypeptides

As noted above, in some cases, a nucleic acid of the present disclosure comprises a nucleotide sequence encoding a CRISPR/Cas effector polypeptide; a system of the present disclosure comprises a nucleic acid comprising a nucleotide sequence encoding a CRISPR/Cas effector polypeptide; and a VLP of the present disclosure comprises a CRISPR/Cas effector polypeptide. Any known CRISPR/Cas effector polypeptide is suitable in the context of a nucleic acid of the present disclosure, a system of the present disclosure, or a VLP of the present disclosure.

Examples of CRISPR/Cas effector polypeptides are CRISPR/Cas endonucleases (e.g., class 2 CRISPR/Cas effector polypeptide such as a type II, type V, or type VI CRISPR/Cas effector polypeptide). Where a CRISPR/Cas effector polypeptide has endonuclease activity, the CRISPR/Cas effector polypeptide may also be referred to as a "CRISPR/Cas endonuclease." A CRISPR/Cas effector polypeptide can also have reduced or undetectable endonuclease activity. A CRISPR/Cas effector polypeptide can also be a fusion CRISPR/Cas effector polypeptide comprising a heterologous fusion partner. In some cases, a suitable CRISPR/Cas effector polypeptide is a class 2 CRISPR/Cas effector polypeptide. In some cases, a suitable CRISPR/Cas effector polypeptide is a class 2 type II CRISPR/Cas effector polypeptide (e.g., a Cas9 protein). In some cases, a suitable CRISPR/Cas effector polypeptide is a class 2 type V CRISPR/Cas endonuclease (e.g., a Cpf1 protein, a C2c1 protein, or a C2c3 protein). In some cases, a suitable CRISPR/Cas effector polypeptide is a class 2 type VI CRISPR/Cas effector polypeptide (e.g., a C2c2 protein; also referred to as a "Cas13a" protein). Also suitable for use is a CasX protein. Also suitable for use is a CasY protein.

In some cases, the CRISPR/Cas effector polypeptide is a Type II CRISPR/Cas effector polypeptide. In some cases, the CRISPR/Cas effector polypeptide is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 8A. In some cases, a Cas9 polypeptide comprises the amino acid sequence depicted in one of FIG. 8A-8F.

In some cases, the Cas9 polypeptide is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 9.

In some cases, the Cas9 polypeptide is a *Campylobacter jejuni* Cas9 (CjCas9) polypeptide. CjCas9 recognizes the 5'-NNNVRYM-3' as the protospacer-adjacent motif (PAM). The amino acid sequence of CjCas9 is set forth in SEQ ID NO:50. In some cases, a suitable Cas9 polypeptide comprises an amino acid sequence having at least 50%, at least 60%, at least 70%, at least 80%, at least 90%, at least 95%, at least 98%, at least 99%, or more than 99%, amino acid sequence identity to the CjCas9 amino acid sequence set forth in SEQ ID NO:50.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 8A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 8A, where amino acids N497, R661, Q695, and Q926 are substituted, e.g., with alanine. In some cases, a suitable Cas9 polypeptide exhibits altered PAM specificity. See, e.g., Kleinstiver et al. (2015) *Nature* 523:481.

In some cases, a suitable CRISPR/Cas effector polypeptide is a type V CRISPR/Cas effector polypeptide. In some cases, a type V CRISPR/Cas effector polypeptide is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in FIG. 10A, FIG. 10B, or FIG. 10C.

In some cases, a suitable CRISPR/Cas effector polypeptide is a CasX or a CasY polypeptide. CasX and CasY polypeptides are described in Burstein et al. (2017) *Nature* 542:237.

In some cases, a suitable CRISPR/Cas effector polypeptide is a fusion protein comprising a CRISPR/Cas effector polypeptide that is fused to a heterologous polypeptide (also referred to as a "fusion partner"). In some cases, a CRISPR/Cas effector polypeptide is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

A nucleic acid that binds to a class 2 CRISPR/Cas effector polypeptide (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

In some cases, a VLP of the present disclosure comprises a CRISPR/Cas effector polypeptide, or both a CRISPR/Cas effector polypeptide and a guide RNA. In some cases, e.g., where a target nucleic acid comprises a deleterious mutation in a defective allele (e.g., a deleterious mutation in a retinal cell target nucleic acid), the CRISPR/Cas effector polypeptide/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, a VLP of the present disclosure comprises: i) an RNA-guided endonuclease; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, a VLP of the present disclosure comprises: i) a CRISPR/Cas effector polypeptide; and ii) 2 or more gRNAs, where the two or more gRNAs provide for multiplexed gene knockout, e.g., each of the 2 or more guide RNAs is targeted to a different gene. In some cases, the guide RNAs are sgRNAs. In some cases, the guide RNAs are dgRNAs.

In some cases, a VLP of the present disclosure comprises: i) an RNA-guided endonuclease; and ii) 2 or more gRNAs, where the two or more gRNAs provide for multiplexed gene knockout, e.g., each of the 2 or more guide RNAs is targeted to a different gene. In some cases, the guide RNAs are sgRNAs. In some cases, the guide RNAs are dgRNAs.

In some cases, a VLP of the present disclosure comprises: i) an RNA-guided endonuclease; and ii) 2 separate sgRNAs, where the 2 separate sgRNAs provide for deletion of a target nucleic acid via non-homologous end joining (NHEJ). In some cases, the guide RNAs are sgRNAs. In some cases, the guide RNAs are dgRNAs.

Class 2 CRISPR/Cas Effector Polypeptides

In class 2 CRISPR systems, the functions of the effector complex (e.g., the cleavage of target DNA) are carried out by a single endonuclease (e.g., see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97); and Shmakov et al. (2017) *Nature Reviews Microbiology* 15:169. As such, the term "class 2 CRISPR/Cas protein" is used herein to encompass the CRISPR/Cas effector polypeptide (e.g., the target nucleic acid cleaving protein) from class 2 CRISPR systems. Thus, the term "class 2 CRISPR/Cas effector polypeptide" as used herein encompasses type II CRISPR/Cas effector polypeptides (e.g., Cas9); type V-A CRISPR/Cas effector polypeptides (e.g., Cpf1 (also referred to a "Cas12a")); type V-B CRISPR/Cas effector polypeptides (e.g., C2c1 (also referred to as "Cas12b")); type V-C CRISPR/Cas effector polypeptides (e.g., C2c3 (also referred to as "Cas12c")); type V-U1 CRISPR/Cas effector polypeptides (e.g., C2c4); type V-U2 CRISPR/Cas effector polypeptides (e.g., C2c8); type V-U5 CRISPR/Cas effector polypeptides (e.g., C2c5); type V-U4 CRISPR/Cas proteins (e.g., C2c9); type V-U3 CRISPR/Cas effector polypeptides (e.g., C2c10); type VI-A CRISPR/Cas effector polypeptides (e.g., C2c2 (also known as "Cas13a")); type VI-B CRISPR/Cas effector polypeptides (e.g., Cas13b (also known as C2c4)); and type VI-C CRISPR/Cas effector polypeptides (e.g., Cas13c (also known as C2c7)). To date, class 2 CRISPR/Cas effector polypeptides encompass type II, type V, and type VI CRISPR/Cas effector polypeptides, but the term is also meant to encompass any class 2 CRISPR/Cas effector polypeptide suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

A type II CRISPR/Cas effector polypeptide is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein comprising a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases, a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive, or has reduced enzymatic activity relative to a wild-type Cas9 protein (e.g., relative to *Streptococcus pyogenes* Cas9).

In some cases, a fusion protein comprises: a) a catalytically inactive Cas9 protein (or other catalytically inactive CRISPR effector polypeptide); and b) a catalytically active endonuclease. For example, in some cases, the catalytically active endonuclease is a FokI polypeptide. FokI is a 579 amino acid bacterial protein comprising a DNA recognition domain and a DNA cleavage domain (catalytic domain), also known as the "FokI nuclease domain" (Li et al (1992) *Proc Natl Acad Sci USA* 89(10):4275-9). The wild type cleavage domain or FokI nuclease domain comprises approximately residues 394-579 of the full length FokI protein. ForI is a dimeric enzyme complex requiring 2 FokI nuclease domains to crease a double strand DNA cleavage event. As one non-limiting example, in some cases, a fusion protein comprises: a) a catalytically inactive Cas9 protein (or other catalytically inactive CRISPR effector polypeptide); and b) a FokI nuclease comprising an amino acid sequence having at least at least 85%, at least 90%, at least 95%, at least 98%, at least 99%, or 100%, amino acid sequence identity to the FokI amino acid sequence provided below; where the FokI nuclease has a length of from about 195 amino acids to about 200 amino acids. In some cases, the FokI nuclease is a nickase, where one of the FokI dimeric complex is inactive.

FokI nuclease amino acid sequence:

```
                                        (SEQ ID NO: 893)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKA

QLTRLNHITNCNGAVLSVEELLIGGEMIKAGTLTLEEVRRKFNNGEIN

F.
```

Assays to determine whether given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like III | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-816.

In other words, in some cases, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-816.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, and are set forth as SEQ ID NOs: 1-4, respectively), or to the corresponding portions in any of the amino acid sequences set forth in SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-816.

In some cases, a suitable Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816. Any Cas9 protein as defined above can be used as a Cas9 polypeptide, as part of a chimeric Cas9 polypeptide (e.g., a Cas9 fusion protein), any of which can be used in an RNP of the present disclosure.

In some cases, a Cas9 protein comprises 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-816.

Examples of various Cas9 proteins (and Cas9 domain structure) and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5): 1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; Shmakov et al., Nat Rev Microbiol. 2017 March; 15(3):169-182; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

Variant Cas9 Proteins—Nickases and dCas9

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as a nuclease defective Cas9 protein or "dCas9" for "dead" Cas9. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 264-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 264-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

In some cases, a variant Cas9 protein has a reduced ability to cleave both the complementary and the non-complementary strands of a double stranded target nucleic acid. As a non-limiting example, in some cases, the variant Cas9 protein harbors mutations at amino acid positions corresponding to residues D10 and H840 (e.g., D10A and H840A) of SEQ ID NO: 5 (or the corresponding residues of any of the proteins set forth as SEQ ID NOs: 6-261 and 264-816) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "dead" Cas9 or simply "dCas9." See, e.g., SEQ ID NO: 264.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-816) can be altered (i.e., substituted). Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-816, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816. In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 5 (the motifs are in Table 1, above, and are set forth as SEQ ID NOs: 1-4, respectively), or to the corresponding portions in any of the amino acid sequences set forth in SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 70% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 75% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 80% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 85% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 90% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 95% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 99% or more amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816. In some cases, a suitable variant Cas9 protein comprises an amino acid sequence having 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 60% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 70% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 75% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 80% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 85% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 90% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 95% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 99% or more amino acid sequence identity to the Cas9 amino acid sequence set forth in SEQ ID NO: 5, or to any of the amino acid sequences set forth as SEQ ID NOs: 6-816. In some cases, a suitable variant Cas9 protein comprises an amino acid sequence having 100% amino acid sequence identity to the Cas9 amino acid sequence set forth in SEQ ID NO: 5, or to any of the amino acid sequences set forth as SEQ ID NOs: 6-816.

Type V and Type VI CRISPR/Cas Effector Polypeptides

In some cases, a suitable CRISPR/Cas effector polypeptide is a type V or type VI CRISPR/Cas effector polypeptide (e.g., Cpf1, C2c1, C2c2, C2c3). Type V and type VI CRISPR/Cas effector polypeptide are a type of class 2 CRISPR/Cas effector polypeptide. Examples of type V CRISPR/Cas effector polypeptides include but are not limited to: Cpf1, C2c1, and C2c3. An example of a type VI CRISPR/Cas effector polypeptide is C2c2. In some cases, a suitable CRISPR/Cas effector polypeptide is a type V CRISPR/Cas endonuclease (e.g., Cpf1, C2c1, C2c3). In some cases, a Type V CRISPR/Cas effector polypeptide is a Cpf1 protein. In some cases, a suitable CRISPR/Cas effector polypeptide is a type VI CRISPR/Cas endonuclease (e.g., Cas13a).

Like type II CRISPR/Cas effector polypeptides, type V and VI CRISPR/Cas effector polypeptides form a complex with a corresponding guide RNA. The guide RNA provides target specificity to CRISPR/Cas effector polypeptide-guide RNA RNP complex by having a nucleotide sequence (a guide sequence) that is complementary to a sequence (the target site) of a target nucleic acid (as described elsewhere herein). The CRISPR/Cas effector polypeptide of the complex provides the site-specific activity. In other words, the CRISPR/Cas effector polypeptide is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., Cpf1, C2c1, C2c2, and C2c3 guide RNAs) can be found in the art, for example, see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97; and Shmakov et al. (2017) *Nature Reviews Microbiology* 15:169.

In some cases, the Type V or type VI CRISPR/Cas effector polypeptide (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas effector polypeptide (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases, a type V CRISPR/Cas effector polypeptide is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs:818-822.

In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 818-822. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 818-822.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 818-822), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 917 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., an E→A substitution) at an amino acid residue corresponding to amino acid 1006 of the Cpf1 amino acid sequence set forth in SEQ ID NO: 818. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822; and comprises an amino acid substitution (e.g., a D→A substitution) at an amino acid residue corresponding to amino acid 1255 of the Cpf1 amino acid sequence set forth in SEQ ID NO: 818.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 818-822.

In some cases, a type V CRISPR/Cas effector polypeptide is a C2c1 protein (examples include those set forth as SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 823-830.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 823-830). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 823-830. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 823-830.

In some cases, the C2c1 protein exhibits reduced enzymatic activity relative to a wild-type C2c1 protein (e.g., relative to a C2c1 protein comprising the amino acid sequence set forth in any of SEQ ID NOs: 823-830), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 823-830.

In some cases, a type V CRISPR/Cas effector polypeptide is a C2c3 protein (examples include those set forth as SEQ ID NOs: 831-834). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 831-834.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 831-834. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 831-834.

In some cases, the C2c3 protein exhibits reduced enzymatic activity relative to a wild-type C2c3 protein (e.g., relative to a C2c3 protein comprising the amino acid sequence set forth in any of SEQ ID NOs: 831-834), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 831-834.

In some cases, a type VI CRISPR/Cas endonuclease is a C2c2 protein (examples include those set forth as SEQ ID NOs: 835-846). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 835-846.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 835-846. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 835-846.

In some cases, the C2c2 protein exhibits reduced enzymatic activity relative to a wild-type C2c2 protein (e.g., relative to a C2c2 protein comprising the amino acid sequence set forth in any of SEQ ID NOs: 835-846), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 835-846.

Examples and guidance related to type V or type VI CRISPR/Cas endonucleases (including domain structure) and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; Shmakov et al., Mol Cell. 2015 Nov. 5; 60(3):385-97; and Shmakov et al., Nat Rev Microbiol. 2017 March; 15(3):169-182; and U.S. patents and patent applications: 9,580,701; 20170073695, 20170058272, 20160362668, 20160362667, 20160298078, 20160289637, 20160215300, 20160208243, and 20160208241, each of which is hereby incorporated by reference in its entirety.

CasX and CasY Proteins

Suitable CRISPR/Cas effector polypeptides include CasX and CasY proteins. See, e.g., Burstein et al. (2017) *Nature* 542:237.

CRISPR/Cas Effector Fusion Polypeptides

In some cases, a CRISPR/Cas effector polypeptide encoded by a nucleic acid of the present disclosure is a CRISPR/Cas effector fusion polypeptide comprising: i) a CRISPR/Cas effector polypeptide; and ii) a heterologous fusion partner.

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases, the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a CRISPR/Cas effector fusion polypeptide includes a heterologous polypeptide that has enzymatic activity that modifies a target nucleic acid (e.g., nuclease activity such as FokI nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, or glycosylase activity).

In some cases, a CRISPR/Cas effector fusion polypeptide includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription, and that are suitable as heterologous fusion partners, include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription, and that are suitable as heterologous fusion partners, include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like. In some cases, the heterologous fusion partner is a reverse transcriptase.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity). In some cases, the fusion partner is a reverse transcriptase acting with a prime editing guide RNA ("pegRNA") that specifies the target and encodes an edit to be introduced into the target DNA (Anzalone et al. (2019) *Nature*: doi.org10.1038/541586-019-1711-4; "Search-and-replace genome editing without double-strand breaks or donor DNA").

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetyl transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

In some cases, a fusion protein comprises: a) a catalytically inactive CRISPR/Cas effector polypeptide (e.g., a catalytically inactive Cas9 polypeptide); and b) a catalytically active endonuclease. For example, in some cases, the catalytically active endonuclease is a FokI polypeptide. As one non-limiting example, in some cases, a fusion protein comprises: a) a catalytically inactive Cas9 protein (or other catalytically inactive CRISPR effector polypeptide); and b) is a FokI nuclease comprising an amino acid sequence having at least at least 85%, at least 90%, at least 95%, at least 98%, at least 99%, or 100%, amino acid sequence identity to the FokI amino acid sequence provided below; where the FokI nuclease has a length of from about 195 amino acids to about 200 amino acids.

FokI nuclease amino acid sequence:

```
                                          (SEQ ID NO: 893)
QLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKA

QLTRLNHITNCNGAVLSVEELLIGGEMIKAGTLTLEEVRRKFNNGEIN

F.
```

In some cases, the FokI polypeptide used is the nuclease catalytic domain. In some cases, two catalytically inactive CRISPR/Cas effector-Fok I nuclease domain fusions are used. An FokI nuclease must dimerize to be active so the use of two fusion proteins allows the formation of an active and dimeric complex.

In some cases, the fusion partner is a deaminase. Thus, in some cases, a CRISPR/Cas effector polypeptide fusion polypeptide comprises: a) a CRISPR/Cas effector polypeptide; and b) a deaminase. In some cases, the CRISPR/Cas effector polypeptide is catalytically inactive. Suitable deaminases include a cytidine deaminase and an adenosine deaminase.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                          (SEQ ID NO: 894)
MSEVEFSHEYWMRHALTLAKRAWDEREVPVGAVLVHNNRVIGEGWNRPI

GRHDPTAHAEIMALRQGGLVMQNYRLIDATLYVTLEPCVMCAGAMIHSR

IGRVVFGARDAKTGAAGSLMDVLHHPGMNHRVEITEGILADECAALLSD

FFRMRRQEIKAQKKAQSSTD
```

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                          (SEQ ID NO: 895)
MRRAFITGVFFLSEVEFSHEYWMRHALTLAKRAWDEREVPVGAVLVHNN

RVIGEGWNRPIGRHDPTAHAEIMALRQGGLVMQNYRLIDATLYVTLEPC

VMCAGAMIHSRIGRVVFGARDAKTGAAGSLMDVLHHPGMNHRVEITEGI

LADECAALLSDFFRMRRQEIKAQKKAQSSTD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

```
                                          (SEQ ID NO: 896)
MGSHMTNDIYFMTLAIEEAKKAAQLGEVPIGAIITKDDEVIARAHNLRE

TLQQPTAHAEHIAIERAAKVLGSWRLEGCTLYVTLEPCVMCAGTIVMSR
```

-continued

IPRVVYGADDPKGGCSGSLMNLLQQSNFNHRAIVDKGVLKEACSTLLTT

FFKNLRANKKSTN:

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

(SEQ ID NO: 897)

MTQDELYMKEAIKEAKKAEEKGEVPIGAVLVINGEIIARAHNLRETEQR

SIAHAEMLVIDEACKALGTWRLEGATLYVTLEPCPMCAGAVVLSRVEKV

VFGAFDPKGGCSGTLMNLLQEERFNHQAEVVSGVLEEECGGMLSAFFRE

LRKKKKAARKNLSE

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

(SEQ ID NO: 898)

MPPAFITGVTSLSDVELDHEYWMRHALTLAKRAWDEREVPVGAVLVHNH

RVIGEGWNRPIGRHDPTAHAEIMALRQGGLVLQNYRLLDTTLYVTLEPC

VMCAGAMVHSRIGRVVFGARDAKTGAAGSLIDVLHHPGMNHRVEIIEGV

LRDECATLLSDFFRMRRQEIKALKKADRAEGAGPAV

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

(SEQ ID NO: 899)

MDEYWMQVAMQMAEKAEAAGEVPVGAVLVKDGQQIATGYNLSISQHDPT

AHAEILCLRSAGKKLENYRLLDATLYITLEPCAMCAGAMVHSRIARVVY

GARDEKTGAAGTVVNLLQHPAFNHQVEVTSGVLAEACSAQLSRFFKRRR

DEKKALKLAQRAQQGIE

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

(SEQ ID NO: 900)

MDAAKVRSEFDEKMMRYALELADKAEALGEIPVGAVLVDDARNIIGE

GWNLSIVQSDPTAHAEIIALRNGAKNIQNYRLLNSTLYVTLEPCTMC

AGAILHSRIKRLVFGASDYKTGAIGSRFHFFDDYKMNHTLEITSGVL

AEECSQKLSTFFQKRREEKKIEKALLKSLSDK

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

(SEQ ID NO: 901)

MRTDESEDQDHRMMRLALDAARAAAEAGETPVGAVILDPSTGEVIAT

AGNGPIAAHDPTAHAEIAAMRAAAAKLGNYRLTDLTLVVTLEPCAMC

AGAISHARIGRVVFGADDPKGGAVVHGPKFFAQPTCHWRPEVTGGVL

ADESADLLRGFFRARRKAKI

In some cases, a suitable adenosine deaminase comprises an amino acid sequence having at least 80%, at least 85%, at least 90%, at least 95%, at least 98%, at least 99%, or 100%, amino acid sequence identity to the following *Geobacter sulfurreducens* TadA amino acid sequence:

(SEQ ID NO: 902)

MSSLKKTPIRDDAYWMGKAIREAAKAAARDEVPIGAVIVRDGAVIGR

GHNLREGSNDPSAHAEMIAIRQAARRSANWRLTGATLYVTLEPCLMC

MGAIILARLERVVFGCYDPKGGAAGSLYDLSADPRLNHQVRLSPGVC

QEECGTMLSDFFRDLRRRKKAKATPALFIDERKVPPEP

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

(SEQ ID NO: 903)

MDSLLMNRRKFLYQFKNVRWAKGRRETYLCYVVKRRDSATSFSLDFG

YLRNKNGCHVELLFLRYISDWDLDPGRCYRVTWFTSWSPCYDCARHV

ADFLRGNPNLSLRIFTARLYFCEDRKAEPEGLRRLHRAGVQIAIMTF

KDYFYCWNTFVENHERTFKAWEGLHENSVRLSRQLRRILLPLYEVDD

LRDAFRTLGL

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 904)

MDSLLMNRRK FLYQFKNVRW AKGRRETYLC YVVKRRDSAT

SFSLDFGYLR NKNGCHVELL FLRYISDWDL DPGRCYRVTW

FTSWSPCYDC ARHVADFLRG NPNLSLRIFT ARLYFCEDRK

AEPEGLRRLH RAGVQIAIMT FKENHERTFK AWEGLHENSV

RLSRQLRRIL LPLYEVDDLR DAFRTLGL.

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

(SEQ ID NO: 905)

MDSLLMNRRK FLYQFKNVRW AKGRRETYLC YVVKRRDSAT

SFSLDFGYLR NKNGCHVELL FLRYISDWDL DPGRCYRVTW

FTSWSPCYDC ARHVADFLRG NPNLSLRIFT ARLYFCEDRK

AEPEGLRRLH RAGVQIAIMT FKDYFYCWNT FVENHERTFK

AWEGLHENSV RLSRQLRRIL LPLYEVDDLR DAFRTLGL.

In some cases, a CRISPR/Cas effector polypeptide fusion polypeptide of the present disclosure comprises a CRISPR/Cas effector polypeptide that exhibits nickase activity. Suitable nickases are described elsewhere herein.

In some cases, a suitable CRISPR/Cas effector polypeptide that exhibits nickase activity comprises an amino acid sequence having at least 80%, at least 85%, at least 90%, at least 95%, at least 98%, at least 99%, or 100%, amino acid sequence identity to the following "nicking high fidelity" Cas9 amino acid sequence:

(SEQ ID NO: 906)

DKKYSIGLAIGTNSVGWAVITDEYKVPSKKFKVLGNTDRHSIKKNLI

GALLFDSGETAEATRLKRTARRRYTRRKNRICYLQEIFSNEMAKVDD

SFFHRLEESFLVEEDKKHERHPIFGNIVDEVAYHEKYPTIYHLRKKL

VDSTDKADLRLIYLALAHMIKFRGHFLIEGDLNPDNSDVDKLFIQLV

QTYNQLFEENPINASGVDAKAILSARLSKSRRLENLIAQLPGEKKNG

LFGNLIALSLGLTPNFKSNFDLAEDAKLQLSKDTYDDDLDNLLAQIG

DQYADLFLAAKNLSDAILLSDILRVNTEITKAPLSASMIKRYDEHHQ

DLTLLKALVRQQLPEKYKEIFFDQSKNGYAGYIDGGASQEEFYKFIK

PILEKMDGTEELLVKLNREDLLRKQRTFDNGSIPHQIHLGELHAILR

RQEDFYPFLKDNREKIEKILTFRIPYYVGPLARGNSRFAWMTRKSEE

TITPWNFEEVVDKGASAQSFIERMTAFDKNLPNEKVLPKHSLLYEYF

TVYNELTKVKYVTEGMRKPAFLSGEQKKAIVDLLFKTNRKVTVKQLK

EDYFKKIECFDSVEISGVEDRFNASLGTYHDLLKIIKDKDFLDNEEN

EDILEDIVLTLTLFEDREMIEERLKTYAHLFDDKVMKQLKRRRYTGW

GALSRKLINGIRDKQSGKTILDFLKSDGFANRNFMALIHDDSLTFKE

DIQKAQVSGQGDSLHEHIANLAGSPAIKKGILQTVKVVDELVKVMGR

HKPENIVIEMARENQTTQKGQKNSRERMKRIEEGIKELGSQILKEHP

VENTQLQNEKLYLYYLQNGRDMYVDQELDINRLSDYDVDHIVPQSFL

KDDSIDNKVLTRSDKNRGKSDNVPSEEVVKKMKNYWRQLLNAKLITQ

RKFDNLTKAERGGLSELDKAGFIKRQLVETRAITKHVAQILDSRMNT

KYDENDKLIREVKVITLKSKLVSDFRKDFQFYKVREINNYHHAHDAY

LNAVVGTALIKKYPKLESEFVYGDYKVYDVRKMIAKSEQEIGKATAK

YFFYSNIMNFFKTEITLANGEIRKRPLIETNGETGEIVWDKGRDFAT

VRKVLSMPQVNIVKKTEVQTGGFSKESILPKRNSDKLIARKKDWDPK

-continued

KYGGFDSPTVAYSVLVVAKVEKGKSKKLKSVKELLGITIMERSSFEK

NPIDFLEAKGYKEVKKDLIIKLPKYSLFELENGRKRMLASAGELQKG

NELALPSKYVNFLYLASHYEKLKGSPEDNEQKQLFVEQHKHYLDEII

EQISEFSKRVILADANLDKVLSAYNKHRDKPIREQAENIIHLFTLTN

LGAPAAFKYFDTTIDRKRYTSTKEVLDATLIHQSITGLYETRIDLSQ

LGGD.

In some cases, a suitable CRISPR/Cas effector polypeptide that exhibits nickase activity comprises an amino acid sequence having at least 80%, at least 85%, at least 90%, at least 95%, at least 98%, at least 99%, or 100%, amino acid sequence identity to the following "nicking enhanced" Cas9 amino acid sequence:

(SEQ ID NO: 907)

DKKYSIGLAIGTNSVGWAVITDEYKVPSKKFKVLGNTDRHSIKKNLI

GALLFDSGETAEATRLKRTARRRYTRRKNRICYLQEIFSNEMAKVDD

SFFHRLEESFLVEEDKKHERHPIFGNIVDEVAYHEKYPTIYHLRKKL

VDSTDKADLRLIYLALAHMIKFRGHFLIEGDLNPDNSDVDKLFIQLV

QTYNQLFEENPINASGVDAKAILSARLSKSRRLENLIAQLPGEKKNG

LFGNLIALSLGLTPNFKSNFDLAEDAKLQLSKDTYDDDLDNLLAQIG

DQYADLFLAAKNLSDAILLSDILRVNTEITKAPLSASMIKRYDEHHQ

DLTLLKALVRQQLPEKYKEIFFDQSKNGYAGYIDGGASQEEFYKFIK

PILEKMDGTEELLVKLNREDLLRKQRTFDNGSIPHQIHLGELHAILR

RQEDFYPFLKDNREKIEKILTFRIPYYVGPLARGNSRFAWMTRKSEE

TITPWNFEEVVDKGASAQSFIERMTNFDKNLPNEKVLPKHSLLYEYF

TVYNELTKVKYVTEGMRKPAFLSGEQKKAIVDLLFKTNRKVTVKQLK

EDYFKKIECFDSVEISGVEDRFNASLGTYHDLLKIIKDKDFLDNEEN

EDILEDIVLTLTLFEDREMIEERLKTYAHLFDDKVMKQLKRRRYTGW

GRLSRKLINGIRDKQSGKTILDFLKSDGFANRNFMQLIHDDSLTFKE

DIQKAQVSGQGDSLHEHIANLAGSPAIKKGILQTVKVVDELVKVMGR

LIREVKVITLKSKLVSDFRKDFQFYKVREINNYHHAHDAYLNAVVGT

HKPENIVIEMARENQTTQKGQKNSRERMKRIEEGIKELGSQILKEHP

VENTQLQNEKLYLYYLQNGRDMYVDQELDINRLSDYDVDHIVPQSFL

ADDSIDNKVLTRSDKNRGKSDNVPSEEVVKKMKNYWRQLLNAKLITQ

RKFDNLTKAERGGLSELDKAGFIKRQLVETRQITKHVAQILDSRMNT

KYDENDKALIKKYPALESEFVYGDYKVYDVRKMIAKSEQEIGKATAK

YFFYSNIMNFFKTEITLANGEIRKAPLIETNGETGEIVWDKGRDFAT

VRKVLSMPQVNIVKKTEVQTGGFSKESILPKRNSDKLIARKKDWDPK

KYGGFDSPTVAYSVLVVAKVEKGKSKKLKSVKELLGITIMERSSFEK

NPIDFLEAKGYKEVKKDLIIKLPKYSLFELENGRKRMLASAGELQKG

NELALPSKYVNFLYLASHYEKLKGSPEDNEQKQLFVEQHKHYLDEII

-continued

```
EQISEFSKRVILADANLDKVLSAYNKHRDKPIREQAENIIHLFTLTN

LGAPAAFKYFDTTIDRKRYTSTKEVLDATLIHQSITGLYETRIDLSQ

LGGD.
```

In some cases, a suitable CRISPR/Cas effector polypeptide that exhibits nickase activity comprises an amino acid sequence having at least 80%, at least 85%, at least 90%, at least 95%, at least 98%, at least 99%, or 100%, amino acid sequence identity to the following "nicking" Cas9 amino acid sequence:

```
                                              (SEQ ID NO: 908)
DKKYSIGLAIGTNSVGWAVITDEYKVPSKKFKVLGNTDRHSIKKNLI

GALLFDSGETAEATRLKRTARRRYTRRKNRICYLQEIFSNEMAKVDD

SFFHRLEESFLVEEDKKHERHPIFGNIVDEVAYHEKYPTIYHLRKKL

VDSTDKADLRLIYLALAHMIKFRGHFLIEGDLNPDNSDVDKLFIQLV

QTYNQLFEENPINASGVDAKAILSARLSKSRRLENLIAQLPGEKKNG

LFGNLIALSLGLTPNFKSNFDLAEDAKLQLSKDTYDDDLDNLLAQIG

DQYADLFLAAKNLSDAILLSDILRVNTEITKAPLSASMIKRYDEHHQ

DLTLLKALVRQQLPEKYKEIFFDQSKNGYAGYIDGGASQEEFYKFIK

PILEKMDGTEELLVKLNREDLLRKQRTFDNGSIPHQIHLGELHAILR

RQEDFYPFLKDNREKIEKILTFRIPYYVGPLARGNSRFAWMTRKSEE

TITPWNFEEVVDKGASAQSFIERMTNFDKNLPNEKVLPKHSLLYEYF

TVYNELTKVKYVTEGMRKPAFLSGEQKKAIVDLLFKTNRKVTVKQLK

EDYFKKIECFDSVEISGVEDRFNASLGTYHDLLKIIKDKDFLDNEEN

EDILEDIVLTLTLFEDREMIEERLKTYAHLFDDKVMKQLKRRRYTGW

GRLSRKLINGIRDKQSGKTILDFLKSDGFANRNFMQLIHDDSLTFKE

DIQKAQVSGQGDSLHEHIANLAGSPAIKKGILQTVKVVDELVKVMGR

HKPENIVIEMARENQTTQKGQKNSRERMKRIEEGIKELGSQILKEHP

VENTQLQNEKLYLYYLQNGRDMYVDQELDINRLSDYDVDHIVPQSFL

KDDSIDNKVLTRSDKNRGKSDNVPSEEVVKKMKNYWRQLLNAKLITQ

RKFDNLTKAERGGLSELDKAGFIKRQLVETRQITKHVAQILDSRMNT

KYDENDKLIREVKVITLKSKLVSDFRKDFQFYKVREINNYHHAHDAY

LNAVVGTALIKKYPKLESEFVYGDYKVYDVRKMIAKSEQEIGKATAK

YFFYSNIMNFFKTEITLANGEIRKRPLIETNGETGEIVWDKGRDFAT

VRKVLSMPQVNIVKKTEVQTGGFSKESILPKRNSDKLIARKKDWDPK

KYGGFDSPTVAYSVLVVAKVEKGKSKKLKSVKELLGITIMERSSFEK

NPIDFLEAKGYKEVKKDLIIKLPKYSLFELENGRKRMLASAGELQKG

NELALPSKYVNFLYLASHYEKLKGSPEDNEQKQLFVEQHKHYLDEII

EQISEFSKRVILADANLDKVLSAYNKHRDKPIREQAENIIHLFTLTN

LGAPAAFKYFDTTIDRKRYTSTKEVLDATLIHQSITGLYETRIDLSQ

LGGD.
```

In some cases, a therapeutic polypeptide is a fusion therapeutic polypeptide comprising: i) a therapeutic polypeptide; and ii) one or more heterologous fusion partners (one or more heterologous fusion polypeptides). In some cases, a fusion therapeutic polypeptide comprises one or more localization signal peptides. In some cases, a fusion CRISPR/Cas effector polypeptide comprises one or more localization signal peptides. Suitable localization signals ("subcellular localization signals") include, e.g., a nuclear localization signal (NLS) for targeting to the nucleus; a sequence to keep the fusion protein out of the nucleus, e.g., a nuclear export sequence (NES); a sequence to keep the fusion protein retained in the cytoplasm; a mitochondrial localization signal for targeting to the mitochondria; a chloroplast localization signal for targeting to a chloroplast; an endoplasmic reticulum (ER) retention signal; and ER export signal; and the like. In some cases, a fusion polypeptide does not include a NLS so that the protein is not targeted to the nucleus (which can be advantageous, e.g., when the target nucleic acid is an RNA that is present in the cytosol).

In some cases, a fusion polypeptide includes (is fused to) a nuclear localization signal (NLS) (e.g., in some cases 2 or more, 3 or more, 4 or more, or 5 or more NLSs). Thus, in some cases, a fusion polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a fusion polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a fusion polypeptide includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO:909); the NLS from nucleoplasmin (e.g., the nucleoplasmin bipartite NLS with the sequence KRPAATKKAGQAKKKK (SEQ ID NO:910)); the c-myc NLS having the amino acid sequence PAAKRVKLD (SEQ ID NO:911) or RQRRNELKRSP (SEQ ID NO:912); the hRNPA1 M9 NLS having the sequence NQSSNFGPMKGGNFGGRSSGPYGGGGQYFAKPRNQGGY (SEQ ID NO:913); the sequence RMRIZFKNKGKDTAELRRRRVEVSVELRKAKKDEQILKRRNV (SEQ ID NO:914) of the IBB domain from importin-alpha; the sequences VSRKRPRP (SEQ ID NO:915) and PPKKARED (SEQ ID NO:916) of the myoma T protein; the sequence PQPKKKPL (SEQ ID NO:917) of human p53; the sequence SALIKKKKKMAP (SEQ ID NO:918) of mouse c-abl IV; the sequences DRLRR (SEQ ID NO:919) and PKQKKRK (SEQ ID NO:920) of the influenza virus NS1; the sequence RKLKKKIKKL (SEQ ID NO:921) of the Hepatitis virus delta antigen; the sequence REKKKFLKRR (SEQ ID NO:922) of the mouse Mx1 protein; the sequence KRKGDEVDGVDEVAKKKSKK (SEQ ID NO:923) of the human poly(ADP-ribose) polymerase; and the sequence RKCLQAGMNLEARKTKK (SEQ ID NO:924) of the steroid hormone receptors (human) glucocorticoid. In some cases, an NLS comprises the amino acid sequence MDSLLMNRRKFLYQFKNVRWAKGRRE- TYLC (SEQ ID NO:925). In general, NLS (or multiple NLSs) are of sufficient strength to drive accumulation of the fusion polypeptide in a detectable amount in the nucleus of a eukaryotic cell. Detection of accumulation in the nucleus may be performed by any suitable technique. For example, a detectable marker may be fused to the fusion polypeptide such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CRISPR/Cas effector polypeptide fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. In some cases, a therapeutic fusion polypeptide includes a PTD. A PTD attached to another molecule, which can range from a small polar molecule to a large macromolecule and/or a nanoparticle, facilitates the molecule traversing a membrane, for example going from extracellular space to intracellular space, or cytosol to within an organelle. In some cases, a PTD is covalently linked to the amino terminus of a polypeptide. In some cases, a PTD is covalently linked to the carboxyl terminus of a polypeptide. In some cases, the PTD is inserted internally in the fusion polypeptide (i.e., is not at the N- or C-terminus of the fusion polypeptide) at a suitable insertion site. In some cases, a subject fusion polypeptide includes (is conjugated to, is fused to) one or more PTDs (e.g., two or more, three or more, four or more PTDs). In some cases, a PTD includes a nuclear localization signal (NLS) (e.g., in some cases 2 or more, 3 or more, 4 or more, or 5 or more NLSs). Thus, in some cases, a fusion polypeptide includes one or more NLSs (e.g., 2 or more, 3 or more, 4 or more, or 5 or more NLSs). In some embodiments, a PTD is covalently linked to a nucleic acid (e.g., a guide nucleic acid, a polynucleotide encoding a guide nucleic acid, a polynucleotide encoding a fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:926); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:927); Transportan GWTLNSAGYLLGKINLKALAALAKKIL (SEQ ID NO:928); KALAWEAKLAKALAKALAKHLAKALAKALKCEA (SEQ ID NO:929); and RQIKIWFQNRRMKWKK (SEQ ID NO:930). Exemplary PTDs include but are not limited to, YGRKKRRQRRR (SEQ ID NO:926), RKKRRQRRR (SEQ ID NO:931); an arginine homopolymer of from 3 arginine residues to 50 arginine residues; Exemplary PTD domain amino acid sequences include, but are not limited to, any of the following: YGRKKRRQRRR (SEQ ID NO:926); RKKRRQRR (SEQ ID NO:932); YARAAARQARA (SEQ ID NO:933); THRLPRRRRRR (SEQ ID NO:934); and GGRRARRRRRR (SEQ ID NO:935). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Anti-CRISPR Polypeptides

In some cases, a VLP of the present disclosure comprises, in addition to a CRISPR-Cas effector polypeptide, an anti-CRISPR (ACR) polypeptide. An ACR can in some cases inhibit a Cas9 polypeptide. Suitable ACR polypeptides include, e.g., AcrIIC1, AcrIIA1, AcrIIA2, AcrIIA3, AcrIIA4, AcrIIC2, AcrIIC3, AcrE1, AcrID1, Acrf10, anti-CRISPR protein 30, Acrf2, and Acrf1. See, e.g., WO 2017/160689; and Nakamura et al. (2019) *Nature Communications* 10:194; Harrington et al. (2017) *Cell* 170:1224; Shin et al. (2017) *Sci. Adv.* 3:e1701620; Zhu et al. (2019) *Mol. Cell* 74:296.

As an example, an AcrIIA4 polypeptide can comprise an amino acid sequence having at least 80%, at least 85%, at least 90%, at least 95%, at least 98%, at least 99%, or 100%, amino acid sequence identity to the following amino acid sequence:

```
                                          (SEQ ID NO: 936)
NDLIREIKNKDYTVKLSGTDSNSITQLIIRVNNDGNEYVISESENES

IVEKFISAFKNGWNQEYEDEEEFYNDMQTITLKSELN.
```

In some cases, the Acr polypeptide is an AcrIIA1 polypeptide. An AcrIIA1 polypeptide can comprise an amino acid sequence having at least 80%, at least 85%, at least 90%, at least 95%, at least 98%, at least 99%, or 100%, amino acid sequence identity to the following amino acid sequence:

```
                                          (SEQ ID NO: 937)
MTIKLLDEFLKKHDLTRYQLSKLTGISQNTLKDQNEKPLNKYTVSIL

RSLSLISGLSVSDVLFELEDIEKNSDDLAGFKHLLDKYKLSFPAQEF

ELYCLIKEFESANIEVLPFTFNRFENEEHVNIKKDVCKALENAITVL

KEKKNELL.
```

In some cases, the Acr polypeptide is an AcrIIA2 polypeptide. An AcrIIA2 polypeptide can comprise an amino acid sequence having at least 80%, at least 85%, at least 90%, at least 95%, at least 98%, at least 99%, or 100%, amino acid sequence identity to the following amino acid sequence:

```
                                          (SEQ ID NO: 938)
MTLTRAQKKY AEAMHEFINM VDDFEESTPD FAKEVLHDSD

YVVITKNEKY AVALCSLSTD ECEYDTNLYL DEKLVDYSTV

DVNGVTYYIN IVETNDIDDL EIATDEDEMK SGNQEIILKS

ELK.
```

Guide RNA

As noted above, in some cases, a system of the present disclosure comprises a CRISPR/Cas effector polypeptide guide RNA or a nucleic acid comprising a nucleotide sequence encoding a CRISPR/Cas effector polypeptide guide RNA.

A nucleic acid molecule that binds to a CRISPR/Cas effector polypeptide protein and targets the complex to a specific location within a target nucleic acid is referred to herein as a "CRISPR/Cas effector polypeptide guide RNA" or simply a "guide RNA."

A guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule. The "targeting segment" is also referred to herein as a "variable region" of a guide RNA. The "protein-binding segment" is also referred to herein as a "constant region" of a guide RNA. In some cases, the guide RNA is a Cas9 guide RNA.

The first segment (targeting segment) of a guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CRISPR/Cas effector polypeptide. The protein-binding segment of a guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the guide RNA (the guide sequence of the guide RNA) and the target nucleic acid.

A guide RNA and a CRISPR/Cas effector polypeptide form a complex (e.g., bind via non-covalent interactions). The guide RNA provides target specificity to the complex by including a targeting segment, which includes a guide sequence (a nucleotide sequence that is complementary to a sequence of a target nucleic acid). The CRISPR/Cas effector polypeptide of the complex provides the site-specific activity (e.g., cleavage activity or an activity provided by the CRISPR/Cas effector polypeptide when the CRISPR/Cas effector polypeptide is a CRISPR/Cas effector polypeptide fusion polypeptide, i.e., has a fusion partner). In other words, the CRISPR/Cas effector polypeptide is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the guide RNA.

The "guide sequence" also referred to as the "targeting sequence" of a guide RNA can be modified so that the guide RNA can target a CRISPR/Cas effector polypeptide to any desired sequence of any desired target nucleic acid, with the exception that the protospacer adjacent motif (PAM) sequence can be taken into account. Thus, for example, a guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a guide RNA includes two separate nucleic acid molecules: an "activator" and a "targeter" and is referred to herein as a "dual guide RNA", a "double-molecule guide RNA", or a "two-molecule guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the guide RNA and a stretch ("duplex-forming segment") of nucleotides that forms one half of the dsRNA duplex of the protein-binding segment of the guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a guide RNA. The exact sequence of a given crRNA or tracrRNA molecule is characteristic of the species in which the RNA molecules are found. A dual guide RNA can include any corresponding activator and targeter pair.

The term "activator" or "activator RNA" is used herein to mean a tracrRNA-like molecule (tracrRNA: "trans-acting CRISPR RNA") of a dual guide RNA (and therefore of a single guide RNA when the "activator" and the "targeter" are linked together by, e.g., intervening nucleotides). Thus, for example, a guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases, the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a dual guide RNA (and therefore of a single guide RNA when the "activator" and the "targeter" are linked together, e.g., by intervening nucleotides). Thus, for example, a guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term “targeter” encompasses naturally occurring crRNAs.

A guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the guide RNA and a stretch (“duplex-forming segment”) of nucleotides that forms one half of the dsRNA duplex of the protein-binding segment of the guide RNA. A corresponding tracrRNA-like molecule (activator) comprises a stretch of nucleotides (a duplex-forming segment) that forms the other half of the dsRNA duplex of the protein-binding segment of the guide RNA. In other words, a stretch of nucleotides of the targeter is complementary to and hybridizes with a stretch of nucleotides of the activator to form the dsRNA duplex of the protein-binding segment of a guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a guide RNA. The particular sequence of a given naturally existing crRNA or tracrRNA molecule is characteristic of the species in which the RNA molecules are found. Examples of suitable activator and targeter are well known in the art.

Targeting Segment of a Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the guide RNA and the target nucleic acid will interact. The targeting segment of a guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al., Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO:939), AAUUUCUGCUGUUGCAGAU (SEQ ID NO:940), AAUUUCCACUGUUGUGGAU (SEQ ID NO:941), AAUUCCUACUGUUGUAGGU (SEQ ID NO:942), AAUUUCUACUAUUGUAGAU (SEQ ID NO:943), AAUUUCUACUGCUGUAGAU (SEQ ID NO:944), AAUUUCUACUUUGUAGAU (SEQ ID NO:945), and AAUUUCUACUUGUAGAU (SEQ ID NO:946). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCAC-UUUCCAGGUGGCAAAGCCCGUUGA GCUUCU-CAAAAAG (SEQ ID NO: 947). In some cases, a C2c1 guide RNA (dual guide or single guide) is an RNA that includes the nucleotide sequence. In some cases, a C2c1 guide RNA (dual guide or single guide) is an RNA that includes the nucleotide sequence GUCUA-GAGGACAGAAUUUUUCAACGGGUGUGC-CAAUGGCCACUUUCCAGGUGGC AAAGCCCGUUGAGCUUCUCAAAAAG (SEQ ID NO:1075). In some cases, a C2c1 guide RNA (dual guide or single guide) is an RNA that includes the nucleotide sequence UCUAGAGGACAGAAUUUUUCAACGGGU-GUGCCAAUGGCCACUUUCCAGGUGGCA AAGCCCGUUGAGCUUCUCAAAAAG (SEQ ID NO:1076). A non-limiting example of an activator RNA (e.g. tracrRNA) of a C2c1 guide RNA (dual guide or single guide) is an RNA that includes the nucleotide sequence ACUUUCCAGGCAAAGCCCGUUGAGCUUCU-CAAAAAG (SEQ ID NO:948). In some cases, a duplex forming segment of a C2c1 guide RNA (dual guide or single guide) of an activator RNA (e.g. tracrRNA) includes the nucleotide sequence AGCUUCUCA (SEQ ID NO:949) or the nucleotide sequence GCUUCUCA (SEQ ID NO:1068) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGAGAAGUGGCACNNNNNNNNNNNNNNNNNNNN (SEQ ID NO:950), where the Ns represent the guide sequence, which will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO:951) or includes the nucleotide sequence CUGAGAAGU (SEQ ID NO:952) or includes the nucleotide sequence UGAGAAGUGGCAC (SEQ ID NO:953) or includes the nucleotide sequence UGAGAAGU (SEQ ID NO:954).

Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; and Shmakov et al., Mol Cell. 2015 Nov. 5; 60(3):385-97.

Nucleic Acid Modifications

In some embodiments, a nucleic acid (e.g., a DNA or an RNA encoding a polypeptide as described herein; a DNA or RNA encoding an RNA guided endonuclease; a guide RNA, etc.) has one or more modifications, e.g., a base modification, a backbone modification, a sugar modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

In some cases, 2% or more of the nucleotides of a nucleic acid (e.g., a guide RNA, etc.) are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are modified). In some cases, 2% or more of the nucleotides of a subject guide RNA are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide RNA are modified). In some cases, 2% or more of the nucleotides of a guide RNA are modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a guide RNA are modified).

In some cases, the number of nucleotides of a subject nucleic acid nucleic acid (e.g., a guide RNA, etc.) that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a subject that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that are modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a nucleic acid (e.g., a guide RNA, etc.) are modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject nucleic acid are modified). In some cases, one or more of the nucleotides of a subject guide RNA are modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject guide RNA are modified). In some cases, one or more of the nucleotides of a guide RNA are modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA are modified).

In some cases, 99% or less of the nucleotides of a nucleic acid (e.g., a guide RNA, etc.) are modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are modified). In some cases, 99% or less of the nucleotides of a subject guide RNA are modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject guide RNA are modified). In some cases, 99% or less of the nucleotides of a guide RNA are modified (e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA are modified).

In some cases, the number of nucleotides of a nucleic acid nucleic acid (e.g., a guide RNA, etc.) that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide RNA that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that are modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a nucleic acid (e.g., a guide RNA, etc.) are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are modified). In some cases, 20 or fewer of the nucleotides of a subject guide RNA are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide RNA are modified). In some cases, 20 or fewer of the nucleotides of a guide RNA are modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a guide RNA are modified).

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stable with respect to attack by single-stranded ribonucleases and is typically 5 to 10-fold less susceptible to DNases than DNA. It is commonly used in antisense oligos as a means to increase stability and binding affinity to the target message.

In some cases, 2% or more of the nucleotides of a nucleic acid (e.g., a guide RNA, etc.) are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2'-O-Methyl modified). In some cases, 2% or more of the nucleotides of a subject guide RNA are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide RNA are 2'-O-Methyl modified). In some cases, 2% or more of the nucleotides of a guide RNA are 2'-O-Methyl modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a guide RNA are 2'-O-Methyl modified).

In some cases, the number of nucleotides of a nucleic acid nucleic acid (e.g., a guide RNA, etc.) that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that are 2'-O-Methyl modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a nucleic acid (e.g., a guide RNA, etc.) are 2'-O-Methyl modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject nucleic acid are 2'-O-Methyl modified). In some cases, one or more of the nucleotides of a guide RNA are 2'-O-Methyl modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject guide RNA are 2'-O-Methyl modified). In some cases, one or more of the nucleotides of a guide RNA are 2'-O-Methyl modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA are 2'-O-Methyl modified).

In some cases, 99% or less of the nucleotides of a nucleic acid (e.g., a guide RNA, etc.) are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2'-O-Methyl modified). In some cases, 99% or less of the nucleotides of a subject guide RNA are 2'-O-Methyl modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject guide RNA are 2'-O-Methyl modified). In some cases, 99% or less of the nucleotides of a guide RNA are 2'-O-Methyl modified (e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA are 2'-O-Methyl modified).

In some cases, the number of nucleotides of a nucleic acid nucleic acid (e.g., a guide RNA, etc.) that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide RNA that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that are 2'-O-Methyl modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a nucleic acid (e.g., a guide RNA, etc.) are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2'-O-Methyl modified). In some cases, 20 or fewer of the nucleotides of a subject guide RNA are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide RNA are 2'-O-Methyl modified). In some cases, 20 or fewer of the nucleotides of a guide RNA are 2'-O-Methyl modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a guide RNA are 2'-O-Methyl modified).

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

In some cases, 2% or more of the nucleotides of a nucleic acid (e.g., a guide RNA, etc.) are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject nucleic acid are 2' Fluoro modified). In some cases, 2% or more of the nucleotides of a subject guide RNA are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a subject guide RNA are 2' Fluoro modified). In some cases, 2% or more of the nucleotides of a guide RNA are 2' Fluoro modified (e.g., 3% or more, 5% or more, 7.5% or more, 10% or more, 15% or more, 20% or more, 25% or more, 30% or more, 35% or more, 40% or more, 45% or more, 50% or more, 55% or more, 60% or more, 65% or more, 75% or more, 80% or more, 85% or more, 90% or more, 95% or more, or 100% of the nucleotides of a guide RNA are 2' Fluoro modified).

In some cases, the number of nucleotides of a nucleic acid nucleic acid (e.g., a guide RNA, etc.) that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that are 2' Fluoro modified is in a range of from 3% to 100% (e.g., 3% to 100%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a nucleic acid (e.g., a guide RNA, etc.) are 2' Fluoro modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject nucleic acid are 2' Fluoro modified). In some cases, one or more of the nucleotides of a subject guide RNA are 2' Fluoro modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA are 2' Fluoro modified). In some cases, one or more of the nucleotides of a guide RNA are 2' Fluoro modified (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA are 2' Fluoro modified).

In some cases, 99% or less of the nucleotides of a nucleic acid (e.g., a guide RNA, etc.) are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid are 2' Fluoro modified). In some cases, 99% or less of the nucleotides of a subject guide RNA are 2' Fluoro modified (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a subject guide RNA are 2' Fluoro modified). In some cases, 99% or less of the nucleotides of a guide RNA are 2' Fluoro modified (e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA are 2' Fluoro modified).

In some cases, the number of nucleotides of a nucleic acid nucleic acid (e.g., a guide RNA, etc.) that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a subject guide RNA that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that are 2' Fluoro modified is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a nucleic acid (e.g., a guide RNA, etc.) are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid are 2' Fluoro modified). In some cases, 20 or fewer of the nucleotides of a subject guide RNA are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide RNA are 2' Fluoro modified). In some cases, 20 or fewer of the nucleotides of a guide RNA are 2' Fluoro modified (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a guide RNA are 2' Fluoro modified).

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3-end. Applications have been described ranging from antisense oligos to hybridization probes to single nucleotide polymorphism (SNP) detection and allele specific polymerase chain reaction (PCR). Due to the large increase in Tm conferred by LNAs, they also can cause an increase in primer dimer formation as well as self-hairpin formation. In some cases, the number of LNAs incorporated into a single oligo is 10 bases or less.

In some cases, the number of nucleotides of a nucleic acid nucleic acid (e.g., a guide RNA, etc.) that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that have an LNA base is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a nucleic acid (e.g., a guide RNA, etc.) have an LNA base (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject nucleic acid have an LNA base). In some cases, one or more of the nucleotides of a subject guide RNA have an LNA base (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject guide RNA have an LNA base). In some cases, one or more of the nucleotides of a guide RNA have an LNA base (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA have an LNA base).

In some cases, 99% or less of the nucleotides of a nucleic acid (e.g., a guide RNA, etc.) have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have an LNA base). In some cases, 99% or less of the nucleotides of a guide RNA have an LNA base (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA have an LNA base). In some cases, 99% or less of the nucleotides of a guide RNA have an LNA base (e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA have an LNA base).

In some cases, the number of nucleotides of a nucleic acid nucleic acid (e.g., a guide RNA, etc.) that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that have an LNA base is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a nucleic acid (e.g., a guide RNA, etc.) have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have an LNA base). In some cases, 20 or fewer of the nucleotides of a subject guide RNA have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide RNA have an LNA base). In some cases, 20 or fewer of the nucleotides of a guide RNA have an LNA base (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a guide RNA have an LNA base).

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some cases, the number of nucleotides of a nucleic acid nucleic acid (e.g., a guide RNA, etc.) that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%). In some cases, the number of nucleotides of a guide RNA that have a phosphorothioate linkage is in a range of from 3% to 99% (e.g., 3% to 99%, 3% to 95%, 3% to 90%, 3% to 85%, 3% to 80%, 3% to 75%, 3% to 70%, 3% to 65%, 3% to 60%, 3% to 55%, 3% to 50%, 3% to 45%, 3% to 40%, 5% to 99%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, or 10% to 40%).

In some cases, one or more of the nucleotides of a nucleic acid (e.g., a guide RNA, etc.) have a phosphorothioate linkage (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject nucleic acid have a phosphorothioate linkage). In some cases, one or more of the nucleotides of a subject guide RNA have a phosphorothioate linkage (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a subject guide RNA have a phosphorothioate linkage). In some cases, one or more of the nucleotides of a guide RNA have a phosphorothioate linkage (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the nucleotides of a guide RNA have a phosphorothioate linkage).

In some cases, 99% or less of the nucleotides of a nucleic acid (e.g., a guide RNA, etc.) have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a subject nucleic acid have a phosphorothioate linkage). In some cases, 99% or less of the nucleotides of a subject guide RNA have a phosphorothioate linkage (e.g., e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA have a phosphorothioate linkage). In some cases, 99% or less of the nucleotides of a guide RNA have a phosphorothioate linkage (e.g., 99% or less, 95% or less, 90% or less, 85% or less, 80% or less, 75% or less, 70% or less, 65% or less, 60% or less, 55% or less, 50% or less, or 45% or less of the nucleotides of a guide RNA have a phosphorothioate linkage).

In some cases, the number of nucleotides of a nucleic acid nucleic acid (e.g., a guide RNA, etc.) that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10). In some cases, the number of nucleotides of a guide RNA that have a phosphorothioate linkage is in a range of from 1 to 30 (e.g., 1 to 25, 1 to 20, 1 to 18, 1 to 15, 1 to 10, 2 to 25, 2 to 20, 2 to 18, 2 to 15, 2 to 10, 3 to 25, 3 to 20, 3 to 18, 3 to 15, or 3 to 10).

In some cases, 20 or fewer of the nucleotides of a nucleic acid (e.g., a guide RNA, etc.) have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject nucleic acid have a phosphorothioate linkage). In some cases, 20 or fewer of the nucleotides of a guide RNA have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a subject guide RNA have a phosphorothioate linkage). In some cases, 20 or fewer of the nucleotides of a guide RNA have a phosphorothioate linkage (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or one, of the nucleotides of a guide RNA have a phosphorothioate linkage).

In some cases, a nucleic acid (e.g., a guide RNA, etc.) has one or more nucleotides that are 2'-O-Methyl modified nucleotides. In some embodiments, a subject nucleic acid (e.g., a guide RNA, etc.) has one or more 2' Fluoro modified nucleotides. In some cases, a subject nucleic acid (e.g., a guide RNA, etc.) has one or more LNA bases. In some cases, a subject nucleic acid (e.g., a guide RNA, etc.) has one or more nucleotides that are linked by a phosphorothioate bond (i.e., the subject nucleic acid has one or more phosphorothioate linkages). In some embodiments, a subject nucleic acid (e.g., a guide RNA, etc.) has a 5' cap (e.g., a 7-methylguanylate cap (m7G)).

In some cases, a nucleic acid (e.g., a DNA or RNA encoding an RNA guided endonuclease, a guide RNA, etc.) has a combination of modified nucleotides. For example, a nucleic acid can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). A nucleic acid can have any combination of modifications. For example, a subject nucleic acid can have any combination of the above described modifications.

In some cases, a guide RNA has one or more nucleotides that are 2'-O-Methyl modified nucleotides. In some embodiments, a guide RNA has one or more 2' Fluoro modified nucleotides. In some embodiments, a guide RNA has one or more LNA bases. In some embodiments, a guide RNA has one or more nucleotides that are linked by a phosphorothioate bond (i.e., the subject nucleic acid has one or more phosphorothioate linkages). In some embodiments, a guide RNA has a 5' cap (e.g., a 7-methylguanylate cap (m7G)).

In some cases, a guide RNA has a combination of modified nucleotides. For example, a guide RNA can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage). A guide RNA can have any combination of modifications. For example, a guide RNA can have any combination of the above described modifications.

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a nucleic acid comprises one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(═O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A nucleic acid can be a nucleic acid mimetic. The term “mimetic” as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general, the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($—CH_2—$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 °C), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methylcytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O $(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2 °C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Donor Nucleic Acid

In some cases, a VLP of the present disclosure comprises, in addition to a CRISPR/Cas effector polypeptide and a guide RNA (or a nucleic acid comprising a nucleotide sequence encoding all or a portion of a guide RNA), a donor nucleic acid (also referred to herein as a "donor DNA template"). In some cases, the donor nucleic acid is a DNA molecule that is present in the VLP. In some cases, a donor nucleic acid is encoded within a nucleic acid of the present disclosure. In some cases, a system of the present disclosure comprises a donor nucleic acid. In some cases, a nucleic acid present in a system of the present disclosure comprises a nucleotide sequence encoding a donor nucleic acid.

By a "donor nucleic acid" or "donor sequence" or "donor polynucleotide" or "donor template" it is meant a nucleic acid sequence to be inserted at the site cleaved by a CRISPR/Cas effector protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair or a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance.

VLPs Comprising a Pseudotyping Envelope Glycoprotein

The present disclosure provides VLPs comprising one or more therapeutic polypeptides, where the VLPs comprise a pseudotyping envelope glycoprotein. The present disclosure provides VLPs comprising a CRISPR/Cas effector polypeptide, where the VLPs comprise a pseudotyping envelope glycoprotein. In some cases, a VLP of the present disclosure comprises: i) a CRISPR/Cas effector polypeptide; and ii) one or more guide RNAs or a nucleic acid comprising a nucleotide sequence encoding one or more guide RNAs. In some cases, a VLP of the present disclosure comprises: i) a CRISPR/Cas effector polypeptide; ii) one or more guide RNAs or a nucleic acid comprising a nucleotide sequence encoding one or more guide RNAs; and iii) a donor DNA template. In some cases, a VLP of the present disclosure comprises: i) a CRISPR/Cas effector polypeptide; and ii) an anti-CRISPR polypeptide.

In some cases, a VLP of the present disclosure comprises: i) retroviral MA, CA, and NC polypeptides; ii) a heterologous polypeptide (e.g., a pseudotyping envelope protein) that provides for binding of the VLP to a target cell; and iii) one or more therapeutic polypeptides encapsidated within the VLP. In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, and NC polypeptides, and p6 polypeptides; and ii) one or more therapeutic polypeptides.

In some cases, a VLP of the present disclosure comprises: i) retroviral MA, CA, and NC polypeptides; ii) a heterologous polypeptide (e.g., a pseudotyping envelope protein) that provides for binding of the VLP to a target cell; and iii) a CRISPR/Cas effector polypeptide encapsidated within the VLP. In some cases, a VLP of the present disclosure comprises, in addition to MA, CA, and NC polypeptides, other viral polypeptides such as a p2 polypeptide, a p1 polypeptide, and a p6 polypeptide. In some cases, a VLP of the present disclosure comprises: i) retroviral MA, CA, and NC polypeptides, and p6 polypeptides; and ii) a CRISPR/Cas effector polypeptide.

Suitable pseudotyping envelop glycoproteins are described in detail above. The pseudotyping viral envelope protein can be, e.g., a Hepatitis B virus (HBV) glycoprotein, a Hepatitis C virus (HCV) glycoprotein, a Marburg virus glycoprotein, an Ebola virus glycoprotein, a VSV-G glycoprotein, an influenza virus hemagglutinin, a SARS-CoV glycoprotein, a respiratory syncytial virus (RSV) glycoprotein, a human parainfluenza virus glycoprotein, a measles virus hemagglutinin and a measles virus fusion glycoprotein, a measles virus fusion glycoprotein, an HTLV-1 glycoprotein, a Ross river virus glycoprotein, a rabies virus glycoprotein, a Mokola virus glycoprotein, a Semliki Forest virus glycoprotein, a Sindbis virus glycoprotein, or a Venezuelan equine encephalitis virus glycoprotein.

In some cases, the pseudotyping viral glycoprotein is selected from a Hepatitis B virus (HBV) glycoprotein, a Hepatitis C virus (HCV) glycoprotein, a Marburg virus glycoprotein, an Ebola virus glycoprotein, a VSV-G glycoprotein. In some cases, the VLP comprises a guide RNA, or a nucleic acid comprising a nucleotide sequence encoding a guide RNA, where the guide RNA comprises a targeting sequence that targets a gene selected from PCSK9, SERPINA1, TTR, FAH, OTC, G6PC, AGXT, F9, and F8. Where the target gene comprises a defect that leads to pathology, in some cases, the VLP comprises a donor template DNA that comprises a nucleotide sequence without the defect.

In some cases, the pseudotyping viral glycoprotein is selected from an influenza virus hemagglutinin, a SARS-CoV glycoprotein, a respiratory syncytial virus glycoprotein, a human parainfluenza virus glycoprotein, and a VSV-G. In some cases, the VLP comprises a guide RNA, or a nucleic acid comprising a nucleotide sequence encoding a guide RNA, where the guide RNA comprises a targeting sequence that targets CFTR. Where the target gene comprises a defect that leads to pathology, in some cases, the VLP comprises a donor template DNA that comprises a nucleotide sequence without the defect.

In some cases, the pseudotyping viral glycoprotein is a measles virus hemagglutinin and/or a measles virus fusion glycoprotein. In some cases, the VLP comprises a guide RNA, or a nucleic acid comprising a nucleotide sequence encoding a guide RNA, where the guide RNA comprises a targeting sequence that targets an HbF gene.

In some cases, the pseudotyping viral glycoprotein is selected from a measles virus hemagglutinin and/or a measles virus fusion glycoprotein, an HTLV-1 glycoprotein, and a VSV-G glycoprotein. In some cases, the VLP comprises a guide RNA, or a nucleic acid comprising a nucleotide sequence encoding a guide RNA, where the guide RNA comprises a targeting sequence that targets a gene selected from PD1, CTLA4, and TCR.

In some cases, the pseudotyping viral glycoprotein is selected from a HIV-1 envelope, a HTLV-1 glycoprotein, a measles virus hemagglutinin and/or a measles virus fusion glycoprotein, and a VSV-G glycoprotein; and wherein the target cell is a CD4+ T cell. In some cases, the VLP comprises a guide RNA, or a nucleic acid comprising a nucleotide sequence encoding a guide RNA, where the guide RNA comprises a targeting sequence that targets a CCR5 gene. In some cases, the VLP comprises one or more guide RNAs, or a nucleic acid comprising a nucleotide sequence encoding one or more guide RNAs, where the one or more guide RNAs comprises a targeting sequence that targets an integrated proviral HIV-1.

In some cases, the pseudotyping viral glycoprotein is a Ross River virus glycoprotein or a VSV-G. In some cases, the VLP comprises a guide RNA, or a nucleic acid comprising a nucleotide sequence encoding a guide RNA, where the guide RNA comprises a targeting sequence that targets a Duchenne muscular dystrophy gene. Where the target gene comprises a defect that leads to pathology, in some cases, the VLP comprises a donor template DNA that comprises a nucleotide sequence without the defect.

In some cases, the pseudotyping viral glycoprotein is selected from an Ebola virus glycoprotein, a Marburg virus glycoprotein, and a VSV-G. In some cases, the VLP comprises a guide RNA, or a nucleic acid comprising a nucleotide sequence encoding a guide RNA, where the guide RNA comprises a targeting sequence that targets a CEP290 gene. Where the target gene comprises a defect that leads to pathology, in some cases, the VLP comprises a donor template DNA that comprises a nucleotide sequence without the defect.

In some cases, the pseudotyping viral glycoprotein is selected from an Ebola virus glycoprotein, a Marburg virus glycoprotein, and a VSV-G. In some cases, the VLP comprises a guide RNA, or a nucleic acid comprising a nucleotide sequence encoding a guide RNA, where the guide RNA comprises a targeting sequence that targets a USH2A gene. Where the target gene comprises a defect that leads to pathology, in some cases, the VLP comprises a donor template DNA that comprises a nucleotide sequence without the defect.

In some cases, the pseudotyping viral glycoprotein is selected from aa rabies glycoprotein, a Mokola virus glycoprotein, a Semliki Forest virus glycoprotein, a Sindbis virus glycoprotein, a Venezuelan equine encephalitis virus glycoprotein, an influenza hemagglutinin glycoprotein, and a VSV-G. In some cases, the VLP comprises a guide RNA, or a nucleic acid comprising a nucleotide sequence encoding a guide RNA, and wherein the guide RNA comprises a targeting sequence that targets a gene selected from Tau/MAPT-1, HTT, SOD1, SOCS3, USP8, DOT1L, ufmylation, SOCS2, SOCS9, SOCS13, SOCS11, and SOCS5.

Compositions

The present disclosure provides a composition comprising a VLP of the present disclosure. The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19$^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

A composition of the present disclosure can include: a) a VLP of the present disclosure; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethanesulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Suitable salts include, e.g., NaCl, $MgCl_2$, KCl, $MgSO_4$, etc.

In some cases, the composition is sterile. In some cases, the composition is suitable for administration to a human subject, e.g., where the composition is sterile and is free of detectable pyrogens and/or other toxins.

A composition of the present disclosure may include other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like. In some cases, a composition of the present disclosure comprises saline.

In some cases, a composition of the present disclosure comprises VLPs of the present disclosure in a concentration of from about $10^5$ VLPs/ml to about $10^{10}$ VLPs/ml, e.g., from about $10^5$ VLPs/ml to about $5\times10^5$ VLPs/ml, from about $5\times10^5$ VLPs/ml to about $10^6$ VLPs/ml, from about $10^6$ VLPs/ml to about $5\times10^6$ VLPs/ml, from about $5\times10^6$ VLPs/ml to about $10^7$ VLPs/ml, from about $10^7$ VLPs/ml to about $5\times10^7$ VLPs/ml, from about $5\times10^7$ VLPs/ml to about $10^8$ VLPs/ml, from about $10^8$ VLPs/ml to about $5\times10^8$ VLPs/ml, from about $5\times10^8$ VLPs/ml to about $10^9$ VLPs/ml, from about $10^9$ VLPs/ml to about $5\times10^9$ VLPs/ml, or from about $5\times10^9$ VLPs/ml to about $10^{10}$ VLPs/ml.

The present disclosure provides a container comprising a VLP composition of the present disclosure, e.g., a liquid composition. The container can be, e.g., a syringe, an ampoule, and the like. In some cases, the container is sterile. In some cases, both the container and the composition are sterile.

The number of VLPs present in a composition of the present disclosure can be quantitated using various methods. For example, an enzyme-linked immunosorbent assay (ELISA) comprising an antibody specific for a lentiviral gag protein such as p24 can be used to determine the number of VLPs in a composition.

The amount of VLPs in a composition of the present disclosure can also be expressed as the volume of a composition of VLPs of the present disclosure that, when contacted with a population of target cells, provides for gene editing in 50% of the target cell population.

Utility

A VLP of the present disclosure finds use in a variety of methods. A VLP of the present disclosure can be used to deliver one or more therapeutic polypeptides to a cell. The cell to which one or more therapeutic polypeptides is being delivered can be an in vitro cell. The cell to which one or more therapeutic polypeptides is being delivered can be an ex vivo cell. The cell to which one or more therapeutic polypeptides is being delivered can be in vivo. For example, a VLP of the present disclosure can be used to deliver a therapeutic antibody for binding an intracellular target polypeptide.

A VLP of the present disclosure can be used to deliver: i) a CRISPR/Cas effector polypeptide; ii) a CRISPR/Cas effector polypeptide and guide RNA; or iii) a CRISPR/Cas effector polypeptide, a guide RNA, and a donor DNA, to a cell, where the CRISPR/Cas effector polypeptide (e.g., when complexed with a guide RNA) can do one or more of the following: (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. The cell to which a CRISPR/Cas effector polypeptide is being delivered can be an in vitro cell. The cell to which a CRISPR/Cas effector polypeptide is being delivered can be an ex vivo cell. The cell to which a CRISPR/Cas effector polypeptide is being delivered can be in vivo.

A cell that serves as a recipient for a VLP of the present disclosure can be any of a variety of cells, including, e.g., in vitro cells; in vivo cells; ex vivo cells; primary cells; cancer cells; animal cells; plant cells; algal cells; fungal cells; etc. A cell that serves as a recipient for a VLP of the present disclosure is referred to as a "host cell" or a "target cell."

Non-limiting examples of cells (target cells) include: a eukaryotic cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a non-human animal cell or derived from a non-human animal cell. A cell can be a non-human mammalian cell or derived from a non-human mammalian cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera*, or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

In some cases, a single dose of a composition comprising a VLP of the present disclosure comprises from about $10^2$ VLPs to about $10^9$ VLPs. For example, a single dose of a composition comprising a VLP of the present disclosure comprises from about $10^2$ VLPs to about $10^3$ VLPs, from about $10^3$ VLPs to about $10^4$ VLPs, from about $10^4$ VLPs to about $10^5$ VLPs, from about $10^5$ VLPs to about $10^6$ VLPs, from about $10^6$ VLPs to about $10^7$ VLPs, from about $10^7$ VLPs to about $10^8$ VLPs, from about $10^8$ VLPs to about $10^9$ VLPs, or from about $10^9$ VLPs to about $10^{10}$ VLPs.

A composition comprising a VLP of the present disclosure can be administered via any of a variety of parenteral and non-parenteral routes of administration. For example, a composition comprising a VLP of the present disclosure can be administered intravenously, intramuscularly, intratumorally, peritumorally, subcutaneously, intraperitoneally, and the like. A VLP of the present disclosure can be administered via convection enhanced delivery (CED) injection.

Delivering a Therapeutic Polypeptide (e.g., a CRISPR/Cas Effector Polypeptide) to a Target Cell Using a VLP Comprising a Targeting Glycoprotein The present disclosure provides methods of delivering one or more therapeutic polypeptides to an individual in need thereof, the methods generally involving administering to the individual an effective amount of a VLP of the present disclosure. In some cases, a composition of the present disclosure is administered to the individual. The present disclosure provides methods of delivering a CRISPR/Cas effector polypeptide to an individual in need thereof, the methods generally involving administering to the individual an effective amount of a VLP of the present disclosure. In some cases, a composition of the present disclosure is administered to the individual.

In some cases, the pseudotyping viral glycoprotein is selected from a Hepatitis B virus (HBV) glycoprotein, a Hepatitis C virus (HCV) glycoprotein, a Marburg virus glycoprotein, an Ebola virus glycoprotein, a VSV-G glycoprotein; and the target cell is a liver cell. In some cases, the VLP comprises a guide RNA, or a nucleic acid comprising a nucleotide sequence encoding a guide RNA, where the guide RNA comprises a targeting sequence that targets a gene selected from PCSK9 (proprotein convertase subtilisin/kexin type 9), SERPINA1 (serpin family A member 1), TTR (transthyretin), FAH (fumarylacetoacetate hydrolase), OTC (ornithine carbamoyltransferase), G6PC (glucose-6-phosphatase catalytic subunit), AGXT (alanine-glyoxylate and serine-pyruvate aminotransferase), F9 (coagulation factor IX), and F8 (coagulation factor VIII). For example, targeting a PCSK9 gene can treat familial hypercholesterolemia. As another example, targeting a SERPINA1 gene can treat alpha-1 antitrypsin deficiency (AATD). As another example, targeting a TTR gene can treat amyloid transthyretin (ATTR) amyloidosis. As another example, targeting a FAH gene can treat hereditary tyrosinemia type 1 (HT1). As another example, targeting an OTC gene can treat ornithine transcarbamylase (OTC) deficiency. As another example, targeting a G6PC gene can treat glycogen storage disease Ia (GSD Ia). As another example, targeting an F9 gene can treat hemophilia type B. As another example, targeting an F8 gene can treat hemophilia type A. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from an influenza virus hemagglutinin, a SARS-CoV glycoprotein, a respiratory syncytial virus glycoprotein, a human parainfluenza virus glycoprotein, and a VSV-G; and the target cell is a lung cell. In some cases, the VLP comprises a guide RNA, or a nucleic acid comprising a nucleotide sequence encoding a guide RNA, where the guide RNA comprises a targeting sequence that targets a CFTR (cystic fibrosis transmembrane conductance regulator) gene. For example, targeting a CFTR gene can treat cystic fibrosis. Where the target gene comprises a defect that leads to pathology, a donor nucleic acid comprising a nucleotide sequence without the defect can be included in the VLP, such that the defect is corrected.

In some cases, the pseudotyping viral glycoprotein is a measles virus hemagglutinin and/or a measles virus fusion glycoprotein, and the target cell is a $CD34^+$ cell. In some cases, the VLP comprises a guide RNA, or a nucleic acid comprising a nucleotide sequence encoding a guide RNA, where the guide RNA comprises a targeting sequence that targets an HbF (fetal hemoglobin) gene. For example, targeting an HbF gene can treat sickle cell disease or beta-thalassemia. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from a measles virus hemagglutinin and/or a measles virus fusion glycoprotein, an HTLV-1 glycoprotein, and a VSV-G glycoprotein; and the target cell is a $CD8^+$ T cell. In some cases, the VLP comprises a guide RNA, or a nucleic acid comprising a nucleotide sequence encoding a guide RNA, where the guide RNA comprises a targeting sequence that targets a gene selected from PD1 (programmed cell death 1), CTLA4 (cytotoxic T-lymphocyte-associated protein 4), and TCR (T-cell receptor). For example, targeting a PD-1 gene, a CTLA-4 gene, or a TCR gene, can be used in the generation of chimeric antigen receptor (CAR)-T cells.

In some cases, the pseudotyping viral glycoprotein is selected from a HIV-1 envelope, a HTLV-1 glycoprotein, a measles virus hemagglutinin, and a VSV-G glycoprotein; and the target cell is a CD4+ T cell. In some cases, the VLP comprises a guide RNA, or a nucleic acid comprising a nucleotide sequence encoding a guide RNA, where the guide RNA comprises a targeting sequence that targets a CCR5 gene, or targets an integrated and proviral HIV-1. Targeting a CCR5 gene can be used to enhance resistance to HIV. Targeting an integrated and proviral HIV-1 can be used to reduce the pool of T cells that are reservoirs for latent HIV.

In some cases, the pseudotyping viral glycoprotein is a Ross River virus glycoprotein or a VSV-G; and the target cell is a skeletal muscle cell. In some cases, the VLP comprises a guide RNA, or a nucleic acid comprising a nucleotide sequence encoding a guide RNA, where the guide RNA comprises a targeting sequence that targets a Duchenne muscular dystrophy (DMD) gene. Targeting a DMD gene can be used to treat Duchenne muscular dystrophy. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from an Ebola virus glycoprotein, a Marburg virus glycoprotein, and a VSV-G; and the target cell is an ocular cell (e.g., in a retinal cell, a photoreceptor cell, etc.). In some cases, the VLP comprises a guide RNA, or a nucleic acid comprising a nucleotide sequence encoding a guide RNA, and wherein the guide RNA comprises a targeting sequence that targets a CEP290 (centrosomal protein 290) gene.

Targeting a CEP290 gene can be used to treat Leber congenital amaurosis 10 (LCA10). Where the target gene comprises a defect that leads to pathology, a donor nucleic acid comprising a nucleotide sequence without the defect can be included in the VLP, such that the defect is corrected.

In some cases, the pseudotyping viral glycoprotein is selected from an Ebola virus glycoprotein, a Marburg virus glycoprotein, and a VSV-G; and the target cell is an auditory cell (e.g., hair cells, cochlear cells, etc.). In some cases, the VLP comprises a guide RNA, or a nucleic acid comprising a nucleotide sequence encoding a guide RNA, where the guide RNA comprises a targeting sequence that targets a USH2A (Usher syndrome 2A) gene. Targeting a USH2A gene can be used to treat Usher Syndrome type 2A. Where the target gene comprises a defect that leads to pathology, a donor nucleic acid comprising a nucleotide sequence without the defect can be included in the VLP, such that the defect is corrected.

In some cases, the pseudotyping viral glycoprotein is selected from aa rabies glycoprotein, a Mokola virus glycoprotein, a Semliki Forest virus glycoprotein, a Sindbis virus glycoprotein, a Venezuelan equine encephalitis virus glycoprotein, an influenza hemagglutinin glycoprotein, and a VSV-G; and wherein the target cell is a central nervous system cell (e.g., neurons (e.g., excitatory and inhibitory neurons); and glial cells (e.g., oligodendrocytes, astrocytes and microglia)). In some cases, the VLP comprises a guide RNA, or a nucleic acid comprising a nucleotide sequence encoding a guide RNA, and wherein the guide RNA comprises a targeting sequence that targets a gene selected from Tau/MAPT-1, HTT (Huntingtin), SOD1 (superoxide dismutase 1), SOCS3 (suppressor of cytokine signaling 3), USP8 (ubiquitin specific peptidase 8), DOT1L (DOT1-like histone lysine methyltransferase), UFM1 (ufmylation; ubiquitin fold modifier 1), SOCS2 (suppressor of cytokine signaling 2), SOCS9 (suppressor of cytokine signaling 9), SOCS13 (suppressor of cytokine signaling 13), SOCS11 (suppressor of cytokine signaling 11), and SOCS5 (suppressor of cytokine signaling 5). For example, targeting a Tau gene can treat Alzheimer's disease. As another example, targeting an HTT gene can treat Huntington Disease. As another example, targeting a SOD1 gene can treat amyotrophic lateral sclerosis. As another example, targeting a Ufmylation, USP8, DOT1L, SOCS2, SOCS3, SOCS9, SOCS13, SOCS11, or SOCS5 gene can treat glioblastoma. Where the target gene comprises a defect that leads to pathology, a donor nucleic acid comprising a nucleotide sequence without the defect can be included in the VLP, such that the defect is corrected.

In some cases, a single dose of a composition comprising a VLP of the present disclosure comprises from about $10^2$ VLPs to about $10^9$ VLPs. For example, a single dose of a composition comprising a VLP of the present disclosure comprises from about $10^2$ VLPs to about $10^3$ VLPs, from about $10^3$ VLPs to about $10^4$ VLPs, from about $10^4$ VLPs to about $10^5$ VLPs, from about $10^5$ VLPs to about $10^6$ VLPs, from about $10^6$ VLPs to about $10^7$ VLPs, from about $10^7$ VLPs to about $10^8$ VLPs, from about $10^8$ VLPs to about $10^9$ VLPs, or from about $10^9$ VLPs to about $10^{10}$ VLPs.

A composition comprising a VLP of the present disclosure can be administered via any of a variety of parenteral and non-parenteral routes of administration. For example, a composition comprising a VLP of the present disclosure can be administered intravenously, intramuscularly, intratumorally, peritumorally, subcutaneously, intraperitoneally, and the like. A VLP of the present disclosure can be administered via convection enhanced delivery (CED) injection.

Examples of Non-Limiting Aspects of the Disclosure

Aspects, including embodiments, of the present subject matter described above may be beneficial alone or in combination, with one or more other aspects or embodiments.

Aspects Set A

Without limiting the foregoing description, certain non-limiting aspects of the disclosure numbered 1-84 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A nucleic acid comprising a nucleotide sequence encoding a virus-like particle (VLP) comprising a fusion polypeptide that comprises: a) a retroviral gag polyprotein comprising a matrix (MA) polypeptide, a capsid (CA) polypeptide, and a nucleocapsid (NC) polypeptide; b) a CRISPR/Cas effector polypeptide; and c) one or more heterologous protease cleavage sites, wherein the one or more heterologous protease cleavage sites is between the gag polyprotein and the CRISPR/Cas effector polypeptide.

Aspect 2. The nucleic acid of aspect 1, wherein the heterologous protease cleavage site is selected from the group consisting of: a TEV cleavage site, a PreScission cleavage site, a human rhinovirus 3C protease cleavage site, an enterokinase cleavage site, an Epstein-Barr virus protease cleavage site, a cathepsin D cleavage site, and/or a thrombin cleavage site.

Aspect 3. The nucleic acid of aspect 1, wherein the gag polypeptide comprises one or more heterologous protease cleavage sites between one or both of: i) the MA polypeptide and the CA polypeptide; and ii) the CA polypeptide and the NC polypeptide.

Aspect 4. The nucleic acid of aspect 1, wherein the retroviral gag polyprotein is a lentiviral gag polyprotein.

Aspect 5. The nucleic acid of aspect 4, wherein the lentiviral gag polyprotein is selected from a bovine immunodeficiency virus gag polyprotein, a simian immunodeficiency virus gag polyprotein, a feline immunodeficiency virus gag polyprotein, a human immunodeficiency virus gag polyprotein, an equine infection anemia virus gag polyprotein, and a caprine arthritis encephalitis virus gag polyprotein.

Aspect 6. The nucleic acid of aspect 4, wherein the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide.

Aspect 7. The nucleic acid of aspect 1, wherein the retroviral gag polyprotein is a gag polyprotein of an alpha retrovirus, a beta retrovirus, a gamma retrovirus, a delta retrovirus, an epsilon retrovirus, or a spumavirus.

Aspect 8. The nucleic acid of any one of aspects 1-7, wherein the CRISPR/Cas effector polypeptide is a type II CRISPR/Cas effector polypeptide.

Aspect 9. The nucleic acid of aspect 8, wherein the type II CRISPR/Cas effector polypeptide is a Cas9 polypeptide.

Aspect 10. The nucleic acid of any one of aspects 1-7, wherein the CRISPR/Cas effector polypeptide is a type V CRISPR/Cas effector polypeptide.

Aspect 11. The nucleic acid of aspect 10, wherein the type V CRISPR/Cas effector polypeptide is a Cas12a, a Cas12b, a Cas12c, a Cas12d, or a Cas12e polypeptide.

Aspect 12. The nucleic acid of any one of aspects 1-7, wherein the CRISPR/Cas effector polypeptide is a type VI CRISPR/Cas effector polypeptide.

Aspect 13. The nucleic acid of aspect 12, wherein the type VI CRISPR/Cas effector polypeptide is a Cas13a polypeptide or a Cas13b polypeptide.

Aspect 14. The nucleic acid of any one of aspects 1-7, wherein the CRISPR/Cas effector polypeptide is a Cas14 polypeptide.

Aspect 15. The nucleic acid of any one of aspects 1-14, wherein the CRISPR/Cas effector polypeptide is a variant that exhibits reduced nucleic acid cleavage activity.

Aspect 16. The nucleic acid of aspect 1-14, wherein the CRISPR/Cas effector polypeptide is a fusion polypeptide comprising: i) a CRISPR/Cas effector polypeptide is a variant that has reduced nucleic acid cleavage activity; and ii) a heterologous fusion polypeptide.

Aspect 17. The nucleic acid of aspect 16, wherein the heterologous fusion polypeptide is a protein modifying enzyme.

Aspect 18. The nucleic acid of aspect 16, wherein the heterologous fusion polypeptide is a nucleic acid modifying enzyme or a reverse transcriptase.

Aspect 19. The nucleic acid of aspect 18, wherein the nucleic acid modifying enzyme is a cytidine deaminase.

Aspect 20. The nucleic acid of any one of aspects 1-19, wherein the CRISPR/Cas effector polypeptide comprises one or more nuclear localization signals.

Aspect 21. The nucleic acid of any one of aspects 1-20, wherein the heterologous protease cleavage site comprises an amino acid sequence selected from the group consisting of ENLYTQS (SEQ ID NO:854), ENAYFQS (SEQ ID NO:883), ENLRFQS (SEQ ID NO:884), ENLFFQS (SEQ ID NO:885), ETVRFQS (SEQ ID NO:886), ETLRFQS (SEQ ID NO:887), ETARFQS (SEQ ID NO:888), ETVYFQS (SEQ ID NO:889), LEVLFQGP (SEQ ID NO:857), and ENVYFQS (SEQ ID NO:890).

Aspect 22. A system comprising:

a) a first nucleic acid comprising a nucleotide sequence encoding a virus-like particle (VLP) comprising a fusion polypeptide that comprises:

i) a lentiviral gag polyprotein comprising a matrix (MA) polypeptide, a capsid (CA) polypeptide, and a nucleocapsid (NC) polypeptide;

ii) a CRISPR/Cas effector polypeptide; and iii) one or more heterologous protease cleavage sites, wherein the one or more heterologous protease cleavage sites is between the gag polyprotein and the CRISPR/Cas effector polypeptide; and b) a second nucleic acid comprising a nucleotide sequence encoding a heterologous protease that cleaves the one or more heterologous protease cleavage sites.

Aspect 23. The system of aspect 22, wherein the nucleotide sequence of the second nucleic acid encodes a polyprotein comprising:

i) a lentiviral gag polyprotein comprising a matrix (MA) polypeptide, a capsid (CA) polypeptide, and a nucleocapsid (NC) polypeptide; and ii) the heterologous protease, wherein the polyprotein comprises one or more heterologous protease cleavage sites between the lentiviral gag polyprotein and the heterologous protease.

Aspect 24. The system of aspect 22, wherein the nucleotide sequence of the second nucleic acid encodes a polyprotein comprising:

i) a lentiviral pol polyprotein comprising a reverse transcriptase and an integrase; and ii) the heterologous protease, wherein the polyprotein comprises one or more heterologous protease cleavage sites between the lentiviral pol polyprotein and the heterologous protease.

Aspect 25. The system of any one of aspects 22-24, comprising:

c) a third nucleic acid comprising a nucleotide sequence encoding a lentiviral gag polyprotein comprising a matrix (MA) polypeptide, a capsid (CA) polypeptide, and a nucleocapsid (NC) polypeptide.

Aspect 26. The system of any one of aspects 22-25, wherein the gag polypeptide comprises one or more heterologous protease cleavage sites between one or both of: i) the MA polypeptide and the CA polypeptide; and ii) the CA polypeptide the NC polypeptide.

Aspect 27. The system of any one of aspects 22-26, wherein the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide.

Aspect 28. The system of any one of aspects 22-27, further comprising a CRISPR/Cas effector polypeptide guide RNA, a nucleic acid comprising a nucleotide sequence encoding the CRISPR/Cas effector polypeptide guide RNA, or a nucleic acid comprising a nucleotide sequence encoding the constant region of a CRISPR/Cas effector polypeptide guide RNA.

Aspect 29. The system of aspect 28, wherein the guide RNA is a single-molecule guide RNA.

Aspect 30. The system of aspect 28 or 29, wherein the CRISPR/Cas effector polypeptide guide RNA comprises one or more of: i) a modified sugar; ii) a modified base; and iii) a modified internucleoside linkage.

Aspect 31. The system of any one of aspects 22-30, comprising:

d) a fourth nucleic acid comprising a nucleotide sequence encoding a pseudotyping viral envelope protein and/or a polypeptide that provides for binding to a target cell.

Aspect 32. The system of any one of aspects 22-30, comprising:

d) a fourth nucleic acid comprising a nucleotide sequence encoding an antibody that binds to a cell surface receptor.

Aspect 33. The system of any one of aspects 22-32, comprising a nucleic acid comprising a nucleotide sequence encoding an inhibitor of an MHC class I antigen presentation pathway.

Aspect 34. The system of any one of aspects 22-33, comprising an Acr nucleic acid comprising a nucleotide sequence encoding an anti-CRISPR (Acr) polypeptide.

Aspect 35. The system of aspect 34, wherein the Acr nucleic acid comprises a nucleotide sequence encoding a polyprotein comprising a lentivirus gag polypeptide and the Acr polypeptide.

Aspect 36. The system of aspect 35, wherein the polyprotein comprises a proteolytic cleavage site between the gag polypeptide and the Acr polypeptide.

Aspect 37. A eukaryotic cell comprising the system of any one of aspects 22-36.

Aspect 38. The eukaryotic cell of aspect 37, wherein the cell is a packaging cell.

Aspect 39. A method of making a virus-like particle (VLP) comprising a CRISPR/Cas effector polypeptide, the method comprising:

a) introducing the system of any one of aspects 22-36 into a packaging cell; and b) harvesting VLPs produced by the packaging cell.

Aspect 40. A virus-like particle (VLP) produced by the method of aspect 39.

Aspect 41. A method of delivering a CRISPR/Cas effector polypeptide to a cell, the method comprising contacting the cell with the VLP of aspect 40.

Aspect 42. A virus-like particle (VLP) comprising:

a) a lentiviral capsid (CA), matrix, (MA), and nucleocapsid (NC) polypeptides;

b) a heterologous polypeptide that provides for binding to a target cell; and c) a CRISPR/Cas effector polypeptide encapsidated within the VLP.

Aspect 43. The VLP of aspect 42, wherein the heterologous polypeptide is a pseudotyping viral envelope protein and/or an antibody specific for an epitope present on the target cell.

Aspect 44. The VLP of aspect 42 or 43, comprising one or more CRISPR/Cas effector guide RNAs or a nucleic acid comprising a nucleotide sequence encoding the one or more CRISPR/Cas effector guide RNAs.

Aspect 45. The VLP of any one of aspects 42-44, comprising a donor DNA or a nucleic acid comprising a nucleotide sequence encoding the donor DNA.

Aspect 46. The VLP of any one of aspects 42-45, wherein the pseudotyping viral envelope protein is selected from a Hepatitis B virus (HBV) glycoprotein, a Hepatitis C virus (HCV) glycoprotein, a Marburg virus glycoprotein, an Ebola virus glycoprotein, a VSV-G glycoprotein, an influenza virus hemagglutinin, a SARS-CoV glycoprotein, a respiratory syncytial virus (RSV) glycoprotein, a human parainfluenza virus glycoprotein, a measles virus hemagglutinin and/or a measles virus fusion glycoprotein, an HTLV-1 glycoprotein, a Ross river virus glycoprotein, a rabies virus glycoprotein, a Mokola virus glycoprotein, a Semliki Forest virus glycoprotein, a Sindbis virus glycoprotein, a Venezuelan equine encephalitis virus glycoprotein, Aspect 47. The VLP of any one of aspects 42-46, wherein the CRISPR/Cas effector polypeptide is a type II CRISPR/Cas effector polypeptide.

Aspect 48. The VLP of aspect 47, wherein the type II CRISPR/Cas effector polypeptide is a Cas9 polypeptide.

Aspect 49. The VLP of any one of aspects 42-46, wherein the CRISPR/Cas effector polypeptide is a type V CRISPR/Cas effector polypeptide.

Aspect 50. The VLP of aspect 49, wherein the type V CRISPR/Cas effector polypeptide is a Cas12a, a Cas12b, a Cas12c, a Cas12d, or a Cas12e polypeptide.

Aspect 51. The VLP of any one of aspects 42-46, wherein the CRISPR/Cas effector polypeptide is a type VI CRISPR/Cas effector polypeptide.

Aspect 52. The VLP of aspect 48, wherein the type VI CRISPR/Cas effector polypeptide is a Cas13a polypeptide or a Cas13b polypeptide.

Aspect 53. The VLP of any one of aspects 42-46, wherein the CRISPR/Cas effector polypeptide is a Cas14 polypeptide.

Aspect 54. The VLP of any one of aspects 42-53, wherein the CRISPR/Cas effector polypeptide is a variant that exhibits reduced nucleic acid cleavage activity.

Aspect 55. The VLP of any one of aspects 42-54, wherein the CRISPR/Cas effector polypeptide is a fusion polypeptide comprising: i) a CRISPR/Cas effector polypeptide is a variant that has reduced nucleic acid cleavage activity; and ii) a heterologous fusion polypeptide.

Aspect 56. The VLP of aspect 55, wherein the heterologous fusion is a protein modifying enzyme.

Aspect 57. The VLP of aspect 55, wherein the heterologous fusion is a nucleic acid modifying enzyme.

Aspect 58. The VLP of aspect 54, wherein the nucleic acid modifying enzyme is a cytidine deaminase.

Aspect 59. The VLP of any one of aspects 42-48, wherein the CRISPR/Cas effector polypeptide comprises one or more nuclear localization signals.

Aspect 60. The VLP of any one of aspects 42-59, comprising a polypeptide that inhibits nucleic acid cleavage activity of the CRISPR/Cas effector polypeptide.

Aspect 61. A method of delivering a CRISPR/Cas effector polypeptide to a target cell, the method comprising contacting the target cell with the VLP of any one of aspects 42-60.

Aspect 62. The method of aspect 61, wherein the target cell is in vitro.

Aspect 63. The method of aspect 61, wherein the target cell is in an individual in vivo, and wherein the method comprising administering a composition comprising the VLP to the individual.

Aspect 64. The method of aspect 63, wherein the pseudotyping viral glycoprotein is selected from a Hepatitis B virus (HBV) glycoprotein, a Hepatitis C virus (HCV) glycoprotein, a Marburg virus glycoprotein, an Ebola virus glycoprotein, a VSV-G glycoprotein; and wherein the target cell is a liver cell.

Aspect 65. The method of aspect 64, wherein the VLP comprises a guide RNA, or a nucleic acid comprising a nucleotide sequence encoding a guide RNA, and wherein the guide RNA comprises a targeting sequence that targets a gene selected from PCSK9, SERPINA1, TTR, FAH, OTC, G6PC, AGXT, F9, and F8.

Aspect 66. The method of aspect 63, wherein the pseudotyping viral glycoprotein is selected from an influenza virus hemagglutinin, a SARS-CoV glycoprotein, a respiratory syncytial virus glycoprotein, a human parainfluenza virus glycoprotein, and a VSV-G; and wherein the target cell is a lung cell.

Aspect 67. The method of aspect 66, wherein the VLP comprises a guide RNA, or a nucleic acid comprising a nucleotide sequence encoding a guide RNA, and wherein the guide RNA comprises a targeting sequence that targets CFTR.

Aspect 68. The method of aspect 63, wherein the pseudotyping viral glycoprotein is a measles virus hemagglutinin, and wherein the target cell is a CD34+ cell.

Aspect 69. The method of aspect 68, wherein the VLP comprises a guide RNA, or a nucleic acid comprising a nucleotide sequence encoding a guide RNA, and wherein the guide RNA comprises a targeting sequence that targets an HbF gene.

Aspect 70. The method of aspect 63, wherein the pseudotyping viral glycoprotein is selected from a measles virus hemagglutinin, an HTLV-1 glycoprotein, and a VSV-G glycoprotein; and wherein the target cell is a CD8+ T cell.

Aspect 71. The method of aspect 70, wherein the VLP comprises a guide RNA, or a nucleic acid comprising a nucleotide sequence encoding a guide RNA, and wherein the guide RNA comprises a targeting sequence that targets a gene selected from PD1, CTLA4, and TCR.

Aspect 72. The method of aspect 63, wherein the pseudotyping viral glycoprotein is selected from a HIV-1 envelope, a HTLV-1 glycoprotein, a measles virus hemagglutinin, and a VSV-G glycoprotein; and wherein the target cell is a CD4+ T cell.

Aspect 73. The method of aspect 72, wherein the VLP comprises a guide RNA, or a nucleic acid comprising a nucleotide sequence encoding a guide RNA, and wherein the guide RNA comprises a targeting sequence that targets a CCR5 gene.

Aspect 74. The method of aspect 72, wherein the VLP comprises one or more guide RNAs, or a nucleic acid comprising a nucleotide sequence encoding one or more guide RNAs, and wherein the one or more guide RNAs comprises a targeting sequence that targets an integrated proviral HIV-1.

Aspect 75. The method of aspect 63, wherein the pseudotyping viral glycoprotein is a Ross River virus glycoprotein or a VSV-G; and wherein the target cell is a skeletal muscle cell.

Aspect 76. The method of aspect 75, wherein the VLP comprises a guide RNA, or a nucleic acid comprising a nucleotide sequence encoding a guide RNA, and wherein the guide RNA comprises a targeting sequence that targets a Duchenne muscular dystrophy gene.

Aspect 77. The method of aspect 63, wherein the pseudotyping viral glycoprotein is selected from an Ebola virus glycoprotein, a Marburg virus glycoprotein, and a VSV-G; and wherein the target cell is an ocular cell.

Aspect 78. The method of aspect 77, wherein the VLP comprises a guide RNA, or a nucleic acid comprising a nucleotide sequence encoding a guide RNA, and wherein the guide RNA comprises a targeting sequence that targets a CEP290 gene.

Aspect 79. The method of aspect 63, wherein the pseudotyping viral glycoprotein is selected from an Ebola virus glycoprotein, a Marburg virus glycoprotein, and a VSV-G; and wherein the target cell is an auditory cell.

Aspect 80. The method of aspect 79, wherein the VLP comprises a guide RNA, or a nucleic acid comprising a nucleotide sequence encoding a guide RNA, and wherein the guide RNA comprises a targeting sequence that targets a USH2A gene.

Aspect 81. The method of aspect 63, wherein the pseudotyping viral glycoprotein is selected from aa rabies glycoprotein, a Mokola virus glycoprotein, a Semliki Forest virus glycoprotein, a Sindbis virus glycoprotein, a Venezuelan equine encephalitis virus glycoprotein, an influenza hemagglutinin glycoprotein, and a VSV-G; and wherein the target cell is a central nervous system cell.

Aspect 82. The method of aspect 81, wherein the VLP comprises a guide RNA, or a nucleic acid comprising a nucleotide sequence encoding a guide RNA, and wherein the guide RNA comprises a targeting sequence that targets a gene selected from Tau/MAPT-1, HTT, SOD1, SOCS3, USP8, DOT1L, ufmylation, SOCS2, SOCS9, SOCS13, SOCS11, and SOCS5.

Aspect 83. A virus-like particle (VLP) comprising:

a) a lentiviral capsid (CA), matrix, (MA), and nucleocapsid (NC) polypeptides;

b) a heterologous polypeptide that provides for binding to a target cell; and c) an anti-CRISPR polypeptide encapsidated within the VLP.

Aspect 84. The VLP of aspect 83, wherein the heterologous polypeptide is a pseudotyping viral envelope protein and/or an antibody specific for an epitope present on the target cell.

Aspects Set B

Without limiting the foregoing description, certain non-limiting aspects of the disclosure numbered 1-113 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A nucleic acid comprising a nucleotide sequence encoding a virus-like particle (VLP) comprising a fusion polypeptide that comprises:

a) a retroviral gag polyprotein comprising a matrix (MA) polypeptide, a capsid (CA) polypeptide, and a nucleocapsid (NC) polypeptide;

b) a therapeutic polypeptide; and c) one or more heterologous protease cleavage sites, wherein the one or more heterologous protease cleavage sites is between the gag polyprotein and the therapeutic polypeptide.

Aspect 2. The nucleic acid of aspect 1, wherein the heterologous protease cleavage site is selected from the group consisting of: a TEV cleavage site, a PreScission cleavage site, a human rhinovirus 3C protease cleavage site, an enterokinase cleavage site, an Epstein-Barr virus protease cleavage site, a cathepsin D cleavage site, and/or a thrombin cleavage site.

Aspect 3. The nucleic acid of aspect 1, wherein the gag polypeptide comprises one or more heterologous protease cleavage sites between one or both of: i) the MA polypeptide and the CA polypeptide; and ii) the CA polypeptide and the NC polypeptide.

Aspect 4. The nucleic acid of aspect 1, wherein the retroviral gag polyprotein is a lentiviral gag polyprotein.

Aspect 5. The nucleic acid of aspect 4, wherein the lentiviral gag polyprotein is selected from a bovine immunodeficiency virus gag polyprotein, a simian immunodeficiency virus gag polyprotein, a feline immunodeficiency virus gag polyprotein, a human immunodeficiency virus gag polyprotein, an equine infection anemia virus gag polyprotein, and a caprine arthritis encephalitis virus gag polyprotein.

Aspect 6. The nucleic acid of aspect 4, wherein the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide.

Aspect 7. The nucleic acid of aspect 1, wherein the retroviral gag polyprotein is a gag polyprotein of an alpha retrovirus, a beta retrovirus, a gamma retrovirus, a delta retrovirus, an epsilon retrovirus, or a spumavirus.

Aspect 8. The nucleic acid of any one of aspects 1-7, wherein the therapeutic polypeptide is selected from a nuclease, a base editor, a recombinase, a transcription factor, an anti-CRISPR polypeptide, a reverse transcriptase, a prime editor, and an antibody.

Aspect 9. The nucleic acid of aspect 8, wherein the nuclease is a CRISPR/Cas effector polypeptide, a zinc finger nuclease (ZFN), a transcription activator like effector nuclease (TALEN), or a MegaTal.

Aspect 10. The nucleic acid of aspect 8, wherein the base editor is a cytidine-specific base editor or an adenine-specific base editor, optionally wherein the base editor is a cytidine deaminase or an adenosine deaminase.

Aspect 11. The nucleic acid of aspect 8, wherein the transcription factor is selected from a CRISPR/Cas effector fusion polypeptide comprising a transcriptional modulator, a zinc finger protein transcription factor (ZFP-TF), and a transcription activator like effector transcription factor (TALE-TF).

Aspect 12. The nucleic acid of any one of aspects 1-7, wherein the therapeutic polypeptide is a CRISPR/Cas effector polypeptide.

Aspect 13. The nucleic acid of aspect 12, wherein the CRISPR/Cas effector polypeptide is a type II CRISPR/Cas effector polypeptide.

Aspect 14. The nucleic acid of aspect 13, wherein the type II CRISPR/Cas effector polypeptide is a Cas9 polypeptide.

Aspect 15. The nucleic acid of aspect 13, wherein the CRISPR/Cas effector polypeptide is a type V CRISPR/Cas effector polypeptide.

Aspect 16. The nucleic acid of aspect 15, wherein the type V CRISPR/Cas effector polypeptide is a Cas12a polypeptide, a Cas12b polypeptide, a Cas12c polypeptide, a Cas12d polypeptide, or a Cas12e polypeptide.

Aspect 17. The nucleic acid of aspect 12, wherein the CRISPR/Cas effector polypeptide is a type VI CRISPR/Cas effector polypeptide.

Aspect 18. The nucleic acid of aspect 17, wherein the type VI CRISPR/Cas effector polypeptide is a Cas13a polypeptide, a Cas13b polypeptide, a Cas13c polypeptide, or a Cas13d polypeptide.

Aspect 19. The nucleic acid of aspect 12, wherein the CRISPR/Cas effector polypeptide is a Cas14a polypeptide, a Cas14b polypeptide, or a Cas14c polypeptide.

Aspect 20. The nucleic acid of aspect 12, wherein the CRISPR/Cas effector polypeptide is a variant that exhibits reduced nucleic acid cleavage activity.

Aspect 21. The nucleic acid of aspect 12, wherein the CRISPR/Cas effector polypeptide is a fusion polypeptide comprising: i) a variant CRISPR/Cas effector polypeptide that exhibits reduced nucleic acid cleavage activity; and ii) a heterologous fusion polypeptide, optionally wherein the heterologous fusion polypeptide is selected from a reverse transcriptase, a protein modifying enzyme, a nucleic acid modifying enzyme, and a transcriptional modulator.

Aspect 22. The nucleic acid of aspect 21, wherein the heterologous fusion polypeptide is a protein modifying enzyme.

Aspect 23. The nucleic acid of aspect 21, wherein the heterologous fusion polypeptide is a nucleic acid modifying enzyme.

Aspect 24. The nucleic acid of aspect 23, wherein the nucleic acid modifying enzyme is a cytidine deaminase or an adenosine deaminase.

Aspect 25. The nucleic acid of aspect 21, wherein the heterologous fusion polypeptide is a transcriptional modulator.

Aspect 26. The nucleic acid of aspect 25, wherein the transcriptional modulator comprises a transcriptional activator or a transcriptional repressor.

Aspect 27. The nucleic acid of any one of aspects 9-25, wherein the CRISPR/Cas effector polypeptide comprises one or more nuclear localization signals.

Aspect 28. The nucleic acid of any one of aspects 1-27, wherein the heterologous protease cleavage site comprises an amino acid sequence selected from the group consisting of ENLYTQS (SEQ ID NO:854), ENAYFQS (SEQ ID NO:883), ENLRFQS (SEQ ID NO:884), ENLFFQS (SEQ ID NO:885), ETVRFQS (SEQ ID NO:886), ETLRFQS (SEQ ID NO:887), ETARFQS (SEQ ID NO:888), ETVYFQS (SEQ ID NO:889), LEVLFQGP (SEQ ID NO:857), and ENVYFQS (SEQ ID NO:890).

Aspect 29. A system comprising:

a) a first nucleic acid comprising a nucleotide sequence encoding a virus-like particle (VLP) comprising a fusion polypeptide that comprises:

i) a lentiviral gag polyprotein comprising a matrix (MA) polypeptide, a capsid (CA) polypeptide, and a nucleocapsid (NC) polypeptide;

ii) a therapeutic polypeptide; and iii) one or more heterologous protease cleavage sites, wherein the one or more heterologous protease cleavage sites is between the gag polyprotein and the therapeutic polypeptide; and b) a second nucleic acid comprising a nucleotide sequence encoding a heterologous protease that cleaves the one or more heterologous protease cleavage sites.

Aspect 30. The system of aspect 29, wherein the nucleotide sequence of the second nucleic acid encodes a polyprotein comprising: i) a lentiviral gag polyprotein comprising a matrix (MA) polypeptide, a capsid (CA) polypeptide, and a nucleocapsid (NC) polypeptide; and ii) the heterologous protease, wherein the polyprotein comprises one or more heterologous protease cleavage sites between the lentiviral gag polyprotein and the heterologous protease.

Aspect 31. The system of aspect 29, wherein the nucleotide sequence of the second nucleic acid encodes a polyprotein comprising: i) a lentiviral pol polyprotein comprising a reverse transcriptase and an integrase; and ii) the heterologous protease, wherein the polyprotein comprises one or more heterologous protease cleavage sites between the lentiviral pol polyprotein and the heterologous protease.

Aspect 32. The system of any one of aspects 29-31, comprising:

c) a third nucleic acid comprising a nucleotide sequence encoding a lentiviral gag polyprotein comprising a matrix (MA) polypeptide, a capsid (CA) polypeptide, and a nucleocapsid (NC) polypeptide.

Aspect 33. The system of any one of aspects 29-32, wherein the gag polypeptide comprises one or more heterologous protease cleavage sites between one or both of: i) the MA polypeptide and the CA polypeptide; and ii) the CA polypeptide the NC polypeptide.

Aspect 34. The system of any one of aspects 29-33, wherein the lentiviral gag polyprotein is a human immunodeficiency virus (HIV) gag polyprotein comprising a MA polypeptide, a CA polypeptide, a p2 polypeptide, an NC polypeptide, a p1 polypeptide, and a p6 polypeptide, and wherein the HIV gag polyprotein comprises one or more heterologous protease cleavage sites between one or more of: i) the MA polypeptide and the CA polypeptide; ii) the CA polypeptide and the p2 polypeptide; iii) the p2 polypeptide and the NC polypeptide; iv) the NC polypeptide and the p1 polypeptide; and v) the p1 polypeptide and the p6 polypeptide.

Aspect 35. The system of any one of aspects 29-34, wherein the therapeutic polypeptide is selected from a nuclease, a base editor, a recombinase, a transcription factor, an anti-CRISPR polypeptide, a reverse transcriptase, a prime editor, and an antibody.

Aspect 36. The system of aspect 35, wherein the nuclease is a CRISPR/Cas effector polypeptide, a zinc finger nuclease (ZFN), a transcription activator-like effector nuclease (TALEN), or a MegaTal.

Aspect 37. The system of aspect 35, wherein the base editor is selected from a cytidine-specific base editor or an adenine-specific base editor, optionally wherein the base editor is a cytidine deaminase or an adenosine deaminase.

Aspect 38. The system of aspect 35, wherein the transcription factor is selected from a CRISPR/Cas effector polypeptide fusion polypeptide comprising a transcriptional modulator, a zinc finger protein transcription factor (ZFP-TF), and a transcription activator like effector transcription factor (TALE-TF).

Aspect 39. The system of any one of aspects 29-34, wherein the therapeutic polypeptide is a CRISPR/Cas effector polypeptide.

Aspect 40. The system of aspect 39, further comprising a CRISPR/Cas effector polypeptide guide RNA, a nucleic acid comprising a nucleotide sequence encoding the CRISPR/Cas effector polypeptide guide RNA, or a nucleic acid comprising a nucleotide sequence encoding the constant region of a CRISPR/Cas effector polypeptide guide RNA.

Aspect 41. The system of aspect 40, wherein the guide RNA is a single-molecule guide RNA.

Aspect 42. The system of aspect 40 or 41, wherein the guide is from a library of guide RNAs.

Aspect 43. The system of aspect 40 or 41, wherein the CRISPR/Cas effector polypeptide guide RNA comprises one or more of: i) a modified sugar; ii) a modified base; and iii) a modified internucleoside linkage.

Aspect 44. The system of any one of aspects 29-43, comprising:

d) a fourth nucleic acid comprising a nucleotide sequence encoding a pseudotyping viral envelope protein and/or a polypeptide that provides for binding to a target cell.

Aspect 45. The system of any one of aspects 29-43, comprising:

d) a fourth nucleic acid comprising a nucleotide sequence encoding an antibody that binds to a cell surface receptor.

Aspect 46. The system of any one of aspects 29-45, comprising a nucleic acid comprising a nucleotide sequence encoding an inhibitor of an MHC class I antigen presentation pathway.

Aspect 47. The system of any one of aspects 29-45, comprising an Acr nucleic acid comprising a nucleotide sequence encoding an anti-CRISPR (Acr) polypeptide.

Aspect 48. The system of aspect 47, wherein the Acr nucleic acid comprises a nucleotide sequence encoding a polyprotein comprising a lentivirus gag polypeptide and the Acr polypeptide.

Aspect 49. The system of aspect 48, wherein the polyprotein comprises a proteolytic cleavage site between the gag polypeptide and the Acr polypeptide.

Aspect 50. A eukaryotic cell comprising the system of any one of aspects 29-49.

Aspect 51. The eukaryotic cell of aspect 50, wherein the cell is a packaging cell.

Aspect 52. A method of making a virus-like particle (VLP) comprising a therapeutic polypeptide, the method comprising:

a) introducing the system of any one of aspects 29-49 into a packaging cell; and b) harvesting VLPs produced by the packaging cell.

Aspect 53. The method of aspect 52, wherein the therapeutic polypeptide is selected from a nuclease, a base editor, a recombinase, a transcription factor, an anti-CRISPR polypeptide, a reverse transcriptase, a prime editor, and an antibody.

Aspect 54. The method of aspect 53, wherein the nuclease is a CRISPR/Cas effector polypeptide, a zinc finger nuclease (ZFN), a transcription activator-like effector nuclease (TALEN), or a MegaTal.

Aspect 55. The method of aspect 53, wherein the base editor is a cytidine-specific base editor or an adenine-specific base editor, optionally wherein the base editor is a cytidine deaminase or an adenosine deaminase.

Aspect 56. The method of aspect 51, wherein the engineered transcription factor is selected from a CRISPR/Cas effector fusion polypeptide comprising a transcriptional modulator, a zinc finger protein transcription factor (ZFP-TF), and a transcription activator-like effector transcription factor (TALE-TF).

Aspect 57. The method of aspect 52, wherein the therapeutic polypeptide is a CRISPR/Cas effector polypeptide.

Aspect 58. A virus-like particle (VLP) produced by the method of any one of aspects 52-57.

Aspect 59. A method of delivering a therapeutic polypeptide to a cell, the method comprising contacting the cell with the VLP of aspect 58.

Aspect 60. A virus-like particle (VLP) comprising:

a) a lentiviral capsid (CA), matrix, (MA), and nucleocapsid (NC) polypeptides;

b) a heterologous polypeptide that provides for binding to a target cell; and c) a therapeutic polypeptide encapsidated within the VLP.

Aspect 61. The VLP of aspect 60, wherein the heterologous polypeptide is a pseudotyping viral envelope protein and/or an antibody specific for an epitope present on the target cell.

Aspect 62. The VLP of aspect 60 or 61, wherein the therapeutic polypeptide is selected from a nuclease, a base editor, a recombinase, a transcription factor, an anti-CRISPR polypeptide, a reverse transcriptase, a prime editor, and an antibody.

Aspect 63. The VLP of aspect 62, wherein the nuclease is a CRISPR/Cas effector polypeptide, a zinc finger nuclease (ZFN), a transcription activator-like effector nuclease (TALEN), or a MegaTal.

Aspect 64. The VLP of aspect 62, wherein the base editor is selected from a cytidine-specific base editor and an adenine-specific base editor, optionally wherein the base editor is a cytidine deaminase or an adenosine deaminase.

Aspect 65. The VLP of aspect 62, wherein the transcription factor is selected from a CRISPR/Cas effector fusion polypeptide, a zinc finger protein transcription factor (ZFP-TF), and a transcription activator-like effector transcription factor (TALE-TF).

Aspect 66. The VLP of aspect 60 or 61, wherein the therapeutic polypeptide is a CRISPR/Cas effector polypeptide.

Aspect 67. The VLP of aspect 66, comprising one or more CRISPR/Cas effector guide RNAs or a nucleic acid comprising a nucleotide sequence encoding the one or more CRISPR/Cas effector guide RNAs.

Aspect 68. The VLP of aspect 66 or aspect 67, comprising a donor DNA or a nucleic acid comprising a nucleotide sequence encoding the donor DNA.

Aspect 69. The VLP of any one of aspects 60-68, wherein the pseudotyping viral envelope protein is selected from a Hepatitis B virus (HBV) glycoprotein, a Hepatitis C virus (HCV) glycoprotein, a Marburg virus glycoprotein, an Ebola virus glycoprotein, a VSV-G glycoprotein, an influenza virus hemagglutinin, a SARS-CoV glycoprotein, a respiratory syncytial virus (RSV) glycoprotein, a human parainfluenza virus glycoprotein, a measles virus hemagglutinin and/or a measles virus fusion glycoprotein, an HTLV-1 glycoprotein, a Ross river virus glycoprotein, a rabies virus glycoprotein, a Mokola virus glycoprotein, a Semliki Forest virus glycoprotein, a Sindbis virus glycoprotein, a Venezuelan equine encephalitis virus glycoprotein, Aspect 70. The VLP of any one of aspects 66-69, wherein the CRISPR/Cas effector polypeptide is a type II CRISPR/Cas effector polypeptide.

Aspect 71. The VLP of aspect 70, wherein the type II CRISPR/Cas effector polypeptide is a Cas9 polypeptide.

Aspect 72. The VLP of any one of aspects 66-69, wherein the CRISPR/Cas effector polypeptide is a type V CRISPR/Cas effector polypeptide.

Aspect 73. The VLP of aspect 72, wherein the type V CRISPR/Cas effector polypeptide is a Cas12a, a Cas12b, a Cas12c, a Cas12d, or a Cas12e polypeptide.

Aspect 74. The VLP of any one of aspects 66-69, wherein the CRISPR/Cas effector polypeptide is a type VI CRISPR/Cas effector polypeptide.

Aspect 75. The VLP of aspect 74, wherein the type VI CRISPR/Cas effector polypeptide is a Cas13a, a Cas13b, a Cas13c, or a Cas13d polypeptide.

Aspect 76. The VLP of any one of aspects 66-69, wherein the CRISPR/Cas effector polypeptide is a Cas14a, a Cas14b, or a Cas14c polypeptide.

Aspect 77. The VLP of any one of aspects 66-76, wherein the CRISPR/Cas effector polypeptide is a variant that exhibits reduced nucleic acid cleavage activity.

Aspect 78. The VLP of any one of aspects 66-77, wherein the CRISPR/Cas effector polypeptide is a fusion polypeptide comprising: i) a CRISPR/Cas effector polypeptide is a variant that has reduced nucleic acid cleavage activity; and ii) a heterologous fusion polypeptide, optionally wherein the heterologous fusion polypeptide is selected from a reverse transcriptase, a protein modifying enzyme, a nucleic acid modifying enzyme, and a transcriptional modulator.

Aspect 79. The VLP of aspect 78, wherein the heterologous fusion polypeptide is a protein modifying enzyme.

Aspect 80. The VLP of aspect 78, wherein the heterologous fusion polypeptide is a nucleic acid modifying enzyme.

Aspect 81. The VLP of aspect 80, wherein the nucleic acid modifying enzyme is a cytidine deaminase or an adenine deaminase.

Aspect 82. The VLP of any one of aspects 60-81, wherein the therapeutic polypeptide comprises one or more nuclear localization signals.

Aspect 83. The VLP of aspect any one of aspects 66-77, comprising a polypeptide that inhibits nucleic acid cleavage activity of the CRISPR/Cas effector polypeptide.

Aspect 84. A method of delivering a therapeutic polypeptide to a target cell, the method comprising contacting the target cell with the VLP of any one of aspects 60-83.

Aspect 85. The method of aspect 84, wherein the target cell is in vitro.

Aspect 86. The method of aspect 84, wherein the target cell is in an individual in vivo, and wherein the method comprises administering a composition comprising the VLP to the individual.

Aspect 87. The method of aspect 83, wherein the pseudotyping viral glycoprotein is selected from a Hepatitis B virus (HBV) glycoprotein, a Hepatitis C virus (HCV) glycoprotein, a Marburg virus glycoprotein, an Ebola virus glycoprotein, a VSV-G glycoprotein; and wherein the target cell is a liver cell.

Aspect 88. The method of any one of aspects 84-87, wherein the therapeutic polypeptide is selected from a nuclease, a base editor, a recombinase, a transcription factor, an anti-CRISPR polypeptide, a reverse transcriptase, a prime editor, and an antibody.

Aspect 89. The method of aspect 88, wherein the nuclease is a CRISPR/Cas effector polypeptide, a zinc finger nuclease (ZFN), a transcription activator like effector nuclease (TALEN), or a MegaTal.

Aspect 90. The method of aspect 88, wherein the base editor is a cytidine-specific base editor or an adenine-specific base editor, optionally wherein the base editor is a cytidine deaminase or an adenosine deaminase.

Aspect 91. The method of aspect 88, wherein the transcription factor is selected from a CRISPR/Cas effector fusion polypeptide, a zinc finger protein transcription factor (ZFP-TF), and a transcription activator like effector transcription factor (TALE-TF).

Aspect 92. The method of any one of aspects 84-87, wherein the therapeutic polypeptide is a CRISPR/Cas effector polypeptide.

Aspect 93. The method of aspect 92, wherein the VLP comprises a guide RNA, or a nucleic acid comprising a nucleotide sequence encoding a guide RNA.

Aspect 94. The method of aspect 93, wherein the guide RNA comprises a targeting sequence that targets a gene selected from PCSK9, SERPINA1, TTR, FAH, OTC, G6PC, AGXT, F9, and F8.

Aspect 95. The method of aspect 87, wherein the pseudotyping viral glycoprotein is selected from an influenza virus hemagglutinin, a SARS-CoV glycoprotein, a respiratory syncytial virus glycoprotein, a human parainfluenza virus glycoprotein, and a VSV-G; and wherein the target cell is a lung cell.

Aspect 96. The method of aspect 95, wherein the VLP comprises a guide RNA, or a nucleic acid comprising a nucleotide sequence encoding a guide RNA, and wherein the guide RNA comprises a targeting sequence that targets CFTR.

Aspect 97. The method of aspect 87, wherein the pseudotyping viral glycoprotein is a measles virus hemagglutinin, and wherein the target cell is a CD34+ cell.

Aspect 98. The method of aspect 97, wherein the VLP comprises a guide RNA, or a nucleic acid comprising a nucleotide sequence encoding a guide RNA, and wherein the guide RNA comprises a targeting sequence that targets an HbF gene.

Aspect 99. The method of aspect 87, wherein the pseudotyping viral glycoprotein is selected from a measles virus hemagglutinin, an HTLV-1 glycoprotein, and a VSV-G glycoprotein; and wherein the target cell is a CD8+ T cell.

Aspect 100. The method of aspect 99, wherein the VLP comprises a guide RNA, or a nucleic acid comprising a nucleotide sequence encoding a guide RNA, and wherein the guide RNA comprises a targeting sequence that targets a gene selected from PD1, CTLA4, and TCR.

Aspect 101. The method of aspect 87, wherein the pseudotyping viral glycoprotein is selected from a HIV-1 envelope, a HTLV-1 glycoprotein, a measles virus hemagglutinin, and a VSV-G glycoprotein; and wherein the target cell is a CD4+ T cell.

Aspect 102. The method of aspect 101, wherein the VLP comprises a guide RNA, or a nucleic acid comprising a nucleotide sequence encoding a guide RNA, and wherein the guide RNA comprises a targeting sequence that targets a CCR5 gene.

Aspect 103. The method of aspect 102, wherein the VLP comprises one or more guide RNAs, or a nucleic acid comprising a nucleotide sequence encoding one or more guide RNAs, and wherein the one or more guide RNAs comprises a targeting sequence that targets an integrated proviral HIV-1.

Aspect 104. The method of aspect 87, wherein the pseudotyping viral glycoprotein is a Ross River virus glycoprotein or a VSV-G; and wherein the target cell is a skeletal muscle cell.

Aspect 105. The method of aspect 104, wherein the VLP comprises a guide RNA, or a nucleic acid comprising a nucleotide sequence encoding a guide RNA, and wherein the guide RNA comprises a targeting sequence that targets a Duchenne muscular dystrophy gene.

Aspect 106. The method of aspect 87, wherein the pseudotyping viral glycoprotein is selected from an Ebola virus glycoprotein, a Marburg virus glycoprotein, and a VSV-G; and wherein the target cell is an ocular cell.

Aspect 107. The method of aspect 106, wherein the VLP comprises a guide RNA, or a nucleic acid comprising a nucleotide sequence encoding a guide RNA, and wherein the guide RNA comprises a targeting sequence that targets a CEP290 gene.

Aspect 108. The method of aspect 87, wherein the pseudotyping viral glycoprotein is selected from an Ebola virus glycoprotein, a Marburg virus glycoprotein, and a VSV-G; and wherein the target cell is an auditory cell.

Aspect 109. The method of aspect 108, wherein the VLP comprises a guide RNA, or a nucleic acid comprising a nucleotide sequence encoding a guide RNA, and wherein the guide RNA comprises a targeting sequence that targets a USH2A gene.

Aspect 110. The method of aspect 87, wherein the pseudotyping viral glycoprotein is selected from aa rabies glycoprotein, a Mokola virus glycoprotein, a Semliki Forest virus glycoprotein, a Sindbis virus glycoprotein, a Venezuelan equine encephalitis virus glycoprotein, an influenza hemagglutinin glycoprotein, and a VSV-G; and wherein the target cell is a central nervous system cell.

Aspect 111. The method of aspect 110, wherein the VLP comprises a guide RNA, or a nucleic acid comprising a nucleotide sequence encoding a guide RNA, and wherein the guide RNA comprises a targeting sequence that targets a gene selected from Tau/MAPT-1, HTT, SOD1, SOCS3, USP8, DOT1L, ufmylation, SOCS2, SOCS9, SOCS13, SOCS11, and SOCS5.

Aspect 112. A virus-like particle (VLP) comprising:

a) a lentiviral capsid (CA), matrix, (MA), and nucleocapsid (NC) polypeptides;

b) a heterologous polypeptide that provides for binding to a target cell; and c) an anti-CRISPR polypeptide encapsidated within the VLP.

Aspect 113. The VLP of aspect 112, wherein the heterologous polypeptide is a pseudotyping viral envelope protein and/or an antibody specific for an epitope present on the target cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Materials and Methods

Plasmids and Cell Lines pCAGGS plasmids were generated to direct the protein expression of "TEV-activated" Gag either (1) fused to Cas9 or (2) fused to TEV protease. Cas9 was fused in-frame to the C-terminus of "TEV-activated" Gag with a TEV Cleavage Site ("TCS", ENLYFQS (SEQ ID NO:880)) separating the Gag polyprotein and Cas9. TEV protease was fused to the C-termini of "TEV-activated" Gag in the pol (−1) reading frame with a TCS separating the two. "TEV-activated" Gag is comprised of HIV-1 gag sequences with three intervening TCS: matrix-TCS-capsid-TCS-SP1-TCS-nucleocapsid-SP2-p6 (see FIG. 2, where breaks in the fusion protein indicate the presence of TEV cleavage sites). The TEV S219V mutant with reduced self-cleavage capability (Kapust et al. (2001) *Protein Engineering* 14:993) was used. "TEV-activated" Gag and TEV sequences were human codon optimized and synthesized as gBlocks (IDT). Cas9 with a C-terminal 3×FLAG tag and 2×SV40 nuclear localization sequences was PCR-amplified from pMJ920 described in Jinek et al. (2013) *eLife* 2:e00471. Plasmids were assembled via Infusion cloning (Takara Bio. Inc.), maxi prepped (QIAGEN) and sequenced prior to use.

Transfection Protocol

Either 293FT (UC Berkeley Cell Culture facility) or Lenti-X 293T cells were maintained in DMEM (Gibco) supplemented with 10% fetal calf serum and 100 U/ml penicillin/streptomycin (Gibco). Cells were plated at 3.8-4× 10^6 cells per 10-cm dish in a total volume of 10m. Cells were allowed to grow to 80-90% confluency, (approximately 24 hours post plating) prior to transfection. Cells were transfected with 7.5 μg "TEV-activated" Gag-Cas9 plasmid, 2.5 μg "TEV-activated" gag-TEV plasmid, 10 μg of a lentiviral-transfer plasmid encoding the sgRNA 5'-AAGTAAAACCTCTACAAATG (SEQ ID NO:1069), and 1 μg of VSV-G envelope plasmid (Addgene #8454). Briefly, plasmids were mixed in 400 μl Opti-Mem media and polyethylenimine (PEI) was added at a 3:1 ratio (63 µg/transfection). Transfection mix was added drop-wise to cells.

Virus-Like Particle Harvest and Concentration

Virus-like particle-containing supernatant was harvested at 48 and 96 hours post transfection. Supernatants were spun at 1500 RPM for 10 minutes and passed through a 0.45 µm syringe filter. Supernatants were either immediately concentrated or stored at 4 °C until concentration. Concentration was performed with a SW 41 Ti rotor in an Optima XL-80K Ultracentrifuge (Beckman-Coulter). Virus-like particle (VLP) concentration was performed by layering VLP-containing supernatant over a 30% sucrose cushion and centrifuging at 25,000 RPM for 1.75-2 hours at 4 °C. Concentrated VLPs were resuspended in Opti-Mem (Gibco).

Results

Figure 3A:
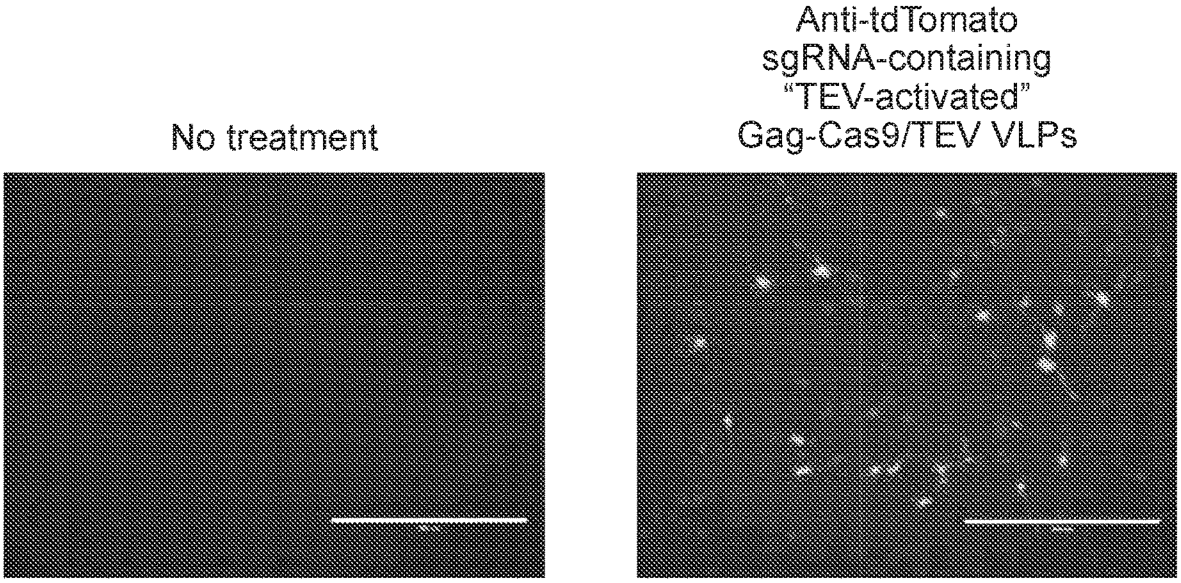
FIG. 3A-3B depict editing efficiency of Cas9-VLPs.
Figure 3B:
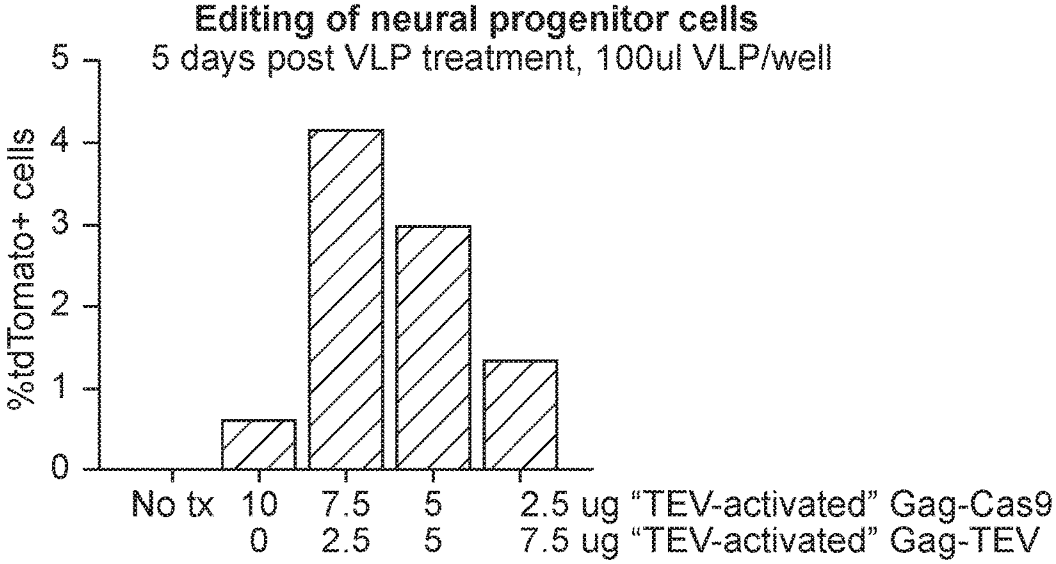

The editing efficiency of VLPs packaging Cas9 was assayed in vitro as described previously, (Staahl et al. (2017) *Nature Biotechnology* 35:431). Briefly, neural progenitor cells (NPCs) were isolated from a mouse harboring to following cassette at the Rosa26 locus: LoxP-STOP-LoxP-tdTomato. The sgRNA 5'-AAGTAAAACCTCTACAAATG (SEQ ID NO:1069) targets within the STOP cassette, thereby resulting in the expression of tdTomato fluorescent protein upon successful genome editing. NPCs were plated at 15,000/well in 96-well plates and allowed to grow for 48 hours. Concentrated VLPs were then added and tdTomato+ edited cells were assayed 3-5 days post treatment. The data are shown in FIG. 3A-3B. Untreated cells exhibited 0.02% tdTomato+ cells while "TEV-activated" Gag-Cas9/TEVa VLP-treated cells exhibited 4.16% tdTomato+ (i.e., edited) cells. This is likely an underestimation of editing efficiency, as at least two edits are required for the expression of tdTomato protein and small frame-shift insertion/deletions are not sufficient for reporter activation, (Staahl et al. (2017), supra).

FIG. 3A-3B. NPCs from Ai9/Ai14 C57Bl/6 mice that contain a floxed transcriptional stop cassette upstream of a tdTomato gene. A "floxed" stop cassette refers to a cassette comprising three transcriptional stop sites (for example, poly A sites) in a row flanked on both sides by loxP sites. A sgRNA that edits the stop cassette (targeting the sequence at the upstream region of the transcriptional stop site) results in the expression of the fluorescent protein tdTomato. Staahl et al. (2017) supra. (A) Untreated NPCs (top) or NPCs five days post treatment with "TEV-activated" Gag-Cas9/TEV VLPs and anti-tdTomato sgRNA (bottom). Representative images are shown. (B) Quantification of tdTomato+ cells (edited cells) by flow cytometry.

Figure 7:
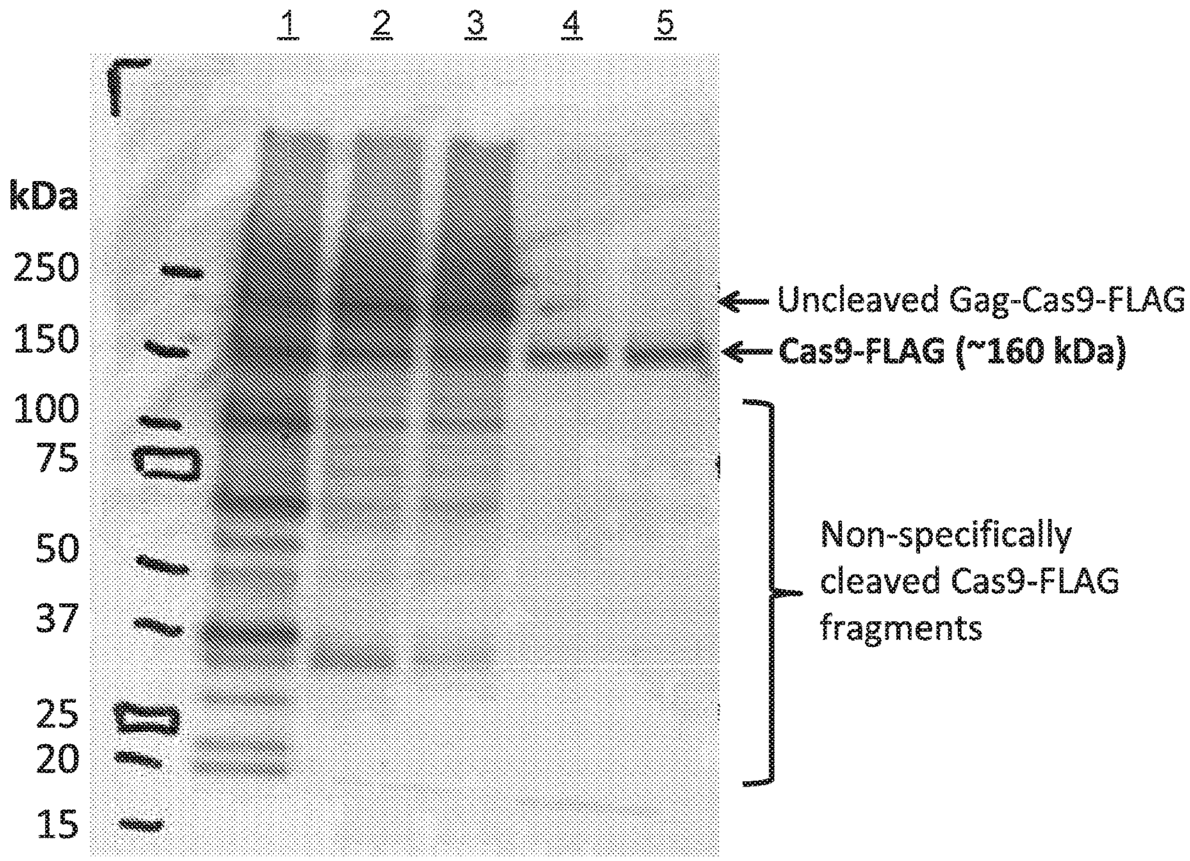
FIG. 7 depicts TEV protease-activated HIV-1 VLP delivery of Cas9.

FIG. 7 depicts a Western blot of the VLPs following production. 20 µl VLP per lane were applied to the gel. The gel was developed with a mouse anti-FLAG antibody and horse radish peroxidase-coupled antibody that binds to mouse antibody, to show the Cas9 proteins. Lane 1: Gag-Cas9, Gag-POL, tdTomato ("tdTom") gRNA; Lane 2: Gag-Cas9, Gag-PR, control gRNA (no RT; no INT); Lane 3: Gag-Cas9, Gag-PR, tdTom gRNA (no RT; no INT); Lane 4: TEV-activated Gag-Cas9, TEV-activated Gag-TEV, control gRNA; Lane 5: TEV-activated Gag-Cas9, TEV-activated Gag-TEV, tdTom gRNA. "POL" polyprotein includes PR (protease), RT (reverse transcriptase), and INT (integrase). Lower bands correspond to Cas9 cleavage products. The blot demonstrates that the particles comprising the HIV-1-activated Cas9 construct (for example, the Gag-Cas9 VLPs shown in lanes 1, 2, and 3) produced a large number of Cas9 proteolytic fragments as compared to the particles comprising the TEV-activated Cas9 construct.

Example 2

Figure 11:
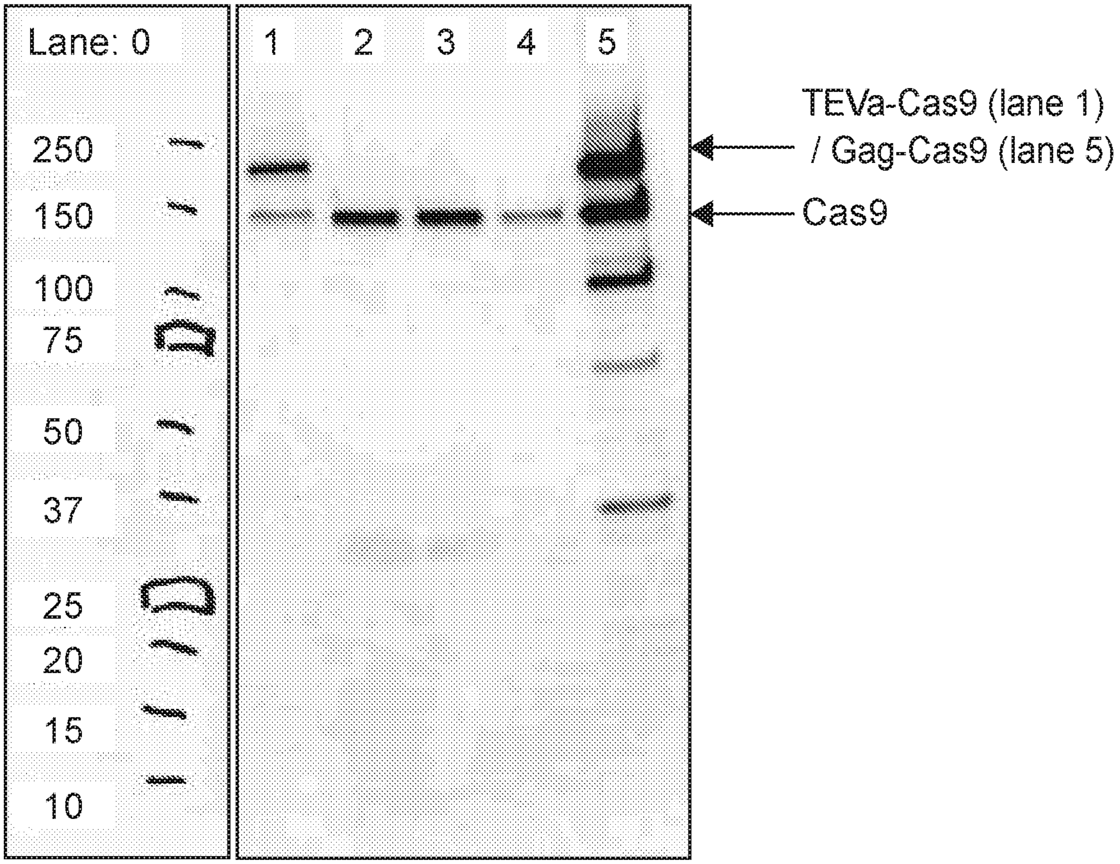
FIG. 11 depicts TEV-mediated release of Cas9 from "TEV-activated" Gag-Cas9.

TEV-mediated release of Cas9 from "TEV-activated" Gag-Cas9, using various amounts of TEV-activated Gag-Cas9 plasmid and TEV-activated Gag-TEV plasmid, was assessed. An anti-FLAG antibody was used for Cas9 detection. TEVa="TEV-activated" Gag. The results are shown in FIG. 11. The sample types shown in FIG. 11 are the same as those shown in FIG. 3B above.

Lane 0 includes molecular weight standards. Lane 1: 10 ug "TEV-activated" Gag-Cas9, no "TEV-activated" Gag-TEV; Lane 2: 7.5 ug "TEV-activated" Gag-Cas9, 2.5 ug "TEV-activated" Gag-TEV; Lane 3: 5 ug "TEV-activated" Gag-Cas9, 5 ug "TEV-activated" Gag-TEV; Lane 4: 2.5 ug "TEV-activated" Gag-Cas9, 7.5 ug "TEV-activated" Gag-TEV; Lane 5: Gag-Cas9, Gag-Pol.

FIG. 11. Western blot detection of VLPs containing Cas9. VLPs were produced either with "TEV-activated" Gag-Cas9 and "TEV-activated" Gag-TEV (lanes 1 through 4) polypeptides or produced with Gag-Cas9 and Gag-pol polypeptides (lane 5). "ug" corresponds to the plasmid amount transfected into producer cells to generate VLPs. "TEV-activated" Gag-TEV can mediate the release of Cas9 from "TEV-activated" gag in VLPs. The blot demonstrates that the use of TEV-activated Cas9 results in the production of generally intact Cas9 protein.

Figure 12:
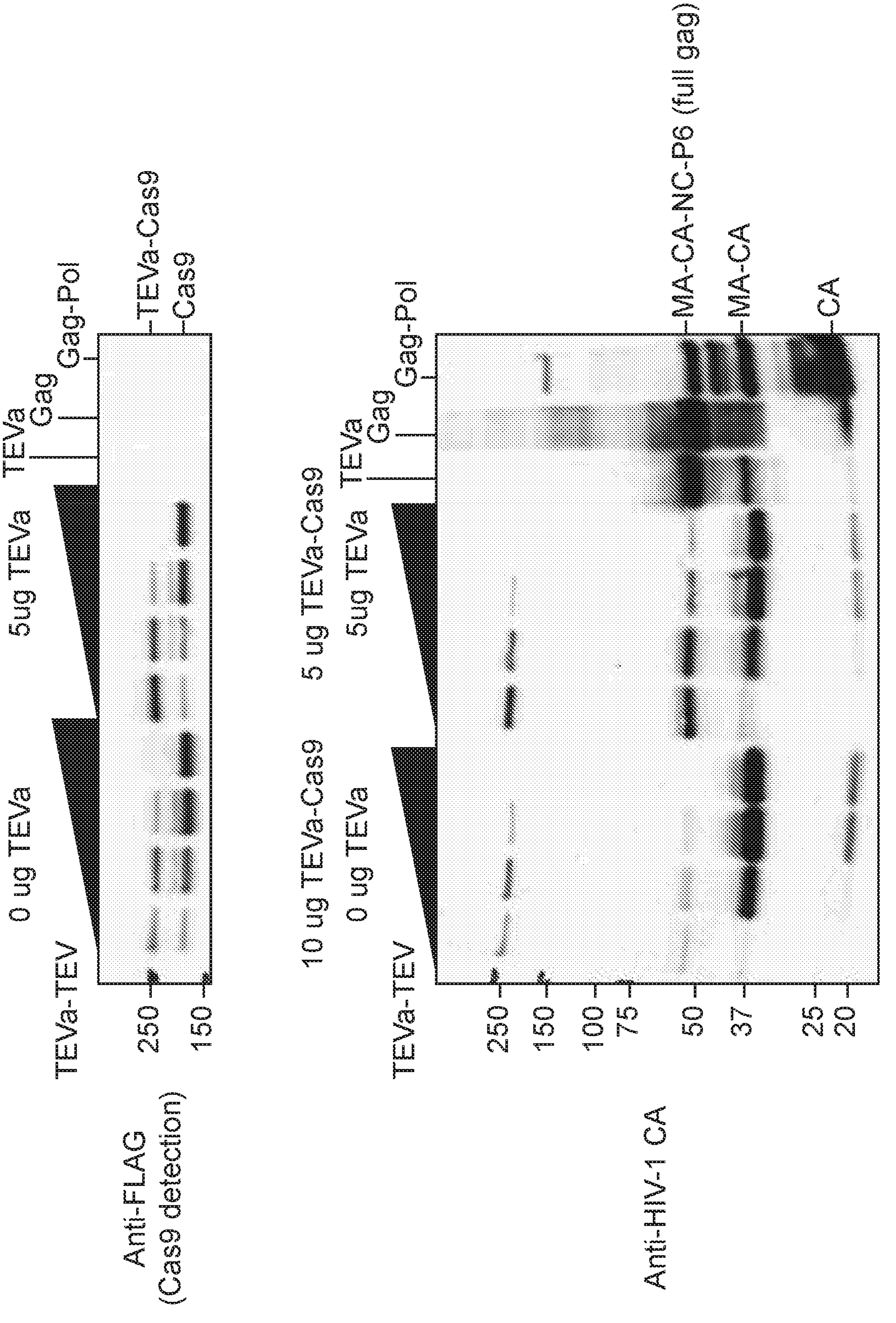
FIG. 12 depicts TEV-mediated proteolytic cleavage of the "TEV-activated" gag-polypeptide.
Figure 13A:
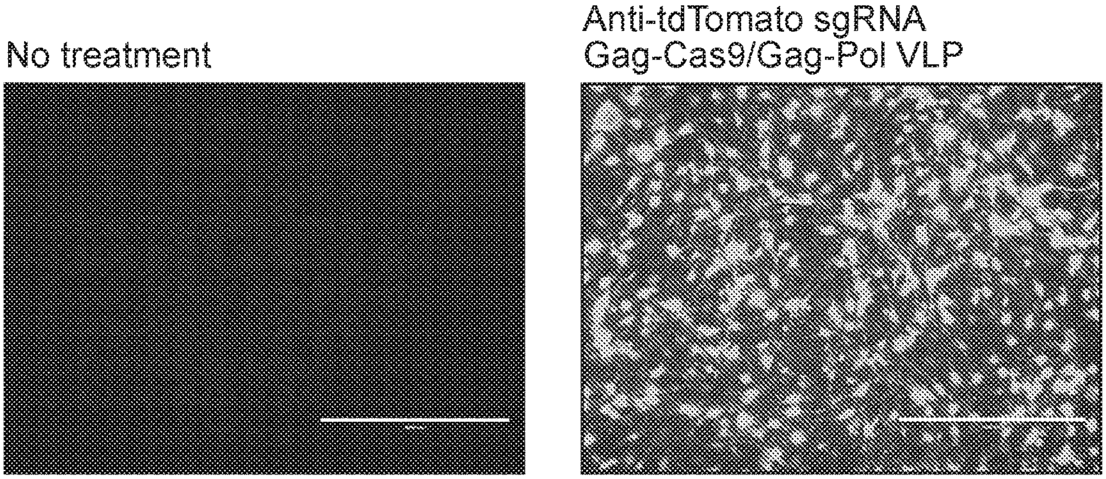
FIG. 13A-13D depict Gag-Cas9 VLPs mediate gene editing in cells in vitro.
Figure 13B:
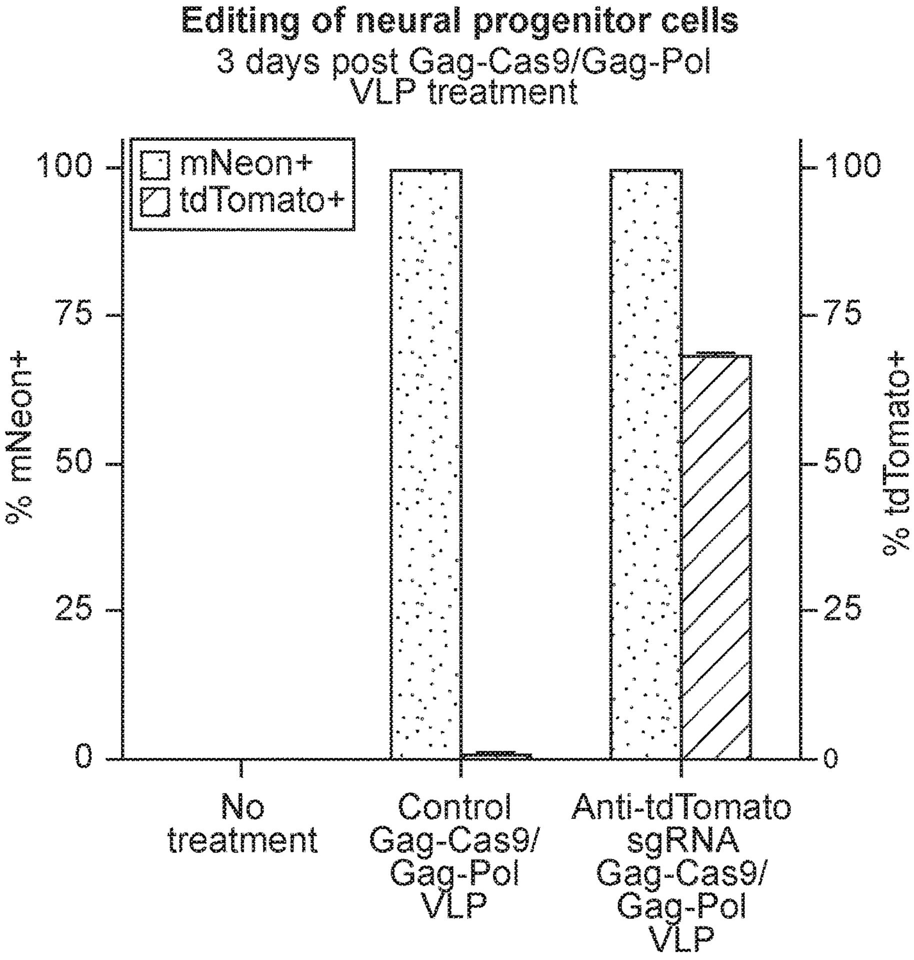
Figure 13C:
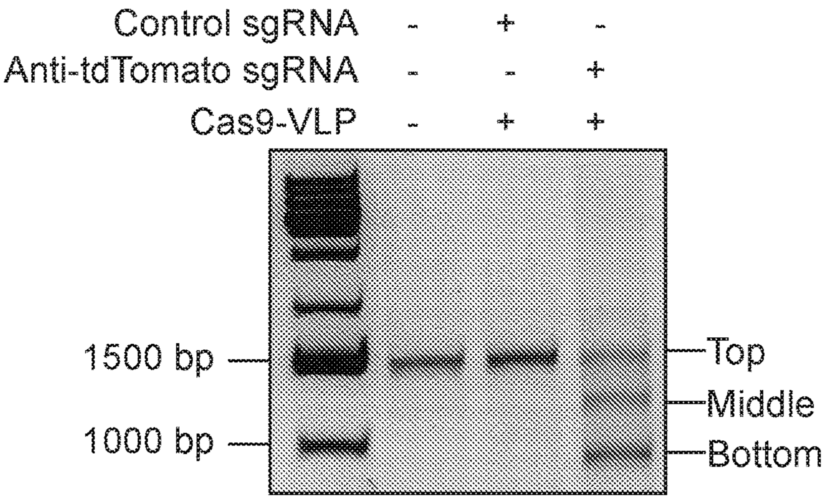
Figure 13D:
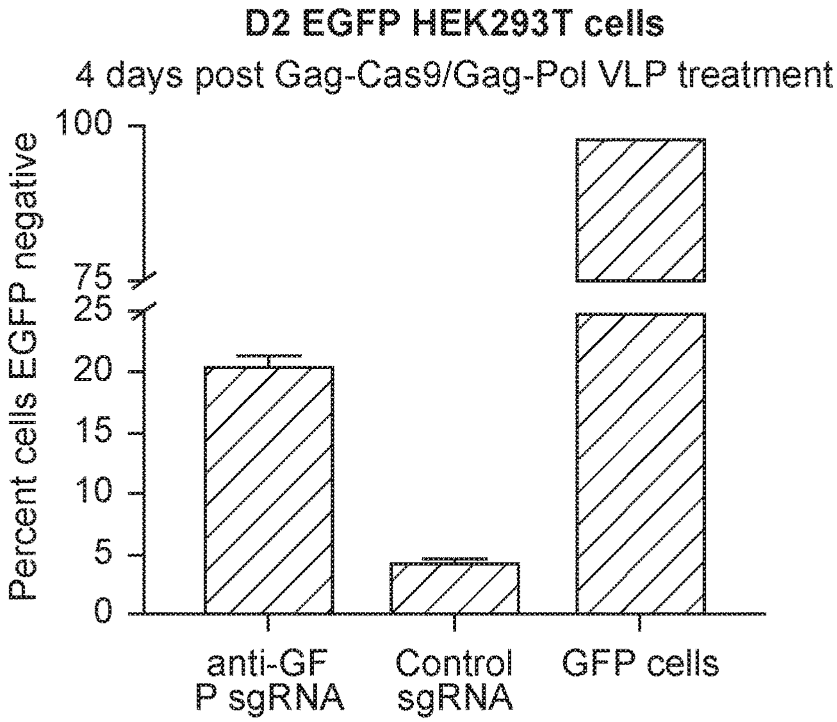

The data provided in FIG. 12 indicate that VLPs composed of "TEV-activated" gag polypeptides are proteolytically processed into individual gag components and free Cas9 by the TEV protease. In the production of these VLPs, a plasmid expressing the MA-CA-NC-p6 fusion lacking the Cas9 sequence ("TEVa") was included during production. The top part of FIG. 12 shows a western blot probed with an anti-FLAG antibody to detect the Cas9 protein. The left half of the blot shows the results with the VLPs produced without any of the TEVa plasmid; the right half of the blot shows the results with the VLPs produced with added TEVa plasmid. The two types of VLPs were used to determine Cas9 release in the presence of increasing amounts of the TEVa-TEV (0, 0.01, 0.1, 1 ug) plasmid transfected into producer cells, which resulted in VLPs with increased levels of proteolytic processing. These results demonstrate that the inclusion of the TEVa-TEV plasmid during VLP production resulted in Cas9 release from the TEVa-Cas9 fusion protein. The bottom part of FIG. 12 shows a western blot in which the CA protein is detected by the antibody. Since the various components of the Gag protein (MA, CA, NC and p6) are separated by TEV protease sites (shown in FIG. 2), cleavage by the TEV protease generates a set of different proteolytic fragments, including CA alone, MA-CA, and MA-CA-NC-P6 (the full gag fusion protein). FIG. 12B depicts the various plasmids that were used in this experiment.

Example 3

Gag-Cas9 VLPs mediate gene editing in cells in vitro. The data are shown in FIG. 13A-13D.

FIG. 13A-13D. Editing efficiency of Gag-Cas9 VLPs in neural progenitor cells (NPCs) from Ai9/Ai14 C57BL/6 mice that contain a floxed transcriptional stop cassette upstream of a tdTomato gene. A sgRNA ("anti-tdTomato") that efficiently edits the stop cassette results in the expression of the fluorescent protein tdTomato, as described above and in Staahl et al. (2017) supra. (FIG. 13A) untreated NPCs (top) or NPCs three days post treatment with Cas9-VLP and anti-tdTomato sgRNA (bottom). Representative images are shown. (FIG. 13B) Quantification of tdTomato cells (edited cells) by flow cytometry. A lentiviral genome encoding the fluorescent protein mNeon and an expression cassette for the anti-tdTomato sgRNA was included during the production of the VLPs used in this experiment; mNeon was quantified to assess the percent of Gag-Cas9 transduced cells. N=3, error bars represent standard error of the mean. The graph shows cells that had been treated with the VLPs produced using the HIV-1 protease (middle data set, also comprising a control sgRNA that does not trigger tdTomato expression), although the cells were transduced by the VLPs (as evidenced by the mNeon signal, left-most bar in each data set), Cas9 cleavage of the tdTomato construct was very low due to the lack of proper guidance to the tdTomato flox site, right-most bar in each data set). In comparison, VLPs produced using the HIV-1 protease (right data set) and produced in the presence of the td-Tomato specific sgRNA, resulted in a similar level of VLP transduction of the NPC as the HIV-1 VLPs but with a large increase in the amount of tdTomato generated signal, indicating efficient Cas9 cleavage of the floxed stop cassette. (FIG. 13C) PCR analysis of the floxed stop cassette of untreated, control Gag-Cas9 VLP (comprising a control sgRNA) treated, or anti-tdTomato sgRNA Cas9-VLP treated NPCs, three days post treatment. Middle and bottom bands indicate efficient editing of the stop cassette locus, and corroborate the results shown in FIG. 13B. (FIG. 13D) Editing efficiency of Gag-Cas9 VLPs in HEK293T cells stably expressing a d2-EGFP (a reporter cell line described in Staahl et al. (2017), supra). Gag-Cas9 VLPs packaging an anti-GFP sgRNA (or control sgRNA) were used to treat d2-EGFP cells overnight in the presence of polybrene. The percentage of GFP negative cells (as a readout of efficient gene editing) was quantified by flow cytometry 4 days post VLP treatment. The left-most bar ("anti-GFP sgRNA") shows the data produced from VLPs comprising the EGFP-specific sgRNA, and indicates that approximately 20% of the HEK293T cells were GFP negative. The left-most bar shows that EGFP-293T cells treated with VLPs packaging anti-GFP sgRNA Cas9 RNPs resulted in 20% GFP knockout by flow cytometry. The middle bar shows editing when the VLPs were produced using the control sgRNA, demonstrating little editing. The right-most bar shows treatment using control 293T cells that do not express EGFP, that were not treated with VLP, where nearly all the cells were GFP negative because no editing took place.

Example 4

Figure 14:
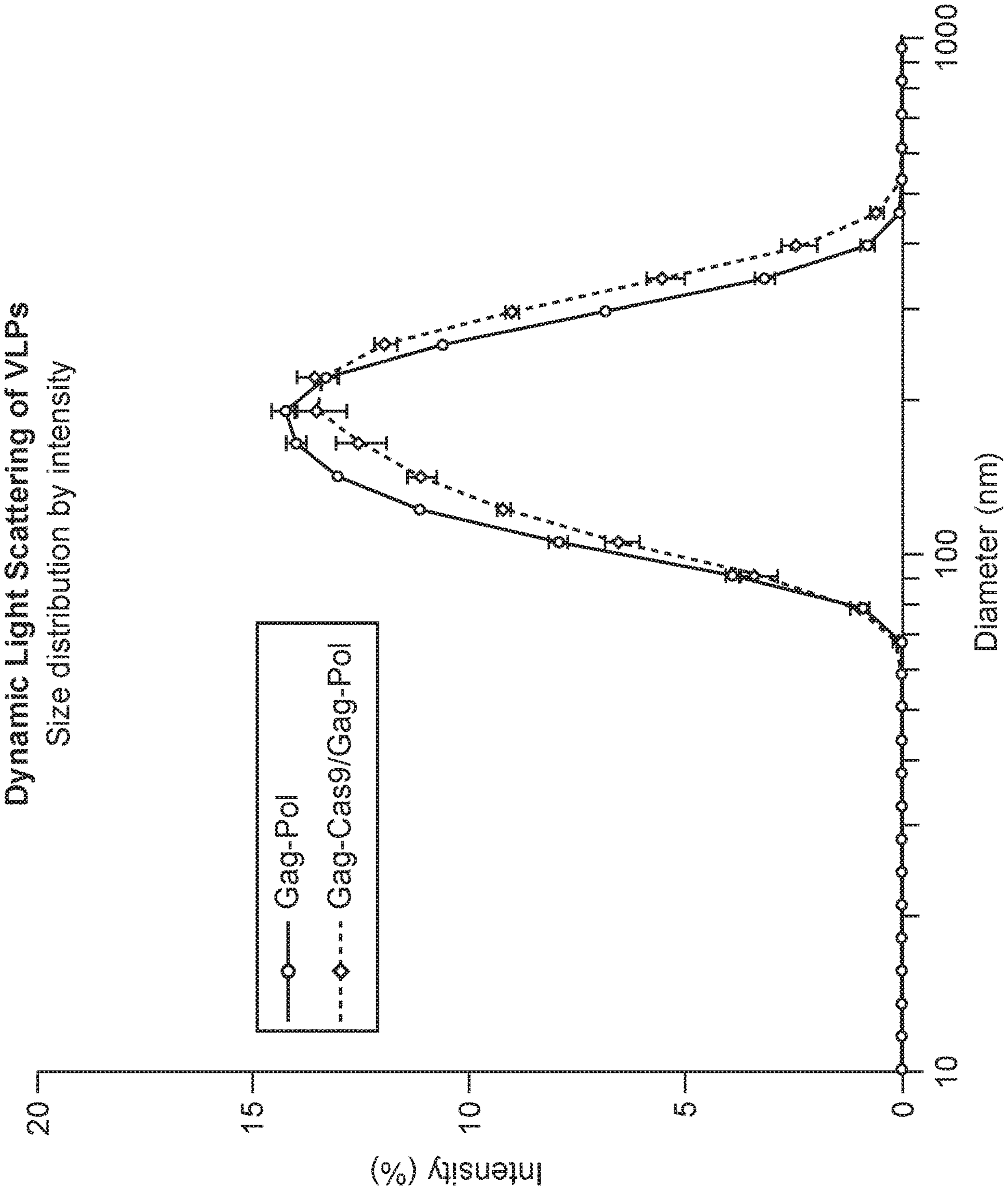
FIG. 14 depicts dynamic light scattering data of VLPs that have packaged Cas9 and VLPs that have not packaged Cas9.

Gag-Cas9 VLPs have a similar diameter to VLPs that have not packaged Cas9. The data are shown in FIG. 14. Dynamic light scattering demonstrates that Gag-Pol VLPs and Gag-Cas9/Gag-Pol VLPs have a similar diameter. The experiment was carried out using a Zetasizer device (Malvern Pananalytical) according to manufacturer's instructions.

Figure 15A:
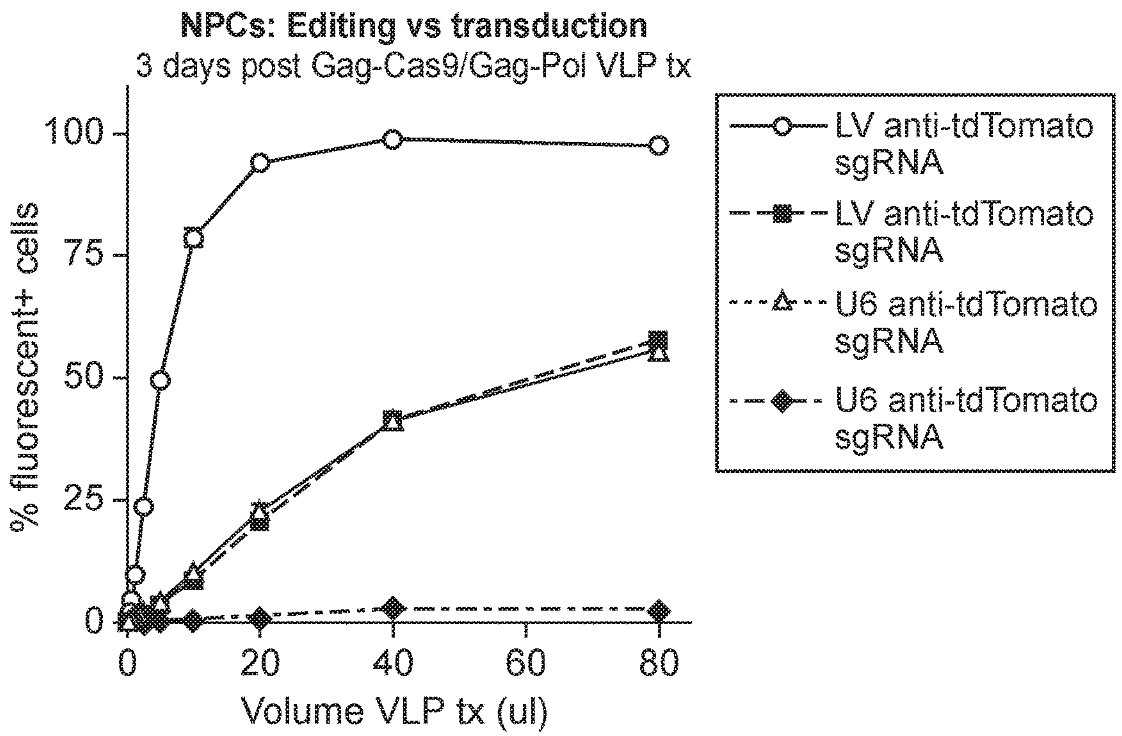
FIGS. 15A and 15B depict gene editing in neural progenitor cells (NPCs) (FIG. 15A) and Jurkat cells (FIG. 15B) treated with: i) Gag-Cas9/Gag-Pol VLPs that co-packaged a lentiviral genome encoding mNeon and an anti-tdTomato sgRNA; or Gag-Cas9/Gag-Pol VLPs that packaged Cas9-sgRNA RNP complexes.

Example 5 sgRNAs can be co-packaged in Gag-Cas9 VLPs to mediate gene editing. The data are shown in FIG. 15A and FIG. 15.B. The data show that lentiviral-mediated expression of a sgRNA in target cells is not required for effective genome editing, but rather that sgRNA can be expressed from a U6-directed expression plasmid during VLP production, generating VLPs comprising ribonucleotide protein complexes (RNPs).

For these studies, two types of Gag-Cas9/Gag-Pol VLPs were generated:

(1): Gag-Cas9/Gag-Pol VLPs that co-packaged a lentiviral genome ("LV anti-tdTomato sgRNA"), which integrates/expresses an mNeon fluorescent gene and the anti-tdTomato sgRNA in target cells (solid lines); and (2): Gag-Cas9/Gag-Pol VLPs that package Cas9-sgRNA ribonucleoprotein complexes ("U6 anti-tdTomato sgRNA"). Producer cells were co-transfected to express the anti-tdTomato sgRNA during VLP production in order for VLP-associated Cas9 to associate with the sgRNA as VLPs bud away from the producer cell (dashed lines).

NPCs were treated with either type of VLPs. The amount of green or red fluorescence was measured.

FIG. 15A. Green lines show the % mNeon+ cells treated with either type of VLP. No mNeon+ cells are observed for "U6 anti-tdTomato sgRNA" treated cells because these particles do not integrate/express an mNeon fluorescent gene upon target cell transduction. Red lines are the quantification of the percent tdTomato+ (i.e. edited) cells treated with either type of VLP.

The data show that equivalent editing was observed, whether the VLPs co-packaged a lentiviral encoding a sgRNA, or packaged Cas9-sgRNA RNPs.

Figure 15B:
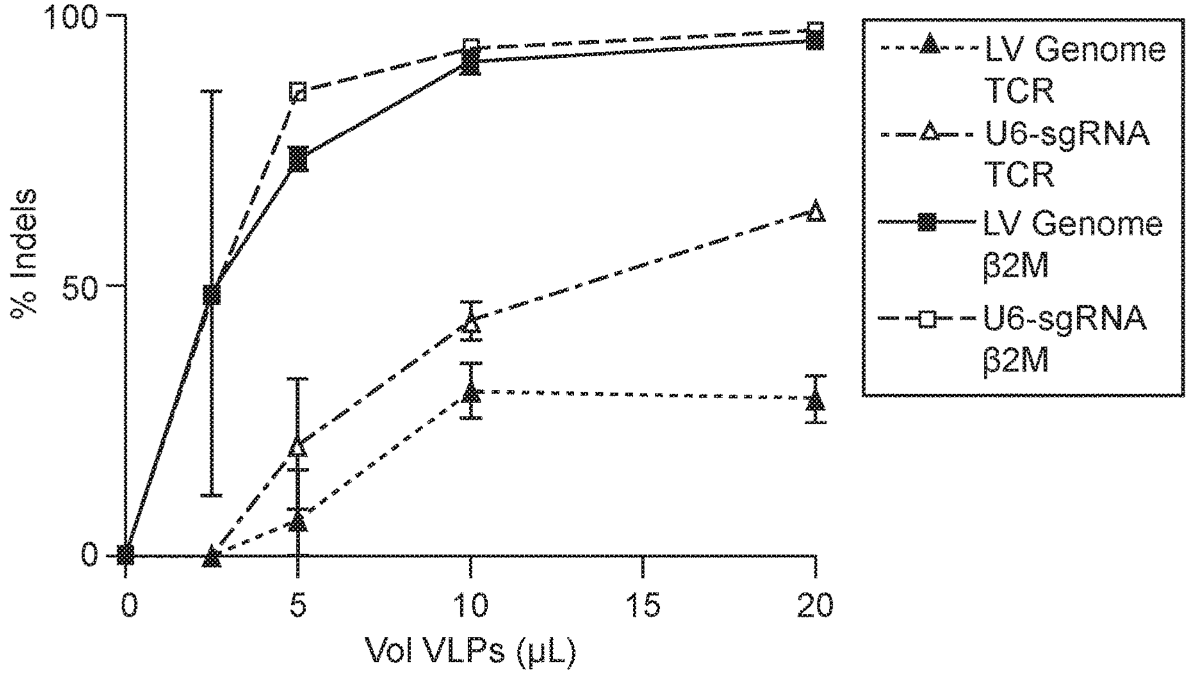

FIG. 15B provides a graph showing editing in Jurkat cells. In this experiment, VLPs comprising Gag-Cas9 and a co-packaged lentivirus genome encoding a guide RNA expression cassette were compared to VLPs comprising Cas9-sgRNA RNPs. Two loci in the T cells were targeted: either the gene encoding the constant region of the T cell receptor ("TCR") alpha chain or the gene encoding beta-2-microglobulin ("β2M"). VSV-G pseudotyped VLPs were produced by transient transfection as described above, and the production supernatant comprising the VLP concentrated into 200 μL Opti-mem® media (Thermo Fisher) by ultracentrifugation. The guide RNA used for TCR was 5'AGAGTCTCTCAGCTGGTACA (SEQ ID NO:1072) while for β2M, the following guide was used: 5' GAGTAGCGCGAGCACAGCTA (SEQ ID NO:1073). DNA was isolated from the treated cells three days post treatment and PCR was performed around the targeted cleavage site. Amplified PCR products were analyzed by the ICE platform (Synthego) to determine the percent editing or indels. The graph shows editing produced by VLPs comprising either RNPs ("U6-sgRNA TCR" and "U6-sgRNA β2M"; dotted lines) or Gag-Cas9 and the lentiviral genomes encoding the sgRNA ("LV Genome TCR" and "LV Genome β2M"; solid lines). The data show that equivalent volumes of VLP of both types results in similar levels of gene editing at the targeted loci.

Example 6

Gag-Cas9 VLPs, in which the Cas9 is released via HIV-1 proteolytic cleavage, mediate gene editing in vivo. The data are shown in FIG. 16.

Convection enhanced delivery (CED) injections of Gag-Cas9 VLPs into the striatum of Ai14 tdTomato mice were performed, and samples were collected for analysis 7 days post treatment. The injections were carried out with 5 μL of concentrated Gag-Cas9 VLPs injected per hemisphere. Tissue samples were collected and 50 μm sections made and fixed using standard methods known in the art, and analyzed by fluorescent microscopy at 4× magnification. Nuclei were stained with DAPI (blue). Upper panel: Gag-Cas9 VLPs co-packaging anti-tdTomato sgRNA. Lower panel: Gag-Cas9 VLPs packaged without sgRNA.

Only Gag-Cas9 VLPs co-packaging the anti-tdTomato sgRNA activate the fluorescent reporter (indicative of genome editing). Thus, the data demonstrated that administration of VLPs comprising the sgRNA (RNP-VLPs) resulted in gene editing in striatal cells in vivo.

The experiments are repeated with the TEV-activated Gag-Cas9 RNP VLPs co-packaged with the anti-tdTomato sgRNAs and demonstrate editing in vivo.

Example 7

Figure 17:
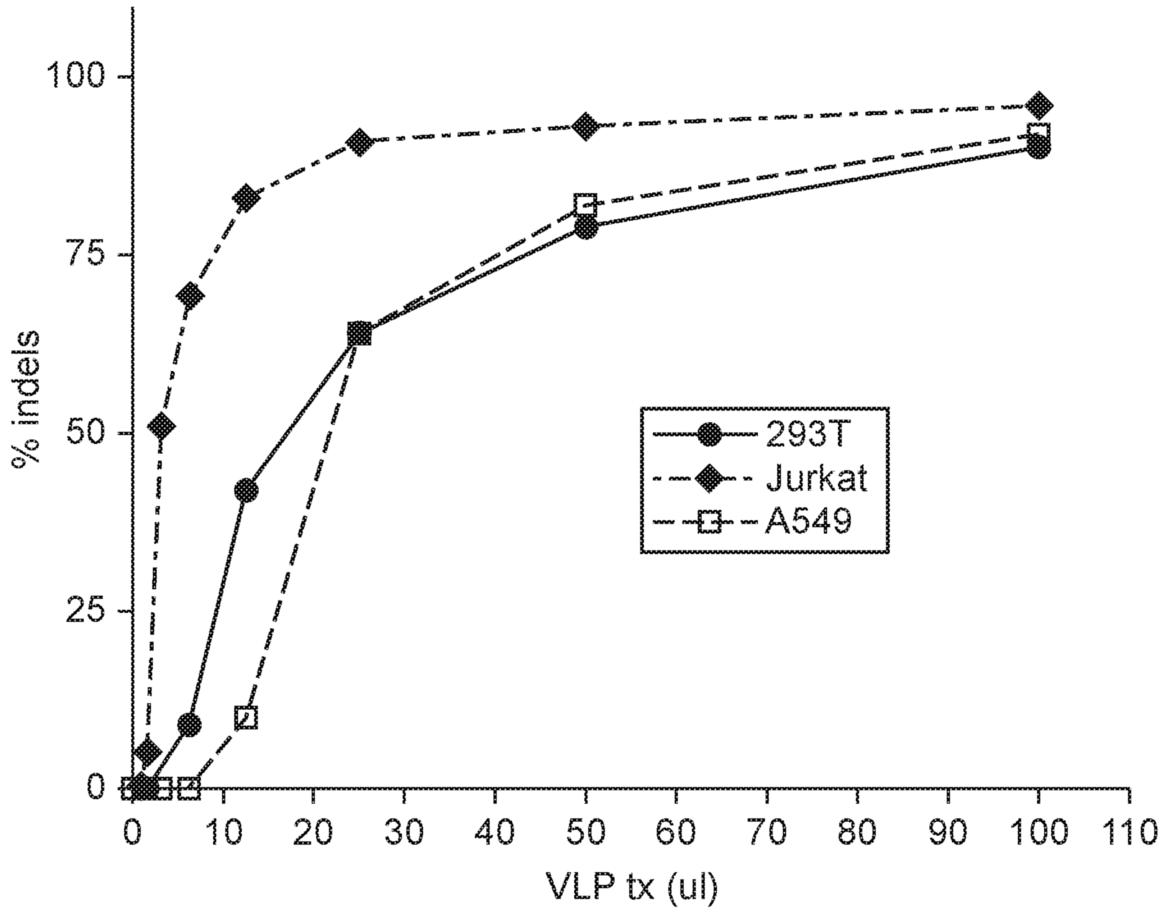
FIG. 17 depicts VLP-mediated editing in immortalized human T cells (Jurkat cells), respiratory epithelial cells (A549 cells) and kidney epithelial cells (293T cells).

The Gag-Cas9 VLPs demonstrated activity in a variety of cell types. The results are shown in FIG. 17. VSV-G pseudotyped RNP-VLPs were produced using transient transfection as described above and concentrated via ultracentrifugation to a volume of 1000 μL in Opti-mem® cell culture medium. Particles comprising Cas9-sgRNA RNPs targeting the beta-2-microglobulin gene (see above) were used to treat the cell types at the indicated volume of VLPs. DNA from the treated cells was isolated three days post treatment and PCR was performed to amplify the region surrounding the targeted cleavage site. The percent editing (indels) was determined using the ICE platform (Synthego). The results (shown in FIG. 17) demonstrated that the VLPs are capable of promoting gene editing in three different cell types: immortalized human T lymphocytes (Jurkat); respiratory epithelial cells (A549); and kidney epithelial cells (HEK293T).

Example 8

Figure 18A:
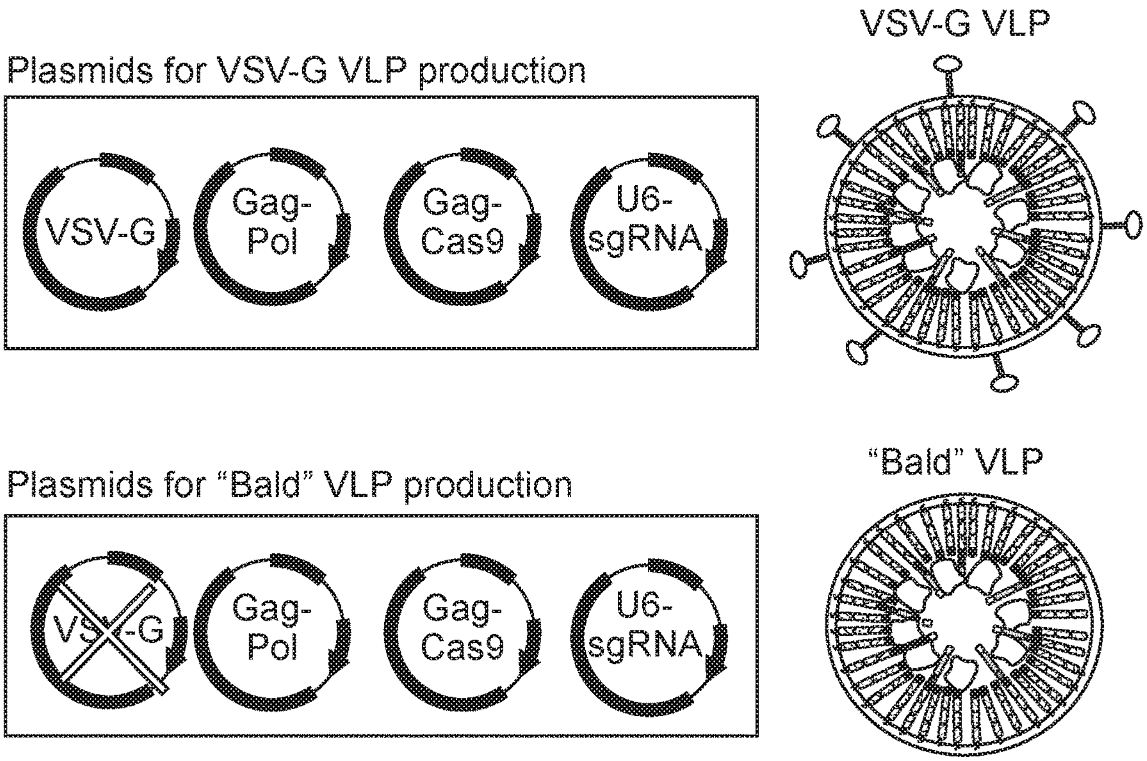
FIG. 18 depicts a comparison of gene editing using VLPs with or without glycoprotein.
Figure 18B:
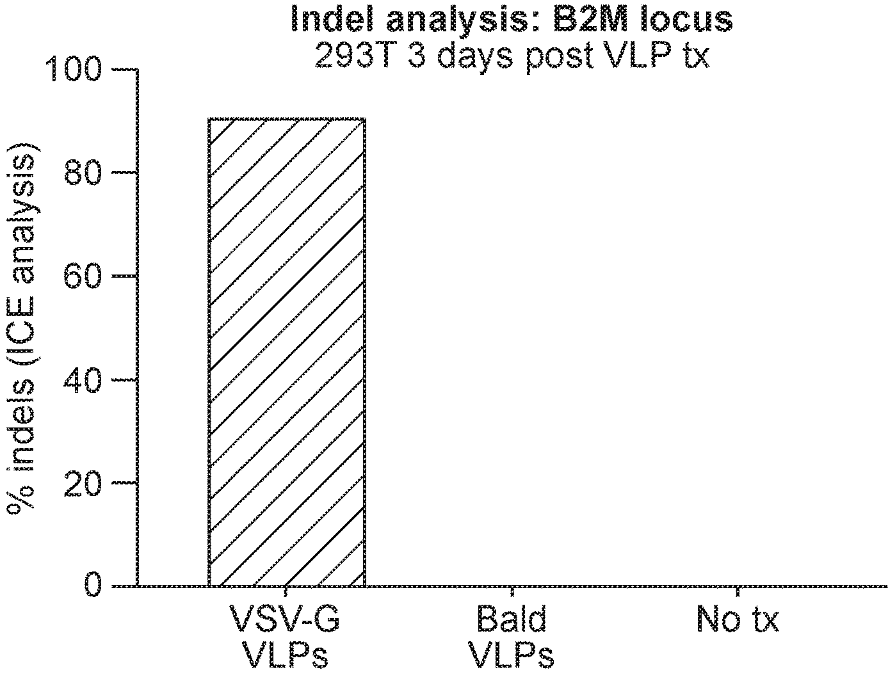

Glycoprotein expression is needed for efficient Gag-Cas9 VLP mediated genome editing. To investigate the requirement for surface glycoprotein expression on genome editing by Cas9 comprising VLPs, experiments were performed using VLPs with and without glycoprotein expression. VSV-G VLPs (Gag-Cas9 VLPs, in which the Gag-Cas9 polyprotein comprises a HIV-1 protease cleavage site to release the Cas9) comprising VSV-G glycoproteins on the surface of the VLP were compared to a second type of VLPs ("Bald" VLPs) that differed from the VSV-G VLPs in that the second type of VLPs lacked the VSV-G glycoprotein on the particle surface. Production of both VSV-G VLPs and "Bald" VLPs was carried out as described above except that the glycoprotein-less VLPs ("Bald" VLPs) were produced without the VSV-G production plasmid (see FIG. 18A). Both VSV-G VLPs and Bald VLPs were produced as RNP-VLPs and included anti-β2M guide RNAs as described above. 100 μL of concentrated VLPs were used to treat HEK293T cells. Three days after treatment, editing efficiency at the β2M locus was evaluated using ICE analysis as described above. The data (shown in FIG. 18B) demonstrated that the VLPs lacking the glycoprotein did not promote gene editing at the target.

Example 9

Delaying the release of the Cas9 from the Gag-Cas9 fusion protein ("Gag-Cas9 polyprotein") until after the polypeptide has been incorporated into the VLP may be beneficial. If the Cas9 is released prior to the budding off of the VLP from the production cell, the released Cas9 may dissipate throughout the cytoplasm of the production cell and not reach optimal concentration inside the VLP. In addition, the Cas9 in TEV-activated VLPs displays high integrity as compared to the Cas9 released in the HIV-1 activated VLPs. The TEV proteolytic site ("TEV cleavage site"; "TCS") was engineered to reduce the efficiency at which the TEV protease cleaved the TCS.

Figure 19A:
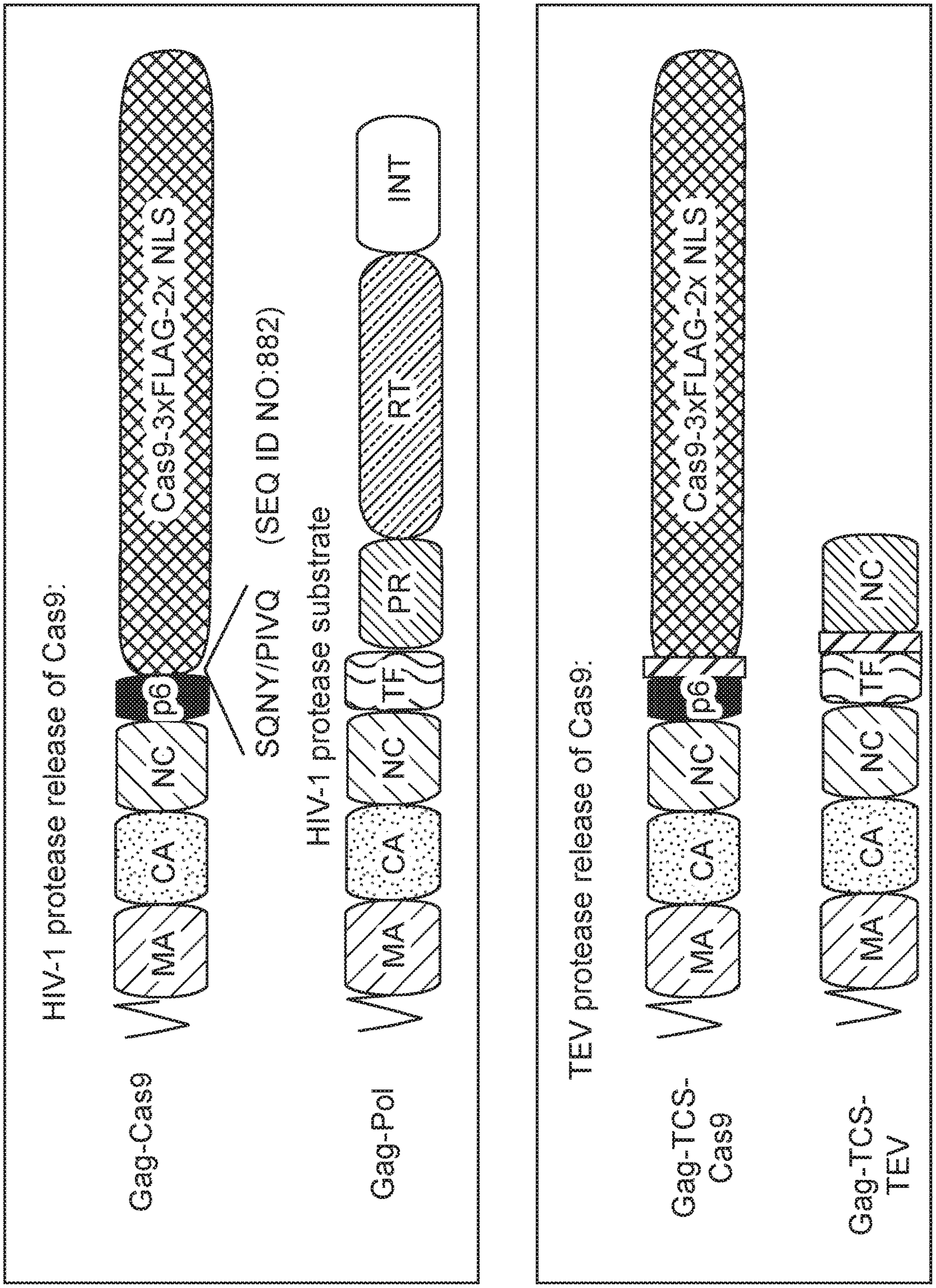
FIGS. 19A-19D demonstrate editing using TEV protease-driven release of Cas9 from Gag.

Comparison of the production vectors for the HIV-1 activated VLPs and the TEV-activated VLPs is shown in FIG. 19A.

The upper panel shows the components of: 1) the "Gag-Cas9" construct: the GAG protein: MA, CA, NC and P6 for the Gag-Cas9 fusion protein in which an HIV-1 protease cleavage site is between the Gag and the Cas9 proteins; and 2) the "Gag-Pol" construct comprising a Gag-Pol fusion protein (comprising the HIV-1 protease (PR)). The Gag-Pol construct has a "TF" or trans-frame region such that the protease is inserted in the minus 1 (−1) reading frame with respect to the Gag portion of the Gag-Cas9 fusion protein. This mirrors the configuration for many viruses and results in a decrease in the amount of protease that is packaged in the VLP. The Cas9 polypeptide was a fusion protein comprising 3 copies of a FLAG epitope ("3× FLAG") and two NLSs ("2× NLS").

The lower panel shows the components of: 1) the "Gag-TCS-Cas9" construct: the GAG protein: MA, CA, NC and P6 for the Gag-Cas9 fusion protein in which a TEV protease cleavage site (TCS) is between the Gag and the Cas9 proteins, and is represented by a narrow rectangle immediately upstream of the Cas9 protein; and 2) the "Gag-TCS-TEV" construct comprising a Gag polyprotein and a TEV protease, in which a TCS is between the Gag and the TEV proteins, and is represented by a narrow rectangle immediately upstream of the TEV protein. The Cas9 polypeptide was a fusion protein comprising 3 copies of a FLAG epitope ("3× FLAG") and two NLSs ("2×NLS"). The Gag-TCS-TEV construct has a "TF" or trans-frame region such that the protease is inserted in the minus 1 (−1) reading frame with respect to the Gag portion of the Gag-TEV fusion protein. Cleavage at the TCS will result in the release of the Cas9 from the Gag-TCS-Cas9 polyprotein or TEV protease from the Gag-TCS-TEV polyprotein. Nucleotide sequences of the Gag-1% TCS-Cas9, Gag-10% TCS-Cas9, Gag-1% TCS-TEV, and Gag-10% TCS-TEV constructs are provided in FIG. 21-24, respectively.

The TCS was engineered to decrease the efficiency of cleavage by TEV at this site. The initial target site used in these experiments, considered to be 100% efficient, was ENLYFQS (SEQ ID NO:880). One engineered site, found to exhibit 10% efficiency, was ENLFFQS (SEQ ID NO:885). An engineered site found to exhibit 1% efficiency was ENVYFQS (SEQ ID NO:890).

VSV-G pseudotyped RNP VLPs were produced; and the amount of released Cas9 was analyzed. All VLPs also comprised sgRNA targeted to the β2M locus. The VLP variants comprised either: 1) Gag-10% TCS-Cas9+Gag-100% TCS-TEV; or 2) Gag-1% TCS-Cas9+Gag-100% TCS-TEV. Release of Cas9 and gene editing efficiency of the VLPs were compared with that of the HIV-1 Gag-Cas9+Gag-Pol VLPs. The data are shown in FIG. 19B and FIG. 19C.

Figure 19B:
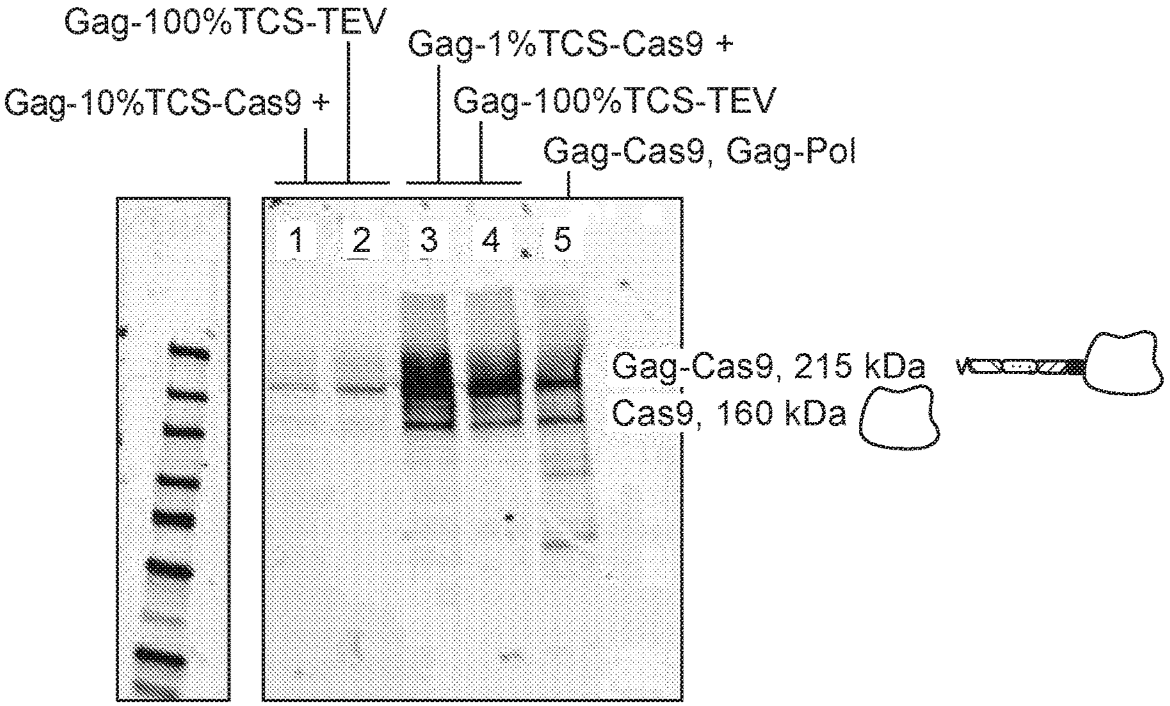
Figure 19C:
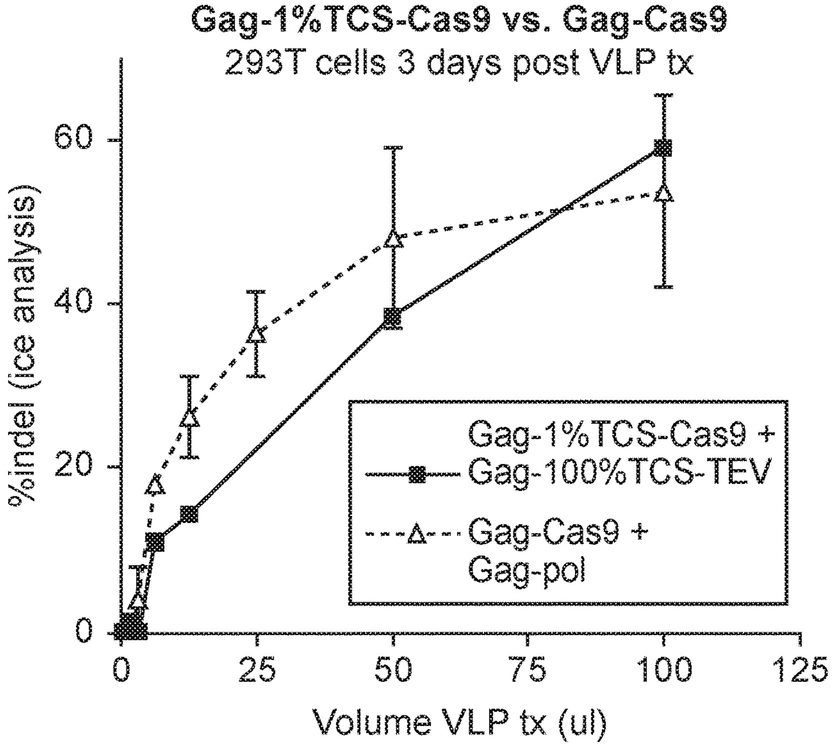
Figure 19D:
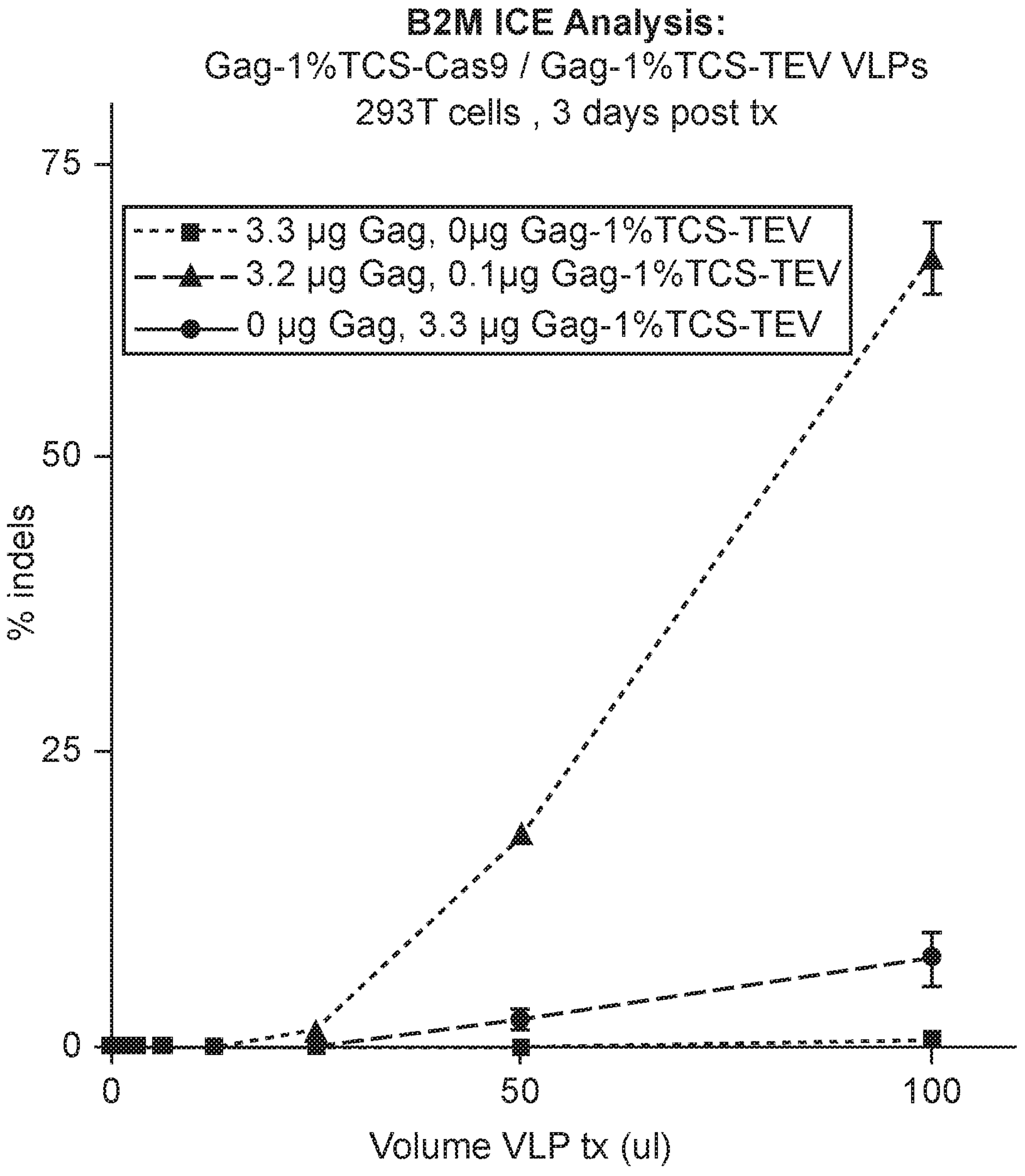

FIG. 19B depicts a western blot of the VLPs in which the Cas9 proteins were detected using an anti-FLAG antibody. Lanes 1 and 2 show the VLPs produced using the Gag-10% TCS-Cas9 while lanes 3 and 4 show VLPs produced using the Gag-1% TCS-Cas9 construct. Lane 5 shows the VLPs produced using the HIV-1 Gag-Cas9 construct. The data demonstrated less degradation of the released Cas9 protein from the TEV VLPs, in agreement with the data shown in FIG. 7. In addition, the TEV activated VLPs showed a higher (or equivalent) quantity of the released Cas9 versus uncleaved Gag-Cas9 fusion protein as compared with the HIV-1 activated VLPs.

Editing efficiency of the TEV-activated RNP VLPs was compared to the HIV-1 activated RNP VLPs in HEK293T cells. Both VLP types comprised sgRNAs specific for the β2M locus, as described above. The VLPs displayed similar editing efficiency as measured by ICE analysis (see FIG. 19C).

VLPs produced using various ratios of Gag-Cas9 and Gag-TEV constructs were compared for gene editing efficiency. In one experiment, three sets of VLPs were produced in which 6.7 μg Gag-1% TCS-Cas9 plasmid was used for VLP production, along with: (i) 3.3 μg Gag+0 μg Gag-1% TCS-TEV; (ii) 3.2 μg Gag+0.1 μg Gag-1% TCS-TEV; and (iii) 0 μg Gag+3.3 μg Gag-1% TCS-TEV. The VLPs were made in producer cells comprising a U6-sgRNA plasmid expressing the β2M specific sgRNA. The VLPs were then tested as described above in HEK293T cells and analyzed for editing efficiency (indels) at the β2M locus by ICE analysis. The results (shown in FIG. 19D) demonstrated that when the TEV comprising plasmid was present in large amounts (VLP iii above), very little gene editing occurred, presumably due to largescale/premature proteolytic release of the Cas9 protein in packaging cells. Also, little editing was detected in the (i) type VLPs, presumably due to a lack of TEV protease to release the Cas9 in the VLP. The (ii) type VLPs showed good editing activity, demonstrating that only small amounts of the TEV protease are required.

Example 10

Delivery of an Acr polypeptide to a cell inhibits Cas9 activity. VLPs were produced comprising an AcrIIa4 polypeptide (Dong et al (2017) *Nature* 546(7658):436-439) that was capable of inhibiting *S. pyogenes* Cas9 in a cell. A Gag-AcrIIa4 fusion protein-encoding plasmid was used during VLP production. The amino acid sequence of the Gag-AcrIIa4 fusion protein is provided in FIG. 25.

Figure 20:
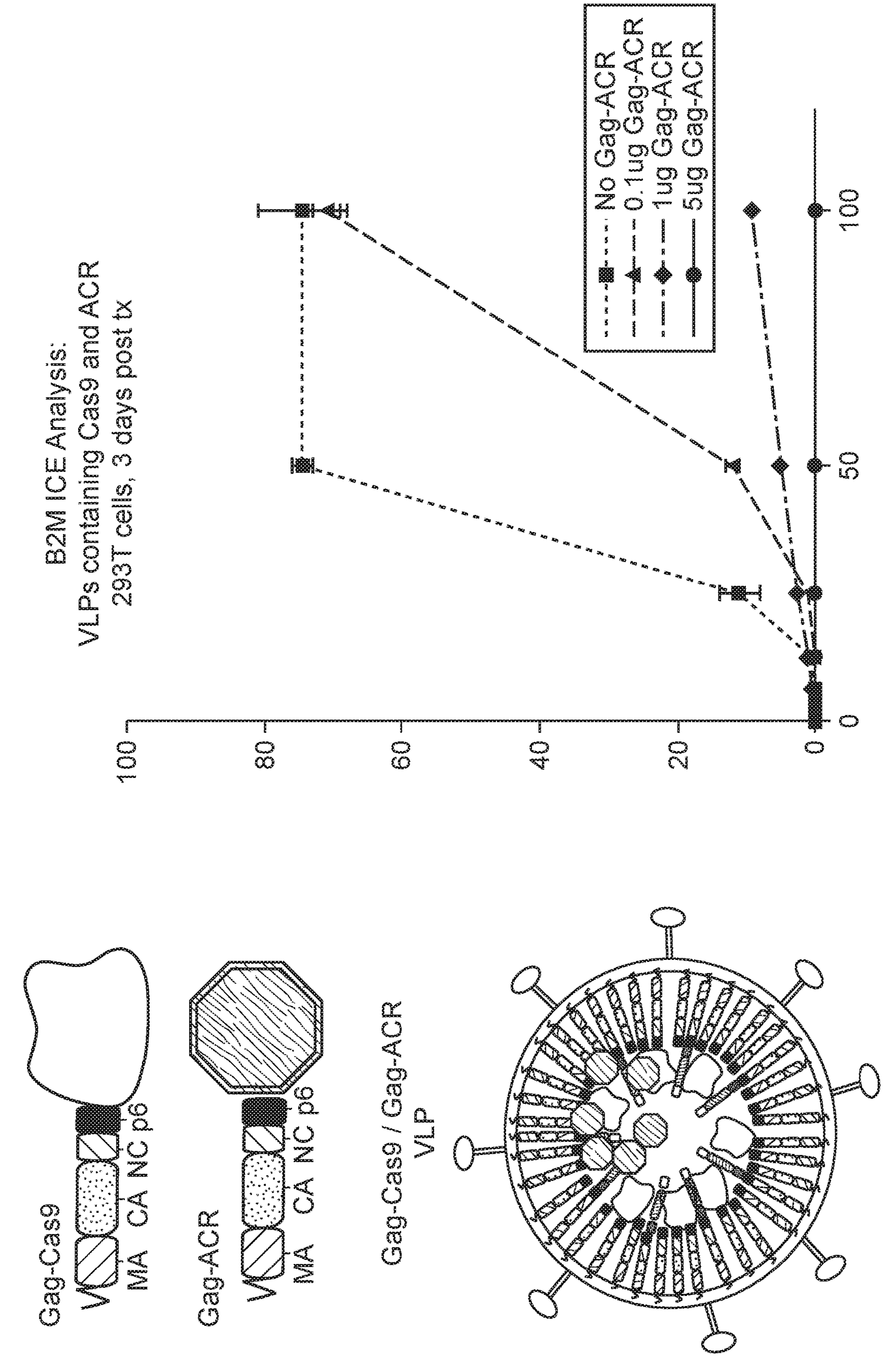
FIG. 20 depicts a graph demonstrating Cas9 inhibition when the VLP co-packages an anti-CRISPR (ACR) polypeptide.

The Gag-Acr fusion protein was incorporated into the VLPs by using 0.1 μg, 1 μg, or 5 μg of Gag-Acr plasmid during VLP production, as described above; and the VLPs were concentrated to a volume of 1000 μL in Opti-Mem® cell culture medium. The VLPs produced also included: a) the Gag-Cas9 plasmid; and b) a U6 expression plasmid driving the production of β2M specific sgRNAs. The VLPs so produced were assayed for Cas9 inhibition in HEK293T cells as follows: The HEK293T cells were treated with the indicated volume of RNP-VLPs and DNA was isolated from the treated cells after three days. Cleavage efficiency (indels) at the β2M locus was measured by ICE analysis as described above. The results, shown in FIG. 20, demonstrated that increasing amounts of the Cas-Acr plasmid produced VLPs with increased inhibition of Cas9.

Example 11: Calculating VLP Titer and Editing Efficiency Vs. MOI

Figure 26:
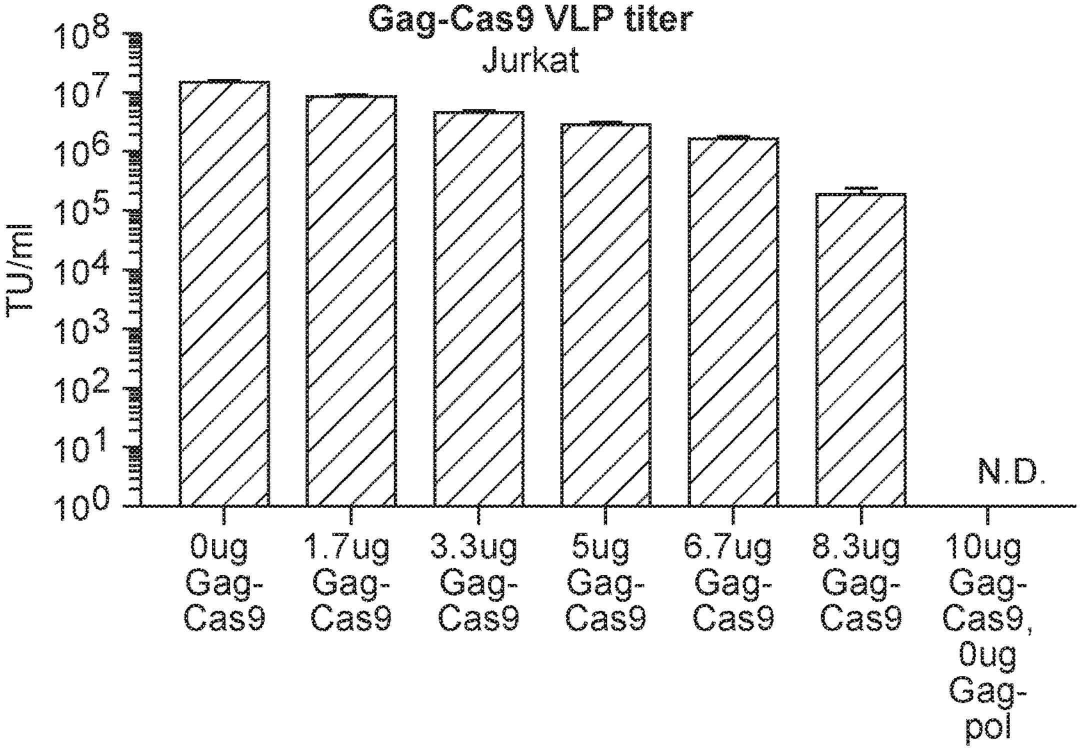
FIG. 26 depicts titration of VLP stocks on Jurkat cells by calculating transducing units per mL (TU/mL) of concentrated medium using VLPs generated with various ratios of Gag-Cas9 to Gag-Pol expression plasmid.

VLPs that integrate/express mNeon in transduced cells and that co-package Cas9-sgRNAs (where the sgRNAs target the β2M gene) were produced using various ratios of Gag-Cas9 to Gag-Pol expression plasmid (total plasmid 10 μg) and concentrated 10× by ultracentrifugation. Jurkat cells were treated with the VLPs (diluted 1:256) and the number of mNeon$^+$ cells was assessed 3 days post treatment, to calculate transducing units per ml (TU/ml). (N.D.=not detected). The data are shown in FIG. 26. The TU/ml is shown for VLPs produced using the following amounts of Gag-Cas9 plasmid and Gag-Pol plasmid (from left to right in FIG. 26): 0 μg Gag-Cas9 plasmid+10 μg Gag-Pol plasmid; 1.7 μg Gag-Cas9 plasmid+8.3 μg Gag-Pol plasmid; 3.3 μg Gag-Cas9 plasmid+6.7 μg Gag-Pol plasmid; 5 μg Gag-Cas9 plasmid+μg Gag-Pol plasmid; 6.7 μg Gag-Cas9 plasmid+3.3 μg Gag-Pol plasmid; 8.3 μg Gag-Cas9 plasmid+1.7 μg Gag-Pol plasmid; and 10 μg Gag-Cas9 plasmid+0 μg Gag-Pol plasmid. The data shown in FIG. 26 indicate that VLP titer (as measured by TU/ml) decreases as VLPs are produced with higher quantities of gag-cas9 expression plasmid.

Editing Efficiency Correlates with Cas9 Incorporation into VLPs.

Figure 27:
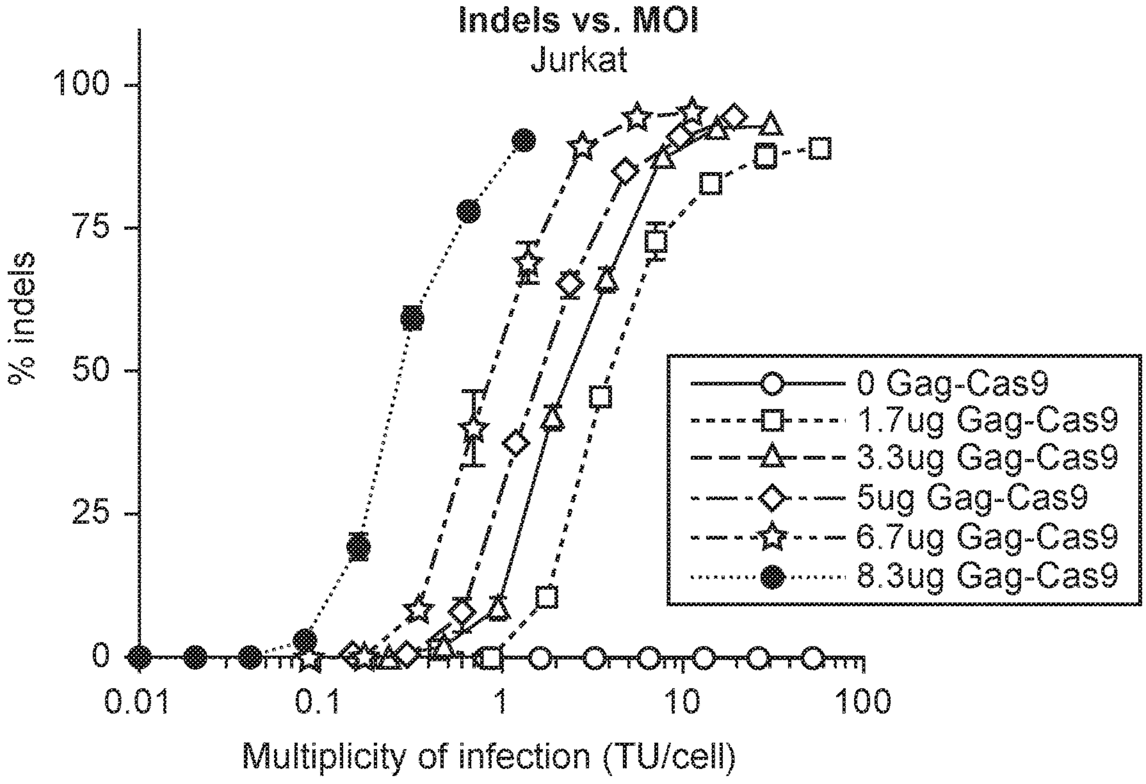
FIG. 27 depicts the percent gene editing (% indels) in Jurkat cells using VLP at various MOI.
Figures 28A, 28B:
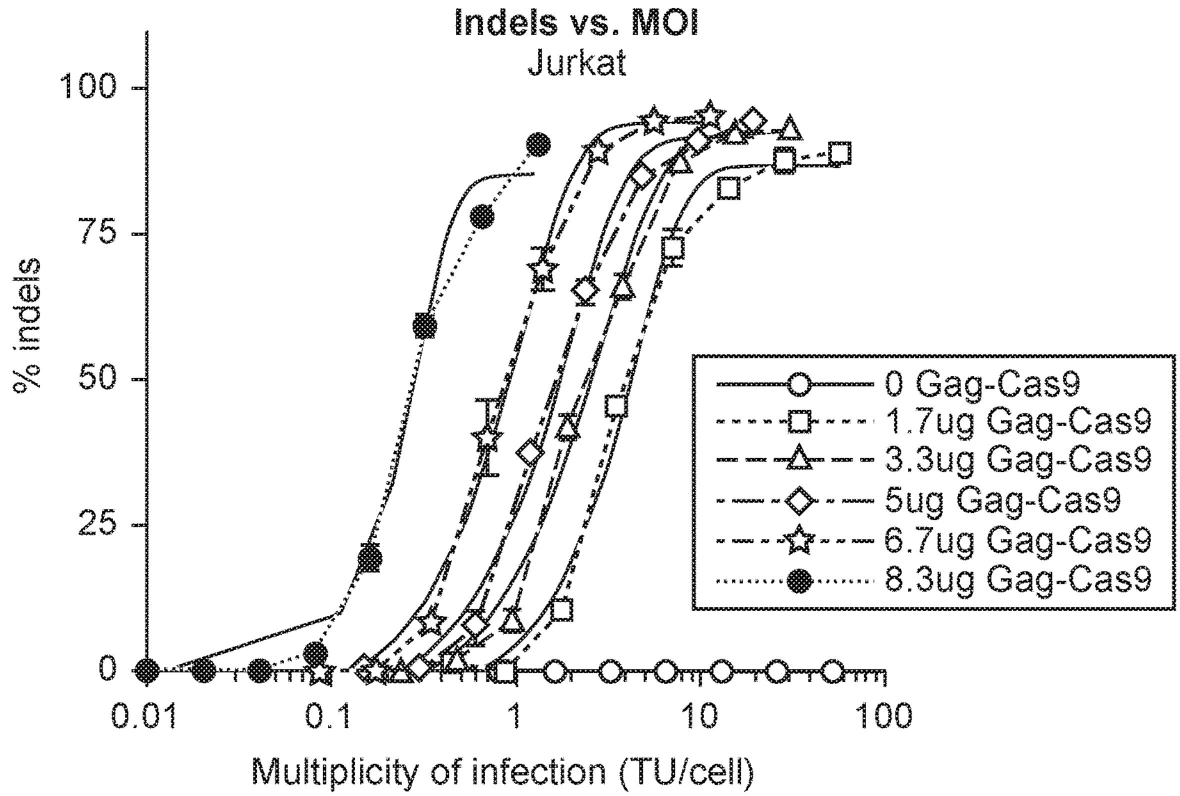
FIG. 28 depicts the percent gene editing (% indels) in Jurkat cells using VLP at various MOI. The MOI to achieve 50% indels was calculated using curve fit analysis.

Jurkat cells were treated with various multiplicities of infection (TU/cell) for each VLP described in FIG. 26. The % indels were assessed 3 days post treatment via Synthego ICE analysis. The data, shown in FIG. 27, indicate that VLPs made with a higher ratio of Gag-Cas9 to Gag-Pol plasmid require a lower multiplicity of infection to induce editing. TU=transducing units. As shown in FIG. 28, the MOI to achieve 50% indels can be calculated via curve fit analysis. FIG. 28A: The data from FIG. 27 curve fit using a four-parameter logistic model to calculate the MOI that results in editing 50% of Jurkat cells in culture. FIG. 28B: Summary table of the MOI to achieve 50% VLP-induced indels by Synthego ICE analysis.

Figure 29:
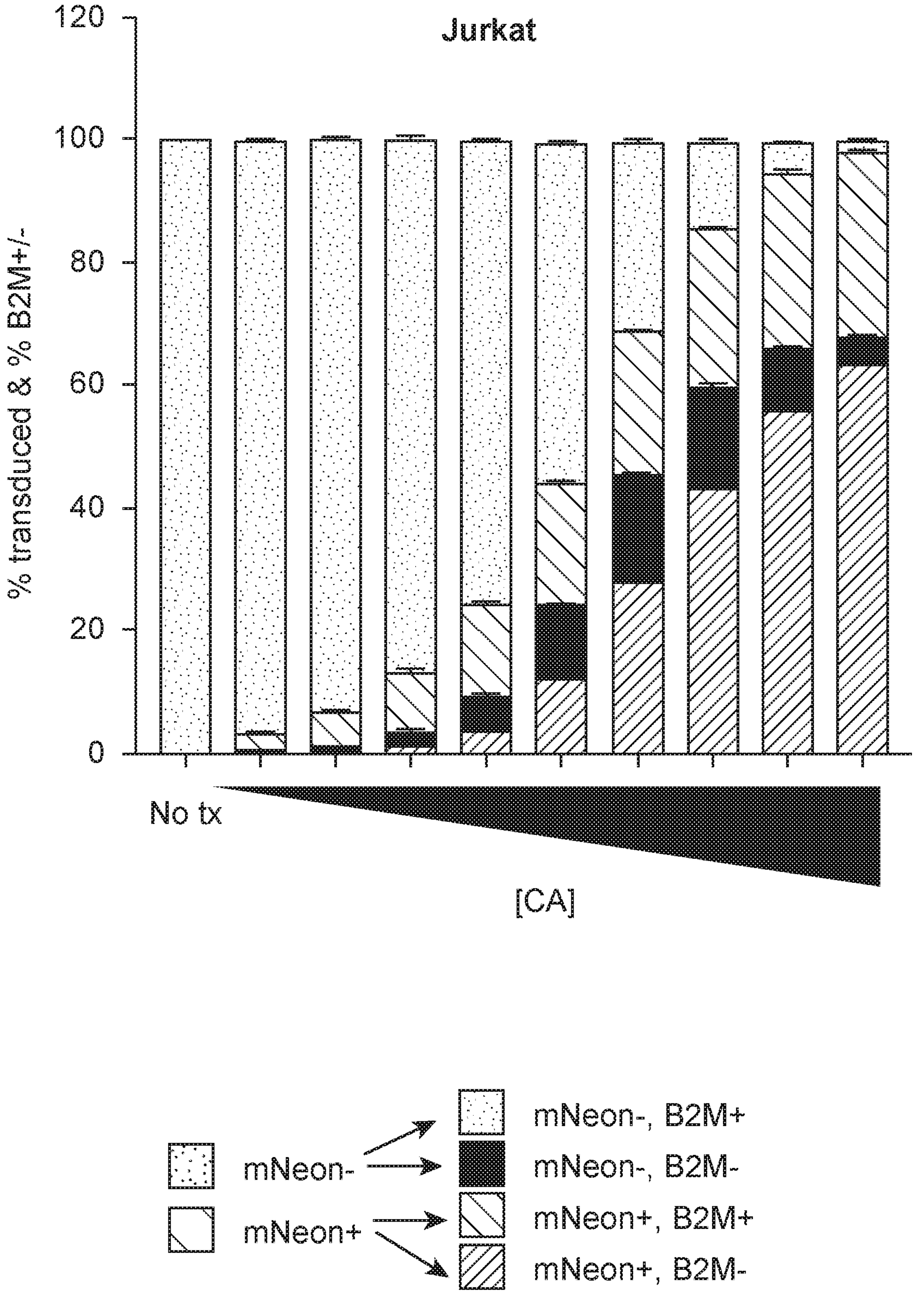
FIG. 29 depicts transduction as a marker for gene-edited Jurkat cells.
Figure 30:
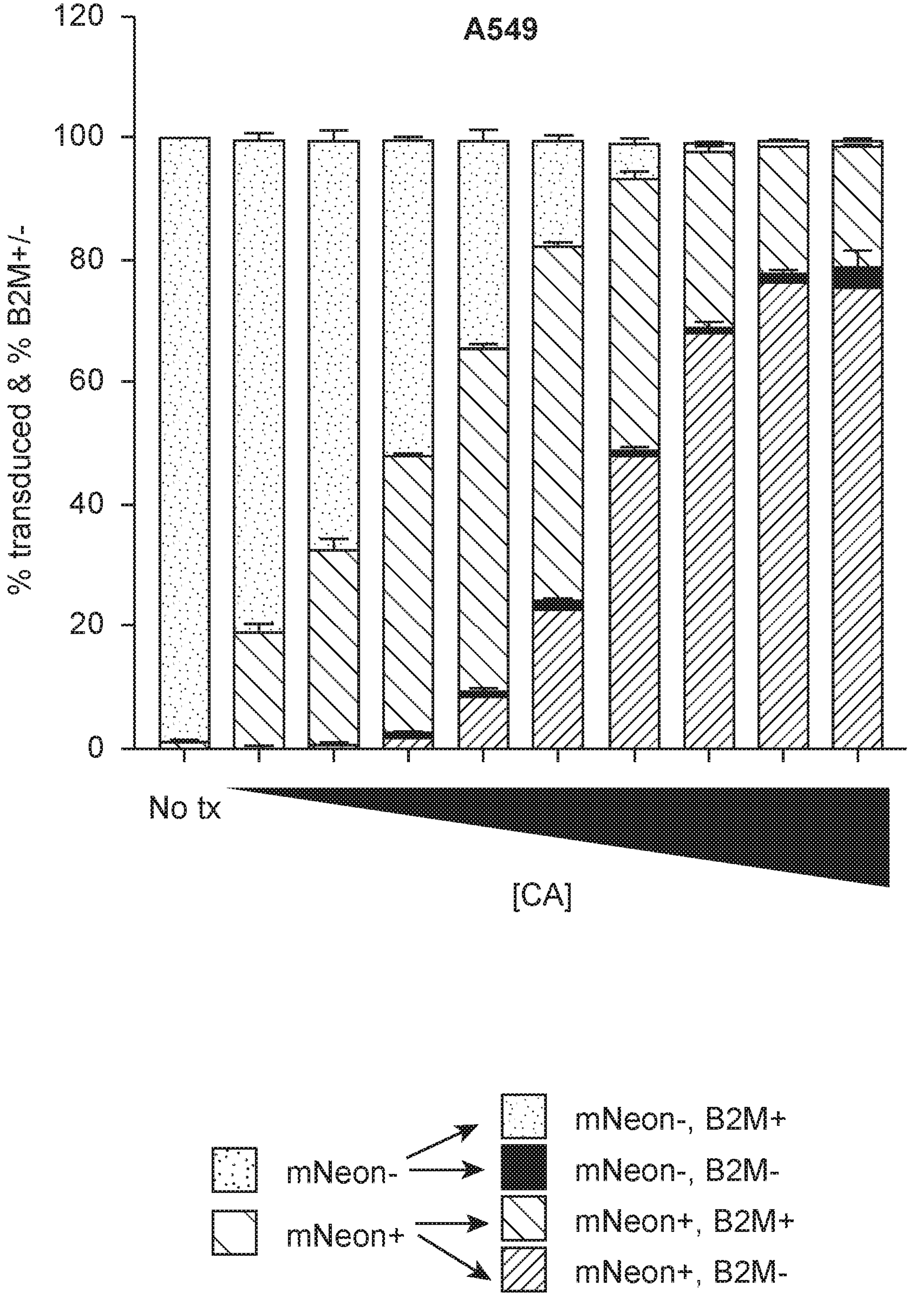
FIG. 30 depicts transduction as a marker for gene-edited A549 cells.

FIG. 29 and FIG. 30 depict transduction as a marker for gene-edited Jurkat cells (FIG. 29) and gene-edited A549 cells (FIG. 30). FIG. 29: VLPs that integrate/express mNeon in transduced cells and co-package Cas9-sgRNAs targeting the β2M gene were produced with 6.7 μg Gag-Cas9 and 3.3 μg Gag-Pol expressing plasmids. Jurkat cells were treated with 2-fold dilutions of VLPs. 6 days post treatment, cells were stained with anti-β2M antibody and cells were quantified by flow cytometry. The rightmost bar represents cells treated with 100 μl of VLPs at 1.04×10^6 pg/ml HIV-1 capsid (CA). FIG. 30: VLPs that integrate/express mNeon in transduced cells and co-package Cas9-sgRNAs targeting the β2M gene were produced with 6.7 μg Gag-Cas9 and 3.3 μg Gag-Pol expressing plasmids. A549 cells were treated with 2-fold dilutions of VLPs. 6 days post treatment, cells were stained with anti-β2M antibody and cells were quantified by flow cytometry. The rightmost bar represents cells treated with 100 μl of VLPs at 1.04×10^6 pg/ml HIV-1 capsid (CA).

Example 12: Gene Editing in Primary Human T Cells

Figure 31:
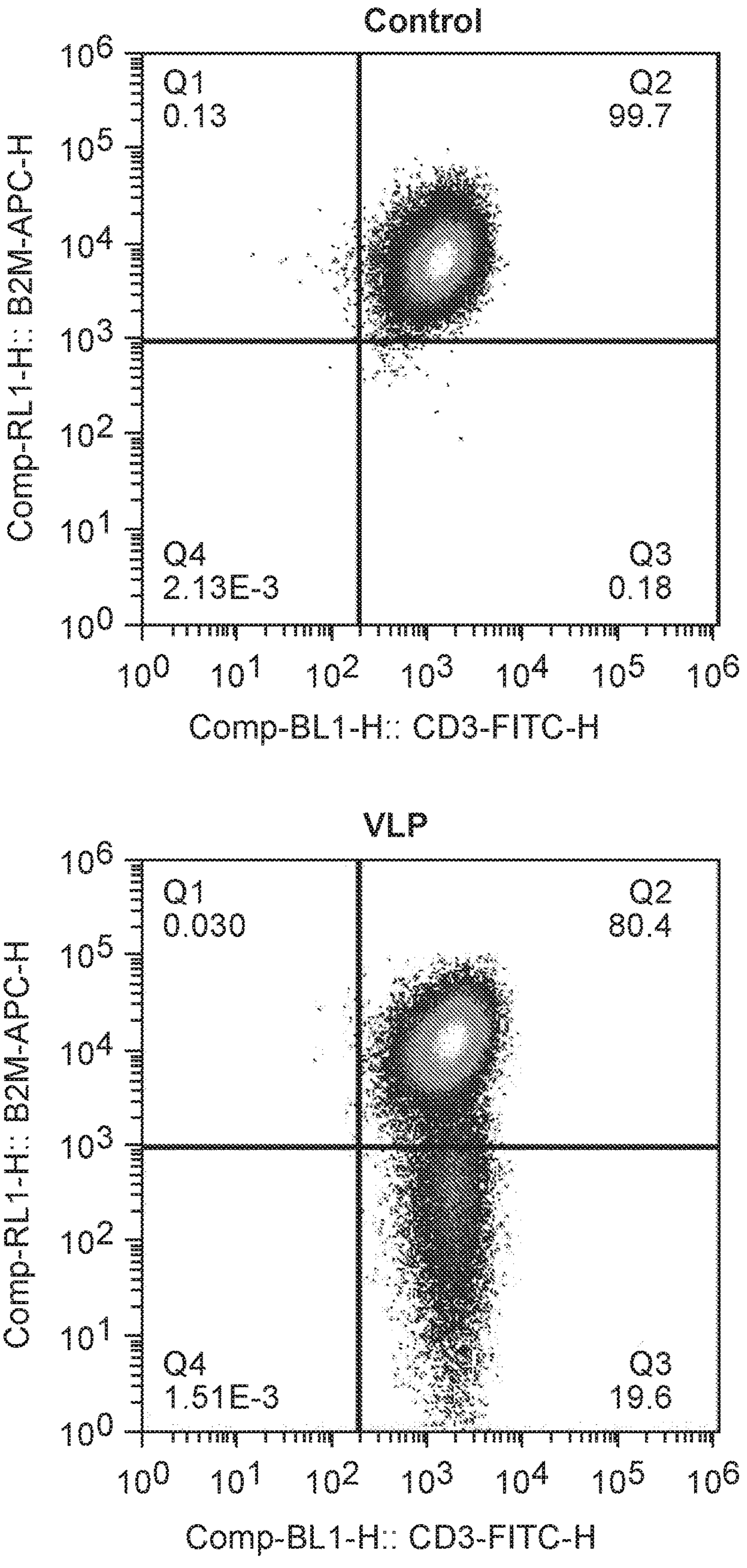
FIG. 31 depicts VLP editing of primary human T cells ex vivo.

VLPs that integrate/express mNeon in transduced cells and co-package Cas9-sgRNAs targeting the β2M gene were produced with 6.7 μg Gag-Cas9 and 3.3 μg Gag-Pol expressing plasmids. Primary human T cells (CD3$^+$) were treated with the VLPs and stained/analyzed for β2M protein expression 4 days post treatment. As shown in FIG. 31, a decrease in β2M positive cells is observed following treatment with the VLPs. The data indicate that VSV-G pseudotyped VLPs are sufficient to mediate editing in primary T cells isolated from human donors.

VLPs Pseudotyped with the HIV-1 Env Glycoprotein Mediate Specific Gene Editing of Primary CD4+ T Cells Ex Vivo.

Figure 32:
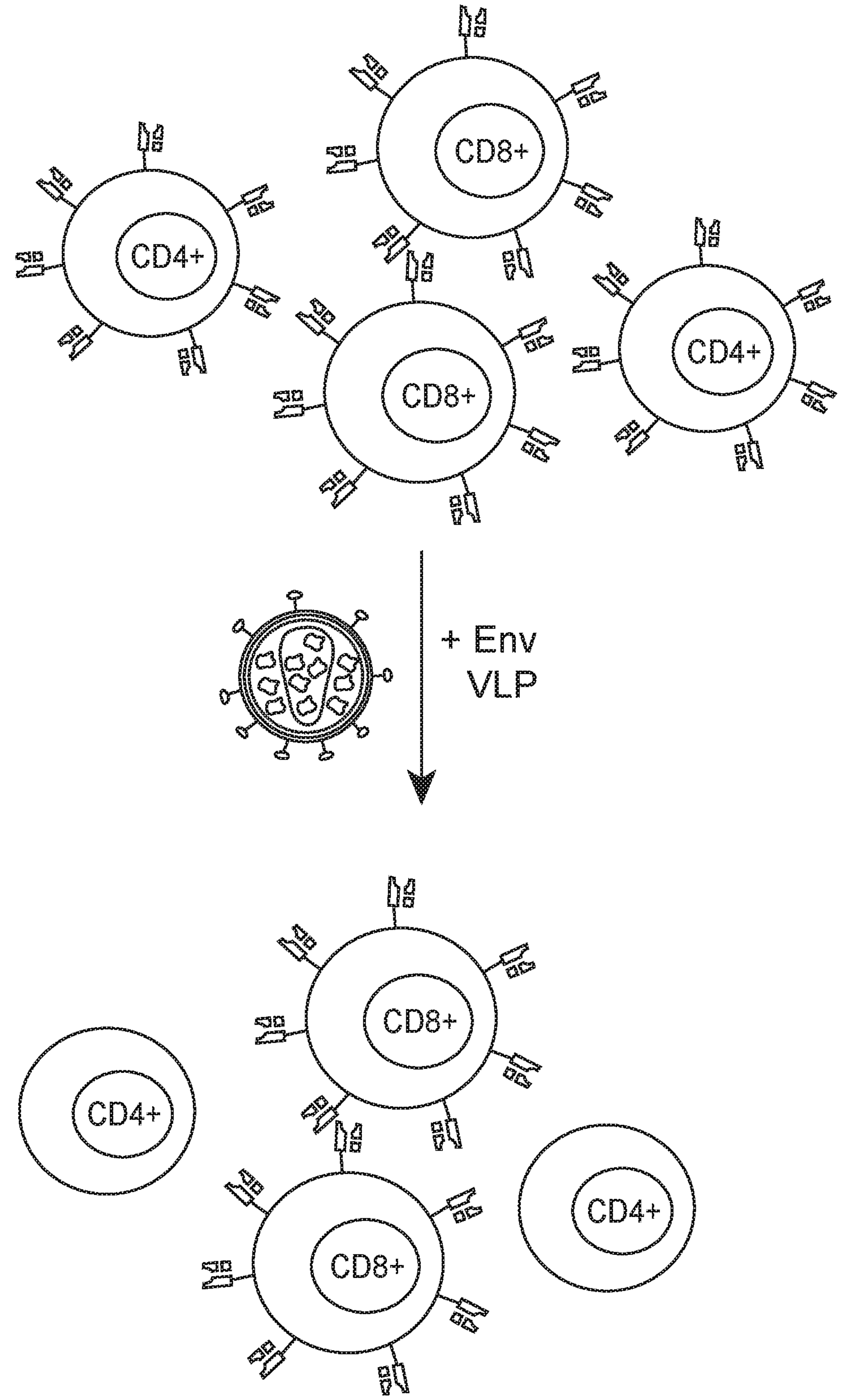
FIG. 32 depicts gene editing of primary $CD4^+$ T cells using VLPs pseudotyped with HIV-1 Env glycoprotein.
Figure 32:
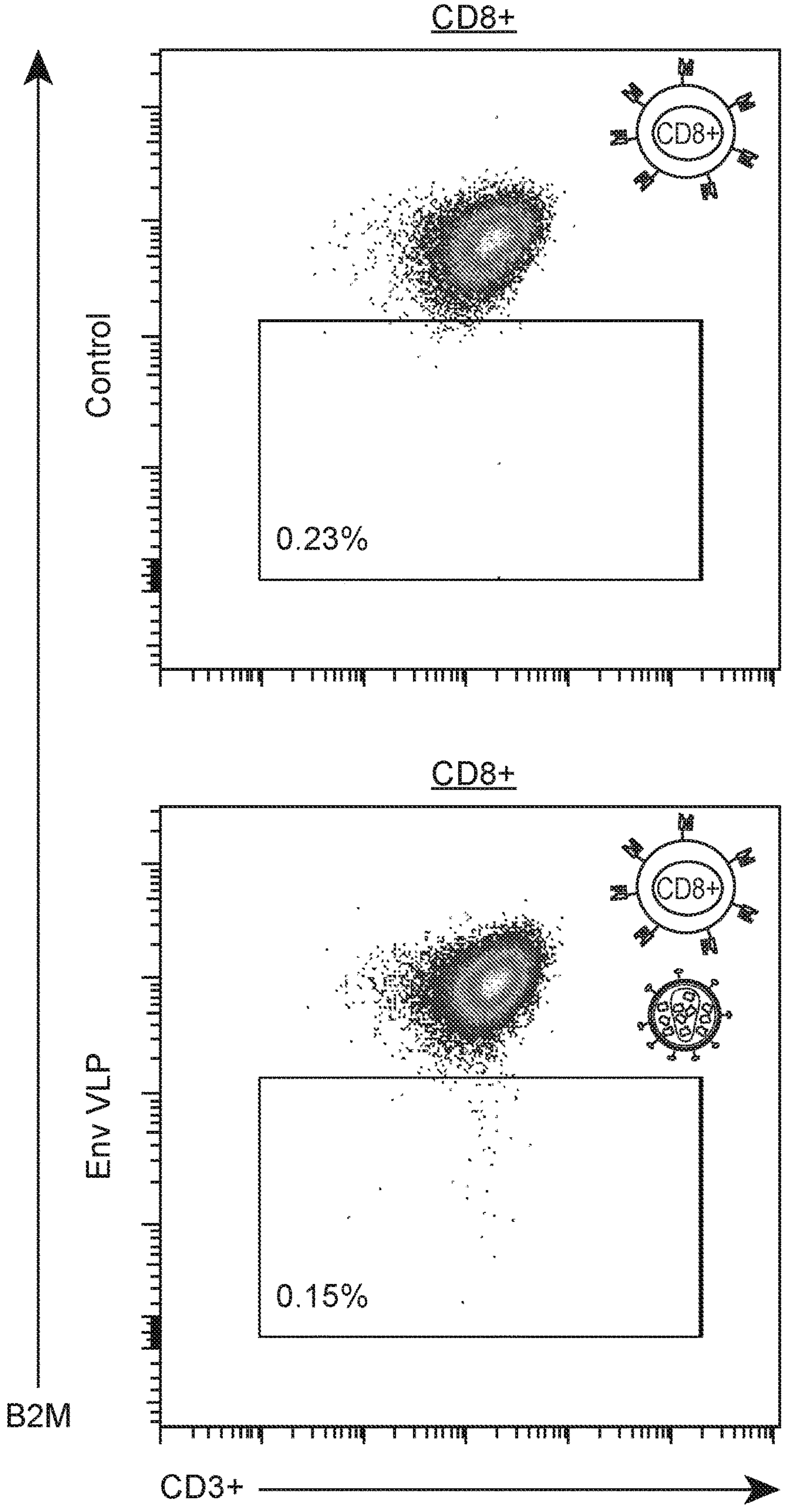
Figure 32:
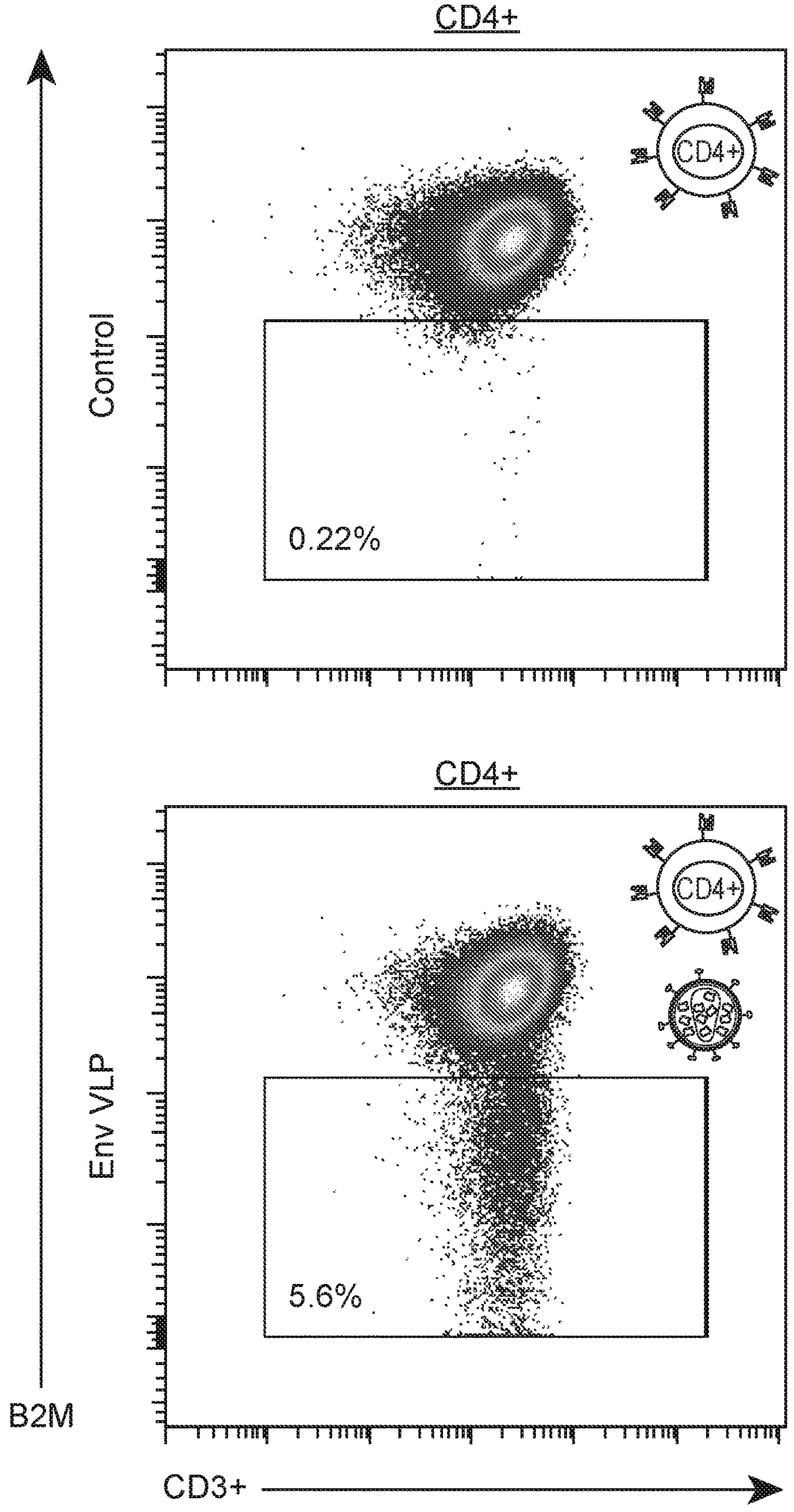

Primary human CD3$^+$ T cells (a mixture of CD4$^+$ and CD8$^+$ cells) were treated with HIV-1 env-pseudotyped VLPs and analyzed for β2M protein expression 4 days post treatment by flow cytometry. The data, shown in FIG. 32, indicate that protein knockout is observed in the $CD4^+$ cells and not in the $CD8^+$ cells.

Example 13: VLPs that Package Anti-CRISPR Proteins (ACRs)

Figure 33:
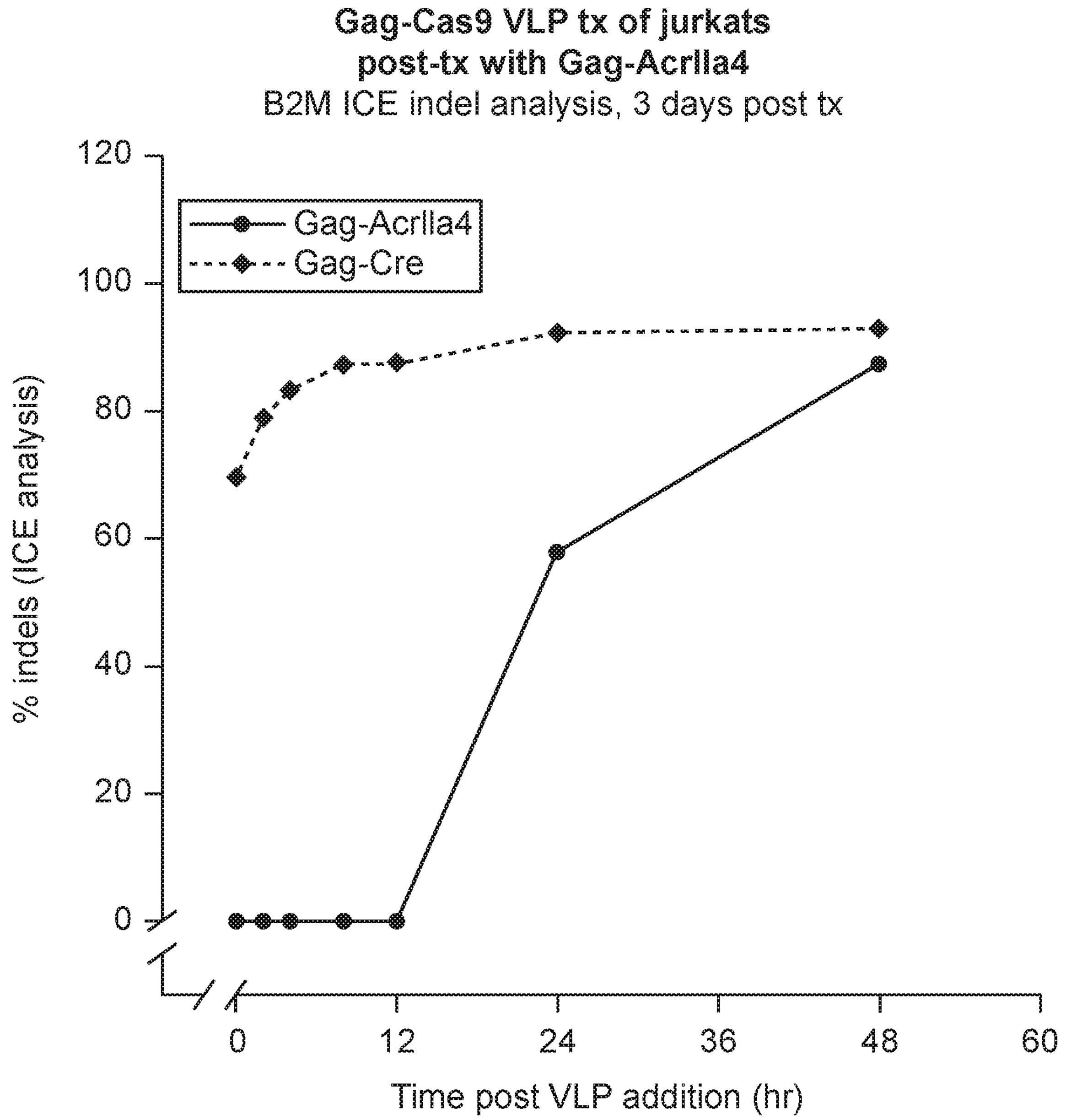
FIG. 33 depicts the effect of anti-CRISPR (Acr), delivered via VLPs, on gene editing in Jurkat cells.

Jurkat cells were treated at time 0 with Gag-Cas9 VLPs that packaged anti-β2M Cas9-sgRNA RNPs. Either Gag-AcrIIa4 or Gag-Cre VLPs were added at the indicated time points. Genomic DNA was isolated at 3 days post time 0 and PCR amplification and Sanger sequencing of the targeted β2M locus was performed. Synthego ICE analysis was used to calculate % indels. The data, shown in FIG. 33, indicate that Gag-AcrIIa4 protected Jurkat cells from Gag-Cas9 mediated editing up to 12 hours post treatment ("post tx").

Example 14: Characterization of VLPs

Gag-Cas9 Particles Induce High Levels of Gene Editing in Various Cell Lines.

Figure 34:
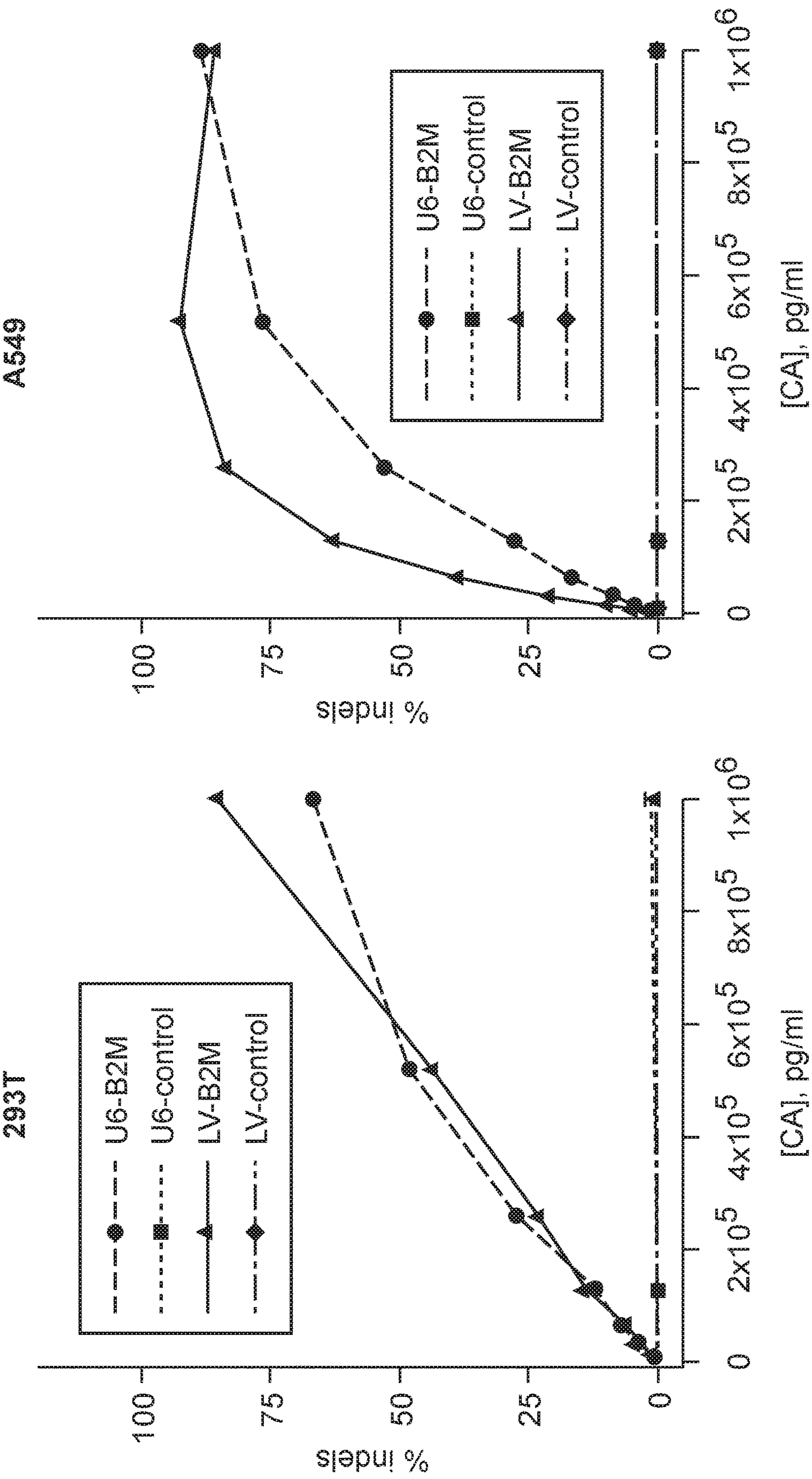
FIG. 34 depicts induction of high levels of gene editing by Gag-Cas9 VLPs in various cell lines.
Figure 34:
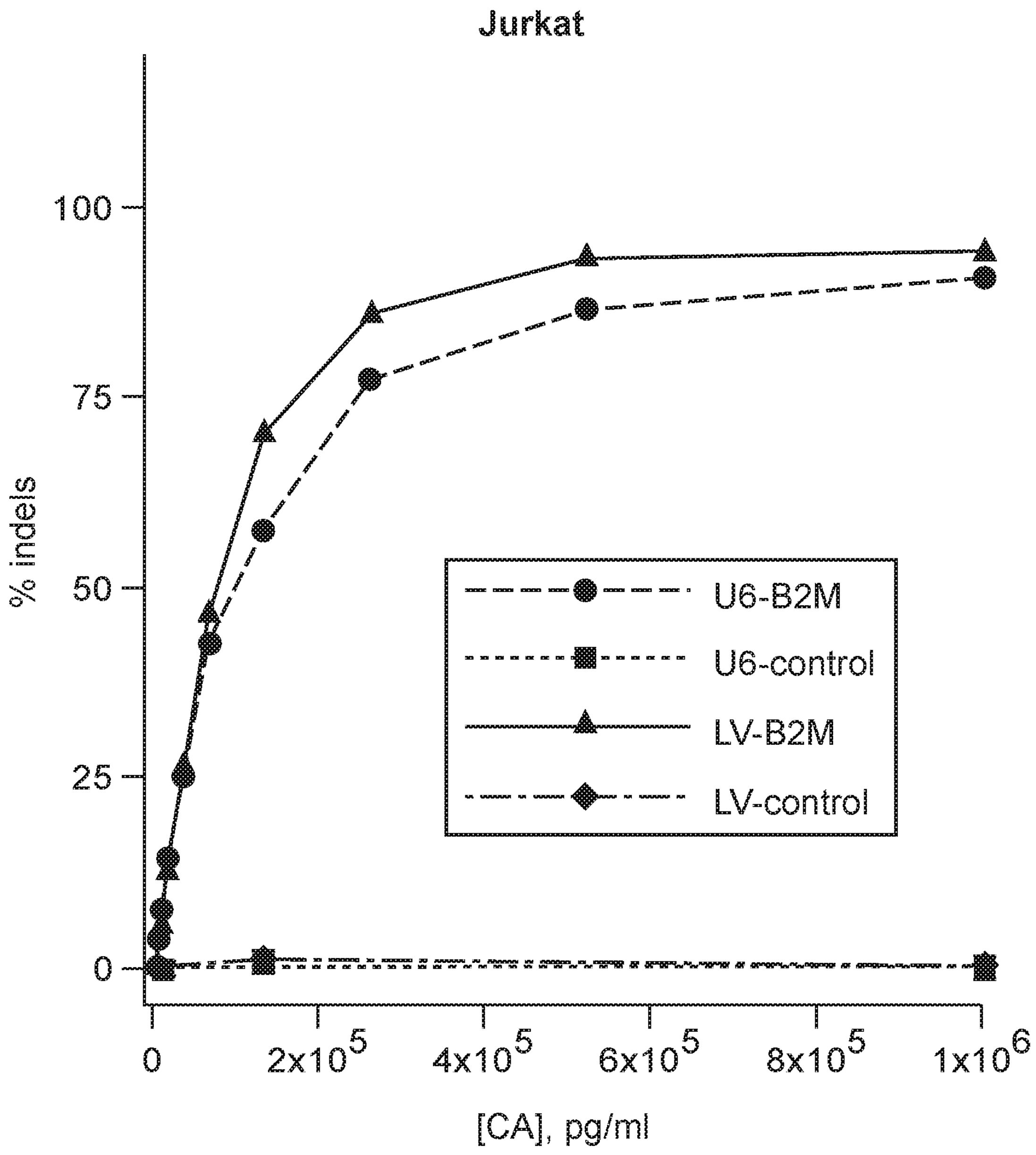

VLPs that solely package sgRNA-Cas9 RNPs targeting the β2M locus ("U6-B2M") or control ("U6-control") or co-package a lentiviral genome ("LV-B2M" and "LV-control") were produced. Samples were normalized by calculating the HIV-1 capsid content by enzyme-linked immunosorbent assay (ELISA). Normalized samples were diluted 2-fold and used to treat 293T, A549, and Jurkat cells in triplicate. DNA was isolated from treated cells after 3 days and amplicon sequencing was performed on a MiSeq. Indel analysis was performed with CRISPResso2. The data are shown in FIG. 34 and indicate that Gag-Cas9 VLPs induce high levels of gene editing in a variety of cell lines.

Pseudotyping Glycoproteins are Essential for VLP Cell Entry.

Figure 35:
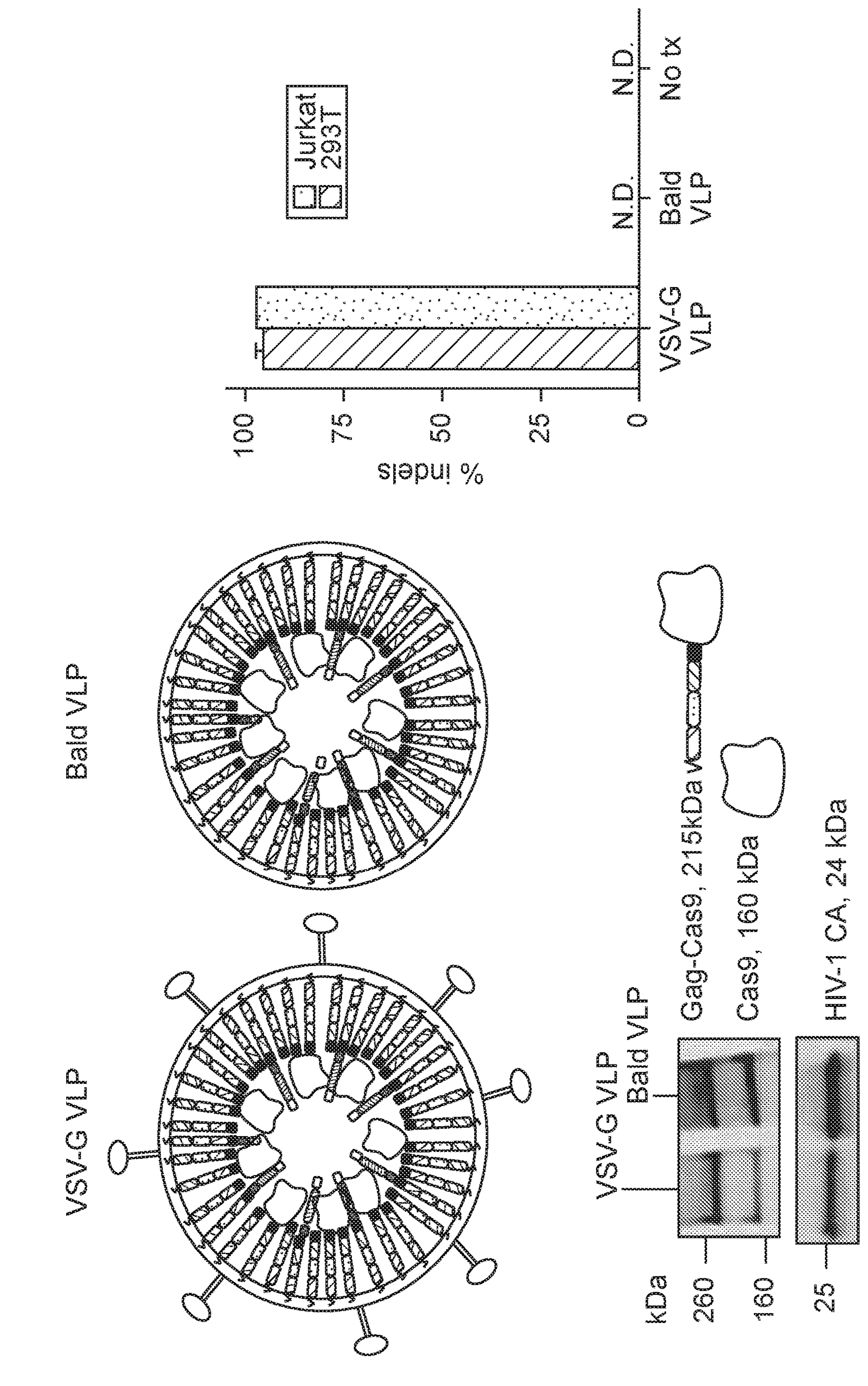
FIG. 35 depicts the effect of pseudotyping glycoproteins on VLP cell entry.

VSV-G or "bald" VLPs packaging sgRNA-Cas9 RNPs targeting the β2M locus were produced. As shown in FIG. 35, both packaged Cas9 protein, as detected by western blot (lower left). Jurkat and 293T cells were treated with either VSV-G or "bald" VLPs. DNA was isolated 3 days post treatment and PCR on the targeted loci was performed and submitted for MiSeq sequencing. As shown in FIG. 35 (right panel), robust editing was observed for the VSV-G pseudotyped particles. No editing was observed in cells treated with the "bald" VLPs. (N.D.=not detected).

Two Different sgRNAs can be Packaged in the Same VLP.

Figure 36:
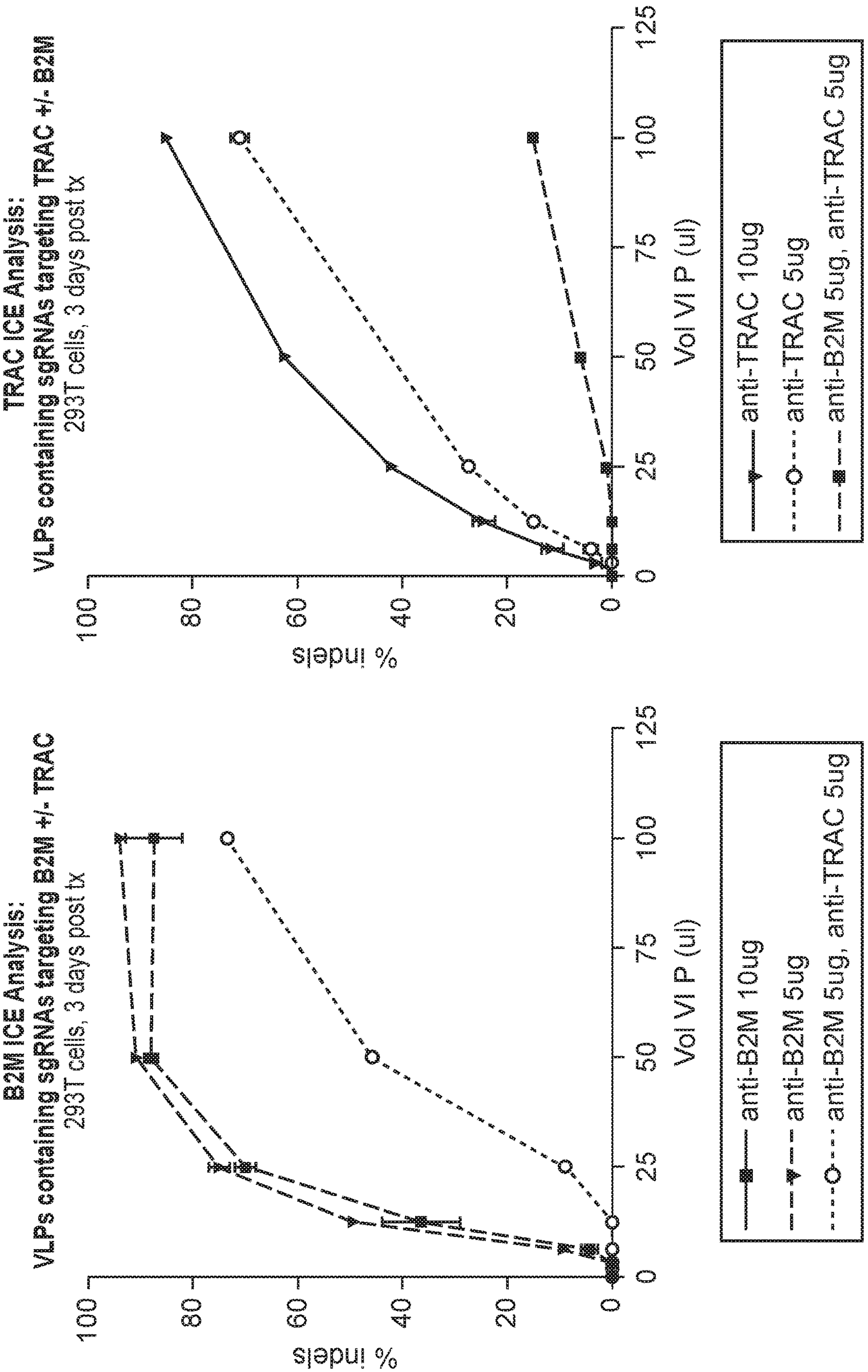
FIG. 36 depicts simultaneous delivery of 2 different sgRNAs using VLPs.

VLPs were produced using various amounts of sgRNA expression plasmid: 10 μg anti-β2M; 5 μg anti-β2M; 10 μg anti-TRAC; 5 μg anti-TRAC; or 5 μg anti-β2M+5 μg anti TRAC. 293T cells were treated with 2-fold dilutions of these VLPs and DNA was isolated 3 days post treatment. PCRs were performed on the targeted β2M and TRAC loci and PCR products were submitted for Sanger sequencing and subsequent ICE analysis. As shown in FIG. 36, when VLPs are produced with 5 μg anti-β2M+5 μg anti TRAC, editing was observed at both loci in treated cells.

VLPs can be Frozen and Maintain Activity.

Figure 37:
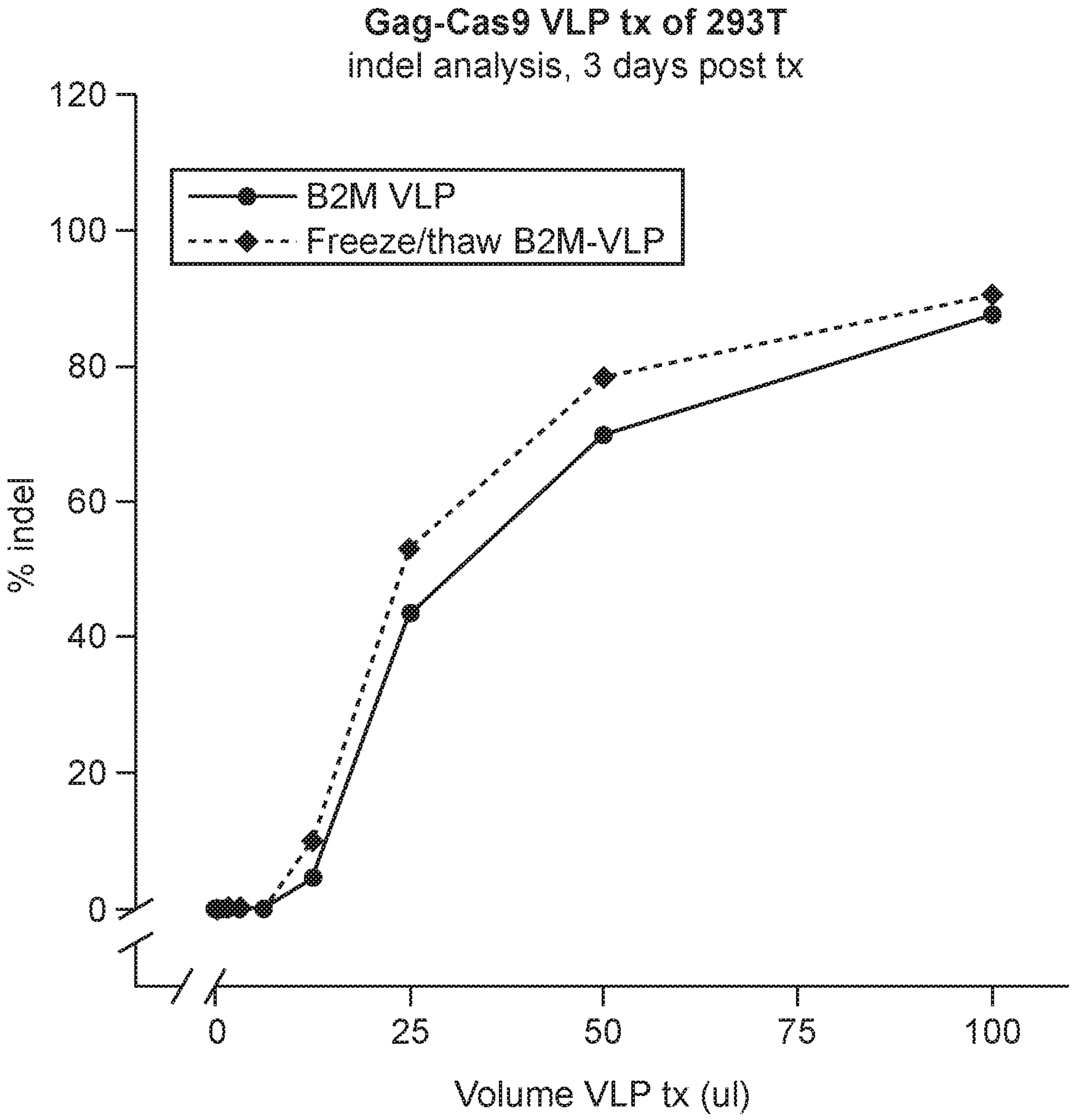
FIG. 37 depicts freeze-thaw stability of VLPs.

VLPs packaging sgRNA-Cas9 RNPs targeting the β2M locus were produced and split into two aliquots. One aliquot was kept at 4 °C for 4 hours and the other was frozen at −80 °C and then re-thawed. Two-fold dilutions of VLPs were performed and used to treat 293T cells. DNA was isolated 3 days post treatment. PCR at the targeted locus was performed and submitted for Sanger sequencing and ICE analysis to determine % indel. As shown in FIG. 37, no loss in editing efficiency was observed when VLPs were frozen prior to use.

Example 15: VLPs and Base Editing

Figure 38:
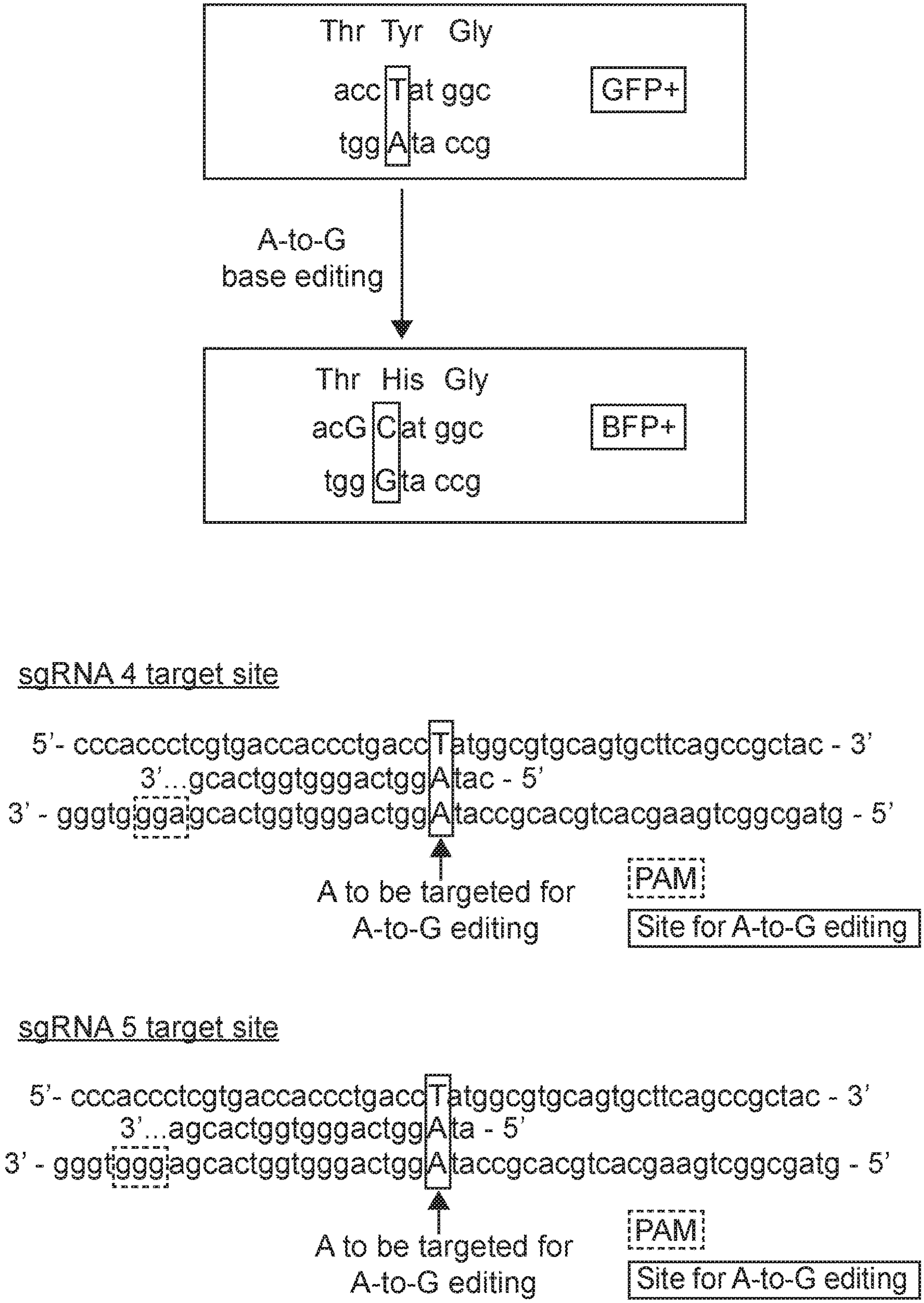
FIG. 38 depicts a fluorescent GFP-to-BFP assay for detecting the activity of base editors.
Figure 42:
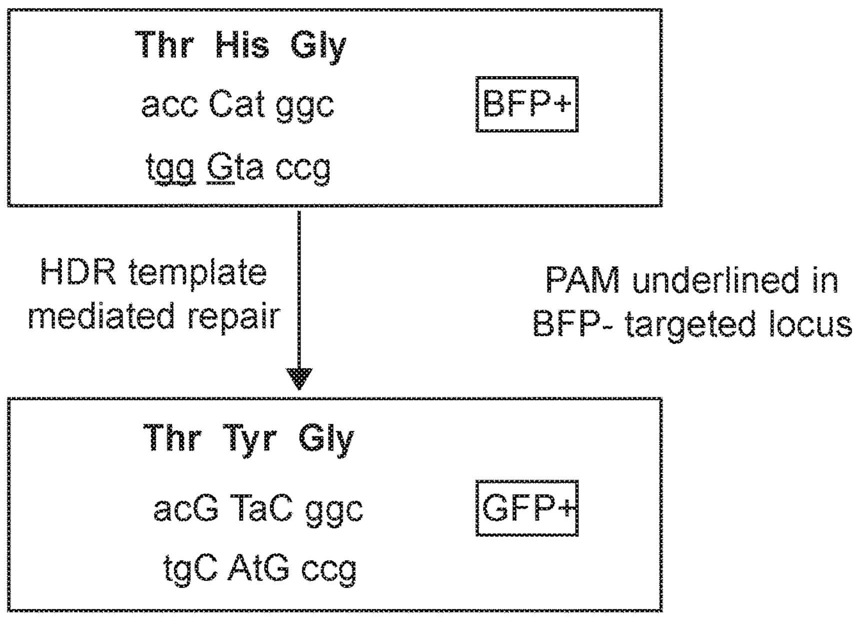
FIG. 42 depicts a fluorescent BFP-to-GFP assay for detecting homology-directed repair (HDR) activity.

Assays outlined in FIG. 38 and FIG. 42 rely upon the ability to change one amino acid in the green fluorescent protein (GFP) gene and achieve a conversion to blue fluorescent protein (BFP), or vice versa. Therefore, cell lines with an integrated BFP/GFP gene can be used to quantify the frequency of gene editing outcomes such as homology-directed repair (HDR) or base editing, where the change from one codon to another can be readily assayed as a switch in fluorescent protein expression.

FIG. 38 depicts a fluorescent GFP-to-BFP assay, using engineered cells (termed "GFP-to-BFP"), for detecting the activity of a base editor. See, e.g., Richardson et al. (2016) *Nat. Biotechnol.* 34:339; Glaser et al. (2016) *Mol. Ther. Nucl. Acids* 5:e334; and Coelho et al. (2018) *BMC Biol.* 16:150. This assay was used to determine VLP-mediated delivery of a base editor. FIG. 38 depicts the targeted codon in a 293T cell line with an integrated copy of GFP. By treating these cells with an A-to-G base editor (such as miniABEmax) directed to the site of the targeted codon via an appropriate sgRNA, the conversion of GFP to BFP can be used to assay the activity of the base editor switching the A:T basepair (indicated in yellow) to a G:C basepair.

Figure 39:
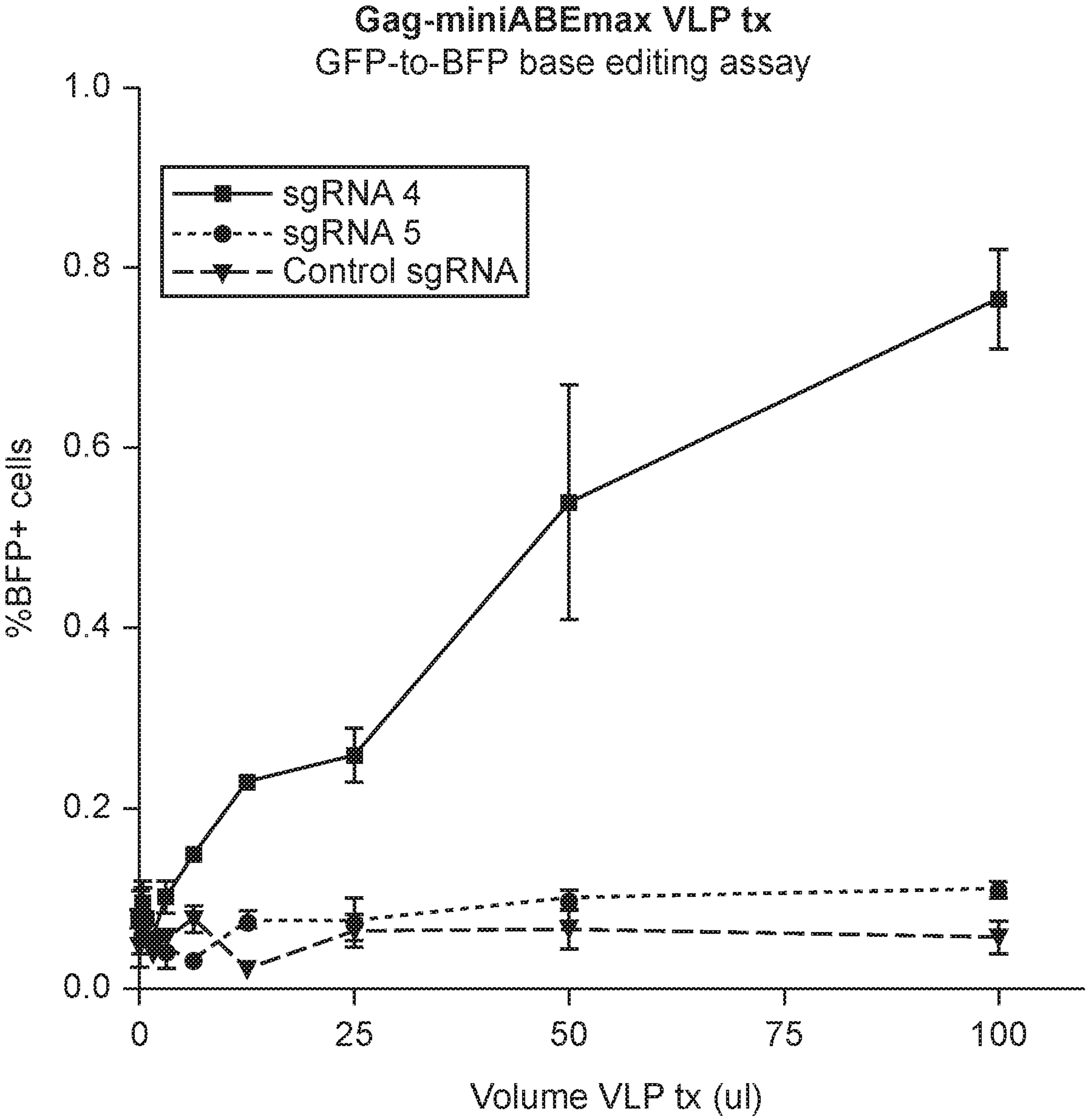
FIG. 39 depicts VLP delivery of a base editor.

Gag-miniABEmax VLPs were produced to package sgRNA-miniABEmax RNPs with sgRNA 4 or sgRNA 5 (see FIG. 38). 2-fold dilutions of VLPs were used to treat GFP-to-BFP cells (see FIG. 38) and fluorescence was analyzed at three days post treatment. % BFP+ cells (indicating successful base editing) was quantified by flow cytometry. The data, shown in FIG. 39, indicate that VLPs using the appropriate sgRNA can be used to deliver a base editor that retains functional activity.

FIG. 40A-40E provides the nucleotide sequence of the Gag-miniABEmax plasmid. FIG. 41 provides the amino acid sequence of the encoded Gag-spacer-miniABEmax-SV40 NLS polypeptide. The spacer between Gag and miniABEmax contains the SQNYPIVQ (SEQ ID NO:882) cleavage site.

Example 16: Homology-Directed Repair

FIG. 42 depicts a fluorescent BFP-to-GFP assay for detecting HDR activity. See, e.g., Richardson et al. (2016) *Nat. Biotechnol.* 34:339. This assay was used detect HDR activity following VLP-mediated delivery. FIG. 42 depicts the targeted codon in a 293T cell line with an integrated copy of BFP. When an HDR template that converts the targeted codon from His to Tyr is supplied in conjunction with Cas9 RNP complexes targeting the BFP gene, successful HDR outcomes can be quantified by measuring the conversion of BFP fluorescence to GFP fluorescence.

Figure 43:
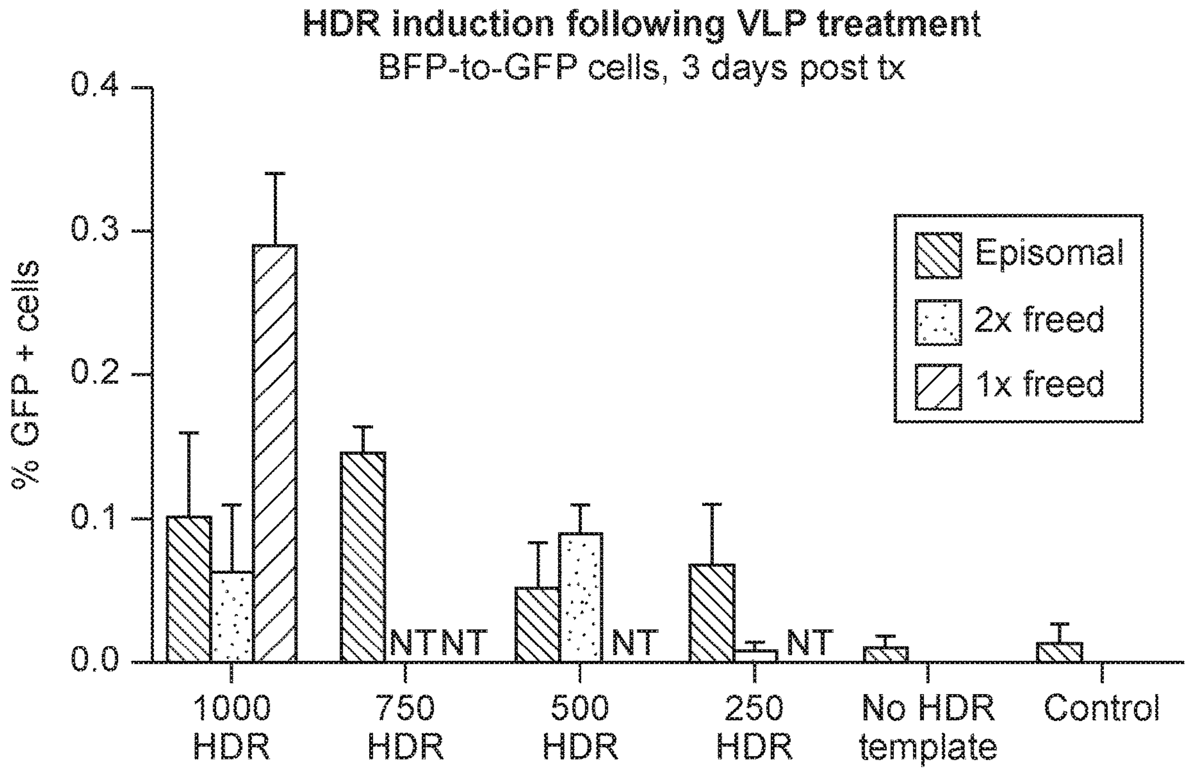
FIG. 43 depicts HDR induction in cells following treatment with VLPs.

FIG. 43 depicts an integration-defective lentiviral (LV) genome as a template for HDR. Non-integrating LV vectors were produced that contain HDR templates that switch the BFP gene to GFP (LV-HDR) upon editing and repair by HDR. LV-HDR VLPs were co-administered with VLPs targeting the BFP locus for editing (sgRNA 5'-gctgaagcactgcacgccat; SEQ ID NO:1074) and GFP+ cells were quantified 3 days post treatment. "Episomal"=HDR template is in the non-integrated LV genome. "2×freed"=sgRNA target sites were cloned to flank the HDR sequence. "1×freed"=a single sgRNA target site was cloned on the 3' end of the HDR sequence. NT=not tested. The data shown in FIG. 43 indicate that a non-integrating lentiviral vector can be used as a template for homology-directed repair in conjunction with the VLP-based delivery of Cas9-sgRNA ribonucleoprotein complexes.

Example 17: VLP Delivery of Cre Protein into Mouse Lungs

Figure 44:
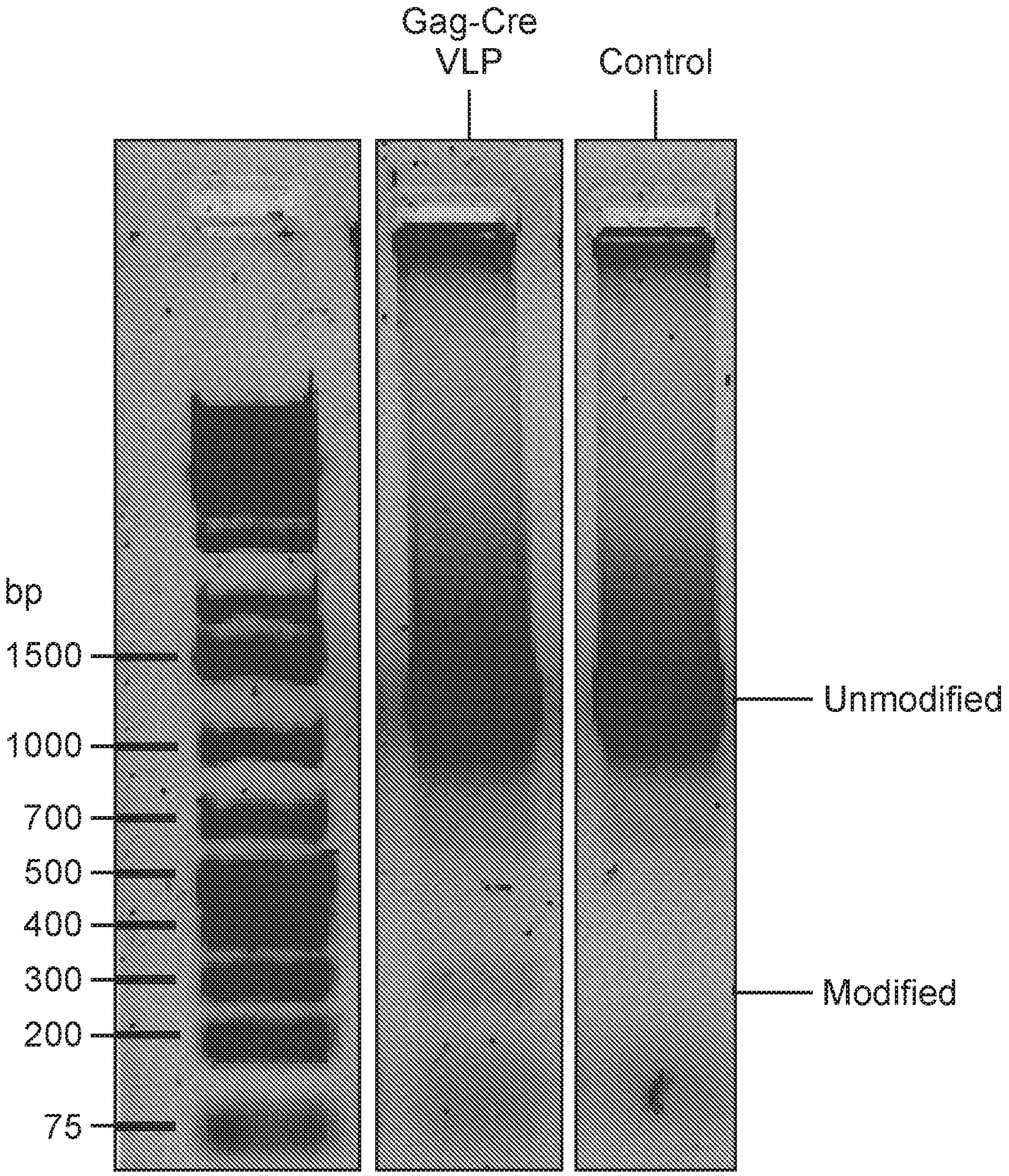
FIG. 44 depicts VLP deliver of Cre protein into mouse lungs in vivo.

VLPs were generated in which the Cre-recombinase protein was fused to the C-terminus of gag ("Gag-Cre VLPs"). Ai9 mice were intratracheally administered 40 μl of Gag-Cre VLPs or 40 μl of phosphate buffered saline as control. DNA was harvested from the lungs 5 days post treatment and PCR was performed using primers that amplify the floxed stop cassette (F: 5'-GCTCCTGGGCAACGTGCTGGTTATTG (SEQ ID NO:1070), R: 5'-TTGATGACCTCCTCGCCCTTGCTCAC (SEQ ID NO:1071)). The expected PCR product sizes for the unmodified and modified loci are 1130 bp and 259 bp, respectively. As shown in FIG. 44, a PCR product corresponding to the modified loci was observed following Gag-Cre VLP administration, demonstrating delivery of the functional Cre-recombinase in vivo.

FIG. 45A-45D provide the nucleotide sequence of the Gag-Cre plasmid. FIG. 46 provides the amino acid sequence of the encoded Gag-spacer-Cre-SV40 NLS polypeptide. The spacer between Gag and Cre contains the SQNYPIVQ (SEQ ID NO:882) cleavage site.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy sequence listing. A copy of the sequence listing is available in electronic form from the USPTO web site (https://seqdata.uspto.gov/docdetail?docId=US12807943B2). An electronic copy of the sequence listing will also be available from the USPTO upon request and payment of the fee set forth in 37 CFR 1.19(b)(3).

What is claimed is:

1. A nucleic acid comprising a nucleotide sequence that encodes a fusion polypeptide, wherein the fusion polypeptide comprises, in N-terminal to C-terminal order:

a) a retroviral gag polyprotein comprising a matrix (MA) polypeptide, a capsid (CA) polypeptide, and a nucleocapsid (NC) polypeptide, wherein:
   i) the MA polypeptide comprises the amino acid sequence of SEQ ID NO: 847;
   ii) the CA polypeptide comprises the amino acid sequence of shown in SEQ ID NO: 848; and
   iii) the NC polypeptide comprises the amino acid sequence of shown in SEQ ID NO: 849;
b) a heterologous protease cleavage site comprising the amino acid sequence SQNYPIVQ (SEQ ID NO: 882); and
c) a therapeutic polypeptide.

2. The nucleic acid of claim 1, wherein the therapeutic polypeptide is selected from a group consisting of nuclease, a base editor, a recombinase, a transcription factor, an anti-CRISPR polypeptide, a reverse transcriptase, a prime editor, and an antibody.

3. The nucleic acid of claim 2, wherein the transcription factor is selected from a group consisting of CRISPR/Cas effector polypeptide fusion polypeptide comprising a transcription modulator, a zinc finger protein transcription factor (ZFP-TF), and a transcription activator like effector transcription factor (TALE-TF).

4. The nucleic acid of claim 1, wherein the therapeutic polypeptide is a Clustered Regularly Interspaced Short Palindromic Repeats (CRISPR)/Cas effector polypeptide.

5. The nucleic acid of claim 4, wherein the CRISPR/Cas effector polypeptide is a type II CRISPR/Cas effector polypeptide, a type VI CRISPR/Cas effector polypeptide, or a type VI CRISPR/Cas polypeptide.

6. The nucleic acid of claim 4, wherein the CRISPR/Cas effector polypeptide is:

a) a variant that exhibits reduced nucleic acid cleavage activity; or
b) a fusion polypeptide comprising: i) a variant CRISPR/Cas effector polypeptide that exhibits reduced nucleic acid cleavage activity; and ii) a heterologous fusion polypeptide.

7. The nucleic acid of claim 4, wherein the CRISPR/Cas effector polypeptide comprises one or more nuclear localization signals (NLSs).

8. The nucleic acid of claim 2, wherein the nuclease is selected from the group consisting of CRISPR/Cas effector polypeptide, a zinc finger nuclease (ZFN), a transcription activator like effector nuclease (TALEN), and a MegaTal.

9. The nucleic acid of claim 2, wherein the base editor is a cytidine-specific base editor or an adenine-specific base editor.

10. The nucleic acid of claim 4, wherein the CRISPR/Cas effector polypeptide is selected from the group consisting of Cas9, Cas12a, Cas12b, Cas12c, Cas12d, Cas12e, Cas13a, Cas13b, Cas13c, Cas13d, Cas14a, Cas14b, and Cas14c polypeptide.

11. The nucleic acid of claim 6, wherein the heterologous fusion polypeptide is a nucleic acid modifying enzyme or a protein modifying enzyme.

12. The nucleic acid of claim 6, wherein the heterologous fusion polypeptide is a transcriptional modulator, a cytidine deaminase, or an adenosine deaminase.

13. A fusion protein comprising, in N-terminal to C-terminal order:

a) a retroviral gag polyprotein comprising a matrix (MA) polypeptide, a capsid (CA) polypeptide, and a nucleocapsid (NC) polypeptide, wherein:
   i) the MA polypeptide comprises the amino acid sequence of SEQ ID NO: 847;

ii) the CA polypeptide comprises the amino acid sequence of SEQ ID NO: 848; and iii) the NC polypeptide comprises the amino acid sequence of SEQ ID NO: 849;

b) a heterologous protease cleavage site comprising the amino acid sequence SQNYPIVQ (SEQ ID NO: 882); and c) a therapeutic polypeptide.

14. A nucleic acid comprising, in N-terminal to C-terminal order:

a) a retroviral gag polyprotein comprising a matrix (MA) polypeptide, a capsid (CA) polypeptide, and a nucleocapsid (NC) polypeptide, wherein:

i) the MA polypeptide comprises the amino acid sequence of SEQ ID NO: 847;

ii) the CA polypeptide comprises the amino acid sequence of SEQ ID NO: 848; and iii) the NC polypeptide comprises the amino acid sequence of SEQ ID NO: 849;

b) a heterologous protease cleavage site comprising the amino acid sequence SQNYPIVQ (SEQ ID NO: 882); and c) a therapeutic polypeptide.

15. A nucleic acid comprising, in N-terminal to C-terminal order:

a) a retroviral gag polyprotein comprising a matrix (MA) polypeptide, a capsid (CA) polypeptide, and a nucleocapsid (NC) polypeptide, wherein:

i) the MA polypeptide comprises the amino acid sequence of SEQ ID NO: 847;

ii) the CA polypeptide comprises the amino acid sequence of SEQ ID NO: 848; and iii) the NC polypeptide comprises the amino acid sequence of SEQ ID NO: 849;

b) a heterologous protease cleavage site comprising the amino acid sequence SQNYPIVQ (SEQ ID NO: 882); and c) a therapeutic polypeptide.

16. The nucleic acid of claim 1, wherein the therapeutic polypeptide comprises a nuclease.

17. The nucleic acid of claim 1, wherein the therapeutic polypeptide comprises a Cas9 polypeptide.

18. The fusion protein of claim 13, wherein the therapeutic polypeptide comprises a nuclease.

19. The fusion protein of claim 13, wherein the therapeutic polypeptide comprises a CRISPR/Cas effector polypeptide.

20. The fusion protein of claim 19, wherein the CRISPR/Cas effector polypeptide wherein the CRISPR/Cas effector polypeptide is: a) a variant that exhibits reduced nucleic acid cleavage activity; or b) a fusion polypeptide comprising: i) a variant CRISPR/Cas effector polypeptide that exhibits reduced nucleic acid cleavage activity; and ii) a heterologous fusion polypeptide.

21. The fusion protein of claim 13, wherein the therapeutic polypeptide comprises a type II CRISPR/Cas effector polypeptide, a type VI CRISPR/Cas effector polypeptide, or a type VI CRISPR/Cas polypeptide.

22. The fusion protein of claim 13, wherein the therapeutic polypeptide comprises a Cas9 polypeptide.

23. The fusion protein of claim 13, wherein the therapeutic polypeptide comprises one or more NLSs.

24. The nucleic acid of claim 7, wherein the one or more NLSs comprise the NLS of a SV40 virus large T-antigen, a human p53 protein, or a combination thereof.

25. The nucleic acid of claim 24, wherein the NLS of the SV40 virus large T-antigen comprises the amino acid sequence PKKKRKV (SEQ ID NO:909), the NLS of the human p53 protein comprises the amino acid sequence PQPKKKPL (SEQ ID NO:917), or the combination of the NLS of the SV40 virus large T-antigen and the NLS of the human p53 protein comprise the amino acid sequences of PKKKRKV (SEQ ID NO:909) and PQPKKKPL (SEQ ID NO:917), respectively.

26. The nucleic acid of claim 7, wherein the one or more NLSs are at the N-terminus, the C-terminus, or both the N-terminus and the C-terminus of the CRISPR/Cas effector polypeptide.

27. The nucleic acid of claim 4, wherein the CRISPR/Cas effector polypeptide comprises a nuclear export sequence (NES).

28. The nucleic acid of claim 14, wherein the CRISPR/Cas effector polypeptide comprises one or more NLSs.

29. The nucleic acid of claim 28, wherein the one or more NLSs comprise the NLS of a SV40 virus large T-antigen, a human p53 protein, or a combination thereof.

30. The nucleic acid of claim 28, wherein the NLS of the SV40 virus large T-antigen comprises the amino acid sequence PKKKRKV (SEQ ID NO:909), the NLS of the human p53 protein comprises the amino acid sequence PQPKKKPL (SEQ ID NO:917), or the combination of the NLS of the SV40 virus large T-antigen and the NLS of the human p53 protein comprise the amino acid sequences of PKKKRKV (SEQ ID NO: 909) and PQPKKKPL (SEQ ID NO:917), respectively.

31. The nucleic acid of claim 28, wherein the one or more NLSs are at the N-terminus, the C-terminus, or both the N-terminus and the C-terminus of the CRISPR/Cas effector polypeptide.

32. The nucleic acid of claim 28, wherein the one or more NLSs comprise two NLSs at the N-terminus and two NLSs at the C-terminus of the CRISPR/Cas effector polypeptide.

33. The nucleic acid of claim 14, wherein the CRISPR/Cas effector polypeptide comprises an NES.

34. The fusion protein of claim 15, wherein the CRISPR/Cas effector polypeptide comprises one or more NLSs.

35. The fusion protein of claim 34, wherein the one or more NLSs comprise the NLS of a SV40 virus large T-antigen, a human p53 protein, or a combination thereof.

36. The fusion protein of claim 34, wherein the NLS of the SV40 virus large T-antigen comprises the amino acid sequence PKKKRKV (SEQ ID NO:909), the NLS of the human p53 protein comprises the amino acid sequence PQPKKKPL (SEQ ID NO:917), or the combination of the NLS of the SV40 virus large T-antigen and the NLS of the human p53 protein comprise the amino acid sequences of PKKKRKV (SEQ ID NO:909) and PQPKKKPL (SEQ ID NO:917), respectively.

37. The fusion protein of claim 34, wherein the one or more NLSs are at the N-terminus, the C-terminus, or both the N-terminus and the C-terminus of the CRISPR/Cas effector polypeptide.

38. The fusion protein of claim 34, wherein the one or more NLSs comprise two NLSs at the N-terminus and two NLSs at the C-terminus of the CRISPR/Cas effector polypeptide.

39. The fusion protein of claim 15, wherein the CRISPR/Cas effector polypeptide comprises an NES.

40. The fusion protein of claim 15, wherein the fusion protein is complexed with a guide RNA.

41. The fusion protein of claim 40, wherein the guide RNA comprises a single-molecule guide RNA (sgRNA).

42. The fusion protein of claim 40, wherein the guide RNA comprises a targeting sequence that targets a gene selected from the list consisting of: PD1, CTLA4, and a T cell receptor (TCR) gene.

43. The fusion protein of claim 42, wherein the TCR gene is a constant region of a TCR alpha chain (TRAC).

44. The nucleic acid of claim 14, wherein the CRISPR/Cas effector polypeptide comprises a Cas9 polypeptide.

45. The fusion protein of claim 15, wherein the CRISPR/Cas effector polypeptide comprises a Cas9 polypeptide.

46. The nucleic acid of claim 17, wherein the Cas9 polypeptide comprises the amino acid sequence set forth in SEQ ID NO: 5.

47. The fusion protein of claim 22, wherein the Cas9 polypeptide comprises the amino acid sequence set forth in SEQ ID NO: 5.

48. The nucleic acid of claim 44, wherein the Cas9 polypeptide comprises the amino acid sequence set forth in SEQ ID NO: 5.

49. The fusion protein of claim 45, wherein the Cas9 polypeptide comprises the amino acid sequence set forth in SEQ ID NO: 5.

50. The nucleic acid of claim 1, wherein the nucleotide sequence that encodes the fusion polypeptide is operably linked to a promoter.

51. The nucleic acid of claim 14, wherein the nucleotide sequence that encodes the fusion polypeptide is operably linked to a promoter.

52. The nucleic acid of claim 6, wherein the heterologous fusion polypeptide is selected from a reverse transcriptase, a protein modifying enzyme, a nucleic acid modifying enzyme, and a transcriptional modulator.

53. The nucleic acid of claim 9, wherein the base editor is a cytidine deaminase.

54. The fusion protein of claim 20, wherein the heterologous fusion polypeptide is selected from a reverse transcriptase, a protein modifying enzyme, a nucleic acid modifying enzyme, and a transcriptional modulator.

* * * * *